(12) United States Patent
Moussa et al.

(10) Patent No.: US 8,093,379 B2
(45) Date of Patent: Jan. 10, 2012

(54) MACROCYCLIC SERINE PROTEASE INHIBITORS

(75) Inventors: Adel Moussa, Burlington, MA (US); Benjamin Alexander Mayes, Boston, MA (US); Elodie Rosinovsky, Brighton, MA (US); Alistair Stewart, Somerville, MA (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 244 days.

(21) Appl. No.: 12/563,072

(22) Filed: Sep. 18, 2009

(65) Prior Publication Data
US 2010/0016578 A1   Jan. 21, 2010

Related U.S. Application Data

(63) Continuation of application No. 12/365,127, filed on Feb. 3, 2009, now Pat. No. 8,003,659.

(60) Provisional application No. 61/026,086, filed on Feb. 4, 2008, provisional application No. 61/083,867, filed on Jul. 25, 2008.

(51) Int. Cl.
C07D 487/04 (2006.01)
C07D 403/12 (2006.01)
C07D 401/14 (2006.01)
C07D 215/38 (2006.01)
C07D 221/02 (2006.01)
C07D 295/00 (2006.01)

(52) U.S. Cl. ........ 540/455; 540/460; 546/159; 546/183; 548/530

(58) Field of Classification Search .................. 540/455, 540/460; 546/159, 183; 548/530
See application file for complete search history.

(56) References Cited

U.S. PATENT DOCUMENTS

| | | | |
|---|---|---|---|
| 5,538,865 A | 7/1996 | Reyes et al. |
| 5,990,276 A | 11/1999 | Zhang et al. |
| 6,004,933 A | 12/1999 | Spruce et al. |
| 6,143,715 A | 11/2000 | Llinas-Brunet et al. |
| 6,265,380 B1 | 7/2001 | Tung et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,410,531 B1 | 6/2002 | Llinas-Brunet et al. |
| 6,420,380 B2 | 7/2002 | Llinas-Brunet et al. |
| 6,448,281 B1 | 9/2002 | Beaulieu et al. |
| 6,479,508 B1 | 11/2002 | Beaulieu et al. |
| 6,534,523 B1 | 3/2003 | Llinas-Brunet et al. |
| 6,608,027 B1 | 8/2003 | Tsamtrozps et al. |
| 6,642,204 B2 | 11/2003 | Llinas-Brunet et al. |
| 6,653,295 B2 | 11/2003 | Glunz et al. |
| 6,727,366 B2 | 4/2004 | Han et al. |
| 6,767,991 B1 | 7/2004 | Llinas-Brunet et al. |
| 6,794,404 B2 | 9/2004 | Beaulieu et al. |
| 6,838,475 B2 | 1/2005 | Arasappan et al. |
| 6,841,566 B2 | 1/2005 | Beaulieu et al. |
| 6,846,802 B2 | 1/2005 | Chen et al. |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,908,901 B2 | 6/2005 | Bailey et al. |
| 6,911,428 B2 | 6/2005 | Zhu et al. |
| 6,919,423 B2 | 7/2005 | Llinas-Brunet et al. |
| 6,995,174 B2 | 2/2006 | Wang et al. |
| 7,012,066 B2 | 3/2006 | Saksena et al. |
| 7,041,698 B2 | 5/2006 | Ripka et al. |
| 7,091,184 B2 | 8/2006 | Llinas-Brunet et al. |
| 7,109,344 B2 | 9/2006 | Arlt |
| 7,119,072 B2 | 10/2006 | Llinas-Brunet et al. |
| 7,125,845 B2 | 10/2006 | Wu et al. |
| 7,132,504 B2 | 11/2006 | Scola et al. |
| 7,135,462 B2 | 11/2006 | Scola et al. |
| 7,148,347 B2 | 12/2006 | Brandenburg et al. |
| 7,169,760 B2 | 1/2007 | Saksena et al. |
| 7,173,004 B2 | 2/2007 | McPhee et al. |
| 7,176,208 B2 | 2/2007 | Nakajima et al. |
| 7,183,302 B2 | 2/2007 | Romine et al. |
| 7,183,374 B2 | 2/2007 | Brenner et al. |

(Continued)

FOREIGN PATENT DOCUMENTS

CA    2370400    8/2003

(Continued)

OTHER PUBLICATIONS

Attwood et al., "The Design and Synthesis of Potent Inhibitors of Hepatitis C Virus NS3-4A Proteinase," *Antiviral Chemistry and Chemotherapy* 1999, vol. 10, pp. 259-273.

(Continued)

*Primary Examiner* — Bruck Kifle
(74) *Attorney, Agent, or Firm* — Jones Day

(57) ABSTRACT

Provided herein are macrocyclic serine protease inhibitor compounds, for example, of Formula I, pharmaceutical compositions comprising the compounds, and processes of preparation thereof. Also provided are methods of their use for the treatment of an HCV infection in a host in need thereof.

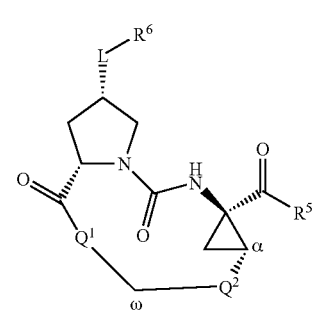

(I)

18 Claims, No Drawings

U.S. PATENT DOCUMENTS

| | | |
|---|---|---|
| 7,189,844 B2 | 3/2007 | Gallou et al. |
| 7,208,600 B2 | 4/2007 | Cottrell et al. |
| 7,253,160 B2 | 8/2007 | Njoroge et al. |
| 7,268,211 B2 | 9/2007 | Gallou et al. |
| 7,273,851 B2 | 9/2007 | Miao et al. |
| 7,309,708 B2 | 12/2007 | Tu et al. |
| 7,323,447 B2 | 1/2008 | Sin et al. |
| 7,351,825 B2 | 4/2008 | Inaba et al. |
| 7,368,452 B2 | 5/2008 | Nakajima et al. |
| RE40,525 E | 9/2008 | Llinas-Brunet et al. |
| 7,439,258 B2 | 10/2008 | Beaulieu et al. |
| 7,442,695 B2 | 10/2008 | Njoroge et al. |
| 7,449,479 B2 | 11/2008 | Wang et al. |
| 7,449,591 B2 | 11/2008 | Brenner et al. |
| 7,470,664 B2 | 12/2008 | Holloway et al. |
| 7,482,501 B2 | 1/2009 | Leitner et al. |
| 7,491,794 B2 | 2/2009 | Blatt et al. |
| 7,504,378 B2 | 3/2009 | Llinas-Brunet et al. |
| 7,511,157 B2 | 3/2009 | Bailey et al. |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0065418 A1 | 5/2002 | Beaulieu et al. |
| 2002/0111313 A1 | 8/2002 | Campbell et al. |
| 2003/0181363 A1 | 9/2003 | Llinas-Brunet et al. |
| 2003/0186895 A1 | 10/2003 | Llinas-Brunet et al. |
| 2003/0187018 A1 | 10/2003 | Llinas-Brunet et al. |
| 2003/0191067 A1 | 10/2003 | Llinas-Brunet et al. |
| 2003/0224977 A1 | 12/2003 | Llinas-Brunet et al. |
| 2003/0232816 A1 | 12/2003 | Beaulieu et al. |
| 2003/0236251 A1 | 12/2003 | Beaulieu et al. |
| 2004/0002448 A1 | 1/2004 | Tsantrizos et al. |
| 2004/0033959 A1 | 2/2004 | Chen et al. |
| 2004/0038872 A1 | 2/2004 | Campbell et al. |
| 2004/0048802 A1 | 3/2004 | Ripka et al. |
| 2004/0072761 A1 | 4/2004 | Campbell et al. |
| 2004/0077551 A1 | 4/2004 | Campbell et al. |
| 2004/0106559 A1 | 6/2004 | Wang et al. |
| 2004/0110126 A1 | 6/2004 | Kukolj et al. |
| 2004/0180815 A1 | 9/2004 | Nakajima et al. |
| 2004/0224900 A1 | 11/2004 | Bailey et al. |
| 2004/0224955 A1 | 11/2004 | Beaulieu et al. |
| 2004/0229777 A1 | 11/2004 | Cerreta et al. |
| 2004/0229818 A1 | 11/2004 | Llinas-Brunet et al. |
| 2004/0248779 A1 | 12/2004 | Dersch et al. |
| 2004/0266668 A1 | 12/2004 | Nakajima et al. |
| 2005/0020503 A1 | 1/2005 | Llinas-Brunet et al. |
| 2005/0049187 A1 | 3/2005 | Brandenburg et al. |
| 2005/0065073 A1 | 3/2005 | Wu et al. |
| 2005/0069522 A1 | 3/2005 | Colonno et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0090450 A1 | 4/2005 | Farmer et al. |
| 2005/0096364 A1 | 5/2005 | Romine et al. |
| 2005/0119453 A1 | 6/2005 | Brenner et al. |
| 2005/0137140 A1 | 6/2005 | Cottrell et al. |
| 2005/0143316 A1 | 6/2005 | Tu et al. |
| 2005/0143580 A1 | 6/2005 | Arlt |
| 2005/0153877 A1 | 7/2005 | Miao et al. |
| 2005/0154186 A1 | 7/2005 | Gallou et al. |
| 2005/0164921 A1 | 7/2005 | Njoroge et al. |
| 2005/0176648 A1 | 8/2005 | Saksena et al. |
| 2005/0187165 A1 | 8/2005 | Scola et al. |
| 2005/0192212 A1 | 9/2005 | Llinas-Brunet et al. |
| 2005/0209135 A1 | 9/2005 | Busacca et al. |
| 2005/0215423 A1 | 9/2005 | Brenner et al. |
| 2005/0261200 A1 | 11/2005 | Miao et al. |
| 2005/0267018 A1 | 12/2005 | Blatt et al. |
| 2005/0267040 A1 | 12/2005 | Scola et al. |
| 2005/0267151 A1 | 12/2005 | Busacca et al. |
| 2006/0009667 A1 | 1/2006 | Herweck et al. |
| 2006/0019905 A1 | 1/2006 | Bailey et al. |
| 2006/0046956 A1 | 3/2006 | Sannigrahi et al. |
| 2006/0046965 A1 | 3/2006 | Bailey et al. |
| 2006/0063915 A1 | 3/2006 | Gallou et al. |
| 2006/0089300 A1 | 4/2006 | Llinas-Brunet et al. |
| 2006/0122123 A1 | 6/2006 | Chaudhary et al. |
| 2006/0172950 A1 | 8/2006 | Wang et al. |
| 2006/0183694 A1 | 8/2006 | Sin et al. |
| 2006/0199773 A1 | 9/2006 | Sausker et al. |
| 2006/0199826 A1 | 9/2006 | Inaba et al. |
| 2006/0252951 A1 | 11/2006 | Leitner et al. |
| 2006/0258868 A1 | 11/2006 | Bailey et al. |
| 2007/0010455 A1 | 1/2007 | Hewawasam et al. |
| 2007/0021330 A1 | 1/2007 | Wu et al. |
| 2007/0021351 A1 | 1/2007 | White et al. |
| 2007/0027071 A1 | 2/2007 | Holloway et al. |
| 2007/0049536 A1 | 3/2007 | Venkatraman et al. |
| 2007/0054842 A1 | 3/2007 | Blatt et al. |
| 2007/0060510 A1 | 3/2007 | Nakajima et al. |
| 2007/0060565 A1 | 3/2007 | Meanwell et al. |
| 2007/0072809 A1 | 3/2007 | Cho et al. |
| 2007/0078081 A1 | 4/2007 | Casarez et al. |
| 2007/0078122 A1 | 4/2007 | Bergstrom et al. |
| 2007/0093414 A1 | 4/2007 | Carini et al. |
| 2007/0093430 A1 | 4/2007 | Chen et al. |
| 2007/0099825 A1 | 5/2007 | D'Andrea et al. |
| 2007/0099929 A1 | 5/2007 | Thede et al. |
| 2007/0105781 A1 | 5/2007 | Lyons et al. |
| 2007/0161574 A1 | 7/2007 | Rosenquist et al. |
| 2007/0161575 A1 | 7/2007 | Miao et al. |
| 2007/0161789 A1 | 7/2007 | Cottrell et al. |
| 2007/0179167 A1 | 8/2007 | Cottrell et al. |
| 2007/0203072 A1 | 8/2007 | Rosenquist et al. |
| 2007/0237818 A1 | 10/2007 | Alton et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0265281 A1 | 11/2007 | Cottens et al. |
| 2007/0281884 A1 | 12/2007 | Sun et al. |
| 2007/0281885 A1 | 12/2007 | Sun et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0019942 A1 | 1/2008 | Seiwert et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0045530 A1 | 2/2008 | Brandl et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0125444 A1 | 5/2008 | Sun et al. |
| 2008/0145334 A1 | 6/2008 | Wang et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0177029 A1 | 7/2008 | Busacca et al. |
| 2008/0181868 A1 | 7/2008 | Sun et al. |
| 2008/0187516 A1 | 8/2008 | Sun et al. |
| 2008/0200497 A1 | 8/2008 | Bailey et al. |
| 2008/0200503 A1 | 8/2008 | Simmen et al. |
| 2008/0242835 A1 | 10/2008 | Shu |
| 2008/0261994 A1 | 10/2008 | Inaba et al. |
| 2008/0262058 A1 | 10/2008 | Simmen et al. |
| 2008/0267916 A1 | 10/2008 | Gai et al. |
| 2008/0267917 A1 | 10/2008 | Niu et al. |
| 2008/0267918 A1 | 10/2008 | Gai et al. |
| 2008/0269228 A1 | 10/2008 | Moore et al. |
| 2008/0269502 A1 | 10/2008 | Gantz et al. |
| 2008/0274080 A1 | 11/2008 | Or et al. |
| 2008/0274082 A1 | 11/2008 | Gai et al. |
| 2008/0279821 A1 | 11/2008 | Niu et al. |
| 2008/0286233 A1 | 11/2008 | Sun et al. |
| 2008/0287449 A1 | 11/2008 | Niu et al. |
| 2008/0292587 A1 | 11/2008 | Sun et al. |
| 2008/0306258 A1 | 12/2008 | Inaba et al. |
| 2008/0311077 A1 | 12/2008 | Chaudhary et al. |
| 2008/0317712 A1 | 12/2008 | Niu et al. |
| 2009/0005387 A1 | 1/2009 | Niu et al. |
| 2009/0023758 A1 | 1/2009 | Wahling et al. |
| 2009/0035267 A1 | 2/2009 | Moore et al. |

| | | | |
|---|---|---|---|
| 2009/0035268 A1 | 2/2009 | Sun et al. | |
| 2009/0035271 A1 | 2/2009 | Sun et al. | |
| 2009/0035272 A1 | 2/2009 | Moore et al. | |
| 2009/0041721 A1 | 2/2009 | Niu et al. | |
| 2009/0047244 A1 | 2/2009 | Parsy et al. | |
| 2009/0047248 A1 | 2/2009 | Sun et al. | |
| 2009/0047252 A1 | 2/2009 | Cai et al. | |
| 2009/0048297 A1 | 2/2009 | Phadke et al. | |
| 2009/0062311 A1 | 3/2009 | Simmen et al. | |
| 2009/0075869 A1 | 3/2009 | Holloway et al. | |
| 2009/0186869 A1* | 7/2009 | Cottell et al. | 514/210.21 |
| 2009/0257978 A1* | 10/2009 | Cho et al. | 424/85.4 |

FOREIGN PATENT DOCUMENTS

| | | |
|---|---|---|
| DE | 19914474 | 10/1999 |
| EP | 1881002 | 1/2008 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/04425 | 1/2002 |
| WO | WO 02/08187 | 1/2002 |
| WO | WO 02/08198 | 1/2002 |
| WO | WO 02/08251 | 1/2002 |
| WO | WO 02/08256 | 1/2002 |
| WO | WO 02/48116 | 6/2002 |
| WO | WO 02/48157 | 6/2002 |
| WO | WO 02/48172 | 6/2002 |
| WO | WO 02/060926 | 8/2002 |
| WO | WO 02/070739 | 9/2002 |
| WO | WO 03/007945 | 1/2003 |
| WO | WO 03/053349 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/014313 | 2/2004 |
| WO | WO 2004/014852 | 2/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/089974 | 10/2004 |
| WO | WO 2004/092203 | 10/2004 |
| WO | WO 2004/093798 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/053735 | 6/2005 |
| WO | WO 2005/053843 | 6/2005 |
| WO | WO 2005/054430 | 6/2005 |
| WO | WO 2005/056182 | 6/2005 |
| WO | WO 2005/058884 | 6/2005 |
| WO | WO 2005/070955 | 8/2005 |
| WO | WO 2005/073195 | 8/2005 |
| WO | WO 2005/073216 | 8/2005 |
| WO | WO 2005/075502 | 8/2005 |
| WO | WO 2005/090383 | 9/2005 |
| WO | WO 2005/095403 | 10/2005 |
| WO | WO 2005/116054 | 12/2005 |
| WO | WO 2006/000085 | 1/2006 |
| WO | WO 2006/005479 | 1/2006 |
| WO | WO 2006/007700 | 1/2006 |
| WO | WO 2006/007708 | 1/2006 |
| WO | WO 2006/020276 | 2/2006 |
| WO | WO 2006/026352 | 3/2006 |
| WO | WO 2006/033851 | 3/2006 |
| WO | WO 2006/043145 | 4/2006 |
| WO | WO 2006/075021 | 7/2006 |
| WO | WO 2006/086381 | 8/2006 |
| WO | WO 2006/119061 | 11/2006 |
| WO | WO 2006/122188 | 11/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/011658 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015855 | 2/2007 |
| WO | WO 2007/016441 | 2/2007 |
| WO | WO 2007/017144 | 2/2007 |
| WO | WO 2007/025307 | 3/2007 |
| WO | WO 2007/030656 | 3/2007 |
| WO | WO 2007/044933 | 4/2007 |
| WO | WO 2007/056120 | 5/2007 |
| WO | WO 2007/015824 | 8/2007 |
| WO | WO 2007/088571 | 8/2007 |
| WO | WO 2007/120595 | 10/2007 |
| WO | WO 2007/121124 | 10/2007 |
| WO | WO 2007/121125 | 10/2007 |
| WO | WO 2007/131966 | 11/2007 |
| WO | WO 2007/143694 | 12/2007 |
| WO | WO 2007/145894 | 12/2007 |
| WO | WO 2007/146695 | 12/2007 |
| WO | WO 2007/148135 | 12/2007 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/033389 | 3/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/070733 | 6/2008 |
| WO | WO 2008/086161 | 7/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106058 | 9/2008 |
| WO | WO 2008/106130 | 9/2008 |

| WO | WO 2008/106139 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005676 | 1/2009 |
| WO | WO 2009/005677 | 1/2009 |
| WO | WO 2009/005690 | 1/2009 |
| WO | WO 2009/010804 | 1/2009 |
| WO | WO 2009/014730 | 1/2009 |
| WO | WO 2009/042668 | 4/2009 |

OTHER PUBLICATIONS

Boyer et al., "Pathogenesis, Diagnosis and Management of Hepatitis C," *J. Hepatol.* 2000, vol. 32(Suppl. 1), pp. 98-112.

Chu et al., "Isolation and Structure of Sch 351633: A Novel Hepatitis C Virus (HCV) NS3 Protease Inhibitor from the Fungus," *Bioorganic and Medicinal Chemistry Letters* 1999, vol. 9, pp. 1949-1952.

Chu et al., "Structure of Sch 68631: A New Hepatitis C Virus Proteinase Inhibitor from Streptomyces sp.," *Tetrahedron Letters* 1996, vol. 37, pp. 7229-7232.

Di Besceglie et al., "The Unmet Challenges of Hepatitis C," *Scientific American*, 1999, vol. 281, pp. 80-85.

Fried et al., "Peginterferon alfa-2a Plus Ribavirin for Chronic Hepatitis C Virus Infection," *N. Engl. J. Med.* 2002, vol. 347, pp. 975-982.

Hadziyannis et al., "Peginterferon-α2a and Ribavirin Combination Therapy in Chronic Hepatitis C," *Ann. Intern. Med.* 2004, vol. 140, pp. 346-355.

Kakiuchi, et al., "Non-peptide Inhibitors of HCV Serine Proteinase," *FEBS Lett.* 1998, vol. 421, pp. 217-220.

Kato et al., "Molecular Cloning of the Human Hepatitis C Cirus Genome from Japanese Patients with Non-A, Non-B Hepatitis," *Proc. Natl. Acad. Sci. USA* 1990, vol. 87, pp. 9524-9528.

Kato, "Molecular Virology of Hepatitis C Virus," *Acta Medica Okayama*, 2001, vol. 55, pp. 133-159.

Kuo et al., "An Assay for Circulating Antibodies to a Major Etiologic Virus of Human Non-A, Non-B Hepatitis," *Science* 1989, vol. 244, pp. 362-364.

Llinas-Brunet et al., "Peptide-based Inhibitors of the Hepatitis C Virus Serine Protease," *Bioorg. Med. Chem. Lett.* 1998, vol. 8, pp. 1713-1718.

Manns et al., "Peginterferon alfa-2b Plus Ribavirin Compared with Interferon alfa-2b Plus Ribavirin for Initial Treatment of Chronic Hepatitis C: a Randomised Trial," *Lancet* 2001, vol. 358, pp. 958-965.

Poynard et al., "Randomised Trial of Interferon α2b Plus Ribavirin for 48 Weeks or for 24 Weeks Versus Interferon α2b Plus Placebo for 48 Weeks for Treatment of Chronic Infection with Hepatitis C Virus," *Lancet* 1998, vol. 352, pp. 1426-1432.

Qasim et al., "Interscaffolding Additivity. Association of $P_I$ Variants of Eglin C and of Turkey Ovomucoid Third Domain with Serine Proteinases," *Biochemistry* 1997, vol. 36, pp. 1598-1607.

Steinkuhler et al., "Product Inhibition of the Hepatitis C Virus NS3 Protease," *Biochemistry* 1998, vol. 37, pp. 8899-8905.

Sudo et al., "Establishment of an in Vitro Assay System for Screening Hepatitis C Virus Protease Inhibitors Using High Performance Liquid Chromatography," *Antiviral Research* 1996, vol. 32, pp. 9-18.

Sudo et al., "Novel Hepatitis C Virus Protease Inhibitors: Thiazolidine Derivatives," *Biochem. Biophys. Res. Commun.* 1997, vol. 238, pp. 643-647.

Takeshita, et al., "An Enzyme-linked Immunosorbent Assay for Detecting Proteolytic Activity of Hepatitis C Virus Proteinase," *Analytical Biochemistry* 1997, vol. 247, pp. 242-246.

Thomas, "Hepatitis C Epidemiology," *Curr. Top. Microbiol. Immunol.* 2000, vol. 242, pp. 25-41.

Velazquez et al., "Design, Synthesis, and Evaluation of Oxygen-Containing Macrocyclic Peptidomimetics as Inhibitors of HCV NS3 Protease," *J. Med. Chem.* 2009, vol. 52, pp. 700-708.

Zeng et al., "Epimerization Reaction of a Substituted Vinylcyclopropane Catalyzed by Ruthenium Carbenes: Mechanistic Analysis," *J. Org. Chem.* 2006, vol. 71, pp. 8864-8875.

* cited by examiner

MACROCYCLIC SERINE PROTEASE INHIBITORS

CROSS REFERENCE TO RELATED APPLICATIONS

This application is a continuation of U.S. application Ser. No. 12/365,127, filed Feb. 3, 2009, which claims the benefit of the priority of U.S. Provisional Application Nos. 61/026,086, filed Feb. 4, 2008, and 61/083,867, filed Jul. 25, 2008, the disclosure of each of which is incorporated herein by reference in its entirety.

FIELD

Provided herein are macrocyclic serine protease inhibitor compounds, pharmaceutical compositions comprising the compounds, and processes of preparation thereof. Also provided are methods of their use for the treatment of an HCV infection in a host in need thereof.

BACKGROUND

Hepatitis C virus (HCV) is known to cause at least 80% of posttransfusion hepatitis and a substantial proportion of sporadic acute hepatitis (Houghton et al., *Science* 1989, 244, 362-364; Thomas, *Curr. Top. Microbiol. Immunol.* 2000, 25-41). Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (Di Besceglie et al., *Scientific American*, 1999, October, 80-85; Boyer et al., *J. Hepatol.* 2000, 32, 98-112).

HCV is an enveloped virus containing a positive-sense single-stranded RNA genome of approximately 9.4 kb (Kato et al., *Proc. Natl. Acad. Sci. USA* 1990, 87, 9524-9528; Kato, *Acta Medico Okayama*, 2001, 55, 133-159). The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as an internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Presently, the most effective HCV therapy employs a combination of alpha-interferon and ribavirin, leading to sustained efficacy in about 40% of patients (Poynard et al., *Lancet* 1998, 352, 1426-1432). Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load (Manns et al, *Lancet* 2001, 358, 958-965; Fried et al., *N. Engl. J. Med.* 2002, 347, 975-982; Hadziyannis et al., *Ann. Intern. Med.* 2004, 140, 346-355). Thus, there is a clear and unmet need to develop effective therapeutics for treatment of HCV infection.

SUMMARY OF THE DISCLOSURE

Provided herein are macrocyclic serine protease inhibitor compounds, pharmaceutical compositions comprising the compounds, and processes of preparation thereof. Also provided are methods of their use for the treatment of an HCV infection in a host in need thereof.

In one embodiment, provided herein is a compound of Formula I:

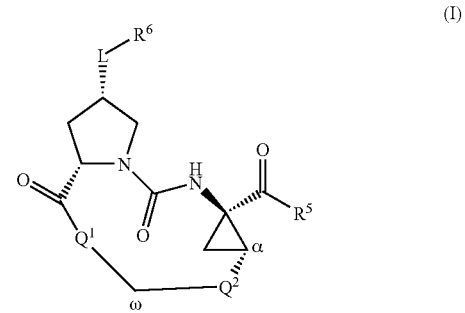

(I)

or a single enantiomer, a racemic mixture, or a mixture of diastereomers thereof; or a pharmaceutically acceptable salt, solvate, or prodrug thereof;

wherein:

$R^5$ is —OH, —NR$^8$R$^9$, —NHS(O)$_2$R$^8$, —NHS(O)$_2$NR$^8$R$^9$, —NHC(O)R$^8$, —NHC(O)NR$^8$R$^9$, —C(O)R$^9$, or —C(O)NR$^8$R$^9$; wherein:

each $R^8$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, C$_{1-6}$ alkyl-C$_{3-7}$ cycloalkylene, —CH$_2$NR$^{8a}$R$^{8b}$, —CH(R$^{8c}$)NR$^{8a}$R$^{8b}$, —CHR$^{8c}$CHR$^{8d}$NR$^{8a}$R$^{8b}$, or —CH$_2$CR$^{8c}$R$^{8d}$NR$^{8a}$R$^{8b}$, wherein:

each $R^{8a}$, $R^{8c}$, and $R^{8d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, or C$_{6-14}$ aryl-C$_{1-6}$ alkylene; and each $R^{8b}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, —S(O)$_k$R$^{11}$, —S(O)$_k$NR$^{11}$R$^{12}$, —C(O)R$^{11}$, —C(O)OR$^{11}$, C(O)NR$^{11}$R$^{12}$, or —C(=NR$^{13}$)NR$^{11}$R$^{12}$; wherein each $R^{11}$, $R^{12}$, and $R^{13}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or $R^{11}$ and $R^{12}$ together with the N atom to which they are attached form heterocyclyl; or $R^{8a}$ and $R^{8b}$ together with the N atom to which they are attached form heterocyclyl; and each $R^9$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or $R^8$ and $R^9$ together with the N atom to which they are attached form heterocyclyl;

$R^6$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

L is a bond, $C_{1-6}$ alkylene, $C_{3-7}$ cycloalkylene, $C_{2-6}$ alkenylene, $C_{2-6}$ alkynylene, X, or —$(CR^{6a}R^{6b})_p$X—; wherein p is an integer of 1, 2, or 3; $R^{6a}$ and $R^{6b}$ are each independently hydrogen, halo, cyano, hydroxyl, or alkoxy; and X is —O—, —C(O)—, —C(O)O—, —OC(O)O—, —C(O)NR$^{14}$—, —C(=NR$^{14}$)NR$^{15}$—, —NR$^{14}$—, —NR$^{14}$C(O)NR$^{15}$—, —NR$^{14}$C(=NR$^{15}$)NR$^{16}$—, —NR$^{14}$S(O)$_k$NR$^{15}$—, —S(O)$_k$—, —S(O)$_k$NR$^{14}$—, —P(O)(OR$^{14}$)—, or —OP(O)(OR$^{14}$)—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

$Q^1$ is —O—, —N(R$^{17}$)—, —C(R$^{18}$R$^{19}$)—, or —CR$^{17}$(NR$^{18}$R$^{19}$)—; wherein:

each $R^{17}$ and $R^{18}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and each $R^{19}$ is independently —R$^{20}$, —C(O)R$^{20}$, —C(O)OR$^{20}$, —C(O)NR$^{21}$R$^{22}$, —C(=NR$^{20}$)NR$^{21}$R$^{22}$, or —S(O)$_k$R$^{20}$; where each $R^{20}$, $R^{21}$, and $R^{22}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{21}$ and $R^{22}$ together with the N atom to which they are attached form heterocyclyl; or $R^{18}$ and $R^{19}$ together with the C or N atom to which they are attached form $C_{3-7}$ cycloalkyl or heterocyclyl;

$Q^2$ is $C_{3-9}$ alkylene, $C_{3-9}$ alkenylene, or $C_{3-9}$ alkynylene, each optionally containing one to three heteroatoms in the chain, independently selected from O, N, and S; and each k is independently an integer of 1 or 2;

wherein each alkyl, alkylene, alkenyl, alkenylene, alkynyl, alkynylene, aryl, cycloalkyl, cycloalkylene, heterocyclyl, and heteroaryl is optionally substituted with one or more groups, each independently selected from cyano, halo, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or —C(O)R$^a$, —C(O)OR$^a$, —C(O)NR$^b$R$^c$, —C(NR$^a$)NR$^b$R$^c$, —OR$^a$, —OC(O)R$^a$, OC(O)OR$^a$, —OC(O)NR$^b$R$^c$, —OC(=NR$^a$)NR$^c$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)$_2$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of cyano, halo, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$, —NR$^e$C(=NR$^h$)NR$^f$R$^g$, —NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, or —S(O)$_2$R$^e$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^f$ and $R^g$ together with the N atom to which they are attached form heterocyclyl.

Also provided herein are pharmaceutical compositions comprising a compound disclosed herein, e.g., a compound of Formula I, including a single enantiomer, a racemic mixture, or a mixture of diastereomers thereof; or a pharmaceutically acceptable salt, solvate, or prodrug thereof; in combination with one or more pharmaceutically acceptable excipients or carriers.

Further provided herein is a method for treating or preventing an HCV infection, which comprises administering to a subject a therapeutically effective amount of a compound disclosed herein, e.g., a compound of Formula I, including a single enantiomer, a racemic mixture, or a mixture of diastereomers thereof; or a pharmaceutically acceptable salt, solvate, or prodrug thereof.

Additionally provided herein is a method for treating, preventing, or ameliorating one or more symptoms of a liver disease or disorder associated with an HCV infection, comprising administering to a subject a therapeutically effective amount of a compound disclosed herein, e.g., a compound of Formula I, including a single enantiomer, a racemic mixture, or a mixture of diastereomers thereof; or a pharmaceutically acceptable salt, solvate, or prodrug thereof.

Provided herein is a method for inhibiting replication of a virus in a host, which comprises administering to the host a therapeutically effective amount of a compound disclosed herein, e.g., a compound of Formula I, including a single enantiomer, a racemic mixture, or a mixture of diastereomers thereof; or a pharmaceutically acceptable salt, solvate, or prodrug thereof.

Provided herein is a method for inhibiting the activity of a serine protease, which comprises contacting the serine protease with a compound disclosed herein, e.g., a compound of Formula I, including a single enantiomer, a racemic mixture, or a mixture of diastereomers thereof; or a pharmaceutically acceptable salt, solvate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "IC$_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with cells, tissues, or organs of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "release controlling excipient" refers to an excipient whose primary function is to modify the duration or place of release of an active substance from a dosage form as compared with a conventional immediate release dosage form.

The term "nonrelease controlling excipient" refers to an excipient whose primary function do not include modifying the duration or place of release of an active substance from a dosage form as compared with a conventional immediate release dosage form.

The term "alkyl" refers to a linear or branched saturated monovalent hydrocarbon radical, wherein the alkylene may optionally be substituted as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene may optionally be substituted as described herein. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "alkenyl" refers to a linear or branched monovalent hydrocarbon radical, which contains one or more, in one embodiment, one to five, carbon-carbon double bonds. The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, carbon-carbon double bonds. The alkenylene may be optionally substituted as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "alkynyl" refers to a linear or branched monovalent hydrocarbon radical, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "alkynylene" refers to a linear or branched divalent hydrocarbon radical, which contains one or more, in one embodiment, one to five, carbon-carbon triple bonds. The alkynylene may be optionally substituted as described herein. The term "alkynylene" also encompasses both linear and branched alkynylene, unless otherwise specified. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene (—C≡C—) and propargylene (—CH$_2$C≡C—). For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms.

The term "cycloalkyl" refers to a cyclic saturated bridged and/or non-bridged monovalent hydrocarbon radical, which may be optionally substituted as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "cycloalkylene" refers to a cyclic saturated bridged and/or non-bridged divalent hydrocarbon radical, which may be optionally substituted as described herein. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene, cyclobutylene, cyclopentylene, cyclohexylene, cycloheptylene, decalinylene, and adamantylene.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents Q as described herein.

The term "arylene" refers to a monocyclic and/or multicyclic divalent aromatic group that contain at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydro-naphthylene (tetralinyl). In certain embodiments, arylene may also be optionally substituted as described herein.

The term "heteroaryl" refers to a monocyclic aromatic group and/or multicyclic aromatic group that contains at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, heteroaryl may also be optionally substituted with one or more substituents Q as described herein.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, heterocyclic may also be optionally substituted with one or more substituents Q as described herein.

The term "alkoxy" refers to an —OR radical, wherein R is, for example, alkyl, alkenyl, alkynyl, cycloalkyl, aryl, heteroaryl, or heterocyclyl, each as defined herein. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2-naphthyloxy. In certain embodiments, alkoxy may also be optionally substituted as described herein.

The term "acyl" refers to a —C(O)R radical, wherein R is, for example, alkyl, alkenyl, alkynyl, cycloalkyl, aryl, heteroaryl, or heterocyclyl, each as defined herein. Examples of acyl groups include, but are not limited to, acetyl, propionyl, butanoyl, isobutanoyl, pentanoyl, hexanoyl, heptanoyl, octanoyl, nonanoyl, decanoyl, dodecanoyl, tetradecanoyl, hexadecanoyl, octadecanoyl, eicosanoyl, docosanoyl, myristoleoyl, palmitoleoyl, oleoyl, linoleoyl, arachidonoyl, benzoyl, pyridinylcarbonyl, and furoyl. In certain embodiments, acyl may also be optionally substituted as described herein.

The term "halogen", "halide" or "halo" refers to fluorine, chlorine, bromine, and/or iodine.

The term "optionally substituted" is intended to mean that a group, such as an alkyl, alkylene, alkenyl, alkenylene, alkynyl, alkynylene, cycloalkyl, cycloalkylene, aryl, arylene, heteroaryl, heterocyclyl group, alkoxy, or acyl, may be substituted with one or more substituents independently selected from, e.g., alkyl, alkylene, alkenyl, alkenylene, alkynyl, alkynylene, cycloalkyl, cycloalkylene, aryl, arylene, heteroaryl, or heterocyclyl, each optionally substituted with one or more, in one embodiment, one, two, three, or four, substituents Q; halo, cyano (—CN), nitro (—NO$_2$), —SR$^a$, —S(O)R$^a$, —S(O)$_2$R$^a$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)$_2$R$^b$, —NR$^a$S(O)R$^b$R$^c$, or —NR$^a$S(O)$_2$R$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of cyano, halo, and nitro; C$_{1-6}$ alkyl, C$_{2-6}$ alkenyl, C$_{2-6}$ alkynyl, C$_{3-7}$ cycloalkyl, C$_{6-14}$ aryl, heteroaryl, and heterocyclyl; and —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$, —NR$^e$C(=NR$^h$)NR$^f$R$^g$, —NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, and —S(O)$_2$R$^e$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^f$ and R$^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

Compounds

HCV has a single positive-stranded RNA genome having about 9.6 kb in length that encodes a large polyprotein having about 3010 amino acids. This precursor polyprotein is then processed into a range of structural proteins, including core protein, C, and envelope glycoproteins, E1 and E2; and non-structural proteins, including NS2, NS3, NS4A, NS4B, NS5A, and NS5B, by host signal peptidases and two viral proteases, NS2-3 and NS3. The NS3 protein contains a trypsin-like serine protease domain at its N-terminus, while its C-terminal domain has helicase activity. Because of its vital role in viral replication, HCV NS3 serine protease has been actively pursued as a drug target for developing a new anti-HCV therapy.

Inhibitors of HCV NS3 protease that have been reported include linear and cyclic peptides and peptide mimetics, and non-peptide molecules (Llinàs-Brunet et al., *Bioorg. Med. Chem. Lett.* 1998, 8, 1713-1718; Steinkühler et al., *Biochemistry* 1998, 37, 8899-8905; U.S. Pat. Nos. 5,538,865; 5,990, 276; 6,143,715; 6,265,380; 6,323,180; 6,329,379; 6,410,531; 6,420,380; 6,534,523; 6,608,027; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; U.S. Pat. App. Pub. Nos.: 2002/0016294, 2002/ 0016442; 2002/0032175; 2002/0037998; 2004/0229777; 2005/0090450; 2005/0153877; 2005/176648; 2006/ 0046956; 2007/0021330; 2007/0021351; 2007/0049536; 2007/0054842; 2007/0060510; 2007/0060565; 2007/ 0072809; 2007/0078081; 2007/0078122; 2007/0093414; 2007/0093430; 2007/0099825; 2007/0099929; 2007/ 0105781; WO 98/17679; WO 98/22496; WO 99/07734; WO 00/09543; WO 00/59929; WO 02/08187; WO 02/08251; WO 02/08256; WO 02/08198; WO 02/48116; WO 02/48157; WO 02/48172; WO 02/60926; WO 03/53349; WO 03/64416; WO 03/64455; WO 03/64456; WO 03/66103; WO 03/99274; WO 03/99316; WO 2004/032827; WO 2004/043339; WO 2005/ 037214; WO 2005/037860; WO 2006/000085; WO 2006/ 119061; WO 2006/122188; WO 2007/001406; WO 2007/ 014925; WO 2007/014926; WO 2007/015824, and WO 2007/056120). However, citation of any reference herein is not an admission that such reference is prior art to the present disclosure.

Provided herein are compounds which are useful for the treatment of HCV infection, which, in one embodiment, can have activity as HCV serine protease inhibitors. Also provided herein are pharmaceutical compositions that comprise the compounds, methods of manufacture of the compounds, and methods of use of the compounds for the treatment of HCV infection in a host in need of treatment.

In one embodiment, provided herein is a compound of Formula I:

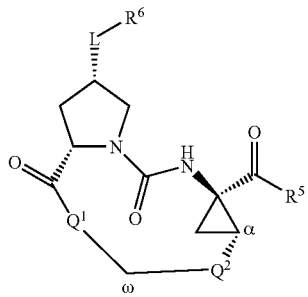

(I)

or a single enantiomer, a racemic mixture, or a mixture of diastereomers thereof; or a pharmaceutically acceptable salt, solvate, or prodrug thereof;
wherein:
$R^5$ is —OH, —$NR^8R^9$, —$NHS(O)_2R^8$, —$NHS(O)_2NR^8R^9$, —$NHC(O)R^8$, —$NHC(O)NR^8R^9$, —$C(O)R^9$, or —$C(O)NR^8R^9$; wherein:
  each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, —$CH_2NR^{8a}R^{8b}$, —$CH(R^{8c})NR^{8a}R^{8b}$, —$CHR^{8c}CHR^{8d}NR^{8a}R^{8b}$, or —$CH_2CR^{8c}R^{8d}NR^{8a}R^{8b}$, wherein:
  each $R^{8a}$, $R^{8c}$, and $R^{8d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, or $C_{6-14}$ aryl-$C_{1-6}$ alkylene; and
  each $R^{8b}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —$S(O)_kR^{11}$, —$S(O)_kNR^{11}R^{12}$, —$C(O)R^{11}$, —$C(O)OR^{11}$, —$C(O)NR^{11}R^{12}$, or —$C(=NR^{13})NR^{11}R^{12}$; wherein each $R^{11}$, $R^{12}$, and $R^{13}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{11}$ and $R^{12}$ together with the N atom to which they are attached form heterocyclyl; or
  $R^{8a}$ and $R^{8b}$ together with the N atom to which they are attached form heterocyclyl; and
each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or
$R^8$ and $R^9$ together with the N atom to which they are attached form heterocyclyl;
$R^6$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
L is a bond, $C_{1-6}$ alkylene, $C_{3-7}$ cycloalkylene, $C_{2-6}$ alkenylene, $C_{2-6}$ alkynylene, X, or —$(CR^{6a}R^{6b})_pX$—; wherein p is an integer of 1, 2, or 3; $R^{6a}$ and $R^{6b}$ are each independently hydrogen, halo, cyano, hydroxyl, or alkoxy; and X is —O—, —C(O)—, —C(O)O—, —OC(O)O—, —C(O)$NR^{14}$—, —$NR^{14}C(O)NR^{15}$—, —C(=$NR^{14}$)$NR^{15}$—, —$NR^{14}C(=NR^{15})NR^{16}$, —$NR^{14}S(O)_kNR^{15}$—, —$S(O)_k$—, —$S(O)_kNR^{14}$—, —P(O)(OR$^{14}$)—, or —OP(O)(OR$^{14}$)—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
$Q^1$ is —O—, —N($R^{17}$)—, —C($R^{18}R^{19}$)—, or —$CR^{17}(NR^{18}R^{19})$—; wherein:
  each $R^{17}$ and $R^{18}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and
  each $R^{19}$ is independently —$R^{20}$, —C(O)$R^{20}$, —C(O)OR$^{20}$, —C(O)NR$^{21}R^{22}$, —C(=NR$^{20}$)NR$^{21}R^{22}$, or —S(O)$_kR^{20}$; where each $R^{20}$, $R^{21}$, and $R^{22}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{21}$ and $R^{22}$ together with the N atom to which they are attached form heterocyclyl; or
  $R^{18}$ and $R^{19}$ together with the C or N atom to which they are attached form cycloalkyl or heterocyclyl;
$Q^2$ is $C_{3-9}$ alkylene, $C_{3-9}$ alkenylene, or $C_{3-9}$ alkynylene, each optionally containing one to three heteroatoms in the chain, independently selected from O, N, and S; and
each k is independently an integer of 1 or 2;
wherein each alkyl, alkylene, alkenyl, alkenylene, alkynyl, alkynylene, aryl, cycloalkyl, cycloalkylene, heterocyclyl, and heteroaryl is optionally substituted with one or more groups, each independently selected from cyano, halo, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or —C(O)$R^a$, —C(O)OR$^a$, —C(O)NR$^bR^c$, —C(NR$^a$)NR$^bR^c$, —OR$^a$, —OC(O)R$^a$, OC(O)OR$^a$, —OC(O)NR$^bR^c$, —OC(=NR$^a$)NR$^bR^c$, —OS(O)R$^a$, —OS(O)$_2R^a$, OS(O)NR$^bR^c$, OS(O)$_2NR^bR^c$, —NR$^bR^c$, —NR$^a$C(O)R$^b$, —NR$^a$C(O)OR$^a$, —NR$^a$C(O)NR$^b$R$^c$, —NR$^a$C(=NR$^d$)NR$^b$R$^c$, —NR$^a$S(O)R$^b$, NR$^a$S(O)$_2$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of cyano, halo, or nitro; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$, —NR$^e$C(=NR$^h$)NR$^f$R$^g$, —NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, or —S(O)$_2$R$^e$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^f$ and R$^g$ together with the N atom to which they are attached form heterocyclyl.

In yet another embodiment, the compound of Formula I has the structure of Formula II:

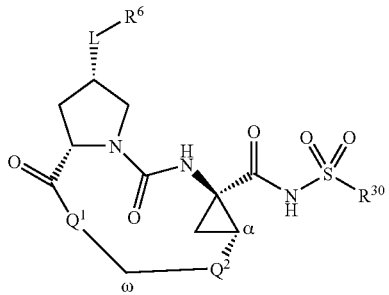

(II)

wherein:
R$^6$, L, Q$^1$, and Q$^2$ are each as defined herein; and
R$^{30}$ is hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, or C$_{1-6}$ alkyl-C$_{3-7}$ cycloalkylene, each optionally substituted with one or more substituents Q; or —CH$_2$NR$^{30a}$R$^{30b}$, —CHR$^{30c}$NR$^{30a}$R$^{30b}$, —CHR$^{30c}$CHR$^{30d}$NR$^{30a}$R$^{30b}$, or —CH$_2$CR$^{30c}$R$^{30d}$NR$^{30a}$R$^{30b}$, wherein:
each R$^{30a}$, R$^{30c}$, and R$^{30d}$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, or C$_{6-14}$ aryl-C$_{1-6}$ alkylene, each optionally substituted with one or more substituents Q; and
each R$^{30b}$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more substituents Q; —S(O)$_k$R$^{11}$, —S(O)$_k$NR$^{11}$R$^{12}$, —C(O)R$^{11}$, —C(O)OR$^{11}$, —C(O)NR$^{11}$R$^{12}$, or —C(=NR$^{13}$)NR$^{11}$R$^{12}$; wherein each R$^{11}$, R$^{12}$, and R$^{13}$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more substituents Q; or R$^{11}$ and R$^{12}$ together with the N atom to which they are attached form heterocyclyl, optionally substituted with one or more substituents Q; or R$^{30a}$ and R$^{30b}$ together with the N atom to which they are attached form heterocyclyl or heteroaryl, each optionally substituted with one or more substituents Q.

In yet another embodiment, the compound of Formula I has the structure of Formula III:

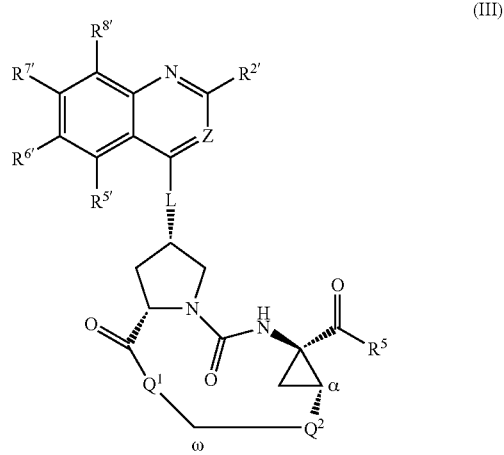

(III)

wherein:
R$^5$, L, Q$^1$, and Q$^2$ are each as defined herein; and
Z is CR$^{3'}$ or N;
R$^{2'}$, R$^{3'}$, R$^{5'}$, R$^{6'}$, R$^{7'}$, and R$^{8'}$ are each independently:
hydrogen, halo, cyano, trifluoromethyl, or nitro;
C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more substituents Q as described herein; or
—C(O)R$^a$, —C(O)OR$^a$, —C(O)NR$^b$R$^c$, —C(NR$^a$)NR$^b$R$^c$, —OR$^a$ —OC(O)R$^a$, —OC(O)OR$^a$, —OC(O)NR$^b$R$^c$, —OC(=NR$^a$)NR$^b$R$^c$, OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)$_2$R$^b$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more substituents Q as described herein; or R$^b$ and R$^c$ together with the N atom to which they are attached form heterocyclyl, optionally substituted with one or more substituents Q as described herein.

In yet another embodiment, the compound of Formula I has the structure of Formula IV:

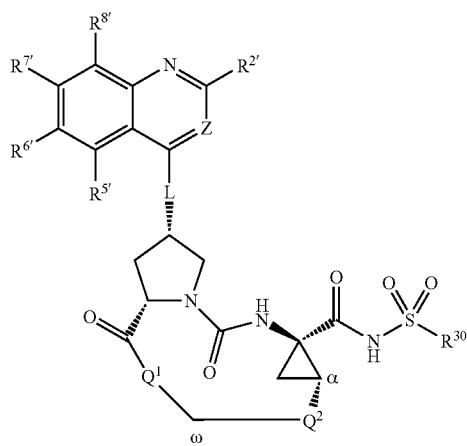

(IV)

wherein $R^{30}$, $R^{2'}$, $R^{3'}$, $R^{5'}$, $R^{6'}$, $R^{7'}$, $R^{8'}$, L, $Q^1$, $Q^2$, and Z are each as defined herein.

In certain embodiments, $Q^2$ is $C_{3-9}$ alkylene. In certain embodiments, $Q^2$ is $C_{3-9}$ alkenylene. In certain embodiments, $Q^2$ is $C_{3-9}$ alkenylene having one carbon-carbon double bond in either cis or trans configuration. In certain embodiments, $Q^2$ is $C_{3-9}$ alkenylene having one carbon-carbon double bond in cis configuration. In certain embodiments, $Q^2$ is $C_{3-9}$ alkynylene.

In certain embodiments, $Q^2$ is selected from the group consisting of:

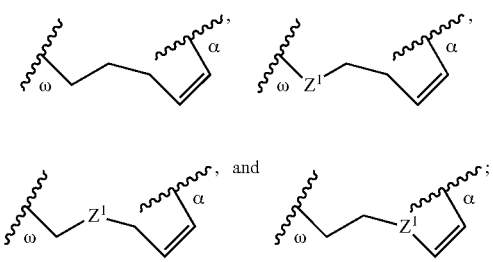

wherein:

$Z^1$ is —O—, —S—, or —N($R^Z$)—, wherein $R^Z$ is hydrogen, $C_{1-6}$ alkyl, aryl, heteroaryl, heterocyclyl, —C(O)$R^{Za}$, —C(O)O$R^{Za}$, —C(O)N$R^{Zb}R^{Zc}$, —S(O)$_2$N$R^{Zb}R^{Zc}$, or —S(O)$_2R^{Za}$; and each $R^{Za}$, $R^{Zb}$, and $R^{Zc}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{Zb}$ and $R^{Zc}$ together with the N atom to which they are attached form heterocyclyl or heteroaryl;

wherein each alkyl, alkenyl, alkynyl, cycloalkyl, aryl, heteroaryl, and heterocyclyl is optionally substituted with one or more substituents Q as described herein.

In one embodiment, the compound of Formula I has the structure of Formula V:

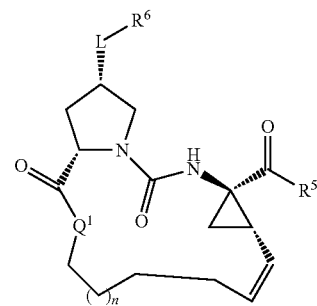

(V)

wherein $R^5$, $R^6$, L, and $Q^1$ are each as defined herein; and n is an integer of 0, 1, 2, 3, 4, or 5.

In yet another embodiment, the compound of Formula V has the structure of Formula VI:

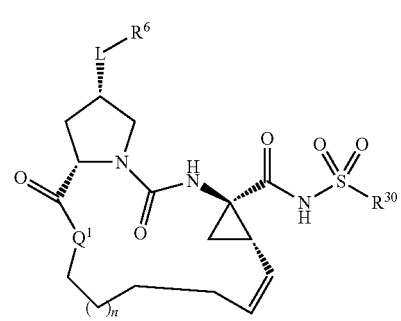

(VI)

wherein $R^6$, $R^{30}$, L, $Q^1$, and n are each as defined herein.

In yet another embodiment, the compound of Formula V has the structure of Formula VII:

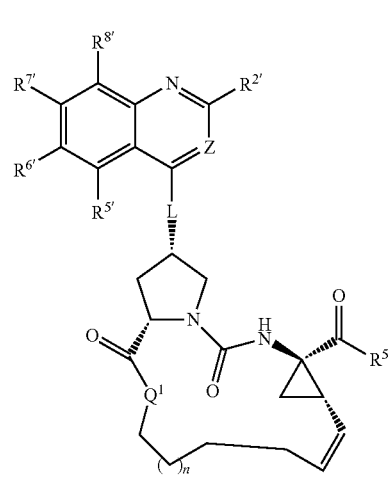

(VII)

wherein $R^5$, $R^{2'}$, $R^{3'}$, $R^{5'}$, $R^{6'}$, $R^{7'}$, $R^{8'}$, L, $Q^1$, Z, and n are each as defined herein.

In yet another embodiment, the compound of Formula V has the structure of Formula VIII:

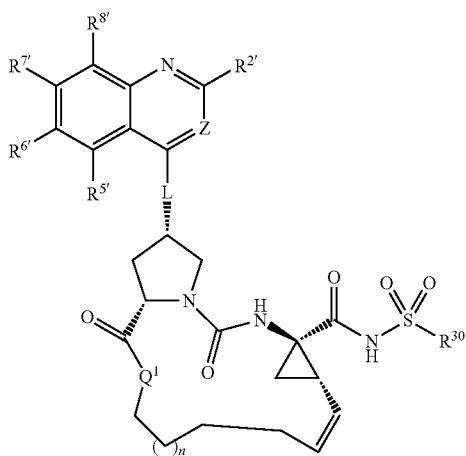

(VIII)

wherein $R^{30}$, $R^{2'}$, $R^{3'}$, $R^{5'}$, $R^{6'}$, $R^{7'}$, $R^{8'}$, L, $Q^1$, Z, and n are each as defined herein.

The groups, $R^5$, $R^6$, $R^{30}$, $R^{2'}$, $R^{3'}$, $R^{5'}$, $R^{6'}$, $R^{7'}$, $R^{8'}$, L, $Q^1$, $Q^2$, and n in Formulae I, II, III, IV, V, VI, VII, and VIII are further defined herein. All combinations of the embodiments provided herein for such groups are within the scope of this disclosure.

In certain embodiments, n is 0, 1, 2, 3, 4, or 5. In certain embodiments, n is 0. In certain embodiments, n is 1. In certain embodiments, n is 2. In certain embodiments, n is 3. In certain embodiments, n is 4. In certain embodiments, n is 5.

In certain embodiments, $R^6$ is hydrogen. In certain embodiments, $R^6$ is $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^6$ is $C_{1-6}$ alkyl, optionally substituted with one or more substituents Q. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q. In certain embodiments, $R^6$ is $C_{3-7}$ cycloalkyl, optionally substituted with one or more substituents Q. In certain embodiments, $R^6$ is $C_{6-14}$ aryl, optionally substituted with one or more substituents Q. In certain embodiments, $R^6$ is heteroaryl, optionally substituted with one or more substituents Q. In certain embodiments, $R^6$ is heterocyclyl, optionally substituted with one or more substituents Q.

In certain embodiments, $R^6$ is selected from the group consisting of:

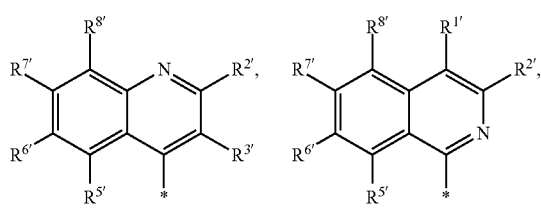

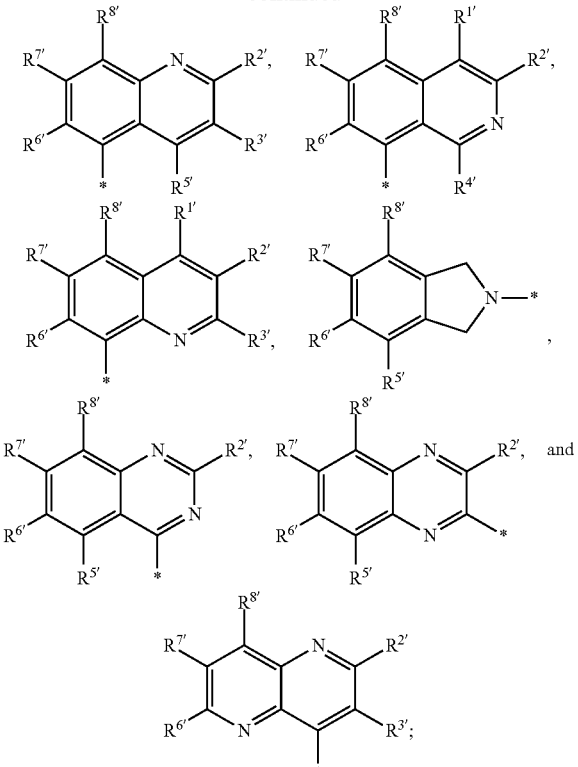

wherein:

$R^{2'}$, $R^{3'}$, $R^{5'}$, $R^{6'}$, $R^{7'}$, and $R^{8'}$ are each as defined herein;

$R^{1'}$ is independently:

hydrogen, halo, cyano, trifluoromethyl, or nitro;

$C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^c R^c$, —N$R^a$C(O)$R^b$, —N$R^a$C(O)O$R^b$, —N$R^a$C(O)N$R^b R^a$, —N$R^a$C(=N$R^d$)N$R^b R^c$, —N$R^a$S(O)$R^b$, —N$R^a$S(O)$_2 R^b$, —N$R^a$S(O)N$R^b R^c$, —N$R^a$S(O)$_2$N$R^b R^c$, —S$R^a$, —S(O)$R^a$, or —S(O)$_2 R^a$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or $R^b$ and $R^c$ together with the N atom to which they are attached form heterocyclyl, optionally substituted with one or more substituents Q as described herein; and each star (*) represents the point of attachment.

In certain embodiments, $R^2$ is $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein. In certain embodiments, $R^{2'}$ is $C_{6-14}$ aryl, heteroaryl, or heterocyclyl, each optionally substituted with one or more substituents Q as described herein.

In certain embodiments, $R^{2'}$ is selected from the group consisting of:

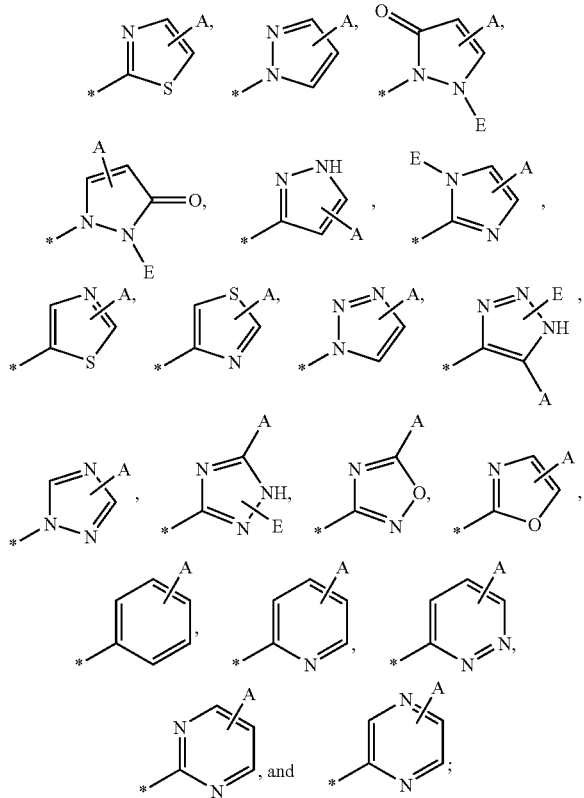

wherein each A is independently hydrogen, halo, cyano, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)$_2$R$^b$, —NR$^a$S(O)NR$^b$R$^c$, NR$^a$S(O)$_2$NR$^b$R$^c$, —SR$^a$, —S(O)R$^a$, or —S(O)$_2$R$^a$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or R$^b$ and R$^c$ together with the N atom to which they are attached form heterocyclyl, optionally substituted with one or more substituents Q as described herein;

each E is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)$_2$R$^b$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or R$^b$ and R$^c$ together with the N atom to which they are attached form heterocyclyl, optionally substituted with one or more substituents Q as described herein; and each star (*) is the point of attachment.

In certain embodiments, A is hydrogen, halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, wherein each alkyl, alkenyl, alkynyl, cycloalkyl, aryl, heteroaryl, and heterocyclyl is optionally substituted with one or more substituents Q as described herein.

In certain embodiments, A is hydrogen, halo, cyano, or nitro; $C_{1-6}$ alkyl, $C_{2-6}$ alkenyl, $C_{2-6}$ alkynyl, $C_{1-6}$ alkoxy, $C_{1-6}$ alkylamine (i.e., —NR$^b$R$^c$, where R$^b$ is hydrogen and R$^c$ is $C_{1-6}$ alkyl), or di($C_{1-6}$ alkyl)amino (i.e., —NR$^b$R$^c$, where R$^b$ and R$^c$ are each independently $C_{1-6}$ alkyl), each optionally substituted with one or more substituents Q as described herein.

In certain embodiments, A is hydrogen or $C_{1-6}$ alkyl, optionally substituted with one or more substituents Q as described herein. In certain embodiments, A is hydrogen. In certain embodiments, A is $C_{1-6}$ alkyl, optionally substituted with one or more substituents Q as described herein. In certain embodiments, A is $C_{2-6}$ alkenyl, optionally substituted with one or more substituents Q as described herein. In certain embodiments, A is $C_{2-6}$ alkynyl, optionally substituted with one or more substituents Q as described herein. In certain embodiments, A is $C_{3-7}$ cycloalkyl, optionally substituted with one or more substituents Q as described herein. In certain embodiments, A is $C_{6-14}$ aryl, optionally substituted with one or more substituents Q as described herein. In certain embodiments, A is heteroaryl, optionally substituted with one or more substituents Q as described herein. In certain embodiments, A is heterocyclyl, optionally substituted with one or more substituents Q as described herein. In certain embodiments, A is —OR$^a$, wherein R$^a$ is as defined herein. In certain embodiments, A is —NR$^b$R$^c$, wherein R$^b$ and R$^c$ are each as defined herein. In certain embodiments, A is isopropylamino.

In certain embodiments, A is hydrogen, cyano, fluoro, methyl, ethyl, n-propyl, isopropyl, isobutyl, isopentyl, trifluoromethyl, ethenyl, ethynyl, cyclopropyl, cyclobutyl, benzyl, 2-morpholin-4-yl-ethyl, methoxy, ethoxy, or isopropylamino. In certain embodiments, A is hydrogen, cyano, methyl, isopropyl, isobutyl, trifluoromethyl, cyclopropyl, cyclobutyl, ethenyl, ethynyl, methoxy, ethoxy, or isopropylamino.

In certain embodiments, E is hydrogen, $C_{1-6}$ alkyl, $C_{2-6}$ alkenyl, $C_{2-6}$ alkynyl, $C_{3-7}$ cycloalkyl, $C_{6-14}$ aryl, heterocyclyl, or heteroaryl, wherein each alkyl, alkenyl, alkynyl, cycloalkyl, aryl, heteroaryl, and heterocyclyl is optionally substituted with one or more substituents Q as described herein. In certain embodiments, E is hydrogen, methyl, ethyl, n-propyl, isopropyl, cyclopropyl, isobutyl, isopentyl, trifluoromethyl, benzyl, 2-morpholin-4-yl-ethyl, cyclobutyl, ethynyl, methoxy, ethoxy, or isopropylamino. In certain embodiments, E is hydrogen, methyl, ethyl, n-propyl, isopropyl, isobutyl, isopentyl, benzyl, or 2-morpholin-4-yl-ethyl.

In certain embodiments, R$^{2'}$ is selected from the group consisting of:

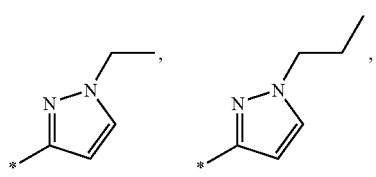

-continued

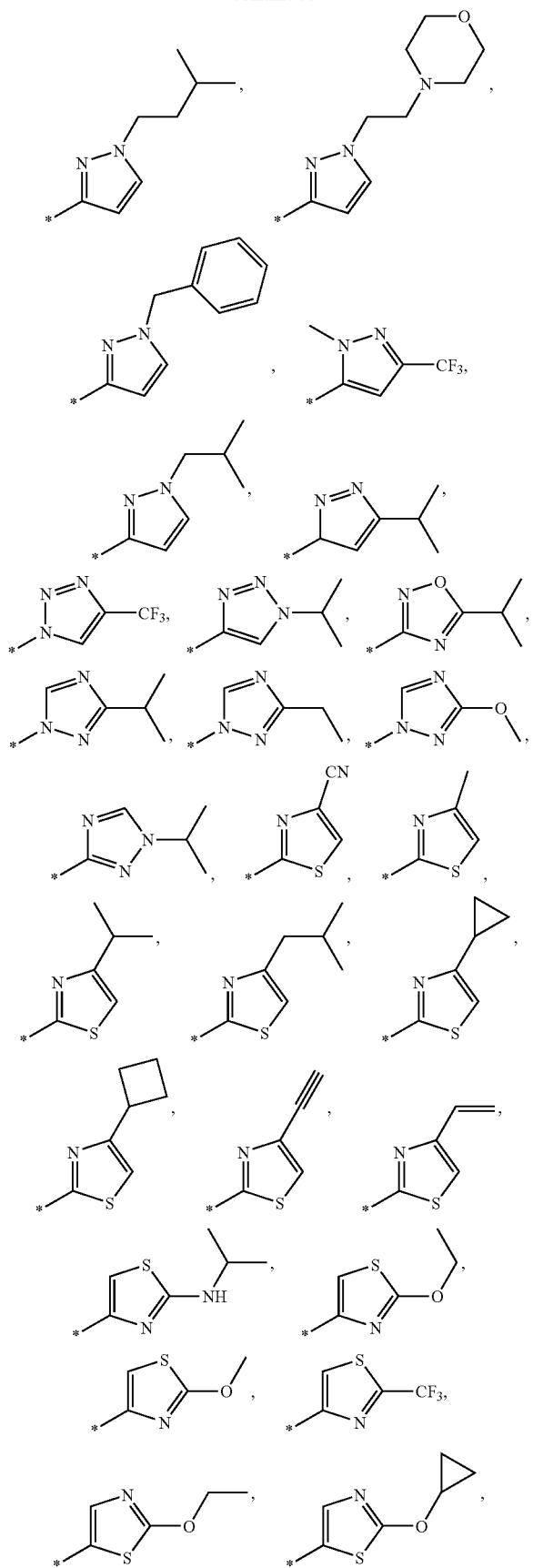

-continued

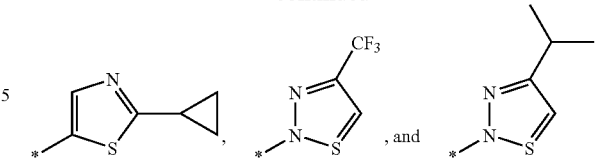

In certain embodiments, L is a bond. In certain embodiments, L is $C_{1-6}$ alkylene, optionally substituted with one or more substituents Q as described herein.

In certain embodiments, L is $-(CR^{6a}R^{6b})_pX-$, wherein $R^{6a}$, $R^{6b}$, X, and p are each as defined herein. In certain embodiments, $R^{6a}$ and $R^{6b}$ are each independently hydrogen or halo. In certain embodiments, L is $-(CR^{6a}R^{6b})_pO-$, wherein $R^{6a}$, $R^{6b}$, and p are each as defined herein. In certain embodiments, L is $-(CR^{6a}R^{6b})_pC(O)-$, wherein $R^{6a}$, $R^{6b}$, and p are each as defined herein. In certain embodiments, L is $-(CR^{6a}R^{6b})_pC(O)O-$, wherein $R^{6a}$, $R^{6b}$, and p are each as defined herein. In certain embodiments, L is $-(CR^{6a}R^{6b})_pOC(O)-$, wherein $R^{6a}$, $R^{6b}$, and p are each as defined herein. In certain embodiments, L is $-(CR^{6a}R^{6b})_pOC(O)O-$, wherein $R^{6a}$, $R^{6b}$, and p are each as defined herein. In certain embodiments, L is $-(CR^{6a}R^{6b})_pC(O)NR^{14}-$, wherein $R^{6a}$, $R^{6b}$, $R^{14}$, and p are each as defined herein. In certain embodiments, L is $-(CR^{6a}R^{6b})_pNR^{14}C(O)-$, wherein $R^{6a}$, $R^{6b}$, $R^{14}$, and p are each as defined herein. In certain embodiments, L is $-(CR^{6a}R^{6b})_pNR^{14}C(O)NR^{15}-$, wherein $R^{6a}$, $R^{6b}$, $R^{14}$, $R^{15}$, and p are each as defined herein. In certain embodiments, L is $-(CR^{6a}R^{6b})_pC(=NR^{14})NR^{15}-$, wherein $R^{6a}$, $R^{6b}$, $R^{14}$, $R^{15}$, and p are each as defined herein. In certain embodiments, L is $-(CR^{6a}R^{6b})_pNR^{14}C(=NR^{15})-$, wherein $R^{6a}$, $R^{6b}$, $R^{14}$, $R^{15}$, and p are each as defined herein. In certain embodiments, L is $-(CR^{6a}R^{6b})_pNR^{14}C(=NR^{15})NR^{16}-$, wherein $R^{6a}$, $R^{6b}$, $R^{14}$, $R^{15}$, $R^{16}$, and p are each as defined herein. In certain embodiments, L is $-(CR^{6a}R^{6b})_pS(O)_k-$, wherein $R^{6a}$, $R^{6b}$, k, and p are each as defined herein. In certain embodiments, L is $-(CR^{6a}R^{6b})_pS(O)_kNR^{15}-$, wherein $R^{6a}$, $R^{6b}$, $R^{14}$, k, and p are each as defined herein. In certain embodiments, L is $-(CR^{6a}R^{6b})_pNR^{14}S(O)_k-$, wherein $R^{6a}$, $R^{6b}$, $R^{14}$, k, and p are each as defined herein. In certain embodiments, L is $-(CR^{6a}R^{6b})_pNR^{14}S(O)_kNR^{15}-$, wherein $R^{6a}$, $R^{6b}$, $R^{14}$, $R^{15}$, k, and p are each as defined herein. In certain embodiments, L is $-(CR^{6a}R^{6b})_pP(O)OR^{14}-$, wherein $R^{6a}$, $R^{6b}$, $R^{14}$, k, and p are each as defined herein. In certain embodiments, L is $-(CR^{6a}R^{6b})_pOP(O)OR^{14}-$, wherein $R^{6a}$, $R^{6b}$, $R^{14}$, k, and p are each as defined herein.

In certain embodiments, L is $-(CH_2)_p-$, wherein p is as defined herein. In certain embodiments, $-CH_2-$. L is In certain embodiments, L is $-(CH_2)_pCF_2-$ or $-CF_2(CH_2)_p-$, wherein p is as defined herein. In certain embodiments, L is $-CF_2-$. In certain embodiments, L is $-(CH_2)_pO-$, wherein p is as defined herein. In certain embodiments, L is $-(CH_2)_pC(O)-$, wherein p is as defined herein. In certain embodiments, L is $-(CH_2)_pC(O)O-$, wherein p is as defined herein. In certain embodiments, L is $-(CH_2)_pOC(O)-$, wherein p is as defined herein. In certain embodiments, L is $-(CH_2)_pC(O)NR^{14}-$, wherein $R^{14}$ and p is as defined herein. In certain embodiments, L is $-(CH_2)_pNR^{14}C(O)-$, wherein $R^{14}$ and p is as defined herein. In certain embodiments, L is $-(CH_2)_pNR^{14}C(O)NR^{15}-$, wherein $R^{14}$, $R^{15}$, and p are as defined herein.

In certain embodiments, p is 1. In certain embodiments, p is 2. In certain embodiments, p is 3.

In certain embodiments, L is $C_{2-6}$ alkenylene, optionally substituted with one or more substituents Q. In certain embodiments, L is $C_{2-6}$ alkynylene, optionally substituted with one or more substituents Q. In certain embodiments, L is $C_{3-7}$ cycloalkylene, optionally substituted with one or more substituents Q.

In certain embodiments, L is —X—, wherein X is as defined herein. In certain embodiments, L is —O—. In certain embodiments, L is —C(O)—. In certain embodiments, L is —C(O)O—. In certain embodiments, L is —OC(O)—. In certain embodiments, L is —OC(O)O—. In certain embodiments, L is —C(O)NR$^{14}$—, wherein R$^{14}$ is as defined herein. In certain embodiments, L is —C(=NR$^{14}$)NR$^{15}$—, wherein R$^{14}$ and R$^{15}$ are each as defined herein. In certain embodiments, L is —NR$^{14}$—, wherein R$^{14}$ is as defined herein. In certain embodiments, L is —NR$^{14}$C(O)—, wherein R$^{14}$ is as defined herein. In certain embodiments, L is —NR$^{14}$C(s)NR$^{15}$—, wherein R$^{14}$ and R$^{15}$ are each as defined herein. In certain embodiments, L is —NR$^{14}$C(O)NR$^{15}$)—, wherein R$^{14}$ and R$^{15}$ are each as defined herein. In certain embodiments, L is —NR$^{14}$C(=NR$^{15}$)NR$^{16}$—, wherein R$^{14}$, R$^{15}$, and R$^{16}$ are each as defined herein. In certain embodiments, L is —NR$^{14}$S(O)$_k$—, wherein R$^{14}$ and k are each as defined herein. In certain embodiments, L is —NR$^{14}$S(O)$_k$NR$^{15}$—, wherein k, R$^{14}$, and R$^{15}$ are each as defined herein. In certain embodiments, L is —S(O)$_k$—, wherein k is as defined herein. In certain embodiments, L is —S(O)$_k$NR$^{14}$—, wherein R$^{14}$ and k are each as defined herein. In certain embodiments, L is —P(O)(OR$^{14}$)—, wherein R$^{14}$ is as defined herein. In certain embodiments, L is —OP(O)(OR$^{14}$)—, wherein R$^{14}$ is as defined herein.

In certain embodiments, each R$^{14}$ and R$^{15}$ is independently hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, each R$^{14}$ and R$^{15}$ is independently hydrogen; $C_{1-6}$ alkyl, or $C_{3-7}$ cycloalkyl, each optionally substituted with one or more substituents Q as described herein. In certain embodiments, R$^{14}$ and R$^{15}$ are hydrogen.

In certain embodiments, R$^{3'}$ is hydrogen. In certain embodiments, R$^{5'}$ is hydrogen. In certain embodiments, R$^{3'}$ and R$^{5'}$ are hydrogen. In certain embodiments, R$^{5'}$ is methoxy.

In certain embodiments, R$^{6'}$ is hydrogen, hydroxyl, cyano, or halo; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —OR$^a$, wherein R$^a$ is $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein.

In certain embodiments, R$^{6'}$ is halo or —OR$^a$, wherein R$^a$ is as defined herein. In certain embodiments, R$^{6'}$ is —OR$^a$, wherein R$^a$ is as defined herein. In certain embodiments, R$^a$ is $C_{1-6}$ alkyl, $C_{3-7}$ cycloalkyl, or $C_{6-14}$ aryl, each optionally substituted with one or more substituents Q as described herein. In certain embodiments, R$^a$ is $C_{1-6}$ alkyl or $C_{3-7}$ cycloalkyl, each optionally substituted with one or more substituents Q as described herein. In certain embodiments, R$^{6'}$ is methoxy. In certain embodiments, R$^{6'}$ is halo. In certain embodiments, R$^{6'}$ is chloro. In certain embodiments, R$^{6'}$ is fluoro. In certain embodiments, R$^{6'}$ is hydrogen.

In certain embodiments, R$^{7'}$ is hydrogen, hydroxyl, cyano, or halo; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —OR$^a$, wherein R$^a$ is $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein.

In certain embodiments, R$^{7'}$ is halo or —OR$^a$, wherein R$^a$ is as defined herein. In certain embodiments, R$^{7'}$ is —OR$^a$, wherein R$^a$ is as defined herein. In certain embodiments, R$^a$ is $C_{1-6}$ alkyl, $C_{3-7}$ cycloalkyl, or $C_{6-14}$ aryl, each optionally substituted with one or more substituents Q as described herein. In certain embodiments, R$^a$ is $C_{1-6}$ alkyl or $C_{3-7}$ cycloalkyl, each optionally substituted with one or more substituents Q as described herein. In certain embodiments, R$^{7'}$ is methoxy. In certain embodiments, R$^{7'}$ is halo. In certain embodiments, R$^{7'}$ is chloro. In certain embodiments, R$^{7'}$ is fluoro. In certain embodiments, R$^{7'}$ is hydrogen.

In certain embodiments, R$^{6'}$ is —OR$^a$ and R$^{7'}$ is hydrogen, wherein R$^a$ is as defined herein. In certain embodiments, R$^{6'}$ is methoxy and R$^{7'}$ is hydrogen.

In certain embodiments, R$^{6'}$ is hydrogen and R$^{7'}$ is —OR$^a$, wherein R$^a$ is as defined herein. In certain embodiments, R$^{6'}$ is hydrogen and R$^{7'}$ is methoxy.

In certain embodiments, R$^{8'}$ is hydrogen, hydroxyl, cyano, or halo; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —OR$^a$, wherein R$^a$ is $C_{1-6}$ alkyl, $C_{2-6}$ alkenyl, $C_{2-6}$ alkynyl, $C_{6-14}$ aryl, $C_{3-7}$ cycloalkyl, heteroaryl, or heterocyclyl, each optionally substituted with one or more substituents Q as described herein. In certain embodiments, R$^{8'}$ is hydrogen, halo, or $C_{1-6}$ alkyl, optionally substituted with one or more substituents Q as described herein. In certain embodiments, R$^{8'}$ is hydrogen.

In certain embodiments, R$^{8'}$ is halo. In certain embodiments, R$^{8'}$ is fluoro. In certain embodiments, R$^{8'}$ is chloro. In certain embodiments, R$^{8'}$ is bromo. In certain embodiments, R$^{8'}$ is iodo.

In certain embodiments, R$^{8'}$ is $C_{1-6}$ alkyl, optionally substituted with one or more substituents Q as described herein. In certain embodiments, R$^{8'}$ is methyl.

In certain embodiments, R$^{5'}$ is hydrogen or methoxy; R$^{6'}$ is hydrogen or methoxy; R$^{7'}$ is hydrogen, chloro, or methoxy; and R$^{8'}$ is hydrogen, chloro, fluoro, bromo, or methyl. In certain embodiments, R$^{5'}$ is methoxy, and R$^{7'}$ is fluoro. In certain embodiments, R$^6$ is methoxy, and R$^{7'}$ is chloro. In certain embodiments, R$^{6'}$ is methoxy, and R$^{8'}$ is methyl. In certain embodiments, R$^{7'}$ is methoxy, and R$^{8'}$ is fluoro. In certain embodiments, R$^{7'}$ is methoxy, and R$^{8'}$ is chloro. In certain embodiments, R$^{7'}$ is methoxy, and R$^{8'}$ is bromo. In certain embodiments, R$^{7'}$ is methoxy, and R$^{8'}$ is methyl.

In certain embodiments, R$^{1'}$ is hydrogen.

In certain embodiments, Q$^1$ is —O—.

In certain embodiments, Q$^1$ is —N(R$^{17}$)—, wherein R$^{17}$ is as defined herein. In one embodiment, R$^{17}$ is hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein. In another embodiment, R$^{17}$ is hydrogen; $C_{1-6}$ alkyl, or $C_{3-7}$ cycloalkyl, each optionally substituted with one or more substituents Q as described herein. In yet another embodiment, R$^{17}$ is hydrogen or $C_{1-6}$ alkyl, optionally substituted with one or more substituents Q as described herein. In yet another embodiment, R$^{17}$ is hydrogen. In yet another embodiment, R$^{17}$ is $C_{1-6}$ alkyl, optionally substituted with one or more substituents Q as described herein. In still another embodiment, R$^{17}$ is methyl.

In certain embodiments, Q$^1$ is —C(R$^{18}$R$^{19}$)—, wherein R$^{18}$ and R$^{19}$ are each as defined herein. In one embodiment, R$^{18}$ and R$^{19}$ are each independently hydrogen; $C_{1-6}$ alkyl, or $C_{3-7}$ cycloalkyl, each optionally substituted with one or more substituents Q as described herein. In another embodiment, $R^{18}$ is hydrogen. In yet another embodiment, $R^{19}$ is hydrogen. In yet another embodiment, $R^{18}$ and $R^{19}$ are hydrogen. In another embodiment, $R^{18}$ is $C_{1-6}$ alkyl, optionally substituted with one or more substituents Q as described herein. In yet another embodiment, $R^{19}$ is $C_{1-6}$ alkyl, optionally substituted with one or more substituents Q as described herein. In still another embodiment, $R^{18}$ and $R^{19}$ are each independently $C_{1-6}$ alkyl, optionally substituted with one or more substituents Q as described herein.

In certain embodiments, $Q^1$ is —$C(R^{18}R^{19})$—, wherein $R^{18}$ and $R^{19}$ together with the C atom to which they are attached form cycloalkyl, optionally substituted with one or more substituents Q as described herein.

In certain embodiments, $Q^1$ is —$CR^{17}(NR^{18}R^{19})$—, wherein $R^{17}$, $R^{18}$, and $R^{19}$ are each as defined herein. In one embodiment, $R^{17}$ and $R^{18}$ are each independently hydrogen; $C_{1-6}$ alkyl, or $C_{3-7}$ cycloalkyl, each optionally substituted with one or more substituents Q as described herein. In another embodiment, $R^{17}$ is hydrogen or $C_{1-6}$ alkyl, optionally substituted with one or more substituents Q as described herein. In yet another embodiment, $R^{17}$ is hydrogen. In yet another embodiment, $R^{17}$ is $C_{1-6}$ alkyl, optionally substituted with one or more substituents Q as described herein. In yet another embodiment, $R^{17}$ is methyl. In one embodiment, $R^{18}$ is hydrogen or $C_{1-6}$ alkyl, optionally substituted with one or more substituents Q as described herein. In yet another embodiment, $R^{18}$ is hydrogen. In yet another embodiment, $R^{18}$ is $C_{1-6}$ alkyl, optionally substituted with one or more substituents Q as described herein. In yet another embodiment, $R^{18}$ is methyl. In yet another embodiment, $R^{17}$ and 18 are hydrogen.

In certain embodiments, $R^{19}$ is hydrogen, —$C(O)R^{20}$, —$C(O)OR^{20}$, —$C(O)NR^{21}R^{22}$, or —$C(=NR^{20})NR^{21}R^{22}$, wherein $R^{20}$, $R^{21}$, and $R^{22}$ are each as defined herein. In certain embodiments, $R^{19}$ is hydrogen. In certain embodiments, $R^{19}$ is —$C(O)R^{20}$, wherein $R^{20}$ is as defined herein. In certain embodiments, $R^{19}$ is —$C(O)NR^{21}R^{22}$, wherein $R^{21}$ and $R^{22}$ are each as defined herein. In certain embodiments, $R^{19}$ is —$C(=O-NR^{20})NR^{21}R^{22}$, wherein $R^{20}$, $R^{22}$, and $R^{21}$ are each as defined herein. In certain embodiments, $R^{21}$ and $R^{22}$ together with the N atom to which they are attached form heterocyclyl, optionally substituted with one or more substituents Q as described herein.

In certain embodiments, $R^{19}$ is —$C(O)OR^{20}$, wherein $R^{20}$ is defined herein. In one embodiment, $R^{20}$ is $C_{1-6}$ alkyl, $C_{3-7}$ cycloalkyl, $C_{6-14}$ aryl, heteroaryl, or heterocyclyl, each optionally substituted with one or more substituents Q as described herein. In yet another embodiment, $R^{20}$ is $C_{1-6}$ alkyl, optionally substituted with one or more substituents Q as described herein. In yet another embodiment, $R^{20}$ is t-butyl. In yet another embodiment, $R^{20}$ is $C_{6-14}$ aryl, optionally substituted with one or more substituents Q as described herein. In still another embodiment, $R^{20}$ is benzyl.

In certain embodiments, $R^{18}$ and $R^{19}$ together with the N atom to which they are attached form heterocyclyl, optionally substituted with one or more substituents Q as described herein.

In certain embodiments, $R^5$ is —OH.

In certain embodiments, $R^5$ is —$NR^8R^9$, wherein $R^8$ and $R^9$ are as defined herein. In certain embodiments, $R^8$ and $R^9$ together with the N atom to which they are attached form heterocyclyl, optionally substituted with one or more substituents Q as described herein.

In certain embodiments, $R^5$ is —$NHS(O)_kR^8$, wherein $R^8$ and k are each as defined herein. In certain embodiments, $R^8$ is $C_{1-6}$ alkyl, $C_{3-7}$ cycloalkyl, $C_{6-14}$ aryl, heteroaryl, heterocyclyl, or $C_{1-6}$ alkyl-$C_{3-7}$ cycloalkylene, each optionally substituted with one or more substituents Q as described herein; or —$CH_2NR^{8a}R^{8b}$, —$CHR^{8c}CHR^{8d}NR^{8a}R^{8b}$, or —$CH_2CR^{8c}R^{8d}NR^{8a}R^{8b}$, wherein $R^{8a}$, $R^{8b}$, $R^{8c}$, and $R^{8d}$ are each as defined herein.

In certain embodiments, $R^8$ is $C_{1-6}$ alkyl, $C_{3-7}$ cycloalkyl, $C_{6-14}$ aryl, heteroaryl, heterocyclyl, or $C_{1-6}$ alkyl-$C_{3-7}$ cycloalkylene, each optionally substituted with one or more substituents Q as described herein; or —$CH_2NR^{8a}R^{8b}$, —$CHR^{8c}CHR^{8d}NR^{8a}R^{8b}$, or —$CH_2CR^{8c}R^{8d}NR^{8a}R^{8b}$, wherein $R^{8a}$, $R^{8b}$, $R^{8c}$, and $R^{8d}$ are each as defined herein. In certain embodiments, $R^8$ is $C_{1-6}$ alkyl, optionally substituted with one or more substituents Q as described herein. In certain embodiments, $R^8$ is methyl. In certain embodiments, $R^8$ is $C_{3-7}$ cycloalkyl, optionally substituted with one or more substituents Q as described herein. In certain embodiments, $R^8$ is cyclopropyl, 1-methylcyclopropyl, 1-ethynylcyclopropyl, cyclobutyl, cyclopentyl, or cyclohexyl. In certain embodiments, $R^8$ is $C_{6-14}$ aryl, optionally substituted with one or more substituents Q as described herein. In certain embodiments, $R^8$ is heteroaryl, optionally substituted with one or more substituents Q as described herein. In certain embodiments, $R^8$ is heterocyclyl, optionally substituted with one or more substituents Q as described herein.

In certain embodiments, $R^8$ is —$CH_2NR^{8a}R^{8b}$, wherein $R^{8a}$ and $R^{8b}$ are each as defined herein. In certain embodiments, $R^8$ is —$CHR^{8c}CHR^{8d}NR^{8a}R^{8b}$, wherein $R^{8a}$, $R^{8b}$, $R^{8c}$, and $R^{8d}$ are each as defined herein. In certain embodiments, $R^8$ is —$CH_2CR^{8c}R^{8d}NR^{8a}R^{8b}$, wherein $R^{8a}$, $R^{8b}$, $R^{8c}$, and $R^{8d}$ are each as defined herein.

In certain embodiments, $R^8$ has the structure of

wherein R' is hydrogen; $C_{1-6}$ alkyl, $C_{2-6}$ alkenyl, $C_{2-6}$ alkynyl, $C_{3-7}$ cycloalkyl, $C_{6-14}$ aryl, halogen, heteroaryl, or heterocyclyl, each optionally substituted with one or more substituents Q as described herein. In one embodiment, R' is $C_{1-6}$ alkyl. In another embodiment, R' is hydrogen. In yet another embodiment, R' is methyl. In yet another embodiment, R' is $C_{2-6}$ alkynyl. In still another embodiment, R' is ethynyl.

Thus, when $R^5$ is —$NHS(O)_2R^8$, $R^5$ has the structure of

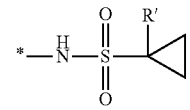

wherein R' is as defined herein. In one embodiment, R' is $C_{1-6}$ alkyl. In another embodiment, R' is hydrogen. In yet another embodiment, R' is methyl. In yet another embodiment, R' is $C_{2-6}$ alkynyl. In still another embodiment, R' is ethynyl.

In certain embodiments, $R^{8a}$ is hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^{8a}$ is hydrogen; $C_{1-6}$ alkyl, or $C_{3-7}$ cycloalkyl, each optionally substituted with one or more substituents Q as described herein. In certain embodiments, $R^{8a}$ is hydrogen. In certain embodiments, $R^{8a}$ is $C_{1-6}$ alkyl, optionally substituted with one or more substituents Q as described herein. In certain embodiments, $R^{8a}$ is methyl. In certain embodiments, $R^{8a}$ is $C_{3-7}$ cycloalkyl, optionally substituted with one or more substituents Q as described described herein. In certain embodiments, $R^{8a}$ is $C_{6-14}$ aryl, optionally substituted with one or more substituents Q as described herein. In certain embodiments, $R^{8a}$ is heteroaryl, optionally substituted with one or more substituents Q as described herein. In certain embodiments, $R^{8a}$ is heterocyclyl, optionally substituted with one or more substituents Q as described herein.

In certain embodiments, $R^{8b}$ is hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or —S(O)$_k$R$^{11}$, —S(O)$_k$NR$^{11}$R$^{12}$, —C(O)R$^{11}$, —C(O)OR$^{11}$, —C(O)NR$^{11}$R$^{12}$, or —C(=NR$^{11}$)NR$^{12}$R$^{13}$, wherein $R^{11}$, $R^{12}$, $R^{13}$, and k are each as defined herein. In certain embodiments, $R^{8b}$ is hydrogen; $C_{1-6}$ alkyl, or $C_{3-7}$ cycloalkyl, each optionally substituted with one or more substituents Q as described herein; or —C(O)R$^{11}$, —C(O)OR$^{11}$, or —C(O)NR$^{11}$R$^{12}$, wherein $R^{11}$ and $R^{12}$ are each as defined herein. In certain embodiments, $R^{8b}$ is hydrogen. In certain embodiments, $R^{8b}$ is $C_{1-6}$ alkyl, optionally substituted with one or more substituents Q as described herein. In certain embodiments, $R^{8b}$ is methyl, ethyl, or isopropyl. In certain embodiments, $R^{8b}$ is $C_{3-7}$ cycloalkyl, optionally substituted with one or more substituents Q as described herein. In certain embodiments, $R^{8b}$ is $C_{6-14}$ aryl, optionally substituted with one or more substituents Q as described herein. In certain embodiments, $R^{8b}$ is phenyl, optionally substituted with one or more substituents Q. In certain embodiments, $R^{8b}$ is $C_{6-14}$ aryl-$C_{1-6}$ alkylene, each optionally substituted with one or more substituents Q as described herein. In certain embodiments, $R^{8b}$ is benzyl. In certain embodiments, $R^{8b}$ is —C(O)R$^{11}$, wherein $R^{8b}$ is as defined herein. In certain embodiments, $R^{8b}$ is —C(O)R$^{11}$, and $R^{11}$ is $C_{1-6}$ alkyl, optionally substituted with one or more substituents Q as described herein. In certain embodiments, $R^{8b}$ is acetyl. In certain embodiments, $R^{8b}$ is —C(O)OR$^{11}$, wherein $R^{11}$ is as defined herein. In certain embodiments, $R^{8b}$ is —C(O)OR$^{11}$, and $R^{11}$ is $C_{1-6}$ alkyl, optionally substituted with one or more substituents Q as described herein. In certain embodiments, $R^{8b}$ is —C(O)O-t-butyl (Boc). In certain embodiments, $R^{8b}$ is —C(O)NR$^{11}$R$^{12}$, wherein $R^{11}$ and $R^{12}$ are each as defined herein.

In certain embodiments, $R^{8c}$ is hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^{8c}$ is hydrogen; $C_{1-6}$ alkyl, or $C_{3-7}$ cycloalkyl, each optionally substituted with one or more substituents Q as described herein. In certain embodiments, $R^{8c}$ is hydrogen. In certain embodiments, $R^{8c}$ is $C_{1-6}$ alkyl, optionally substituted with one or more substituents Q as described herein. In certain embodiments, $R^{8c}$ is methyl. In certain embodiments, $R^{8c}$ is $C_{3-7}$ cycloalkyl, optionally substituted with one or more substituents Q as described herein. In certain embodiments, $R^{8c}$ is $C_{6-14}$ aryl, optionally substituted with one or more substituents Q as described herein. In certain embodiments, $R^{8c}$ is heteroaryl, optionally substituted with one or more substituents Q as described herein. In certain embodiments, $R^{8c}$ is heterocyclyl, optionally substituted with one or more substituents Q as described herein.

In certain embodiments, $R^{8d}$ is hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^{8d}$ is hydrogen; $C_{1-6}$ alkyl, or $C_{3-7}$ cycloalkyl, each optionally substituted with one or more substituents Q as described herein. In certain embodiments, $R^{8d}$ is hydrogen. In certain embodiments, $R^{8d}$ is $C_{1-6}$ alkyl, optionally substituted with one or more substituents Q as described herein. In certain embodiments, $R^{8d}$ is methyl. In certain embodiments, $R^{8d}$ is $C_{3-7}$ cycloalkyl, optionally substituted with one or more substituents Q as described herein. In certain embodiments, $R^{8d}$ is $C_{6-14}$ aryl, optionally substituted with one or more substituents Q as described herein. In certain embodiments, $R^{8d}$ is heteroaryl, optionally substituted with one or more substituents Q as described herein. In certain embodiments, $R^{8d}$ is heterocyclyl, optionally substituted with one or more substituents Q as described herein.

In certain embodiments, $R^{30}$ is $C_{1-6}$ alkyl, $C_{3-7}$ cycloalkyl, $C_{6-14}$ aryl, heteroaryl, heterocyclyl, or $C_{1-6}$ alkyl-$C_{3-7}$ cycloalkylene, each optionally substituted with one or more substituents Q as described herein; or —CH$_2$NR$^{30a}$R$^{30b}$, —CHR$^{30c}$CHR$^{30d}$NR$^{30a}$R$^{30b}$, or —CH$_2$CR$^{30c}$R$^{30d}$NR$^{30a}$R$^{30b}$, wherein $R^{30a}$, $R^{30b}$, $R^{30c}$, and $R^{30d}$ are each as defined herein. In certain embodiments, $R^{30}$ is $C_{1-6}$ alkyl, optionally substituted with one or more substituents Q as described herein. In certain embodiments, $R^{30}$ is methyl. In certain embodiments, $R^{30}$ is $C_{3-7}$ cycloalkyl, optionally substituted with one or more substituents Q as described herein. In certain embodiments, $R^{30}$ is cyclopropyl, 1-methylcyclopropyl, cyclobutyl, cyclopentyl, or cyclohexyl. In certain embodiments, $R^{30}$ is $C_{6-14}$ aryl, optionally substituted with one or more substituents Q as described herein. In certain embodiments, $R^{30}$ is heteroaryl, optionally substituted with one or more substituents Q as described herein. In certain embodiments, $R^{30}$ is heterocyclyl, optionally substituted with one or more substituents Q as described herein.

In certain embodiments, $R^{30}$ is —CH$_2$NR$^{30a}$R$^{30b}$, wherein $R^{30a}$ and $R^{30b}$ are each as defined herein. In certain embodiments, $R^{30}$ is —CH$_2$CR$^{30c}$R$^{30d}$NR$^{30a}$R$^{30b}$, wherein $R^{30a}$, $R^{30b}$, $R^{30c}$, and $R^{30d}$ are each as defined herein. In certain embodiments, $R^{30}$ is —CHR$^{30c}$CHR$^{30d}$NR$^{30a}$R$^{30b}$, wherein $R^{30a}$, $R^{30b}$, $R^{30c}$, and $R^{30d}$ are each as defined herein.

In certain embodiments, $R^{30}$ has the structure of

wherein R' is hydrogen; $C_{1-6}$ alkyl, $C_{2-6}$ alkenyl, $C_{2-6}$ alkynyl, $C_{6-14}$ aryl, $C_{3-7}$ cycloalkyl, heteroaryl, or heterocyclyl, each optionally substituted with one or more substituents Q as described herein. In one embodiment, R' is $C_{1-6}$ alkyl. In another embodiment, R' is hydrogen. In yet another embodiment, R' is methyl. In yet another embodiment, R' is $C_{2-6}$ alkynyl. In still another embodiment, R' is ethynyl.

In certain embodiments, $R^{30a}$ is hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^{30a}$ is hydrogen; $C_{1-6}$ alkyl, or $C_{3-7}$ cycloalkyl, each optionally substituted with one or more substituents Q as described herein. In certain embodiments, $R^{30a}$ is hydrogen. In certain embodiments, $R^{30a}$ is $C_{1-6}$ alkyl, optionally substituted with one or more substituents Q as described herein. In certain embodiments, $R^{30a}$ is methyl. In certain embodiments, $R^{30a}$ is $C_{3-7}$ cycloalkyl, optionally substituted with one or more substituents Q as described herein. In certain embodiments, $R^{30a}$ is $C_{6-14}$ aryl, optionally substituted with one or more substituents Q as described herein. In certain embodiments, $R^{30a}$ is heteroaryl, optionally substituted with one or more substituents Q as described herein. In certain embodiments, $R^{30a}$ is heterocyclyl, optionally substituted with one or more substituents Q as described herein.

In certain embodiments, $R^{30b}$ is hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or $-S(O)_kR^{11}$, $-S(O)_kNR^{11}R^{12}$, $-C(O)R^{11}$, $-C(O)OR^{11}$, $-C(O)NR^{11}R^{12}$, or $-C(=NR^{11})NR^{12}R^{13}$, wherein $R^{11}$, $R^{12}$, $R^{13}$, and k are each as defined herein. In certain embodiments, $R^{30b}$ is hydrogen; $C_{1-6}$ alkyl, or $C_{3-7}$ cycloalkyl, each optionally substituted with one or more substituents Q as described herein; or $-C(O)R^{11}$, $-C(O)OR^{11}$, or $-C(O)NR^{11}R^{12}$, wherein $R^{11}$ and $R^{12}$ are each as defined herein. In certain embodiments, $R^{30b}$ is hydrogen. In certain embodiments, $R^{30b}$ is $C_{1-6}$ alkyl, optionally substituted with one or more substituents Q as described herein. In certain embodiments, $R^{30b}$ is methyl, ethyl, or isopropyl. In certain embodiments, $R^{30b}$ is $C_{3-7}$ cycloalkyl, optionally substituted with one or more substituents Q as described herein. In certain embodiments, $R^{30b}$ is $C_{6-14}$ aryl, optionally substituted with one or more substituents Q as described herein. In certain embodiments, $R^{30b}$ is phenyl, optionally substituted with one or more substituents Q. In certain embodiments, $R^{30b}$ is $C_{6-14}$ aryl-$C_{1-6}$ alkylene, each optionally substituted with one or more substituents Q as described herein. In certain embodiments, $R^{30b}$ is benzyl. In certain embodiments, $R^{30b}$ is $-C(O)R^{11}$, wherein $R^{11}$ is as defined herein. In certain embodiments, $R^{30b}$ is $-C(O)R^{11}$, and $R^{11}$ is $C_{1-6}$ alkyl, optionally substituted with one or more substituents Q as described herein. In certain embodiments, $R^{30b}$ is acetyl. In certain embodiments, $R^{30b}$ is $-C(O)OR^{11}$, wherein $R^{11}$ is as defined herein. In certain embodiments, $R^{30b}$ is $-C(O)OR^{11}$, and $R^{11}$ is $C_{1-6}$ alkyl, optionally substituted with one or more substituents Q as described herein. In certain embodiments, $R^{30b}$ is $-C(O)$O-t-butyl (Boc). In certain embodiments, $R^{30b}$ is $-C(O)NR^{11}R^{12}$, wherein $R^{11}$ and $R^{12}$ are each as defined herein.

In certain embodiments, $R^{30c}$ is hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^{30c}$ is hydrogen; $C_{1-6}$ alkyl, or $C_{3-7}$ cycloalkyl, each optionally substituted with one or more substituents Q as described herein. In certain embodiments, $R^{30c}$ is hydrogen. In certain embodiments, $R^{30c}$ is $C_{1-6}$ alkyl, optionally substituted with one or more substituents Q as described herein. In certain embodiments, $R^{30c}$ is methyl. In certain embodiments, $R^{30c}$ is $C_{3-7}$ cycloalkyl, optionally substituted with one or more substituents Q as described herein. In certain embodiments, $R^{30c}$ is $C_{6-14}$ aryl, optionally substituted with one or more substituents Q as described herein. In certain embodiments, $R^{30c}$ is heteroaryl, optionally substituted with one or more substituents Q as described herein. In certain embodiments, $R^{30c}$ is heterocyclyl, optionally substituted with one or more substituents Q as described herein.

In certain embodiments, $R^{30d}$ is hydrogen; $C_{1-6}$ alkyl, $C_{3-7}$ cycloalkyl, $C_{6-14}$ aryl, heteroaryl, or heterocyclyl, each optionally substituted with one or more substituents Q as described herein. In certain embodiments, $R^{30d}$ is hydrogen; $C_{1-6}$ alkyl, or $C_{3-7}$ cycloalkyl, each optionally substituted with one or more substituents Q as described herein. In certain embodiments, $R^{30d}$ is hydrogen. In certain embodiments, $R^{30d}$ is $C_{1-6}$ alkyl, optionally substituted with one or more substituents Q as described herein. In certain embodiments, $R^{30d}$ is methyl. In certain embodiments, $R^{30d}$ is $C_{3-7}$ cycloalkyl, optionally substituted with one or more substituents Q as described herein. In certain embodiments, $R^{30d}$ is $C_{6-14}$ aryl, optionally substituted with one or more substituents Q as described herein. In certain embodiments, $R^{30d}$ is heteroaryl, optionally substituted with one or more substituents Q as described herein. In certain embodiments, $R^{30d}$ is heterocyclyl, optionally substituted with one or more substituents Q as described herein.

In certain embodiments, k is 1. In certain embodiments, k is 2.

In certain embodiments, Z is $CR^{3'}$. In certain embodiments, Z is CH. In certain embodiments, Z is N.

In one embodiment, provided herein is a compound of Formula (IX):

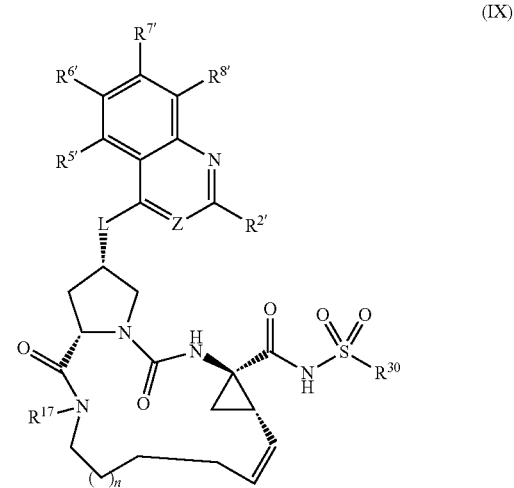

(IX)

wherein $R^{17}$, $R^{30}$, $R^{2'}$, $R^{5'}$, $R^{6'}$, $R^{7'}$, $R^{8'}$, L, and n are each as defined herein; and Z is CH or N. In one embodiment, L is $-O-$. In another embodiment, $R^{17}$ is $C_{1-6}$ alkyl. In yet another embodiment, $R^{17}$ is methyl. In yet another embodiment, $R^{17}$ is $C_{1-6}$ alkyl and L is $-O-$. In still another embodiment, $R^{17}$ is methyl and L is $-O-$.

In yet another embodiment, provided herein is a compound of Formula (X):

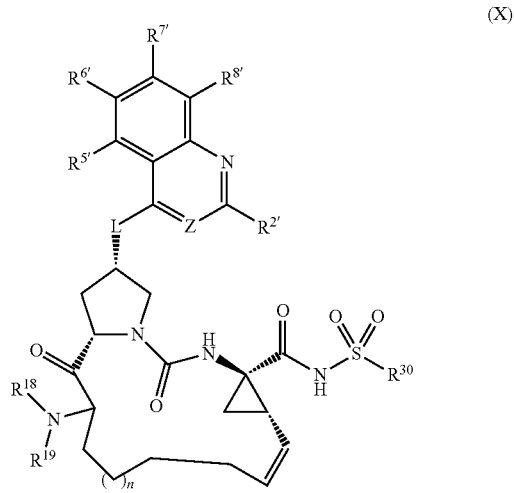

(X)

wherein $R^{18}$, $R^{19}$, $R^{30}$, $R^{2'}$, $R^{5'}$, $R^{6'}$, $R^{7'}$, $R^{8'}$, L, and n are each as defined herein; and Z is CH or N. In one embodiment, L is $-O-$. In another embodiment, $R^{18}$ is hydrogen. In yet another embodiment, $R^{18}$ is hydrogen and L is $-O-$.

In one embodiment, provided herein is the compound of Formula IX or X, wherein each $R^{17}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{30}$ is independently $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, or $C_{1-6}$ alkyl-$C_{3-7}$ cycloalkylene, each optionally substituted with one or more substituents Q; or —CH$_2$NR$^{30a}$R$^{30b}$, —CHR$^{30c}$NR$^{30a}$R$^{30b}$, —CHR$^{30c}$CHR$^{30d}$NR$^{30a}$R$^{30b}$, or —CH$_2$CR$^{30c}$R$^{30d}$NR$^{30a}$R$^{30b}$, wherein:

each $R^{30a}$, $R^{30c}$, and $R^{30d}$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, or $C_{6-14}$ aryl-$C_{1-6}$ alkylene, each optionally substituted with one or more substituents Q; and each $R^{30b}$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; —S(O)$_k$R$^{11}$, —S(O)$_k$NR$^{11}$R$^{12}$, —C(O)R$^{11}$, —C(O)OR$^{11}$, —C(O)NR$^{11}$R$^{12}$, or —C(=NR$^{13}$)NR$^{11}$R$^{12}$; wherein each $R^{11}$, $R^{12}$, and $R^{13}$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or $R^{11}$ and $R^{12}$ together with the N atom to which they are attached form heterocyclyl, optionally substituted with one or more substituents Q; or $R^{30a}$ and $R^{30b}$ together with the N atom to which they are attached form heterocyclyl or heteroaryl, each optionally substituted with one or more substituents Q;

each $R^{2'}$, $R^{5'}$, $R^{6'}$, $R^{7'}$, and $R^{8'}$ is independently:

hydrogen, halo, cyano, trifluoromethyl, or nitro;

$C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, OS(O)R$^a$, —OS(O)$_2$R$^a$, —OS(O)NR$^b$R$^c$, —OS(O)$_2$NR$^b$R$^c$, —NR$^b$R$^c$, NR$^a$C(O)R$^b$, —NR$^a$C(O)OR$^b$, NR$^a$C(O)NR$^b$R$^c$, —NR$^a$C(=NR$^d$)NR$^b$R$^c$, —NR$^a$S(O)R$^b$, —NR$^a$S(O)$_2$R$^b$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or $R^b$ and $R^c$ together with the N atom to which they are attached form heterocyclyl, optionally substituted with one or more substituents Q;

each L is independently a bond, $C_{1-6}$ alkylene, $C_{3-7}$ cycloalkylene, $C_{2-6}$ alkenylene, $C_{2-6}$ alkynylene, X, or —(CR$^{6a}$R$^{6b}$)$_p$X—; wherein p is an integer of 1, 2, or 3; $R^{6a}$ and $R^{6b}$ are each independently hydrogen, halo, cyano, hydroxyl, or alkoxy; and X is —O—, —C(O)—, —C(O)O—, —OC(O)O—, —C(O)NR$^{14}$—, —C(=NR$^{14}$)NR$^{15}$—, —NR$^{14}$—, —NR$^{14}$C(O)NR$^{15}$—, —NR$^{14}$C(NR$^{15}$)NR$^{16}$—, —NR$^{14}$S(O)$_k$NR$^{15}$—, —S(O)$_k$—, —S(O)$_k$NR$^{14}$—, —P(O)OR$^{14}$—, or —OP(O)OR$^{14}$— where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each Z is independently CH or N; and each n is independently an integer of 0, 1, 2, 3, 4, or 5.

In another embodiment, provided herein is the compound of Formula IX or X, wherein:

each $R^{17}$ is independently hydrogen, $C_{1-6}$ alkyl, $C_{3-7}$ cycloalkyl, $C_{6-14}$ aryl, heteroaryl, or heterocyclyl;

each $R^{30}$ is independently $C_{1-6}$ alkyl, $C_{3-7}$ cycloalkyl, $C_{6-14}$ aryl, heteroaryl, heterocyclyl, or $C_{1-6}$ alkyl-$C_{3-7}$ cycloalkylene, each optionally substituted with one or more substituents Q; or —CH$_2$NR$^{30a}$R$^{30b}$, —CHR$^{30c}$NR$^{30a}$R$^{30b}$, —CHR$^{30c}$CHR$^{30d}$NR$^{30a}$R$^{30b}$, or —CH$_2$CR$^{30c}$R$^{30d}$NR$^{30a}$R$^{30b}$, wherein:

each $R^{30a}$, $R^{30c}$, and $R^{30d}$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, or $C_{6-14}$ aryl-$C_{1-6}$ alkylene, each optionally substituted with one or more substituents Q; and each $R^{30b}$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; —S(O)$_k$R$^{11}$, —S(O)$_k$NR$^{11}$R$^{12}$, —C(O)R$^{11}$, —C(O)OR$^{11}$, —C(O)NR$^{11}$R$^{12}$, or —C(=NR$^{13}$)NR$^{11}$R$^{12}$; wherein each $R^{11}$, $R^{12}$, and $R^{13}$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or $R^{11}$ and $R^{12}$ together with the N atom to which they are attached form heterocyclyl, optionally substituted with one or more substituents Q; or $R^{30a}$ and $R^{30b}$ together with the N atom to which they are attached form heterocyclyl or heteroaryl, each optionally substituted with one or more substituents Q;

each $R^{2'}$, $R^{5'}$, $R^{6'}$, $R^{7'}$, and $R^{8'}$ is independently:

hydrogen, halo, cyano, trifluoromethyl, or nitro;

$C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$ —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^a$, —NR$^a$C(=NR$^d$)NR$^b$R$^c$, —NR$^a$S(O)R$^b$, —NR$^a$S(O)$_2$R$^b$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q as described herein; or $R^b$ and $R^c$ together with the N atom to which they are attached form heterocyclyl, optionally substituted with one or more substituents Q;

each L is independently a bond, X, or —(CR$^{6a}$R$^{6b}$)$_p$X—; wherein p is an integer of 1, 2, or 3; $R^{6a}$ and $R^{6b}$ are each independently hydrogen or halo; and X is —O—, —C(O)—, —C(O)O—, —OC(O)O—, —C(O)NR$^{14}$—, —C(=NR$^{14}$)NR$^{15}$—, —NR$^{14}$—, —NR$^{14}$C(O)NR$^{15}$—, —NR$^{14}$C(=NR$^{15}$)NR$^{16}$—, —NR$^{14}$S(O)$_k$NR$^{15}$—, —S(O)$_k$—, or —S(O)$_k$NR$^{14}$—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each Z is independently CH or N; and each n is independently an integer of 1, 2, 3, 4, or 5.

In yet another embodiment, provided herein is the compound of Formula IX or X, wherein:

each $R^{17}$ is independently hydrogen, $C_{1-6}$ alkyl, $C_{3-7}$ cycloalkyl, $C_{6-14}$ aryl, heteroaryl, or heterocyclyl;

each $R^{30}$ is independently $C_{1-6}$ alkyl, $C_{3-7}$ cycloalkyl, $C_{6-14}$ aryl, or $C_{1-6}$ alkyl-$C_{3-7}$ cycloalkylene, each optionally substituted with one or more substituents Q;

each $R^{2'}$ is independently $C_{6-14}$ aryl, heteroaryl, or heterocyclyl, each optionally substituted with one or more substituents Q;

each $R^{5'}$, $R^{6'}$, $R^{7'}$, and $R^{8'}$ is independently hydrogen, halo, cyano, methanesulfonamido, $C_{1-6}$ alkyl, or $C_{3-7}$ cycloalkyl, each optionally substituted with one or more substituents Q; or —$OR^a$, wherein each $R^a$ is independently $C_{1-6}$ alkyl, $C_{3-7}$ cycloalkyl, $C_{6-14}$ aryl, heteroaryl, or heterocyclyl, each optionally substituted with one or more substituents Q;

each L is independently a bond, X, or —$(CR^{6a}R^{6b})_pX$—; wherein p is an integer of 1, 2, or 3; $R^{6a}$ and $R^{6b}$ are each independently hydrogen or halo; and X is —O—, —C(O)—, —C(O)O—, —OC(O)O—, —C(O)NR$^{14}$—, —C(=NR$^{14}$)NR$^{15}$—, —NR$^{14}$—, —NR$^{14}$C(O)NR$^{15}$—, —NR$^{14}$C(=NR$^{15}$)NR$^{16}$—, —NR$^{14}$S(O)$_k$NR$^{15}$—, —S(O)$_k$—, or —S(O)$_k$NR$^{14}$—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each Z is independently CH or N; and each n is independently an integer of 1, 2, 3, 4, or 5.

In yet another embodiment, provided herein is the compound of Formula IX or X, wherein:

each $R^{17}$ is independently $C_{1-6}$ alkyl or $C_{3-7}$ cycloalkyl;

each $R^{30}$ is independently $C_{1-6}$ alkyl, $C_{3-7}$ cycloalkyl, $C_{6-14}$ aryl, or $C_{1-6}$ alkyl-$C_{3-7}$ cycloalkylene, each optionally substituted with one or more substituents Q;

each $R^{2'}$ is independently $C_{6-14}$ aryl, heteroaryl, or heterocyclyl, each optionally substituted with one or more substituents Q;

each $R^{5'}$, $R^{6'}$, $R^{7'}$, and $R^{8'}$ is independently hydrogen, halo, cyano, $C_{1-6}$ alkyl, or $C_{3-7}$ cycloalkyl, each optionally substituted with one or more substituents Q; or —$OR^a$, wherein each $R^a$ is independently $C_{1-6}$ alkyl or $C_{3-7}$ cycloalkyl, each optionally substituted with one or more substituents Q;

each L is independently —O—, —C(O)—, —C(O)O—, —OC(O)O—, —C(O)NR$^{14}$—, or —NR$^{14}$—, where $R^{14}$ is hydrogen, $C_{1-6}$ alkyl or $C_{3-7}$ cycloalkyl;

each Z is independently CH or N; and each n is independently an integer of 1, 2, 3, 4, or 5.

In yet another embodiment, provided herein is the compound of Formula IX or X, wherein:

each $R^{17}$ is independently $C_{1-6}$ alkyl;

each $R^{30}$ is independently $C_{1-6}$ alkyl or $C_{3-7}$ cycloalkyl optionally substituted with one or more substituents Q;

each $R^{2'}$ is independently $C_{6-14}$ aryl, heteroaryl, or heterocyclyl, each optionally substituted with one or more substituents Q;

each $R^{5'}$, $R^{6'}$, $R^{7'}$, and $R^{8'}$ is independently halo, cyano, methanesulfonamido, $C_{1-6}$ alkyl, or $C_{3-7}$ cycloalkyl, each optionally substituted with one or more substituents Q; or —$OR^a$, wherein each $R^a$ is independently $C_{1-6}$ alkyl or $C_{3-7}$ cycloalkyl, each optionally substituted with one or more substituents Q;

L is —O—;

each Z is independently CH or N; and each n is independently an integer of 1, 2, or 3.

In yet another embodiment, provided herein is the compound of Formula IX or X, wherein:

each $R^{17}$ is independently $C_{1-6}$ alkyl;

each $R^{30}$ is independently $C_{1-6}$ alkyl, or $C_{3-7}$ cycloalkyl optionally substituted with $C_{1-6}$ alkyl or $C_{2-6}$ alkynyl;

each $R^{2'}$ is independently $C_{6-14}$ aryl or heteroaryl, each optionally substituted with one or more substituents selected from the group consisting of cyano, fluoro, methyl, isopropyl, trifluoromethyl, cyclopropyl, cyclobutyl, ethenyl, and ethynyl;

each $R^{5'}$, $R^{6'}$, $R^{7'}$, and $R^{8'}$ is independently hydrogen, halo, methanesulfonamido; $C_{1-6}$ alkyl, optionally substituted with one to three fluoro groups; —$OR^a$, wherein $R^a$ is $C_{1-6}$ alkyl, optionally substituted with one to three fluoro groups;

L is —O—;

each Z is independently CH or N; and each n is independently an integer of 1, 2, or 3.

In yet another embodiment, provided herein is the compound of Formula IX or X, wherein:

each $R^{17}$ is independently methyl or ethyl;

each $R^{30}$ is independently methyl, cyclopropyl, 1-methylcyclopropyl, or 1-ethynylcyclopropyl;

each $R^{2'}$ is independently phenyl, 4-fluorophenyl, 2-isopropylaminothiazol-4-yl, 2-isopropylthiazol-4-yl, 2-trifluoromethylthiazol-4-yl, 4-cyanothiazol-2-yl, 4-methylthiazol-2-yl, 4-trifluoromethylthiazol-2-yl, 4-isopropylthiazol-2-yl, 4-cyclopropylthiazol-2-yl, 4-cyclobutylthiazol-2-yl, 4-ethenylthiazol-2-yl, 4-ethynylthiazol-2-yl, 3-isopropylpyrazol-1-yl, 3-trifluoromethylpyrazol-1-yl, or 5-isopropyl-isoxazol-3-yl;

each $R^{5'}$ is independently hydrogen or methoxy;

each $R^{6'}$ is independently hydrogen, chloro, or methoxy;

each $R^{7'}$ is independently hydrogen, methoxy, difluoromethoxy, trifluoromethoxy, methanesulfonamido, or chloro;

each $R^{8'}$ is independently hydrogen, methyl, difluoromethyl, fluoro, chloro, or bromo;

L is —O—;

each Z is independently CH or N; and each n is independently an integer of 1, 2, or 3.

In still another embodiment, provided herein is the compound of Formula IX or X, wherein:

each $R^{17}$ is independently methyl or ethyl;

each $R^{30}$ is independently methyl, cyclopropyl, 1-methylcyclopropyl, or 1-ethynylcyclopropyl;

each $R^{2'}$ is independently phenyl, 4-fluorophenyl, 2-isopropylaminothiazol-4-yl, 2-isopropylthiazol-4-yl, 2-trifluoromethylthiazol-4-yl, 4-cyanothiazol-2-yl, 4-methylthiazol-2-yl, 4-trifluoromethylthiazol-2-yl, 4-isopropylthiazol-2-yl, 4-cyclopropylthiazol-2-yl, 4-cyclobutylthiazol-2-yl, 4-ethenylthiazol-2-yl, 4-ethynylthiazol-2-yl, 3-isopropylpyrazol-1-yl, 3-trifluoromethylpyrazol-1-yl, or 5-isopropyl-isoxazol-3-yl;

each $R^{5'}$ is independently hydrogen or methoxy;

each $R^{6'}$ is independently hydrogen or methoxy;

each $R^{7'}$ is independently hydrogen, chloro, or methoxy;

each $R^{8'}$ is independently hydrogen, methyl, fluoro, chloro, or bromo;

L is —O—;

each Z is independently CH or N; and each n is independently an integer of 1, 2, or 3.

In one embodiment, provided herein is a compound selected from the group consisting of

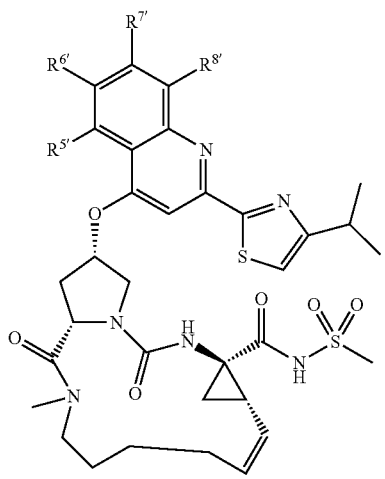

63a: $R^{5'}$ = H, $R^{6'}$ = H, $R^{7'}$ = OCH$_3$, $R^{8'}$ = H;
63b: $R^{5'}$ = H, $R^{6'}$ = H, $R^{7'}$ = OCH$_3$, $R^{8'}$ = CH$_3$;
63c: $R^{5'}$ = H, $R^{6'}$ = H, $R^{7'}$ = OCH$_3$, $R^{8'}$ = F;
63d: $R^{5'}$ = H, $R^{6'}$ = H, $R^{7'}$ = OCH$_3$, $R^{8'}$ = Cl;
63e: $R^{5'}$ = OCH$_3$, $R^{6'}$ = H, $R^{7'}$ = OCH$_3$, $R^{8'}$ = H;
63f: $R^{5'}$ = H, $R^{6'}$ = OCH$_3$, $R^{7'}$ = H, $R^{8'}$ = CH$_3$;
63g: $R^{5'}$ = H, $R^{6'}$ = OCH$_3$, $R^{7'}$ = Cl, $R^{8'}$ = H; and
63h: $R^{5'}$ = H, $R^{6'}$ = H, $R^{7'}$ = OCH$_3$, $R^{8'}$ = Br;

and pharmaceutically acceptable salts, solvates, and prodrugs thereof.

In another embodiment, provided herein is a compound selected from the group consisting of

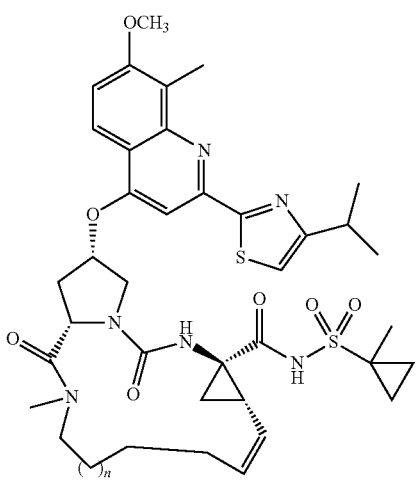

76a: n = 2; and
76b: n = 3;

and pharmaceutically acceptable salts, solvates, and prodrugs thereof.

In yet another embodiment, provided herein is a compound selected from the group consisting of

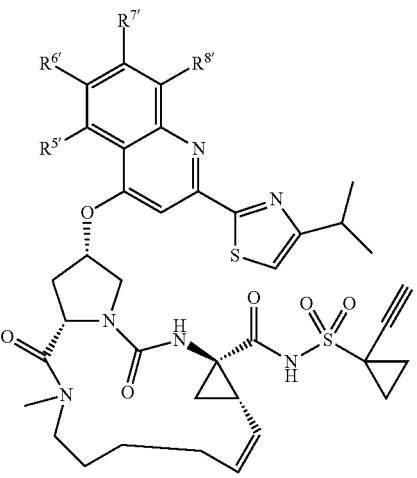

83a: $R^{5'}$ = H, $R^{6'}$ = H, $R^{7'}$ = OCH$_3$, $R^{8'}$ = H;
83b: $R^{5'}$ = H, $R^{6'}$ = H, $R^{7'}$ = OCH$_3$, $R^{8'}$ = CH$_3$;
83c: $R^{5'}$ = H, $R^{6'}$ = H, $R^{7'}$ = OCH$_3$, $R^{8'}$ = F;
83d: $R^{5'}$ = H, $R^{6'}$ = H, $R^{7'}$ = OCH$_3$, $R^{8'}$ = Cl;
83e: $R^{5'}$ = OCH$_3$, $R^{6'}$ = H, $R^{7'}$ = OCH$_3$, $R^{8'}$ = H;
83f: $R^{5'}$ = H, $R^{6'}$ = OCH$_3$, $R^{7'}$ = H, $R^{8'}$ = CH$_3$;
83g: $R^{5'}$ = H, $R^{6'}$ = OCH$_3$, $R^{7'}$ = Cl, $R^{8'}$ = H; and
83h: $R^{5'}$ = H, $R^{6'}$ = H, $R^{7'}$ = OCH$_3$, $R^{8'}$ = Br;

and pharmaceutically acceptable salts, solvates, and prodrugs thereof.

In yet another embodiment, the compound of Formula I is selected from the group consisting of:

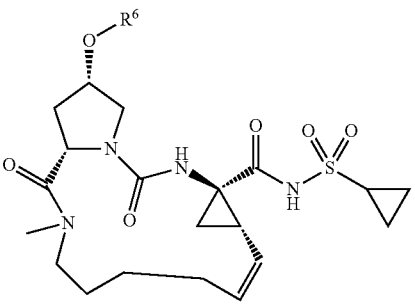

and pharmaceutically acceptable salts, solvates, and prodrugs thereof;

| Cmpd# | $R^6$ |
|---|---|
| 62a | 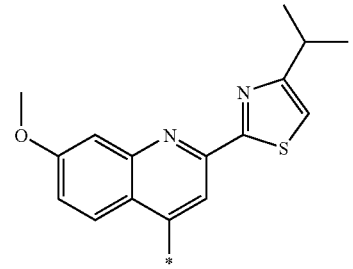 |

37
-continued
| Cmpd# | R⁶ |
|---|---|
| 62b | 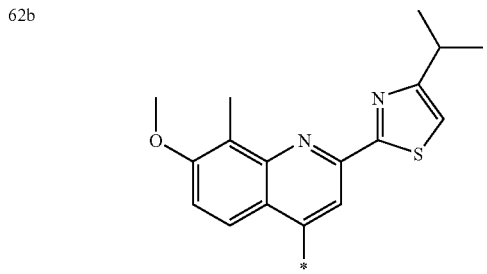 |
| 62c | 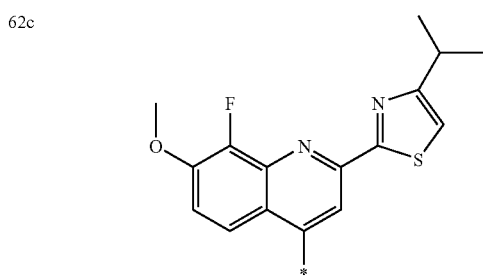 |
| 62d | 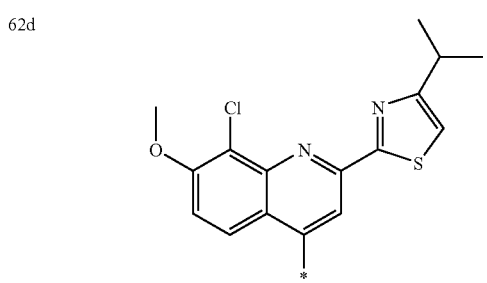 |
| 62e | 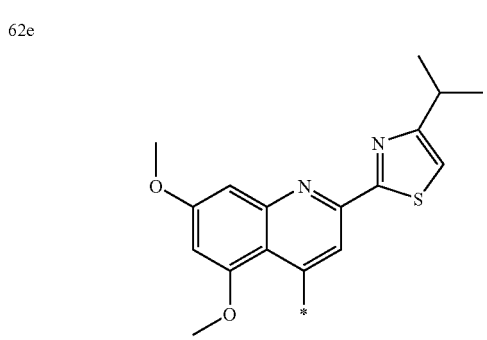 |
| 62f | 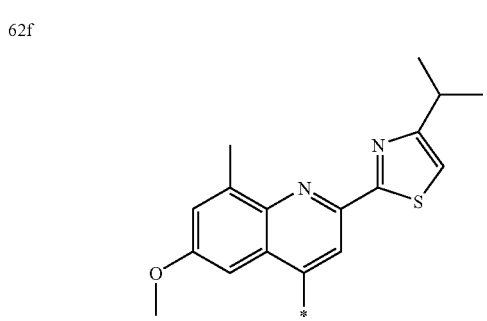 |
38
-continued
| Cmpd# | R⁶ |
|---|---|
| 62g | 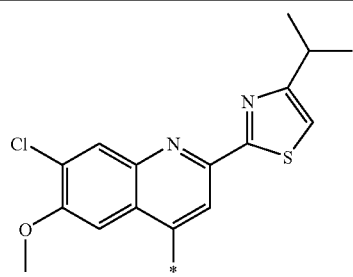 |
| 62h | 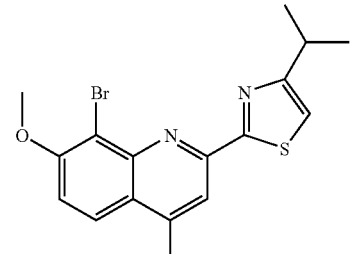 |
| 69a | 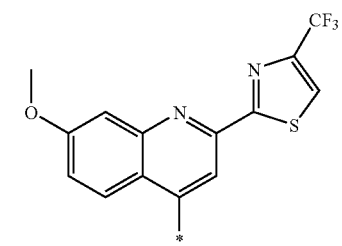 |
| 69b | 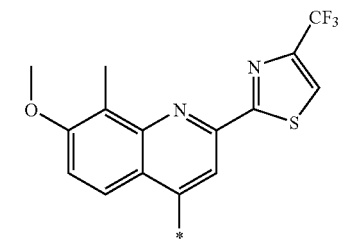 |
| 69c | 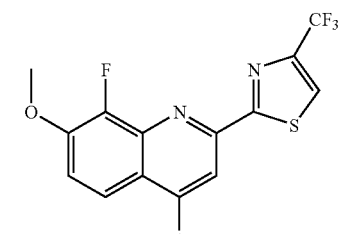 |
| 69d | 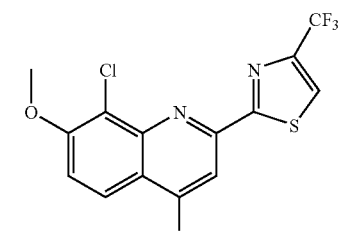 |

-continued
| Cmpd# | R⁶ |
|---|---|
| 69e | 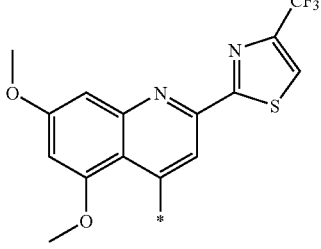 |
| 69f | 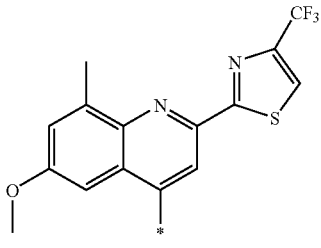 |
| 69g | 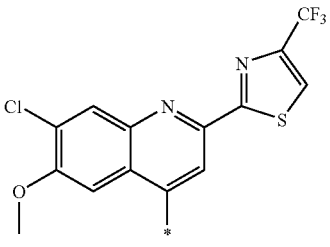 |
| 69h | 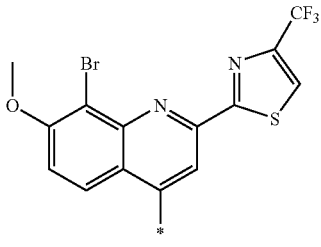 |
| 91e | 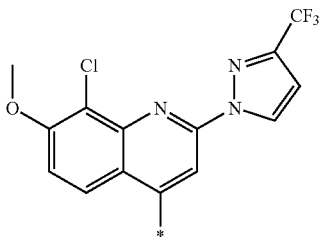 |
| 91f | 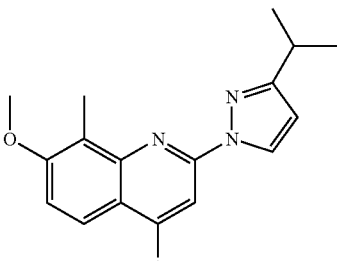 |
-continued
| Cmpd# | R⁶ |
|---|---|
| 91g | 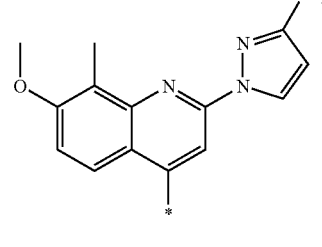 |
| G₁ | 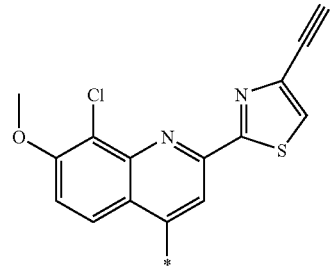 |
| G₃ | 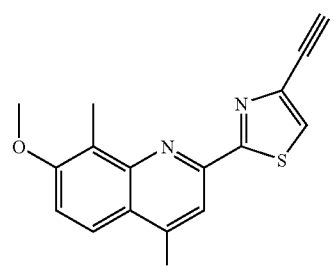 |
| O₁ | 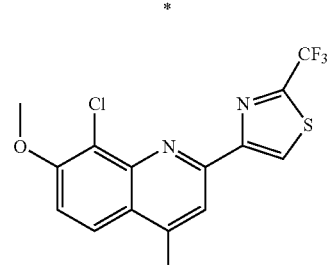 |
| O₃ | 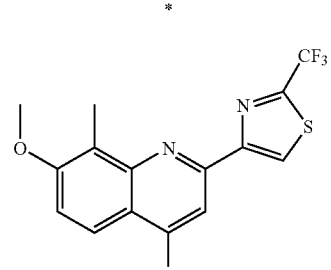 |
| T₁ | 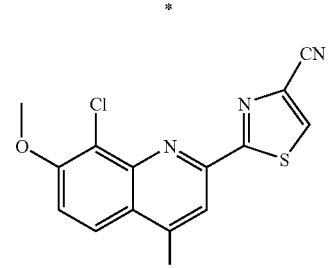 |

| Cmpd# | R⁶ | | Cmpd# | R⁶ |
|---|---|---|---|---|
| AC₁ | (8-chloro-7-methoxyquinolin-2-yl)-4-cyclopropylthiazole structure | | 56a | (7-methoxyquinolin-2-yl)-4-isopropylthiazole structure |
| AC₂ | (8-chloro-7-methoxyquinolin-2-yl)-4-cyclobutylthiazole structure | | 56b | (7-methoxy-8-methylquinolin-2-yl)-4-isopropylthiazole structure |
| AN | (8-chloro-7-methoxyquinolin-2-yl)-4-methylthiazole structure | | 56c | (8-fluoro-7-methoxyquinolin-2-yl)-4-isopropylthiazole structure |
| | | | 56d | (8-chloro-7-methoxyquinolin-2-yl)-4-isopropylthiazole structure |
| | | | 56e | (5,7-dimethoxyquinolin-2-yl)-4-isopropylthiazole structure |

In still another embodiment, the compound of Formula I is selected from the group consisting of:

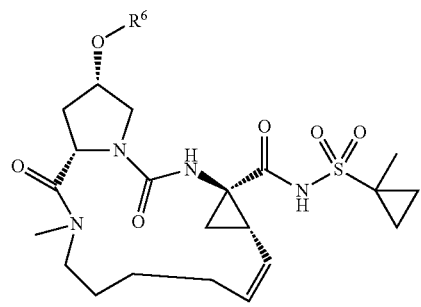

and pharmaceutically acceptable salts, solvates, and prodrugs thereof;

-continued
| Cmpd# | R⁶ |
|---|---|
| 56f | 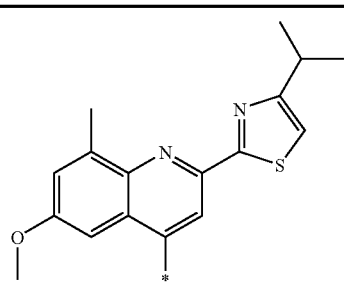 |
| 56g | 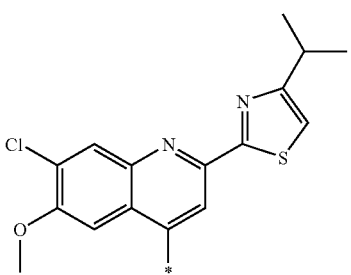 |
| 56h | 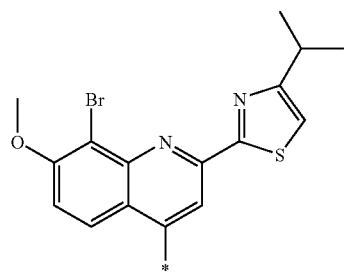 |
| 68a | 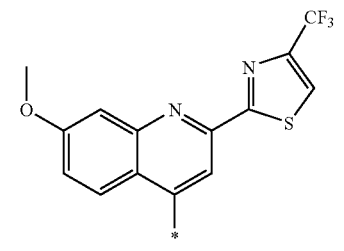 |
| 68b | 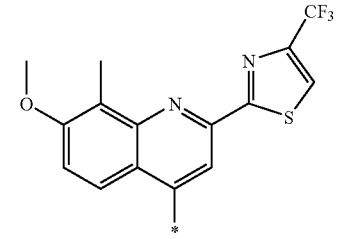 |
| 68c | 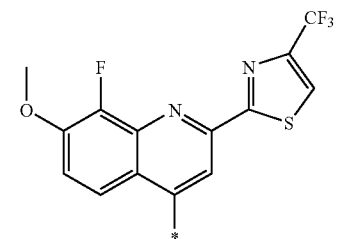 |
-continued
| Cmpd# | R⁶ |
|---|---|
| 68d | 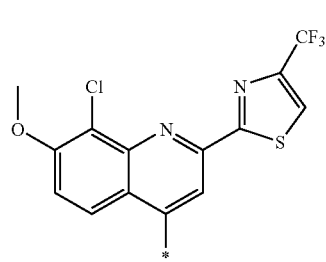 |
| 68e | 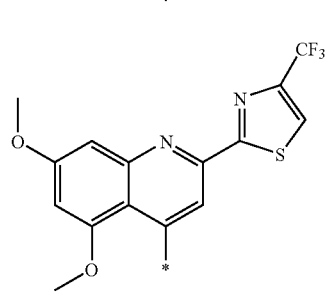 |
| 68f | 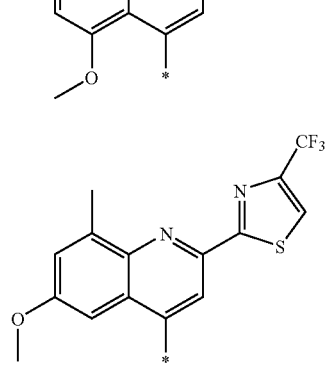 |
| 68g | 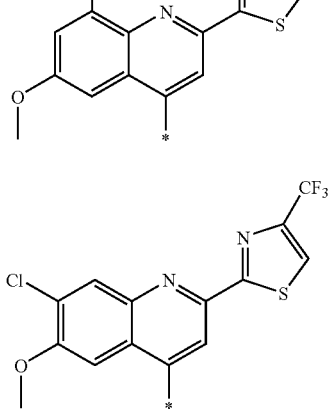 |
| 68h | 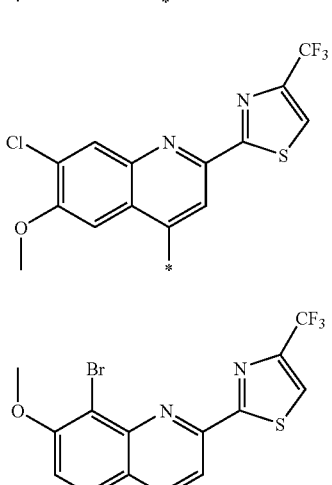 |
| 91a | 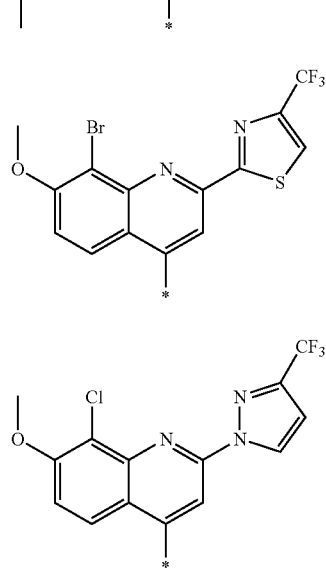 |

| Cmpd# | R⁶ |
|---|---|
| 91b | 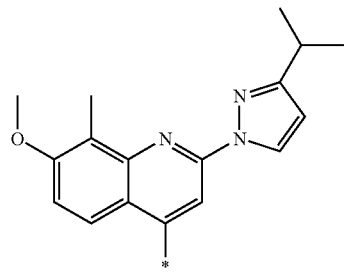 |
| 91c | 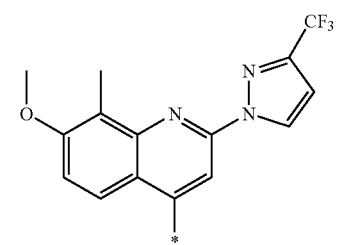 |
| 91d | 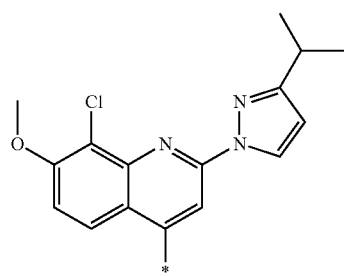 |
| 96a | 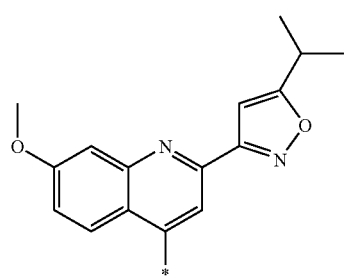 |
| 96b | 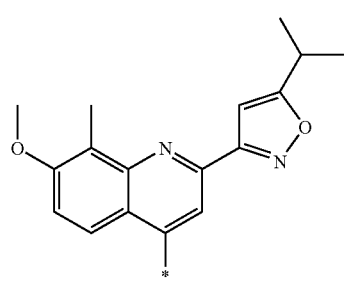 |
| Cmpd# | R⁶ |
|---|---|
| 96c | 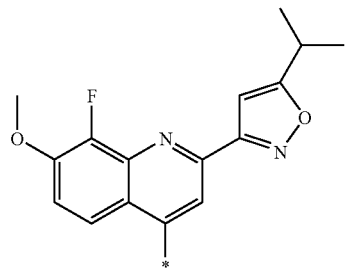 |
| 96d | 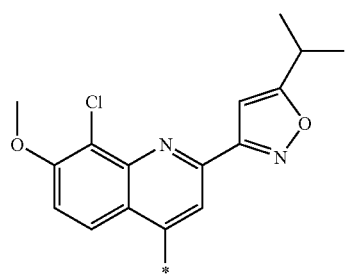 |
| 96e | 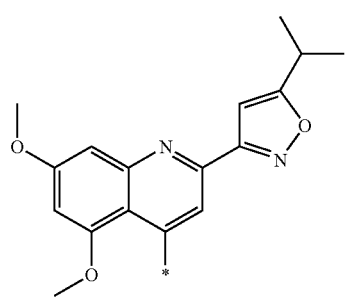 |
| 96f | 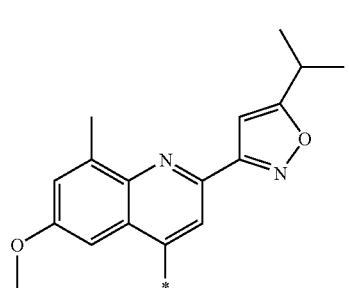 |
| 96g | 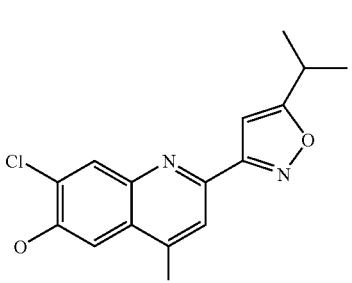 |

| Cmpd# | R⁶ |
|---|---|
| 96h | (8-bromo-7-methoxyquinolin-2-yl with 5-isopropylisoxazol-3-yl) |
| 101a | (7-methoxyquinolin-2-yl with 2-isopropylthiazol-4-yl) |
| 101b | (7-methoxy-8-methylquinolin-2-yl with 2-isopropylthiazol-4-yl) |
| 101c | (8-fluoro-7-methoxyquinolin-2-yl with 2-isopropylthiazol-4-yl) |
| 101d | (8-chloro-7-methoxyquinolin-2-yl with 2-isopropylthiazol-4-yl) |

| Cmpd# | R⁶ |
|---|---|
| 101e | (5,7-dimethoxyquinolin-2-yl with 2-isopropylthiazol-4-yl) |
| 101f | (6-methoxy-8-methylquinolin-2-yl with 2-isopropylthiazol-4-yl) |
| 101g | (7-chloro-6-methoxyquinolin-2-yl with 2-isopropylthiazol-4-yl) |
| 101h | (8-bromo-7-methoxyquinolin-2-yl with 2-isopropylthiazol-4-yl) |
| 110a | (7-methoxyquinazolin-2-yl with 4-isopropylthiazol-2-yl) |

49
-continued

| Cmpd# | R⁶ |
|---|---|
| 110b | (structure) |
| 110c | (structure) |
| 110d | (structure) |
| 110e | (structure) |
| 110f | (structure) |

50
-continued

| Cmpd# | R⁶ |
|---|---|
| 110g | (structure) |
| 110h | (structure) |
| 121 | (structure) |
| 122 | (structure) |
| 123 | (structure) |

| Cmpd# | R[6] |
|---|---|
| 124 | 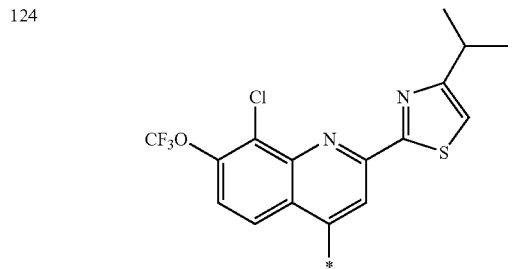 |
| 125 | 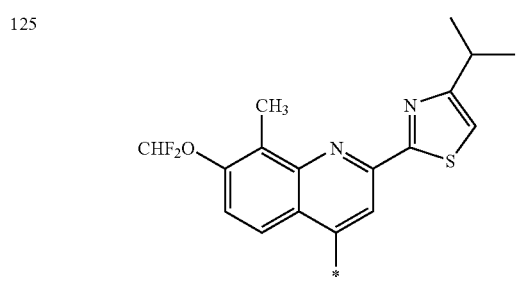 |
| 126 | 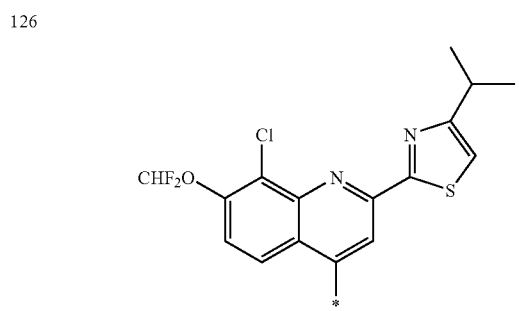 |
| 127 | 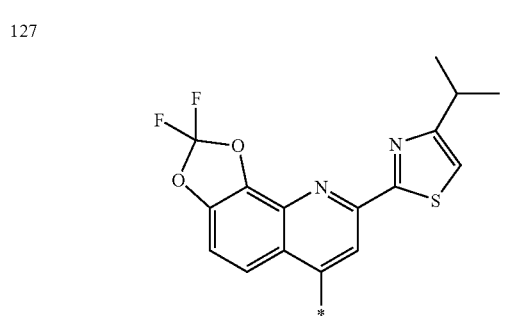 |
| 128 | 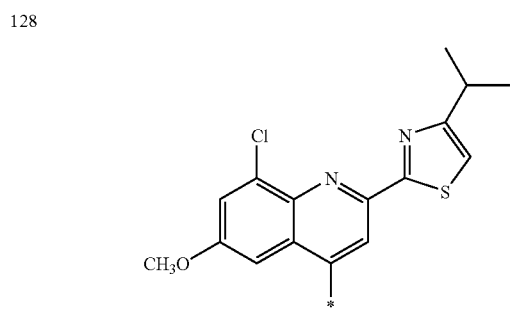 |
| Cmpd# | R[6] |
|---|---|
| 129 | 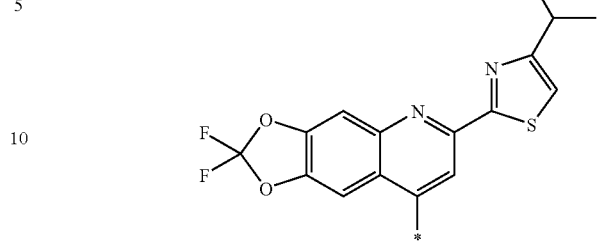 |
| 130 | 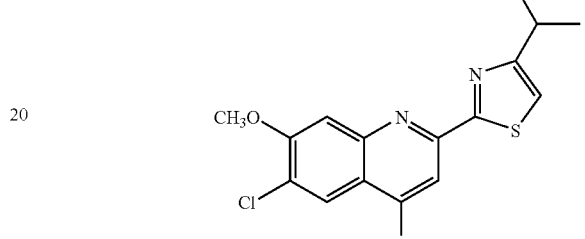 |
| 131 | 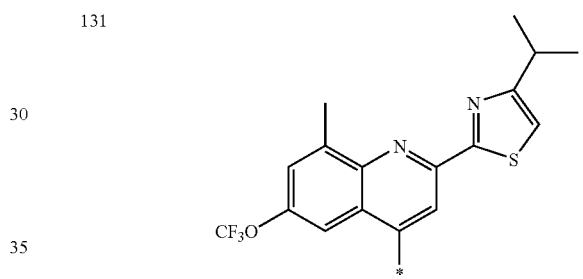 |
| 132 | 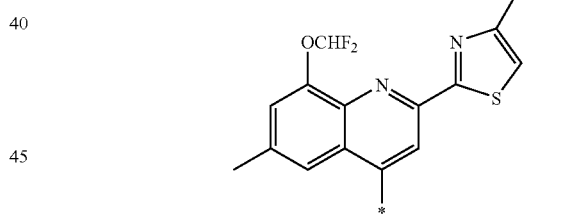 |
| 133 | 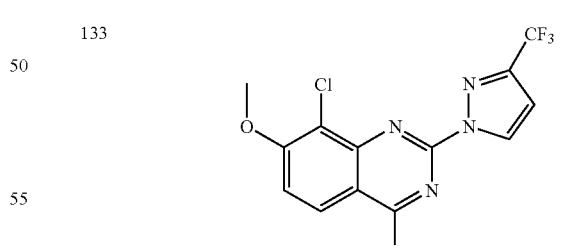 |
| 134 | 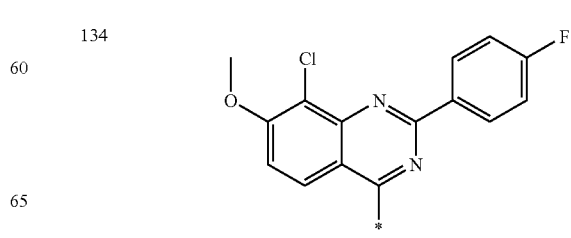 |

| Cmpd# | R⁶ |
|---|---|
| 135 | (structure: H₃CO₂S-NH-quinoline(8-Me)-thiazole-CF₃) |
| G₂ | (structure: 8-Cl-7-methoxy-quinoline-thiazole-C≡CH) |
| G₄ | (structure: 7-methoxy-8-methyl-quinoline-thiazole-C≡CH) |
| O₂ | (structure: 8-Cl-7-methoxy-quinoline-thiazole(2-CF₃)) |
| O₄ | (structure: 7-methoxy-8-methyl-quinoline-thiazole(2-CF₃)) |
| T₂ | (structure: 8-Cl-7-methoxy-quinoline-thiazole-CN) |
| AC₃ | (structure: 8-Cl-7-methoxy-quinoline-thiazole-cyclobutyl) |
| AH | (structure: 8-Cl-7-methoxy-quinoline-thiazole-vinyl) | wherein the symbol * indicates the point of attachment.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible via a low energy barrier, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The heterocyclic moiety that is fused with the macrocyclic ring in the compound provided herein contains two chiral centers as indicated by star symbols. As result, the heterocyclic moiety may exist in four different stereoisomeric forms as shown below, including two cis isomers, (i) and (ii), and two trans isomers, (iii) and (iv).

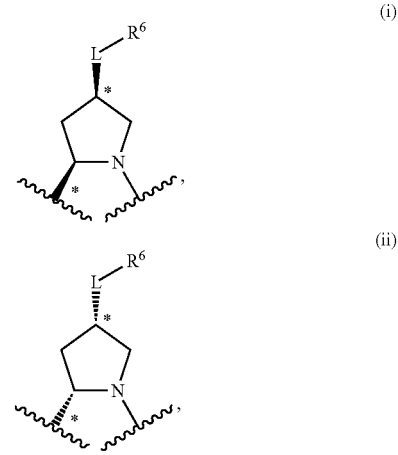

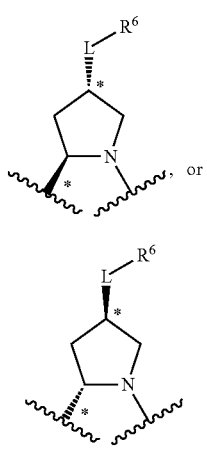

In certain embodiments, the heterocyclic moiety in the compound provided herein is in a cis configuration, (i), (ii), or a mixture thereof. In certain embodiments, the heterocyclic moiety in the compound provided herein is in cis configuration (i). In certain embodiments, the heterocyclic moiety in the compound provided herein is in cis configuration (ii). In certain embodiments, the heterocyclic moiety in the compound provided herein is in cis configuration (i) and (ii).

In certain embodiments, the heterocyclic moiety in the compound provided herein is in a trans configuration, (iii), (iv), or a mixture thereof. In certain embodiments, the heterocyclic moiety in the compound provided herein is in trans configuration (iii). In certain embodiments, the heterocyclic moiety in the compound provided herein is in trans configuration (iv). In certain embodiments, the heterocyclic moiety in the compound provided herein is in trans configuration (iii) and (iv).

In certain embodiments, the heterocyclic moiety in the compound provided herein is in configuration (i), (iii), or a mixture thereof. In certain embodiments, the heterocyclic moiety in the compound provided herein is in configuration (i). In certain embodiments, the heterocyclic moiety in the compound provided herein is in configuration (iii). In certain embodiments, the heterocyclic moiety in the compound provided herein is in configuration (i) and (iii).

In certain embodiments, the heterocyclic moiety in the compound provided herein is in configuration (ii), (iv), or a mixture thereof. In certain embodiments, the heterocyclic moiety in the compound provided herein is in configuration (ii). In certain embodiments, the heterocyclic moiety in the compound provided herein is in configuration (iv). In certain embodiments, the heterocyclic moiety in the compound provided herein is in configuration (ii) and (iv).

The heterocyclic moiety of a particular configuration can readily be introduced by selecting a chiral starting material that will yield the desired chirality. For example, various chiral 4-hydroxyl prolines are available commercially, including cis-4-hydroxy-D-proline, cis-4-hydroxy-L-proline, and trans-4-L-proline.

The compounds provided herein may be enantiomerically pure, such as a single enantiomer or a single diastereomer, or be stereoisomeric mixtures, such as a racemic mixture or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compound provided herein can be prepared, isolated, or obtained by any method known to one of skill in the art. For an example, a compound of Formula I can be prepared as shown in Scheme 1.

N-Protected 4-hydroxyproline 1 with a desired stereochemistry is coupled with an amine with a terminal carbon-carbon double bond to form amide 2. Compound 2 is then converted into a free amine by removing the N-protecting group on its proline moiety with a Lewis acid, such as trifluoroacetic acid, followed by coupling with a cyclopropylamine to yield compound 3, which is then protected with a hydroxyl protecting group, such as TBDMSCl, and cyclized in the presence of a metathesis catalyst to yield macrocyclic compound 4. The hydroxyl protecting group of compound 4 is removed to yield compound 5 with a free hydroxyl group. At this point, a variety of $R^6$-L group can be introduced at the hydroxyl position using various chemistries, such as coupling reactions to form ester, carbonate, or carbamate with the hydroxyl group, or nucleophilic substitution reactions to form ether, amine, or thioether. A nucleophilic substitution reaction to form an ether linkage is illustrated in Scheme 1. Compound 5 reacts with $R^6$OH under Mitsunobu condition with inversion of the stereochemistry at the position of the hydroxyl group to produce compound 6 with oxy as L in Formula I as provided herein. The ethyl protecting group is removed from the carboxyl group of compound 6 to yield a free acid, which is readily coupled with a variety of amines to form desired macrocyclic serine protease inhibitors, such as sulfonamide 7.

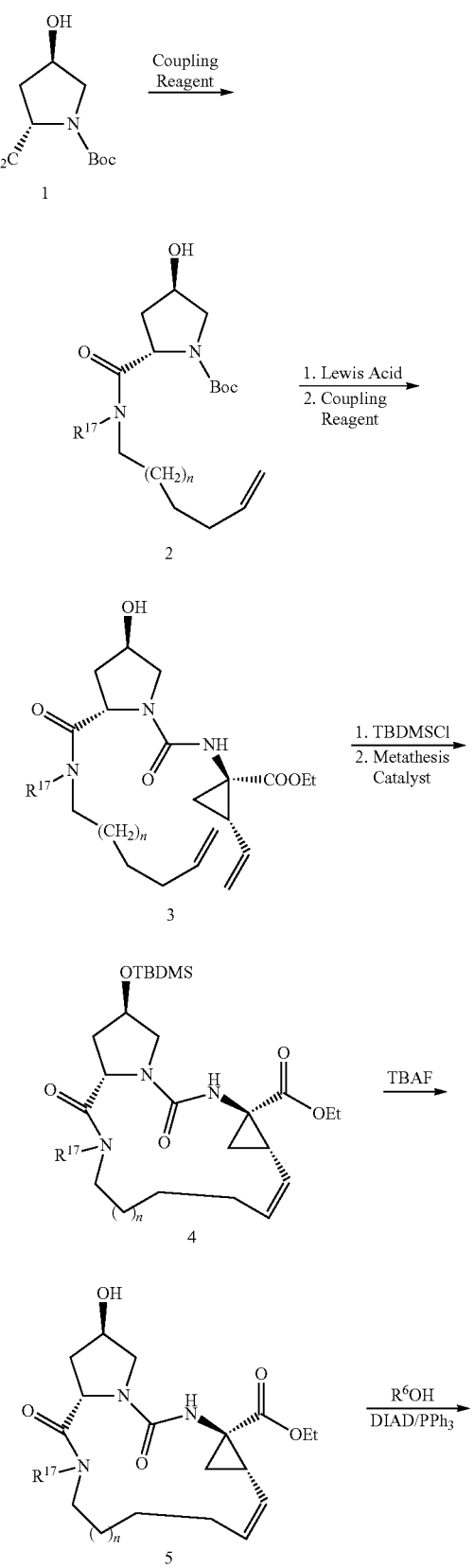

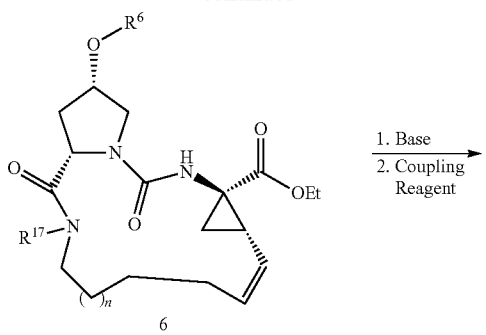

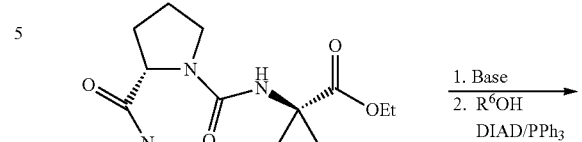

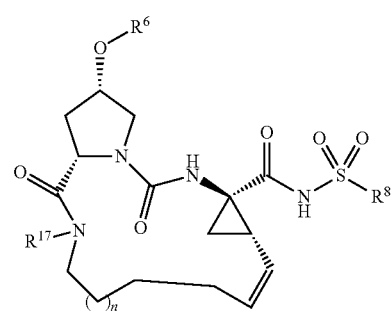

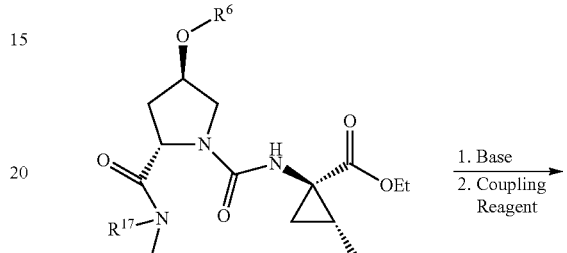

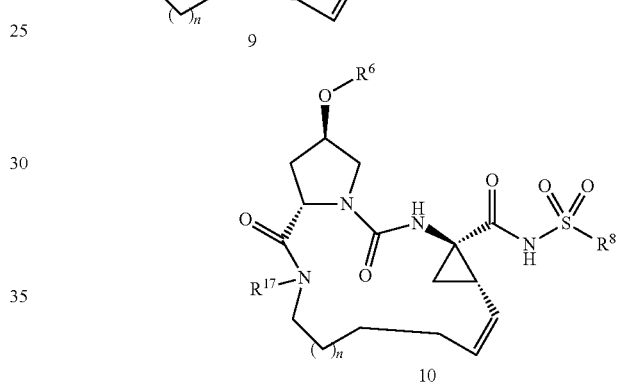

An alternative strategy is shown in Scheme 2, where double inversion of the stereochemistry at the position of the hydroxyl group is employed to retain its original stereochemistry. Compound 5 is first converted into para-nitrobenzoyl (PNB) ester 8 under Mitsunobu condition with the first inversion of the stereochemistry at the position of the hydroxyl group. The PNB ester 8 is hydrolyzed, and then reacts with $R^6OH$ under Mitsunobu condition with the second inversion of the stereochemistry at the position of the hydroxyl group to yield compound 10 with retention of its original stereochemistry at the position of hydroxyl group.

The starting materials used in the synthesis of the compounds provided herein are either commercially available or can be readily prepared. For example, beta amino sulfonamide is synthesized as shown in Scheme 3 and quinoline derivatives are synthesized as shown in Scheme 4, wherein A, $R^{5'}$, $R^{6'}$, $R^{7'}$, and $R^{8'}$ are as defined herein.

Scheme 2

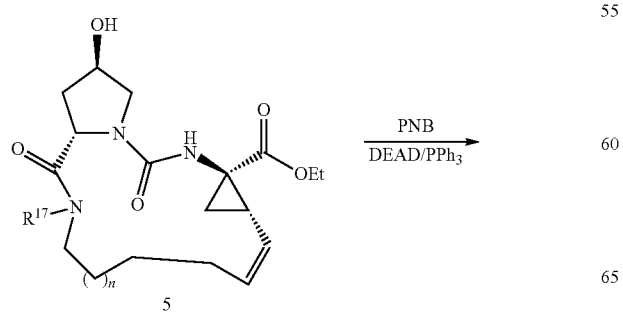

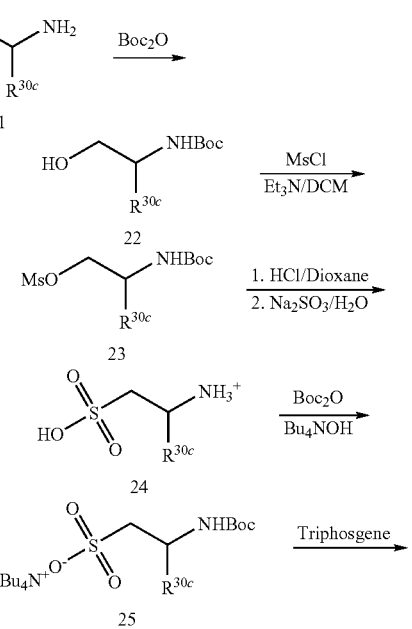

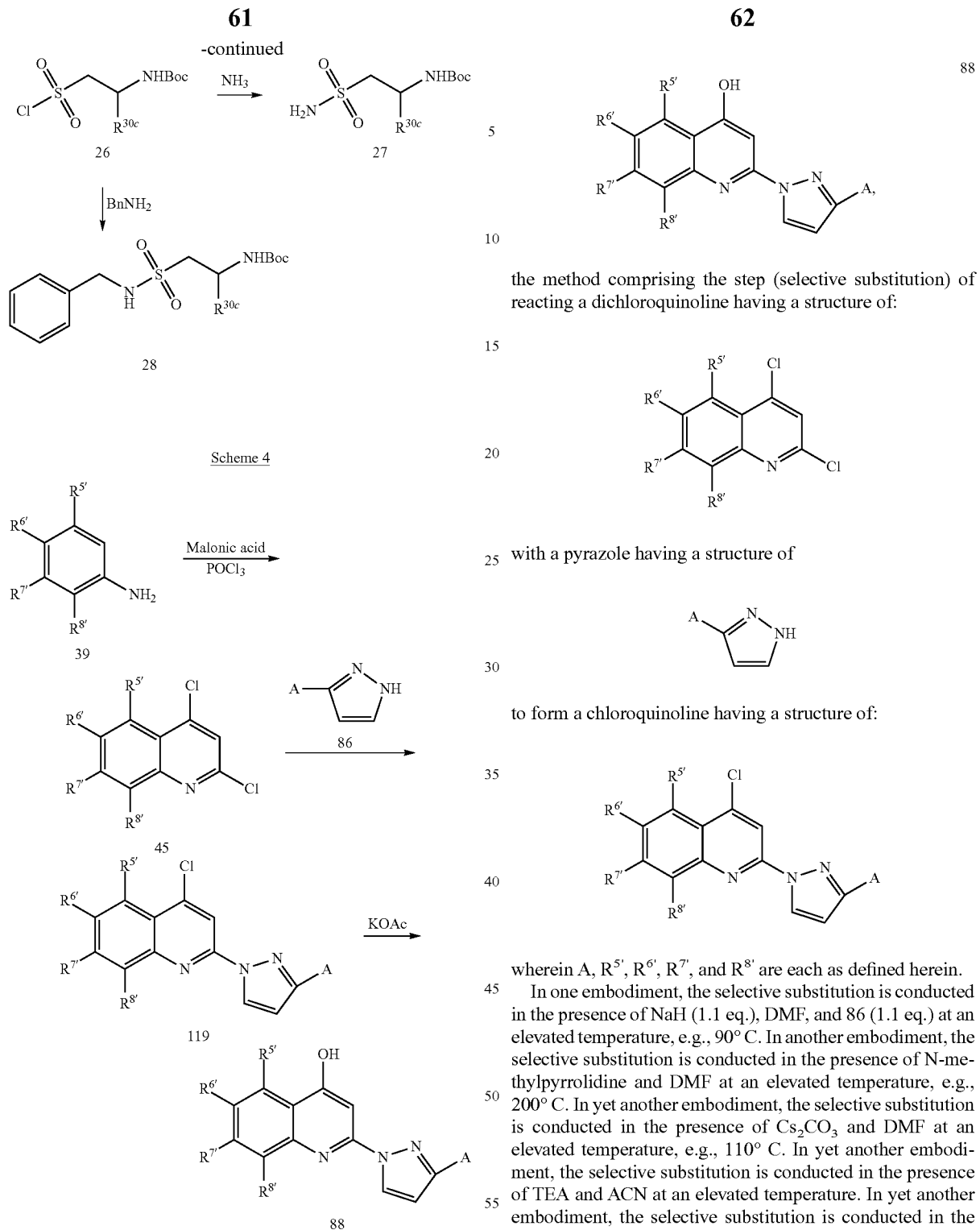

For the syntheses of quinoline derivatives, dichloroquinolines are prepared via the condensation of analine 39 and malonic acid. Selective substitution of the chloro group at the 2 position with pyrazole 86 yields compound 119 in a single step without a protecting group. The chloro at the 4 position of compound 119 is then converted to hydroxyl in the presence of a base, including, but not limited to, NaOH, KOH, KOAc, and NaOAc.

Provided herein is a method of preparing a quinoline having a structure of:

the method comprising the step (selective substitution) of reacting a dichloroquinoline having a structure of:

with a pyrazole having a structure of to form a chloroquinoline having a structure of:

wherein A, $R^{5'}$, $R^{6'}$, $R^{7'}$, and $R^{8'}$ are each as defined herein.

In one embodiment, the selective substitution is conducted in the presence of NaH (1.1 eq.), DMF, and 86 (1.1 eq.) at an elevated temperature, e.g., 90° C. In another embodiment, the selective substitution is conducted in the presence of N-methylpyrrolidine and DMF at an elevated temperature, e.g., 200° C. In yet another embodiment, the selective substitution is conducted in the presence of $Cs_2CO_3$ and DMF at an elevated temperature, e.g., 110° C. In yet another embodiment, the selective substitution is conducted in the presence of TEA and ACN at an elevated temperature. In yet another embodiment, the selective substitution is conducted in the presence of EtN(iPr)$_2$ and dioxane at a temperature from room temperature to 140° C. In yet another embodiment, the selective substitution is conducted in toluene at an elevated temperature. In still another embodiment, the selective substitution is conducted in the absence of any solvents at an elevated temperature, e.g., 120° C.

In another embodiment, the method further comprises the step of converting the chloro to hydroxyl in the presence of a base. Suitable bases include, but are not limited to, NaOH, KOH, NaOAc, and KOAc. In one embodiment, the base is NaOH. In another embodiment, the base is KOH. In yet another embodiment, the base is NaOAc. In still another embodiment, the base is KOAc.

Provided herein is a method of preparing compound 129a. As shown in Scheme 4a, the method comprises the steps of (a) reacting compound 127a with CDI to form compound 128a and (b) coupling compound 128a with compound 128 b to form compound 129a.

Provided herein is also a method of preparing a macrocyclic serine protease inhibitor provided herein, e.g., compound 7, as shown in Scheme 4b. The method comprises the step of converting compound 129a into compound 7 in the presence of a ring closure metathesis (RCM) catalyst. In one embodiment, the RCM catalyst is Zhan 1B catalyst.

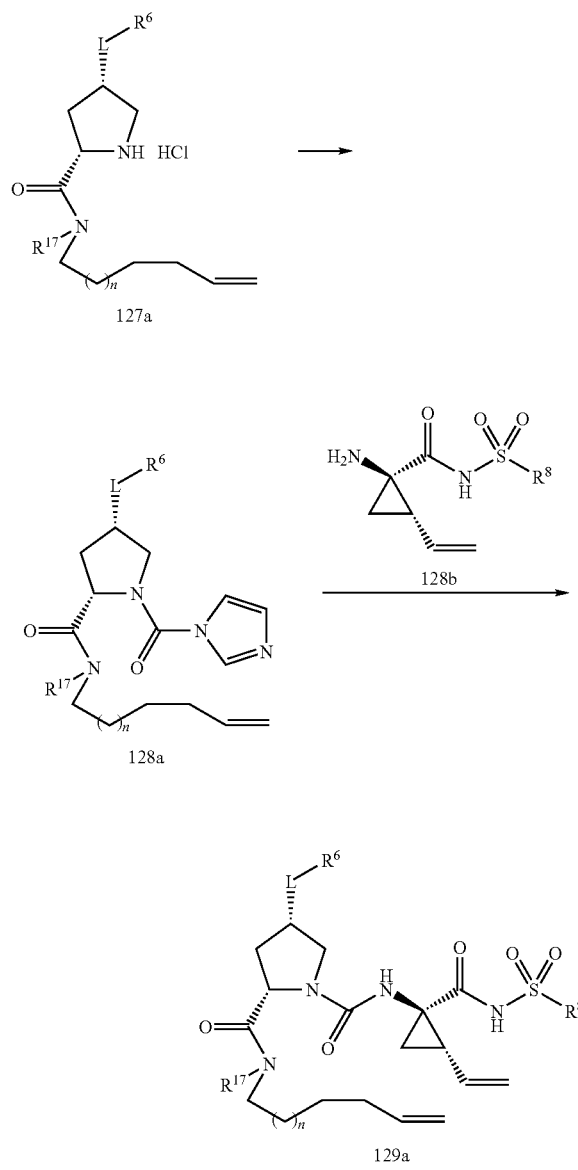

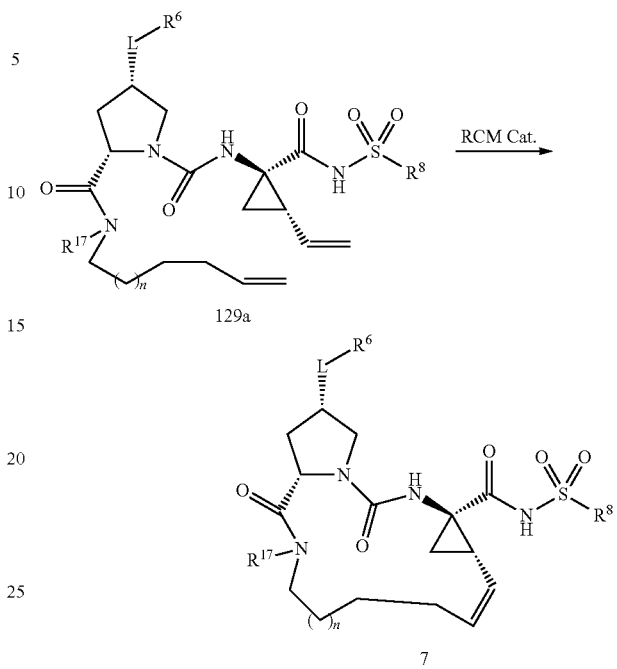

Pharmaceutical Compositions

Provided herein are pharmaceutical compositions comprising a compound provided herein as an active ingredient, including a single enantiomer, a racemic mixture, or a mixture of diastereomers thereof; or a pharmaceutically acceptable salt, solvate, or prodrug thereof, in combination with a pharmaceutically acceptable vehicle, carrier, diluent, or excipient, or a mixture thereof. In certain embodiments, the pharmaceutical composition comprises at least one release controlling excipient or carrier. In certain embodiments, the pharmaceutical composition comprises at least one nonrelease controlling excipient or carrier. In certain embodiments, the pharmaceutical composition comprises at least one release controlling and at least one nonrelease controlling excipients or carriers.

The compound provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, including a single enantiomer, a racemic mixture, or a mixture of diastereomers thereof; or a pharmaceutically acceptable salt, solvate, or prodrug thereof; and one or more pharmaceutically acceptable excipients or carriers.

In another embodiment, the pharmaceutical compositions are provided in a dosage form for parenteral administration, which comprise a compound provided herein, including a single enantiomer, a racemic mixture, or a mixture of diastereomers thereof; or a pharmaceutically acceptable salt, solvate, or prodrug thereof; and one or more pharmaceutically acceptable excipients or carriers.

In yet another embodiment, the pharmaceutical compositions are provided in a dosage form for topical administration, which comprise a compound provided herein, including a single enantiomer, a racemic mixture, or a mixture of diastereomers thereof; or a pharmaceutically acceptable salt, solvate, or prodrug thereof; and one or more pharmaceutically acceptable excipients or carriers.

The pharmaceutical compositions provided herein may be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted-, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(-)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082;

6,048,736; 6,039,975; 6,004,534; 5,985,307; 5,972,366; 5,900,252; 5,840,674; 5,759,542; and 5,709,874.

Methods of Use

Provided herein are methods for treating or preventing a hepatitis C viral infection in a subject, which comprises administering to a subject a therapeutically effective amount of a compound provided herein, including a single enantiomer, a racemic mixture, or a mixture of diastereomers thereof; or a pharmaceutically acceptable salt, solvate, or prodrug thereof. In one embodiment, the subject is a mammal. In another embodiment, the subject is a human.

Additionally, provided herein is a method for inhibiting replication of a virus in a host, which comprises contacting the host with a therapeutically effective amount of the compound of Formula I, including a single enantiomer, a racemic mixture, or a mixture of diastereomers thereof; or a pharmaceutically acceptable salt, solvate, or prodrug thereof. In one embodiment, the host is a cell. In another embodiment, the host is a human cell. In yet another embodiment, the host is a mammal. In still another embodiment, the host is human.

In certain embodiments, administration of a therapeutically effective amount of a compound provided herein, including a single enantiomer, a racemic mixture, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the replication of the virus relative to a subject without administration of the compound, as determined at 1 day, 2 days, 3 days, 4 days, 5 days, 10 days, 15 days, or 30 days after the administration by a method known in the art, e.g., determination of viral titer.

In certain embodiments, administration of a therapeutically effective amount of a compound provided herein, including a single enantiomer, a racemic mixture, or a mixture of diastereomers thereof; or a pharmaceutically acceptable salt, solvate, or prodrug thereof, results in a 1, 2, 3, 4, 5, 10, 15, 20, 25, 50, 75, 100-fold or more reduction in the replication of the virus relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein, including a single enantiomer, a racemic mixture, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the viral titer relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein, including a single enantiomer, a racemic mixture, or a mixture of diastereomers thereof; or a pharmaceutically acceptable salt, solvate, or prodrug thereof, results in a 1, 2, 3, 4, 5, 10, 15, 20, 25, 50, 75, 100 or more fold reduction in the viral titer relative to a subject without administration of the compound, as determined at 1 day, 2 days, 3 days, 4 days, 5 days, 10 days, 15 days, or 30 days after the administration by a method known in the art.

Further provided herein is a method for inhibiting the replication of an HCV virus, which comprises contacting the virus with a therapeutically effective amount of a compound provided herein, including a single enantiomer, a racemic mixture, or a mixture of diastereomers thereof; or a pharmaceutically acceptable salt, solvate, or prodrug thereof.

In certain embodiments, the contacting of the virus with a therapeutically effective amount of a compound provided herein, including a single enantiomer, a racemic mixture, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the virus with a therapeutically effective amount of a compound provided herein, including a single enantiomer, a racemic mixture, or a mixture of diastereomers thereof; or a pharmaceutically acceptable salt, solvate, or prodrug thereof, results in a 1, 2, 3, 4, 5, 10, 15, 20, 25, 50, 75, 100 or more fold reduction in the viral titer relative to the virus without such contact, as determined at 1 day, 2 days, 3 days, 4 days, 5 days, 10 days, 15 days, or 30 days after the initial contact, by a method known in the art.

Also provided herein is a method for treating, preventing, or ameliorating one or more symptoms of a liver disease or disorder associated with an HCV infection, comprising administering to a subject a therapeutically effective amount of the compound provided herein, including a single enantiomer, a racemic mixture, or a mixture of diastereomers thereof; or a pharmaceutically acceptable salt, solvate, or prodrug thereof. Non-limiting examples of diseases associated with HCV infection include chronic hepatitis, cirrhosis, hepatocarcinoma, or extra hepatic manifestation.

Provided herein is a method for inhibiting the activity of a serine protease, which comprises contacting the serine protease with an effective amount of a compound provided herein, including a single enantiomer, a racemic mixture, or a mixture of diastereomers thereof; or a pharmaceutically acceptable salt, solvate, or prodrug thereof. In one embodiment, the serine protease is hepatitis C NS3 protease.

Depending on the condition, disorder, or disease, to be treated and the subject's condition, a compound provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

Combination Therapy

The compounds provided herein may also be combined or used in combination with other therapeutic agents useful in the treatment and/or prevention of an HCV infection.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of HCV can emerge after prolonged treatment with an antiviral agent. Drug resistance most typically occurs due to the mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameters of the drug can be altered by such combination or alternation therapy. In general, combination therapy is typically preferred over alternation therapy because it induces multiple simultaneous stresses on the virus.

In certain embodiments, the compound provided herein is combined with one or more agents selected from the group consisting of an interferon, ribavirin, amantadine, an interleukin, a NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme.

In certain embodiments, the compound provided herein is combined with a HCV protease inhibitor, including, but not limited to, Medivir HCV protease inhibitor (Medivir/Tibotec); ITMN-191 (InterMune), SCH 503034 (Schering), VX950 (Vertex); substrate-based NS3 protease inhibitors as disclosed in WO 98/22496; Attwood et al., *Antiviral Chemistry and Chemotherapy* 1999, 10, 259-273; DE 19914474; WO 98/17679; WO 99/07734; non-substrate-based NS3 protease inhibitors, such as 2,4,6-trihydroxy-3-nitro-benzamide derivatives (Sudo et al., *Biochem. Biophys. Res. Commun.* 1997, 238, 643-647), RD3-4082, RD3-4078, SCH 68631, and a phenanthrenequinone (Chu et al., *Tetrahedron Letters* 1996, 37, 7229-7232); SCH 351633 (Chu et al., *Bioorganic and Medicinal Chemistry Letters* 1999, 9, 1949-1952); Eglin c, a potent serine protease inhibitor (Qasim et al., *Biochemistry* 1997, 36, 1598-1607).

Other suitable protease inhibitors for the treatment of HCV include those disclosed in, for example, U.S. Pat. No. 6,004,933, which discloses a class of cysteine protease inhibitors of HCV endopeptidase 2.

Additional hepatitis C virus NS3 protease inhibitors include those disclosed in, for example, Llinàs-Brunet et al., *Bioorg. Med. Chem. Lett.* 1998, 8, 1713-1718; Steinkühler et al., *Biochemistry* 1998, 37, 8899-8905; U.S. Pat. Nos. 5,538,865; 5,990,276; 6,143,715; 6,265,380; 6,323,180; 6,329,379; 6,410,531; 6,420,380; 6,534,523; 6,608,027; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; U.S. Pat. App. Pub. Nos.: 2002/0016294, 2002/0016442; 2002/0032175; 2002/0037998; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781; WO 98/17679; WO 98/22496; WO 99/07734; WO 00/09543; WO 00/59929; WO 02/08187; WO 02/08251; WO 02/08256; WO 02/08198; WO 02/48116; WO 02/48157; WO 02/48172; WO 02/60926; WO 03/53349; WO 03/64416; WO 03/64455; WO 03/64456; WO 03/66103; WO 03/99274; WO 03/99316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; WO 2007/015824, and WO 2007/056120.

Other protease inhibitors include thiazolidine derivatives, such as RD-1-6250, RD4 6205, and RD4 6193, which show relevant inhibition in a reverse-phase HPLC assay with an NS3/4A fusion protein and NS5A/5B substrate (Sudo et al., *Antiviral Research* 1996, 32, 9-18); thiazolidines and benzanilides identified in Kakiuchi et al., *FEBS Lett.* 1998, 421, 217-220; Takeshita et al., *Analytical Biochemistry* 1997, 247, 242-246.

Suitable helicase inhibitors include, but are not limited to, those disclosed in U.S. Pat. No. 5,633,358; and WO 97/36554.

Suitable nucleotide polymerase inhibitors include, but are not limited to, gliotoxin (Ferrari et al., *Journal of Virology* 1999, 73, 1649-1654), and the natural product cerulenin (Lohmann et al., *Virology* 1998, 249, 108-118).

Suitable interfering RNA (iRNA) based antivirals include, but are not limited to, short interfering RNA (siRNA) based antivirals, such as Sirna-034 and those described in WO/03/070750, WO 2005/012525, and U.S. Pat. Pub. No. 2004/0209831.

Suitable antisense phosphorothioate oligodeoxynucleotides (S-ODN) complementary to sequence stretches in the 5' non-coding region (NCR) of HCV virus include, but are not limited to those described in Alt et al., *Hepatology* 1995, 22, 707-717, and nucleotides 326-348 comprising the 3' end of the NCR and nucleotides 371-388 located in the core coding region of HCV RNA (Alt et al., *Archives of Virology* 1997, 142, 589-599; Galderisi et al., *Journal of Cellular Physiology* 1999, 181, 251-257);

Suitable inhibitors of IRES-dependent translation include, but are not limited to, those described in Japanese Pat. Pub. Nos.: JP 08268890 and JP 10101591.

Suitable ribozymes include those disclosed in, for example, U.S. Pat. Nos. 6,043,077; 5,869,253 and 5,610,054.

Suitable nucleoside analogs include, but are not limited to, the compounds described in U.S. Pat. Nos. 6,660,721; 6,777,395; 6,784,166; 6,846,810; 6,927,291; 7,094,770; 7,105,499; 7,125,855; and 7,202,224; U.S. Pat. Pub. Nos. 2004/0121980; 2005/0009737; 2005/0038240; and 2006/0040890; WO 99/43691; WO 01/32153; WO 01/60315; WO 01/79246; WO 01/90121, WO 01/92282, WO 02/18404; WO 02/32920, WO 02/48165, WO 02/057425; WO 02/057287; WO 2004/002422, WO 2004/002999, and WO 2004/003000.

Other miscellaneous compounds that can be used as second agents include, for example, 1-amino-alkylcyclohexanes (U.S. Pat. No. 6,034,134), alkyl lipids (U.S. Pat. No. 5,922,757), vitamin E and other antioxidants (U.S. Pat. No. 5,922,757), squalene, amantadine, bile acids (U.S. Pat. No. 5,846,964), N-(phosphonacetyl)-L-aspartic acid (U.S. Pat. No. 5,830,905), benzenedicarboxamides (U.S. Pat. No. 5,633,388), polyadenylic acid derivatives (U.S. Pat. No. 5,496,546), 2',3'-dideoxyinosine (U.S. Pat. No. 5,026,687), benzimidazoles (U.S. Pat. No. 5,891,874), plant extracts (U.S. Pat. Nos. 5,725,859; 5,837,257; and 6,056,961), and piperidines (U.S. Pat. No. 5,830,905).

In certain embodiments, one or more compounds provided herein are administered in combination or alternation with an anti-hepatitis C virus interferon, including, but not limited to, INTRON® A (interferon alfa-2b) and PEGASYS® (Peginterferon alfa-2a); ROFERON® A (recombinant interferon alfa-2a), INFERGEN® (interferon alfacon-1), and PEG-INTRON® (pegylated interferon alfa-2b). In one embodiment, the anti-hepatitis C virus interferon is INFERGEN®, IL-29 (PEG-Interferon lambda), R7025 (Maxy-alpha), BELEROFON®, oral interferon alpha, BLX-883 (LOCTERON®), omega interferon, MULTIFERON®, medusa interferon, ALBUFERON®, or REBIF®.

In certain embodiments, one or more compounds provided herein are administered in combination or alternation with an anti-hepatitis C virus polymerase inhibitor, such as ribavirin, viramidine, NM 283 (valopicitabine), PSI-6130, R1626, HCV-796, or R7128.

In certain embodiments, the one or more compounds provided herein are administered in combination with ribavirin and an anti-hepatitis C virus interferon, such as INTRON® A (interferon alfa-2b), PEGASYS® (Peginterferon alfa-2a), ROFERON® A (recombinant interferon alfa-2a), INFERGEN® (interferon alfacon-1), and PEG-INTRON® (pegylated interferon alfa-2b), In certain embodiments, one or more compounds provided herein are administered in combination or alternation with an anti-hepatitis C virus protease inhibitor, such as ITMN-191, SCH 503034, VX950 (telaprevir), or Medivir HCV protease inhibitor.

In certain embodiments, one or more compounds provided herein are administered in combination or alternation with an anti-hepatitis C virus vaccine, including, but not limited to, TG4040, PEVIPRO™, CGI-5005, HCV/MF59, GV1001, IC41, and INNO0101 (E1).

In certain embodiments, one or more compounds provided herein are administered in combination or alternation with an anti-hepatitis C virus monoclonal antibody, such as AB68 or XTL-6865 (formerly HepX-C); or an anti-hepatitis C virus polyclonal antibody, such as cicavir.

In certain embodiments, one or more compounds provided herein are administered in combination or alternation with an anti-hepatitis C virus immunomodulator, such as ZADAXIN® (thymalfasin), NOV-205, or oglufanide.

In certain embodiments, one or more compounds provided herein are administered in combination or alternation with NEXAVAR®, doxorubicin, PI-88, amantadine, JBK-122, VGX-410C, MX-3253 (celgosivir), SUVUS (BIVN-401 or virostat), PF-03491390 (formerly IDN-6556), G126270, UT-231B, DEBIO-025, EMZ702, ACH-0137171, MitoQ, ANA975, AVI-4065, bavituximab (tarvacin), ALINIA® (nitrazoxanide) or PYN17.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In certain embodiments, the pharmaceutical compositions provided herein further comprise a second antiviral agent as described herein. In one embodiment, the second antiviral is selected from the group consisting of an interferon, ribavirin, an interleukin, an NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme. In another embodiment, the second antiviral agent is an interferon. In yet another embodiment, the t interferon is selected from the group consisting of pegylated interferon alpha 2a, interferon alfacon-1, natural interferon, ALBUFERON®, interferon beta-1a, omega interferon, interferon alpha, interferon gamma, interferon tau, interferon delta, and interferon gamma-1b.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a racemic mixture, or a mixture of diastereomers thereof; or a pharmaceutically acceptable salt, solvate, or prodrug thereof.

In certain embodiments, the kit includes a container comprising a dosage form of the compound provided herein, including a single enantiomer, a racemic mixture, or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); ACN, (acetonitrile); CDCl$_3$ (deuterated chloroform); DCE (dichloroethane); DCM (dichloromethane); DMF (N,N-dimethylformamide); DMSO (dimethylsulfoxide); DMSO-d$_6$ (deuterated dimethylsulfoxide); EtOAc (ethyl acetate); MeOH (methanol); THF (tetrahydrofuran); DIPEA (N,N-diisopropylethylamine); TEA (triethylamine); DBU (1,8-diazabicyclo[5.4.0] undec-7-ene); CDI (carbonyldiimidazole); EDCI or EDC (N'-ethyl-N-(3-dimethylaminopropyl)-carbodiimide); P$_2$O$_5$, (phosphorus pentoxide); TBAF (tetrabutylammonium fluoride); TBTU (O-(benzotriazol-1-yl)-N,N,N',N'-tetramethyluronium tetrafluoroborate); Me (methyl); Et (ethyl); iPr (isopropyl); tBu (tert-butyl); Boc (tert-butoxylcarbony); Bn (benzyl); PMB (p-methoxybenzyl); TsO (tosylate); DEAD (diethylazodicarboxylate), DIAD (diisopropylazodicarboxylate), PPh$_3$ (triphenylphosphine), PNBA (p-nitrobenzoic acid), PNB (p-nitrobenzoyl), and Zhan IB catalyst ((1,3-dimesitylimidazolidin-2-yl)(5-(N,N-dimethylsulfamoyl)-2-isopropoxybenzylidene)ruthenium(V) chloride).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated in Schemes 4 to 18 are intended to exemplify the applicable chemistry through the use of specific examples and are not indicative of the scope of the disclosure.

Example 1

Preparation of N-methyl-ω-alkenyl-1-amine tosylate salts 32

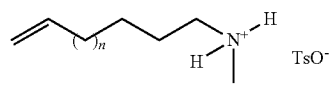

32a: n = 1
32b: n = 2
32c: n = 3

The synthesis of N-methyl-ω-alkenyl-1-amine tosylate salts 32 are shown in Scheme 5.

Step A: Preparation of 2,2,2-trifluoro-N-(hex-5-enyl)-N-methylacetamide 31a. Sodium hydride (60% dispersion in mineral oil, 31.5 g, 1.28 eq.) was slowly added under nitrogen atmosphere to a solution of N-methyl-2,2,2-trifluoroacetamide (100 g, 1.28 eq.) in DMF (500 mL) at 0° C. The reaction mixture was stirred for 90 min at 0° C., and then 6-bromo-1-hexene (100 g, 1 eq.) was added dropwise over 45 min. The reaction mixture was allowed to warm up to room temperature, and stirred for 3 days at room temperature. The reaction mixture was then poured into water and extracted tree time with EtOAc. The combined organics layers were dried over anhydrous sodium sulphate and concentrated under reduced pressure. The residue was purified by flash chromatography on silica gel to produce compound 31a as colorless oil in 56% yield.

$^1$H NMR (DMSO-d$_6$, 400 MHz) δ 1.27-1.38 (m, 2H), 1.48-1.60 (m, 2H), 2.00-2.06 (m, 2H), 2.93-3.07 (2 m, 3H), 3.35-3.40 (m, 2H), 4.92-5.04 (m, 2H), 5.73-5.83 (m, 1H).

Scheme 5

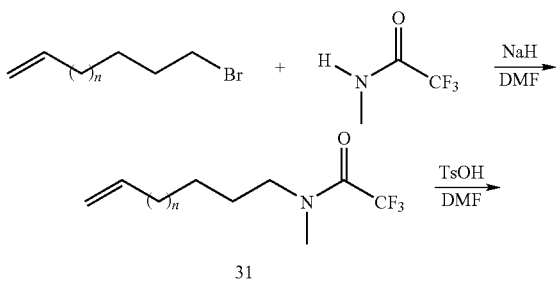

31

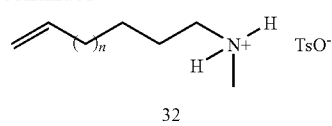

Step B: N-Methylhex-5-en-1-amine tosylate salt 32a. At room temperature, compound 31a (71.88 g, 1 eq.) and p-toluene sulfonic acid (74.4 g, 1.2 eq.) were dissolved in MeOH (640 mL). The reaction mixture was refluxed for 7 days. The solvent was then removed under vacuum, and the residue was recrystallized in acetone. The product was isolated by filtration, dried over $P_2O_5$ to give compound 32a as a white powder in 76% yield.

$^1$H NMR (CDCl$_3$, 400 MHz): δ 1.38 (q, J=7.76 Hz, 2H), 1.71 (q, J=7.76 Hz, 2H), 1.99 (q, J=6.98 Hz, 2H), 2.38 (s, 3H), 2.70 (t, J=5.17 Hz, 3H), 2.87-2.93 (m, 2H), 4.92-4.99 (m, 2H), 5.67-5.73 (m, 1H), 7.20 (d, J=7.76 Hz, 2H), 7.75 (d, J=7.76 Hz, 2H), 8.62 (br s, 2H).

Step C: N-Methylhept-5-en-1-amine tosylate salt 32b. Compound 32b was synthesized from 7-bromo-heptene as a white solid in quantitative yield, following the procedure as described for compound 32a.

$^1$H NMR (CDCl$_3$, 400 MHz) δ 1.38 (q, J=7.76 Hz, 2H), 1.71 (q, J=7.76 Hz, 2H), 1.80 (q, J=6.98 Hz, 2H), 1.99 (q, J=6.98 Hz, 2H), 2.38 (s, 3H), 2.70 (t, J=5.17 Hz, 3H), 2.87-2.93 (m, 2H), 4.92-4.99 (m, 2H), 5.67-5.73 (m, 1H), 7.20 (d, J=7.76 Hz, 2H), 7.75 (d, J=7.76 Hz, 2H), 8.62 (br s, 2H).

Step D: N-Methyloct-5-en-1-amine tosylate salt 32c. Compound 32c was synthesized from 7-bromo-octene as a white powder in quantitative yield, following the procedure as described for compound 32a.

$^1$H NMR (CDCl$_3$, 400 MHz) δ 1.38 (q, J=7.76 Hz, 2H), 1.71 (q, J=7.76 Hz, 2H), 1.80 (q, J=6.98 Hz, 2H), 1.90 (q, J=6.9 Hz, 2H), 1.99 (q, J=6.98 Hz, 2H), 2.38 (s, 3H), 2.70 (t, J=5.17 Hz, 3H), 2.87-2.93 (m, 2H), 4.92-4.99 (m, 2H), 5.67-5.73 (m, 1H), 7.20 (d, J=7.76 Hz, 2H), 7.75 (d, J=7.76 Hz, 2H), 8.62 (brs, 2H).

Example 2

Preparation of 1-((1R,2S)-1-(ethoxycarbonyl)-2-vinylcyclopropylcarbamoyl)-3-methyl-1H-imidazol-3-ium iodide

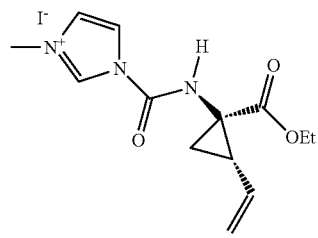

The synthesis of 1-((1R,2S)-1-(ethoxycarbonyl)-2-vinyl-cyclopropyl-carbamoyl)-3-methyl-1H-imidazol-3-ium iodide 34 is shown in Scheme 6.

Scheme 6

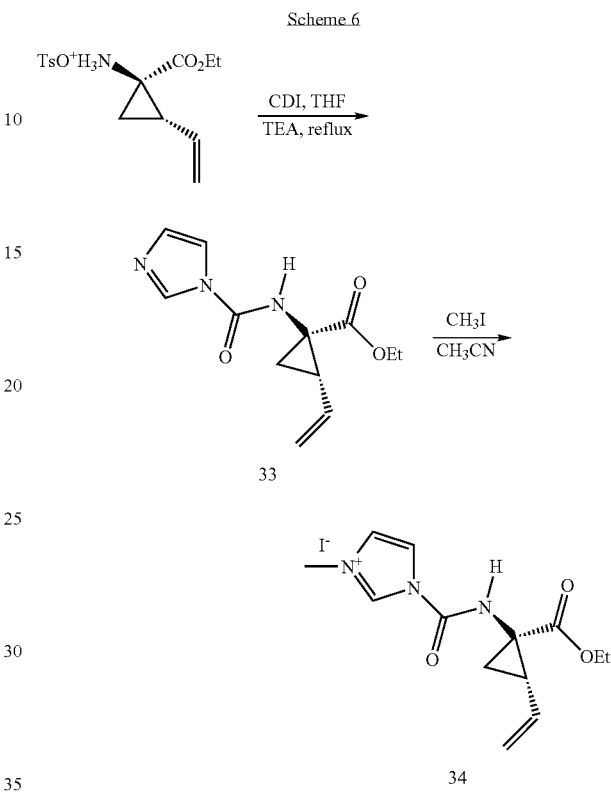

Step A: Preparation of (1R,2S)-ethyl 1-(1H-imidazole-1-carboxamido)-2-vinylcyclopropanecarboxylate 33. Under nitrogen, (1R,2S)-ethyl 1-amino-2-vinylcyclopropanecarboxylate tosylate salt (5 g, 1 eq.) and CDI (2.7 g, 1.1 eq.) were dissolved in THF (50 mL) containing TEA (2.3 mL, 1.1 eq.). The reaction mixture was then refluxed overnight. The solvent was removed under reduced pressure. The residue was dissolved in DCM, and washed twice with water. The organic layer was dried over sodium sulfate and then concentrated. The residue was purified by chromatography on silica gel to yield compound 33 as pale yellow oil in 70% yield.

$^1$H NMR (DMSO-d$_6$, 400 MHz): δ 1.13 (t, J=7.11 Hz, 3H), 1.54 (dd, J=5.43 and 9.57 Hz, 1H), 1.74 (dd, J=5.43 and 8.28 Hz, 1H), 2.35 (q, J=8.54 Hz, 1H), 4.08-4.13 (q, J=7.11 Hz, 2H), 5.13-5.16 (dd, J=10.41 and 1.84 Hz, 1H), 5.32-5.36 (dd, J=17.13 and 1.73 Hz, 1H), 5.63-5.71 (m, 1H), 7.02 (s, 1H), 7.65 (s, 1H), 8.23 (s, 1H), 9.31 (s, 1H); MS (ESI$^+$): m/z 250.2 (MH$^+$).

Step B: Preparation of 1-((1R,2S)-1-(ethoxycarbonyl)-2-vinylcyclopropyl-carbamoyl)-3-methyl-1H-imidazol-3-ium iodide 34. Under nitrogen, methyl iodide (1.9 mL, 4 eq.) was added to a solution of compound 33 (2 g, 1 eq.) in ACN (16 mL). The reaction mixture was stirred at room temperature for 2 hrs. The solvent was removed under reduced pressure to yield compound 34 as yellow oil, which was used directly in the next step without further purification.

Example 3

Preparation of 2-(4-isopropylthiazol-2-yl)-substituted quinolin-4-ols 43

43a: $R^{5'}$ = H, $R^{6'}$ = H, $R^{7'}$ = OCH$_3$, $R^{8'}$ = H
43b: $R^{5'}$ = H, $R^{6'}$ = H, $R^{7'}$ = OCH$_3$, $R^{8'}$ = CH$_3$
43c: $R^{5'}$ = H, $R^{6'}$ = H, $R^{7'}$ = OCH$_3$, $R^{8'}$ = F
43d: $R^{5'}$ = H, $R^{6'}$ = H, $R^{7'}$ = OCH$_3$, $R^{8'}$ = Cl
43e: $R^{5'}$ = OCH$_3$, $R^{6'}$ = H, $R^{7'}$ = OCH$_3$, $R^{8'}$ = H
43f: $R^{5'}$ = H, $R^{6'}$ = OCH$_3$, $R^{7'}$ = H, $R^{8'}$ = CH$_3$
43g: $R^{5'}$ = H, $R^{6'}$ = OCH$_3$, $R^{7'}$ = Cl, $R^{8'}$ = H
43h: $R^{5'}$ = H, $R^{6'}$ = H, $R^{7'}$ = OCH$_3$, $R^{8'}$ = Br

The syntheses of compounds 43 are shown in Schemes 7 to 9, where $R^{5'}$, $R^{6'}$ $R^{7'}$, and $R^{8'}$ in compounds 39 to 42 and 45 to 47 are the same as defined in compounds 43.

Method 1:

Step A: Preparation of 1-bromo-3-methylbutan-2-one 35. To a solution of 3-methyl-2-butanone (40.7 g, 1 eq.) in ethanol (391 mL) was added bromide (62.4 g, 0.83 eq.) under nitrogen at 0° C. over 30 min. The reaction mixture was stirred at 0° C. for 4 hrs, then quenched with 1M aqueous sodium metabisulfite (100 mL) and extracted with petroleum ether (750 mL). The organic layer was washed twice with water (100 mL), twice with a cold saturated aqueous bicarbonate, and then brine. The organic layer was dried over sodium sulfate and then concentrated under reduced pressure. The product was purified by distillation under vacuum to yield compound 35 as colourless oil in 42% yield.

$^1$H NMR (CDCl$_3$, 400 MHz): δ 1.17 (d, J=6.98 Hz, 6H), 2.99 (m, J=6.98 Hz, 1H), 3.99 (s, 2H).

Scheme 7

Scheme 8

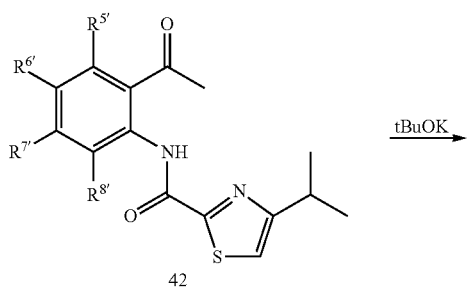 tBuOK → 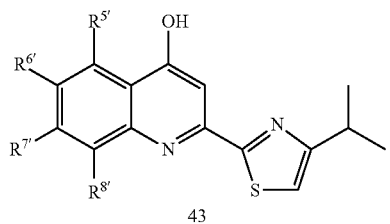

Step B: Preparation of ethyl 4-isopropylthiazole-2-carboxylate 36. A solution of compound 35 (3.5 g, 1.25 eq.) and ethylthioxamate (2.3 g, 1 eq.) in ethanol (40 mL) was heated to 80° C. for 6 hrs, and then cooled to 0° C. The reaction mixture was diluted with water and EtOAc, and then neutralized to pH 7 with $NH_3$ (28%). The aqueous layer was extracted with EtOAc. The combined organic layers were dried over sodium sulfate and then removed under reduced pressure. The residue was purified by chromatography on silica gel to yield compound 36 as yellow oil in quantitative yield.

$^1$H NMR (DMSO-$d_6$, 400 MHz): δ 1.25 (d, J=6.73 Hz, 6H), 1.31 (t, J=7.24 Hz, 3H), 3.11 (hep, J=6.73 Hz, 1H), 4.35 (q, J=7.24 Hz, 2H), 7.72 (s, 1H).

Step C: Preparation of 4-isopropylthiazole-2-carboxylic acid, lithium salt 37. To a solution of compound 36 (26 g, 1 eq.) in a mixture of MeOH (78 mL) and THF (260 mL), lithium hydroxide (2.8 g, 0.9 eq.) was added. The reaction mixture was stirred at room temperature overnight. The solvents were then removed under reduced pressure. The residue was triturated with petroleum ether (500 mL), filtrated, washed with petroleum ether, and dried under vacuum to yield compound 37 as a beige solid in 56% yield.

$^1$H NMR (DMSO-$d_6$, 400 MHz): δ 1.21 (d, J=6.73 Hz, 6H), 2.95 (hep, J=6.73 Hz, 1H), 7.19 (s, 1H).

Step D: Preparation of 4-isopropylthiazole-2-carbonyl chloride 38. Oxalyl chloride (2.9 g, 1.5 eq.) was added dropwise under nitrogen at 0° C. to a suspension of compound 37 (1.8 g, 1 eq.) in DCM (25 mL) and DMF (50 μL). The reaction mixture was stirred at 0° C. for 30 min and then at room temperature for additional 90 min. Lithium chloride salt was removed from the reaction mixture through filtration. The solvent was then removed under reduced pressure to give compound 38 as yellow oil in quantitative yield, which was stored under nitrogen and used directly in the next step without further purification.

Step E: Preparation of 1-(2-amino-4-methoxyphenyl)ethanone 40a. Trichloroborane (IM) in DCM (82 mL, 1 eq.) was added dropwise to a solution of meta-anisidine 39a (10 g, 1 eq.) in toluene (56 mL) under nitrogen at 0-5° C. over 1 hr. After stirred for 10 min at 0° C., ACN (5.2 mL, 1.20 eq.) was added. After the reaction mixture was stirred for additional 1 hr at 0° C., aluminium(III) chloride (11.9 g, 1.1 eq.) was added at 0° C. The reaction mixture was stirred at 50° C. for 16 hrs. The reaction mixture was then cooled down to 0° C., and propan-2-ol (38 mL) was added over 10 min, followed by addition of water (110 mL) over 30 min. The reaction mixture was heated to 50° C. for 3 hrs. After cooling down to 0° C., aqueous solution of sodium hydroxide (25%) was added. The aqueous layer was extracted with toluene (100 mL). The combined organic layers were washed with NaOH (25%), brine, and dried over sodium sulfate. The solvent was removed to yield compound 40a as a yellow solid in 63% yield.

$^1$H NMR (CDCl$_3$, 400 MHz): δ 2.52 (s, 3H), 3.80 (s, 3H), 6.07 (d, J=2.43, 1H), 6.23 (dd, J=2.43 and 8.98 Hz, 1H), 6.43 (br s, 2H), 7.63 (d, J=8.98 Hz).

Step F: Preparation of 1-(2-amino-3-methyl-4-methoxyphenyl)ethanone 40b. Compound 40b was synthesized from 3-methoxy-2-methylaniline 39b as a yellow solid in 23% yield, according to the procedure as described for compound 40a.

MS (ESI, EI$^+$): m/z=180 (MH$^+$).

Step G: Preparation of 1-(2-amino-4-chloro-5-methoxyphenyl)-ethanone 40g. Compound 40g was synthesized from 3-chlor-4-methoxy-aniline 39g as a brown solid in 50% yield, according to the procedure as described for compound 40a.

MS (ESI, EI$^+$): m/z=200 (MH$^+$).

Step H: Preparation of N-(3,5-dimethoxy-phenyl)-4-isopropylthiazole-2-carboxamide 41e. To a stirred solution of compound 37 (1.38 g, 7.8 mmol) in DCM (50 mL) under nitrogen was added oxalyl chloride (1.16 g, 9.1 mmol). The reaction mixture was stirred at room temperature for 90 min. The solution was filtered under nitrogen and washed with DCM. The filtrate was concentrated under reduced pressure and the residue was dissolved in dioxane (20 mL). 3,5-Dimethoxyaniline (1 g, 6.5 mmol) in dioxane (9 mL) was added dropwise. The reaction mixture was stirred at room temperature for 90 min. Solvent was removed under reduced pressure and the crude material was purified by chromatography on silica gel (EtOAc/DCM) to yield compound 41e as a white solid in 90% yield.

$^1$H NMR (CDCl$_3$, 400 MHz) δ 1.35 (s, 3H), 1.37 (s, 3H), 3.14-3.17 (m, 1H), 3.82 (s, 6H), 6.30 (brs, 1H), 6.97 (d, J=2.30 Hz, 2H), 7.19 (s, 1H); MS (ESI, EI$^+$) m/z=307 (MH$^+$).

Step I. Preparation of N-(2-acetyl-5-methoxyphenyl)-4-isopropylthiazole-2-carboxamide 42a. Under nitrogen, a solution of compound 40a (3 g, 1 eq.) in 1,4-dioxane (30 mL) was added at 0° C. to a solution of compound 38 (4.1 g, 1.2 eq.) in 1,4-dioxane. The reaction mixture was stirred at room temperature overnight. The solvent was removed under reduced pressure and the residue was purified by chromatography on silica gel to yield compound as a beige solid 42a in 75% yield.

$^1$H NMR (CDCl$_3$, 400 MHz): δ (ppm) 1.43 (d, J=6.98 Hz, 6H), 2.65 (s, 3H), 3.26 (hep, J=6.98 Hz, 1H), 3.92 (s, 3H), 6.69 (dd, J=2.59 and 8.80 Hz, 1H), 7.2 (d, J=0.84, 1H), 7.87 (d, J=8.9 Hz, 1H), 8.58 (d, J=2.59 Hz, 1H), 13.5 (br s, 1H); MS (ESI, EI$^+$): m/z=319 (MH$^+$).

Step J. Preparation of N-(6-acetyl-2-methyl-3-methoxyphenyl)-4-isopropylthiazole-2-carboxamide 42b. Compound 42b was synthesized from compound 40b and compound 38 as a beige solid in 66% yield, according to the procedure as described for compound 42a.

MS (ESI, EI+): m/z=333 (MH+).

Step K: Preparation of N-(6-acetyl-2-fluoro-3-methoxyphenyl)-4-isopropylthiazole-2-carboxamide 42c. Compound 42c was synthesized from 1-(2-amino-3-fluoro-4-methoxyphenyl)ethanone and compound 38 as a beige solid in 84% yield, according to the procedure as described for compound 42a.

MS (ESI, EI+): m/z=337 (MH+).

Step L: Preparation of N-(6-acetyl-2-chloro-3-methoxyphenyl)-4-isopropylthiazole-2-carboxamide 42d. Compound 42d was synthesized from 1-(2-amino-3-chloro-4-methoxyphenyl)ethanone and compound 38 as a beige solid in 80% yield, according to the procedure as described for compound 42a.

$^1$H NMR (CDCl$_3$, 400 MHz) δ (ppm) 1.47 (s, 3H), 1.48 (s, 3H), 2.57 (s, 3H), 3.34-3.41 (quint, J=6.90 Hz, 1H), 3.98 (s, 3H), 6.86 (d, J=8.48 Hz, 1H), 7.64 (d, J=8.48 Hz, 1H), 8.07 (s, 1H); MS (ESI, EI−) m/z=351 (MH−); MS (ESI, EI+): m/z=353 (MH+).

Step M: Preparation of N-(2-acetyl-3,5-dimethoxy-phenyl)-4-isopropylthiazole-2-carboxamide 42e. To a suspension of Et$_2$AlCl (1.61 g, 12.04 mmol) in DCM at 0° C. was added acetyl chloride (630 mg, 8.02 mmol). The mixture was stirred at 0° C. for 30 min. Compound 41e (1.23 g, 4.01 mmol) was then added and the reaction mixture was stirred at 80° C. for 90 min. The reaction was poured in ice and DCM was added. The organic layers were separated, dried over Na$_2$SO$_4$, filtered, and concentrated under reduced pressure. The crude product was purified by chromatography on silica gel (EtOAc/DCM) to yield compound 42e as a white solid in 82% yield.

$^1$H NMR (CDCl$_3$, 400 MHz) δ 1.41 (s, 3H), 1.43 (s, 3H), 2.63 (s, 3H), 3.20-3.27 (m, 1H), 3.89 (s, 3H), 3.90 (s, 3H), 6.27 (d, J=2.30, 1H), 7.19 (s, 1H), 8.12 (d, J=2.30 Hz, 1H).

Step N: Preparation of N-(6-acetyl-3-chloro-4-methoxyphenyl)-4-isopropylthiazole-2-carboxamide 42g. Compound 42g was synthesized from compounds 38 and 40g as a beige solid in 69% yield, according to the procedure as described for compound 42a.

MS (ESI, EI+): m/z=354 (MH+).

Step O: Preparation of 2-(4-isopropylthiazol-2-yl)-7-methoxyquinolin-4-ol 43a. To a solution of compound 42a (4.312 g, 1 eq.) in tBuOH (60 mL) was added potassium t-butoxide (3.8 g, 2.5 eq.) under nitrogen. The mixture was stirred at 70° C. for 16 hrs, and then cooled down to 0° C. and quenched with MeOH (10 mL) and acetic acid (2.5 mL). The solvent was removed under reduced pressure and the residue was triturated in a mixture of MeOH/water, isolated by filtration, washed with ACN, and then petroleum ether to yield compound 43a as a yellow solid in 71% yield.

$^1$H NMR (DMSO-d$_6$, 400 MHz): δ 1.32 (d, J=6.98 Hz, 6H), 3.14 (m, 1H), 3.89 (s, 3H), 7.06 (br s, 1H), 7.50-7.66 (m, 3H), 8 (d, J=9.05 Hz, 1H), 11.62 (br s, 1H); MS (ESI, EI+): m/z 301 (MH+).

Step P: Preparation of 2-(4-isopropylthiazol-2-yl)-7-methoxy-8-methylquinolin-4-ol 43b. Compound 43b was synthesized from compound 42b as a yellow solid in 60% yield, according to the procedure as described for compound 43a.

MS (ESI, EI+): m/z=315 (MH+).

Step Q: Preparation of 2-(4-isopropylthiazol-2-yl)-8-fluoro-7-methoxyquinolin-4-ol 43c. Compound 43c was synthesized from compound 42c as a yellow solid in 90% yield, according to the procedure as described for compound 43a.

MS (ESI, EI+): m/z=319 (MH+).

Step R: Preparation of 2-(4-isopropylthiazol-2-yl)-5,7-dimethoxyquinolin-4-ol 43e. Compound 43e was synthesized from compound 42e as a yellow solid in 60% yield, according to the procedures as described for compound 43a.

$^1$H NMR (CDCl$_3$, 400 MHz) δ 1.37 (s, 3H), 1.39 (s, 3H), 3.15-3.22 (m, 1H), 3.95 (s, 3H), 4.05 (s, 3H), 6.45 (s, 1H), 7.03 (s, 2H), 7.62 (brs, 1H), 9.55 (s, 1H); MS (ESI, EI+): m/z 331 (MH+).

Step S: Preparation of 7-chloro-2-(4-isopropylthiazol-2-yl)-6-methoxyquinolin-4-ol 43g. Compound 43g was synthesized from compound 42g as a yellow solid in 70% yield, according to the procedures as described for compound 43a.

MS (ESI, EI+): m/z=335 (MH+).

Step T: Preparation of 8-bromo-7-methoxy-2-(4-isopropyl-thiazol-2-yl)-quinolin-4-ol 43h. Compound 43h was synthesized according to the procedures as described for compounds 42a and 43a and in WO 2007014919, the disclosure of which is incorporated herein by reference in its entirety.

MS (ESI, EI+): m/z=380 (MH+).

Method B:

Step AA: Preparation of 4-isopropyl-2-tributylstannanyl-thiazole 44. To a stirred solution of 4-isopropylthiazole (9 g, 71 mmol) in anhydrous THF (100 mL) at −78° C. was added nBuLi (40 mL, 99 mmol). The reaction was stirred for 1 hr and the temperature reached −40° C. The reaction mixture was cooled to −78° C. and tri-n-butyltinchloride (23 g, 71 mmol) was added. The reaction mixture was stirred at room temperature for 48 hrs. Water was added and solvent was evaporated under reduced pressure. The residue was partioned between water and EtOAc. Organics were dried over Na$_2$SO$_4$, filtered, and concentrated under reduced pressure to yield compound 44 as colorless oil in 55% yield.

$^1$H NMR (CDCl$_3$, 400 MHz) δ 0.88-1.62 (m, 27H), 1.40 (s, 3H), 1.42 (s, 3H), 3.17-3.24 (m, 1H).

Step AB: Preparation of 2,4,8-trichloro-7-methoxyquinoline 45d. A mixture of 2-chloro-3-methoxyaniline hydrochloride 39d (15 g, 1 eq.), malonic acid (12.06 g, 1.5 eq.), and phosphorus oxochloride (80 mL) was refluxed for 16 hrs. The reaction mixture was slowly poured into water and extracted with DCM. The organic layer was dried over Na$_2$SO$_4$, filtered, and concentrated under reduced pressure. The crude material was purified on silica pad, eluted with DCM, to yield compound 45d as a white solid in 74% yield.

$^1$H NMR (CDCl$_3$, 376 MHz) δ 4.10 (s, 3H), 7.43 (t, J=4.88 Hz, 2H), 8.12 (d, J=9.48 Hz, 1H).

Step AC: Preparation of 2,4-dichloro-8-methyl-7-methoxyquinoline 45b. Compound 45b was synthesized from 2-methyl-3-methoxyaniline hydrochloride 39b and malonic acid as a white powder in 43% yield, following the procedure as described for compound 45d.

$^1$H NMR (CDCl$_3$, 376 MHz) δ 2.62 (s, 3H), 4.03 (s, 3H), 7.34 (s, 1H), 7.37 (d, J=9.02 Hz, 1H), 8.05 (d, J=9.02 Hz, 1H).

Scheme 9

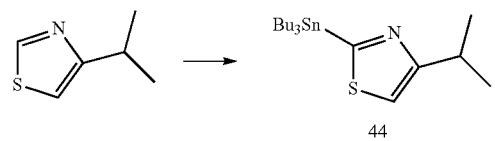

-continued

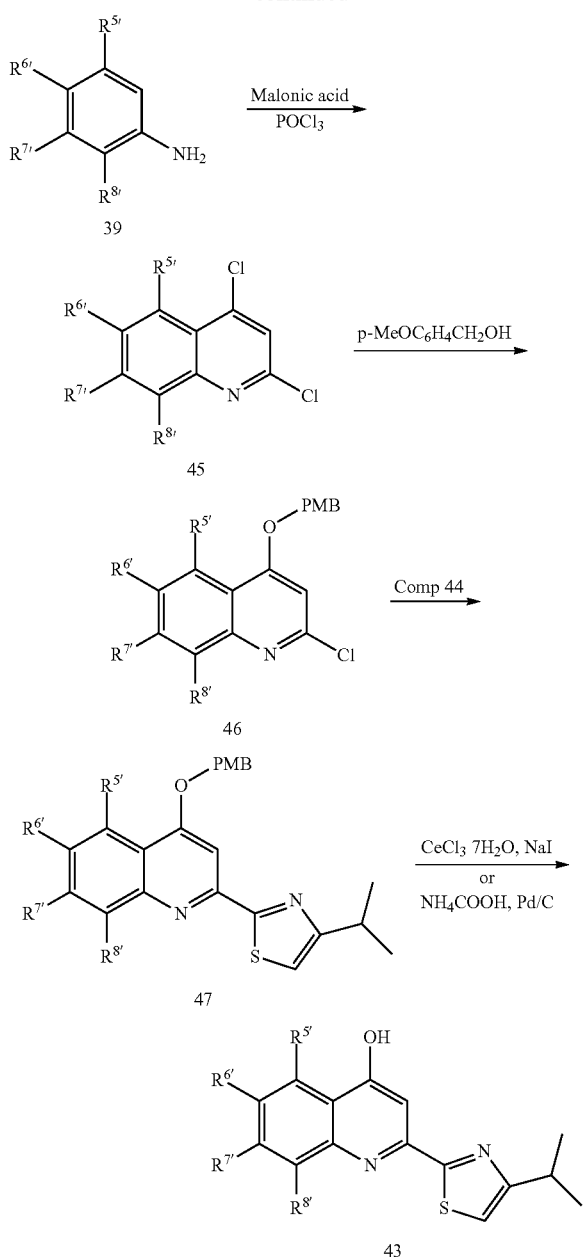

Step AD: Preparation of 2,4-dichloro-6-methoxy-8-methyl-quinoline 45f. A mixture of 4-methoxy-2-methyl aniline 39f (5 g, 36.45 mmol), malonic acid (5.68 g, 54.67 mmol) in phosphorus oxide trichloride (36 mL) was refluxed for 16 hrs. The reaction mixture was then poured dropwise into cooled water (400 mL), extracted with ethyl acetate, washed with brine, dried over Na$_2$SO$_4$, filtered, concentrated under reduced pressure, and purified by chromatography on silica gel (DCM) to yield compound 45f as a beige solid in 43% yield.

$^1$H NMR (CDCl$_3$, 400 MHz) δ 2.72 (s, 3H), 3.95 (s, 3H), 7.27-7.28 (m, 2H), 7.47 (s, 1H).

Step AE: Preparation of 2,8-dichloro-7-methoxy-4-(4-methoxy-benzyloxy)-quinoline 46d. NaH (60% in oil) (670 mg, 1.2 eq.) was added portionwise to a stirred solution of p-methoxybenzylalcohol (2.31 g, 1.2 eq.) and 15-crown-5 (3.32 mL, 1.2 eq.) in anhydrous DMF (10 mL). The mixture was stirred at room temperature for 30 min. Compound 45d (3.66 g, 1 eq.) in anhydrous DMF (25 mL) was then added and the reaction mixture was stirred at room temperature for 16 hrs. The reaction mixture was then poured into water (300 mL), extracted with EtOAC, dried over Na$_2$SO$_4$, filtered, and concentrated under reduced pressure. The crude material was purified by chromatography on silica gel (petroleum ether/DCM, 50/50) to give compound 46d as a yellow solid in 38% yield.

$^1$H NMR (CDCl$_3$, 376 MHz) δ 3.86 (s, 3H), 4.05 (s, 3H), 5.20 (s, 2H), 6.77 (s, 1H), 6.98 (d, J=8.53 Hz, 2H), 7.23 (d, J=9.41, 1H), 7.42 (d, J=8.53 Hz, 2H), 8.08 (d, J=9.41 Hz, 1H).

Step AF: Preparation of 2-chloro-8-methyl-7-methoxy-4-(4-methoxy-benzyloxy)-quinoline 46b. Compound 46b was synthesized from compound 45b as a white powder in 50% yield, following the procedure as described for compound 46d.

$^1$H NMR (CDCl$_3$, 376 MHz) δ 2.60 (s, 3H), 3.85 (s, 3H), 3.97 (s, 3H), 5.18 (s, 2H), 6.69 (s, 1H), 6.97 (d, J=8.57 Hz, 1H), 7.19 (d, J=8.57 Hz, 1H), 7.42 (d, J=8.57 Hz, 1H), 8.02 (d, J=8.57 Hz, 1H).

Step AG: Preparation of 2-chloro-6-methoxy-4-(4-methoxybenzyloxy)-8-methyl-quinoline 46f. Compound 46f was synthesized from compound 45f as a white solid in 58% yield, following the procedure as described for compound 46a.

$^1$H NMR (CDCl$_3$, 400 MHz) δ 2.68 (s, 3H), 3.80 (s, 3H), 3.83 (s, 3H), 5.11 (s, 2H), 6.72 (s, 1H), 6.97 (d, J=9.03 Hz, 2H), 7.15 (dd, J=3.01 Hz and J=0.96 Hz, 1H), 7.20 (d, J=3.00 Hz, 1H), 7.40 (d, J=9.03 Hz, 2H).

Step AH: Preparation of 2-(4-isopropyl-thiazol-2-yl)-6-methoxy-4-(4-methoxy-benzyloxy)-8-methyl-quinoline 47f. Compound 44 (100 mg, 0.29 mmol), compound 46f (242 mg, 0.35 mmol), and potassium carbonate (48 mg, 0.35 mmol) in degassed anhydrous DMF were stirred under microwave radiations at 80° C. for 1 hr. Solvent was removed under reduced pressure and the crude material was purified by chromatography on silica gel (Petroleum ether/DCM) to yield compound 47f as yellow powder in 63% yield.

$^1$H NMR (CDCl$_3$, 400 MHz) δ 1.40 (s, 3H), 1.42 (s, 3H), 2.80 (s, 3H), 3.17-3.24 (m, 1H), 3.85 (s, 3H), 3.89 (s, 3H), 5.31 (s, 2H), 6.99 (d, J=9.10 Hz, 2H), 7.00 (s, 1H), 7.21 (m, 1H), 7.31 (d, J=2.93 Hz, 1H), 7.49 (d, J=9.10 Hz, 2H), 7.79 (s, 1H).

Step AI: Preparation of 4-hydroxy-[2-(4-isopropyl-thiazol-2-yl)]-6-methoxy-8-methyl-quinoline 43f. Compound 47f (1.23 g, 2.82 mmol), cesium trichloride (1.58 g, 4.23 mmol), and sodium iodide (423 mg, 2.82 mmol) in ACN (26 mL) were stirred at 85° C. for 1 hr. The mixture was then filtered through celite and the solvent was evaporated. The brown solid obtained was suspended in water, pH was adjusted at 5 with 1N HCl. The mixture was extracted with DCM, dried over Na$_2$SO$_4$, filtered, concentrated under reduced pressure, and purified by chromatography on silica gel (petroleum ether/DCM) to yield compound 43f as a brown solid in 55% yield.

$^1$H NMR (CDCl$_3$, 400 MHz) δ 1.40 (d, J=6.91 Hz, 6H), 2.80 (s, 3H), 3.17-3.24 (m, 1H), 3.89 (s, 3H), 7.00 (s, 1H), 7.21 (m, 1H), 7.55 (s, 1H), 7.79 (s, 1H), 9.56 (brs, 1H).

Example 4

Preparation of Macrocyclic Compounds 56

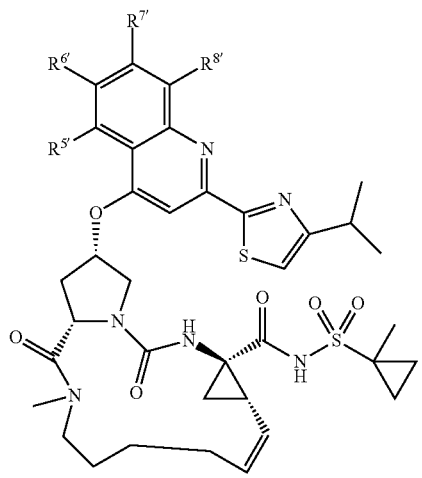

56a: R$^{5'}$ = H, R$^{6'}$ = H, R$^{7'}$ = OCH$_3$, R$^{8'}$ = H
56b: R$^{5'}$ = H, R$^{6'}$ = H, R$^{7'}$ = OCH$_3$, R$^{8'}$ = CH$_3$
56c: R$^{5'}$ = H, R$^{6'}$ = H, R$^{7'}$ = OCH$_3$, R$^{8'}$ = F
56d: R$^{5'}$ = H, R$^{6'}$ = H, R$^{7'}$ = OCH$_3$, R$^{8'}$ = Cl
56e: R$^{5'}$ = OCH$_3$, R$^{6'}$ = H, R$^{7'}$ = OCH$_3$, R$^{8'}$ = H
56f: R$^{5'}$ = H, R$^{6'}$ = OCH$_3$, R$^{7'}$ = H, R$^{8'}$ = CH$_3$
56g: R$^{5'}$ = H, R$^{6'}$ = OCH$_3$, R$^{7'}$ = Cl, R$^{8'}$ = H
56h: R$^{5'}$ = H, R$^{6'}$ = H, R$^{7'}$ = OCH$_3$, R$^{8'}$ = Br

The syntheses of macrocyclic compounds 56 are illustrated in Scheme 10, where R$^{5'}$, R$^{6'}$, R$^{7'}$, and R$^{8'}$ in compounds 54 and 55 are the same as defined in compounds 56.

Scheme 10

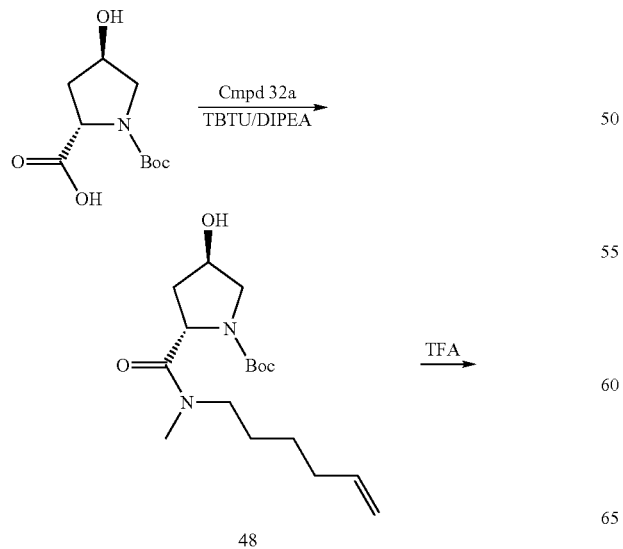

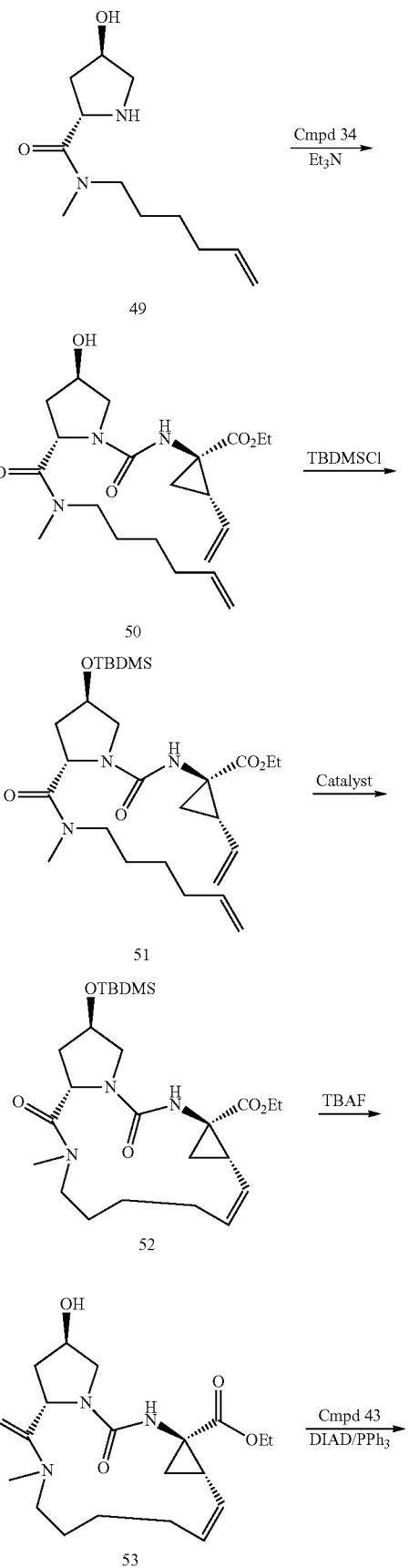

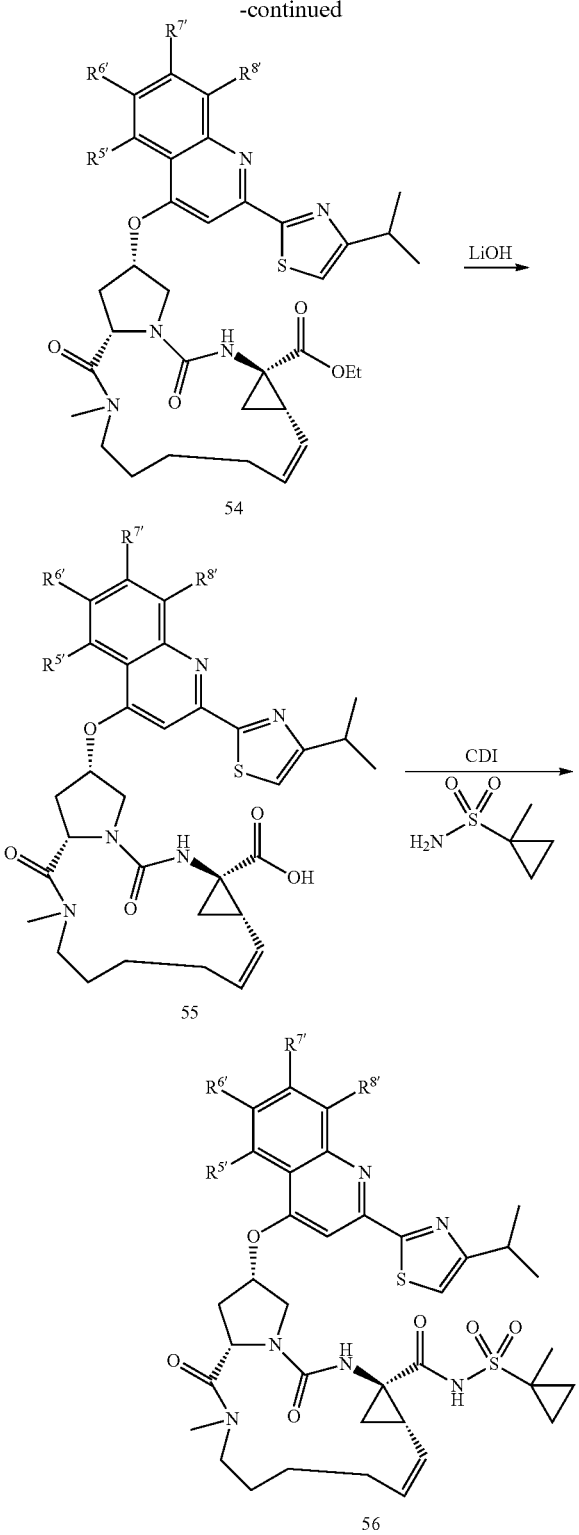

under nitrogen at 0° C. The reaction mixture was stirred overnight at room temperature, and then quenched with water and extracted with diethyl ether. The organic layer was washed with brine, dried over magnesium sulfate, and concentrated under reduced pressure. The residue was purified by chromatography on silica gel to yield compound 48 as a rose powder in 95% yield.

$^1$H NMR (DMSO-$d_6$, 400 MHz): δ 1.29-1.3 (m, 9H), 1.33-1.55 (m, 4H), 1.70-1.80 (m, 1H), 1.97-2.12 (m, 3H), 2.77-2.97 (m, 3H), 3.15-3.40 (m, 4H), 4.22 (br s, 1H), 4.50-4.62 (m, 1H), 4.90-5.04 (m, 3H), 5.71-5.83 (m, 1H); MS (ESI$^+$): m/z=327 (MH$^+$).

Step B: Preparation of (2S,4R)—N-(hex-5-enyl)-4-hydroxy-N-methylpyrrolidine-2-carboxamide 49. Trifluoroacetic acid was added dropwise to a solution of compound 48 (1 g, 1 eq.) in DCM (10 mL). The reaction mixture was stirred for 3 hrs at room temperature, and then trifluoroacetic acid was removed under reduced pressure. The residue was co-evaporated with toluene to yield compound 49 as pale yellow oil in quantitative yield.

MS (ESI$^+$): m/z=227 (MH$^+$).

Step C: Preparation of (1R)-1-{[2(S)-(hex-5-enyl-methyl-carbamoyl)-4(R)-hydroxy-pyrrolidine-N-carbonyl]amino}-2(R)-vinyl-cyclopropanecarboxylic acid ethyl ester 50. Triethylamine (1.3 mL, 3 eq.) was added at room temperature under nitrogen to a mixture of compound 34 (0.7 g, 1 eq.) and compound 49 (1.2 g, 1 eq.) in DCM (15 mL). The reaction mixture was stirred overnight at room temperature and then quenched with 1M aqueous hydrochloric acid. The organic layer was dried over sodium sulfate and concentrated under reduced pressure. The residue was purified by chromatography on silica gel to yield compound 50 as a white solid in 70% yield.

$^1$H NMR (DMSO-$d_6$, 400 MHz): δ 1.10-1.14 (td, J=7.07 and 2.01 Hz, 3H), 1.15-1.17 (m, 1H), 1.22-1.30 (m, 1H), 1.33-1.41 (m, 2H), 1.42-1.50 (m, 1H), 1.54-1.57 (m, 1H), 1.71-1.79 (m, 1H), 1.97-2.07 (m, 4H), 2.74 (s, 1H), 2.97 (s, 2H), 3.11 (d, J=10.24 Hz, 1H), 3.15-3.21 (m, 1H), 3.43-3.48 (m, 1H), 3.91-4.07 (m, 2H), 4.29-4.30 (m, 1H), 4.65-4.69 (d, J=6.50 Hz, 1H), 4.90-4.96 (m, 3H), 5.00-5.06 (m, 2H), 5.19-5.25 (dd, J=17.04 and 6.50 Hz, 1H), 5.51-5.61 (m, 1H), 5.71-5.83 (m, 1H), 7.08 (s, 1H); MS (ESI$^-$): m/z=406 (MH$^-$).

Step D: Preparation of (1R)-1-{[2(S)-(hex-5-enyl-methyl-carbamoyl)-4(R)-tert-butyldimethylsilyloxy-pyrrolidine-N-carbonyl]-amino}-2(R)-vinyl-cyclopropanecarboxylic acid ethyl ester 51. Under nitrogen atmosphere, the tert-butyldimethylsilyl chloride was added to a solution of compound 50 (750 mg, 1 eq.) and TEA (537 μL, 1 eq.) in DCM (6 mL). The reaction mixture was stirred overnight at room temperature and quenched with water. The organic layer was washed with brine, dried on sodium sulfate, and concentrated under reduced pressure. The residue was purified by chromatography on silica gel to yield compound 51 in 70% yield.

$^1$H NMR (DMSO-$d_6$, 400 MHz): δ 0.03 (s, 6H), 0.83 (s, 9H), 1.09-1.13 (td, J=7.09 and 2.24 Hz, 3H), 1.14-1.18 (m, 1H), 1.21-1.29 (m, 2H), 1.32-1.41 (m, 2H), 1.54-1.57 (m, 2H), 1.80-1.86 (m, 2H), 1.91-2.09 (m, 4H), 2.75 (s, 1H), 2.97 (s, 2H), 3.06-3.19 (m, 2H), 3.47-3.57 (m, 1H), 3.94-4.07 (m, 2H), 4.48-4.52 (m, 1H), 4.66-4.71 (m, 1H), 4.90-5.06 (m, 2H), 5.19-5.25 (dd, J=17.24 and 7.39 Hz, 1H), 5.51-5.61 (m, 1H), 5.75-5.83 (m, 1H), 7.12 (s, 1H); MS (ESI$^+$): m/z=522 (MH$^+$).

Step A: Preparation of (2S,4R)-tert-butyl 2-(N-(hex-5-enyl)-N-methyl-carbamoyl)-4-hydroxypyrrolidine-1-carboxylate 48. To a cold solution of cis-N-Boc-4-hydroxy-L-proline (10 g, 1 eq.), O-(benzotriazol-1-yl)-N,N,N',N'-tetramethyluronium tetrafluoroborate (TBTU 15.5 g, 1.12 eq.) and compound 32a (13.6 g, 1.1 eq.) in DMF (80 mL) containing DIPEA (29.4 mL, 3.9 eq.) was added dropwise Step E: Preparation of (Z)-(4R,6S,15S,17R)-2,14-dioxo-13-N-methyl-17-tert-butyldimethylsilyloxy-1,3,13-triazatricyclo[13.3.0.0]octadec-7-ene-4-carboxylic acid ethyl ester 52. To a solution of compound 51 (708 mg, 1 eq.) in DCE (700 mL) (degassed for 45 min by bubbling nitrogen), the catalyst (Hoveyda-Grubbs Catalyst 2nd generation) (6%) was added. The reaction mixture was flushed with nitrogen for 15 min. After refluxed for 3 hrs, the reaction mixture was cooled down to room temperature, and poured onto a silica pad and eluted with EtOAc and then with EtOAc/MeOH. The crude product was purified by chromatography on silica gel to yield compound 52 as a yellow powder in 51% yield.

$^1$H NMR (DMSO-$d_6$, 400 MHz): δ 1.05 (s, 6H), 0.85 (s, 9H), 1.01-1.07 (m, 1H), 1.11-1.15 (t, J=7.29 Hz, 3H), 1.16-1.21 (m, 1H), 1.22-1.28 (m, 1H), 1.39-1.43 (m, 2H), 1.55-1.59 (m, 1H), 1.63-1.77 (m, 2H), 1.87-2.02 (m, 3H), 2.53-2.60 (m, 1H), 2.89 (s, 3H), 3.02-3.05 (dd, J=9.67 and 2.97 Hz, 1H), 3.50-3.53 (dd, J=10.04 and 6.01 Hz, 1H), 3.90-3.99 (m, 1H), 4.00-4.11 (m, 1H), 4.28-4.34 (td, J=13.20 and 3.04 Hz, 1H), 4.58-4.60 (m, 1H), 4.66-4.69 (dd, J=13.20 and 3.04 Hz, 1H), 5.32-5.38 (m, 1H), 5.40-5.47 (m, 1H), 7.04 (s, 1H); MS (ESI, EI$^+$): m/z=494 (MH$^+$).

Step F: Preparation of (Z)-(4R,6S,15S,17R)-2,14-dioxo-17-hydroxy-13-N-methyl-1,3,13-triazatricyclo[13.3.0.0]octadec-7-ene-4-carboxylic acid ethyl ester 53. Under nitrogen atmosphere and at room temperature, a solution of TBAF (1M in THF, 1.3 mL, 2 eq.) was added dropwise to a solution of compound 52 (330 mg, 1 eq.) in THF (2 mL). The reaction mixture was stirred for 2 hrs at room temperature. The solvent was removed under reduced pressure. The residue was dissolved in DCM, washed twice with brine, dried over sodium sulfate, and concentrated under vacuum. The residue was purified by chromatography on silica gel to yield compound 53 as a brown solid in 94% yield.

$^1$H NMR (DMSO-$d_6$, 400 MHz): δ 1.02-1.07 (m, 1H), 1.12-1.15 (t, J=6.89 Hz, 3H), 1.20-1.27 (m, 2H), 1.33-1.38 (m, 1H), 1.40-1.43 (dd, J=4.50 and 4.76 Hz, 1H), 1.56-1.59 (dd, J=4.50 and 4.96 Hz, 1H), 1.65-1.69 (m, 1H), 1.73-1.79 (m, 2H), 1.94-2.05 (m, 2H), 2.54-2.66 (m, 1H), 2.89 (s, 3H), 3.07 (d, J=10.32 Hz, 1H), 3.34-3.37 (dd, J=4.97 and 4.90 Hz, 1H), 3.90-3.98 (m, 1H), 4.04-4.12 (m, 1H), 4.29-4.33 (m, 1H), 4.36-4.38 (m, 1H), 4.65-4.68 (dd, J=5.55 and 2.60 Hz, 1H), 5.00 (d, J=4.68 Hz, 1H), 5.32-5.37 (m, 1H), 5.40-5.47 (m, 1H), 6.95 (s, 1H); MS (ESI, EI$^+$): m/z=380 (MH$^+$).

Step G: Preparation of (Z)-(4R,6S,15S,17S)-17-[8-fluoro-7-methoxy-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid ethyl ester 54c. To a solution compound 53 (240 mg, 1 eq.), compound 43c (201 mg, 1 eq.), and triphenylphosphine (331 mg, 2 eq) in THF (60 mL) was added dropwise DIAD (249 μL, 2 eq.) under nitrogen at 0° C. The reaction mixture was stirred at room temperature overnight. The solvent was then evaporated. The residue was dissolved in EtOAc, washed with a NaHCO$_3$ saturated solution and brine, and dried on sodium sulfate. The solvent was removed under reduced pressure and the residue was purified by chromatography on silica gel to yield compound 54c in 61% yield.

MS (ESI, EI$^+$): m/z=680 (MH$^+$).

Step H: Preparation of (Z)-(4R,6S,15S,17S)-17-[7-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid ethyl ester 54a. Compound 54a was synthesized from compound 53 and compound 43a in 68% yield, following the procedure as described for compound 54c.

MS (ESI, EI$^+$): m/z=662 (MH$^+$).

Step I. Preparation of (Z)-(4R,6S,15S,17S)-17-[7-methoxy-8-methyl-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid ethyl ester 54b. Compound 54b was synthesized from compound 53 and compound 43b in 42% yield, following the procedure as described for compound 54c.

MS (ESI, EI$^+$): m/z=676 (MH$^+$)

Step J: Preparation of (Z)-(4R,6S,15S,17S)-17-[8-chloro-7-methoxy-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid ethyl ester 54d. Compound 54d was synthesized from compound 53 and compound 43d in 48% yield, following the procedure as described for compound 54c.

MS (ESI, EI$^+$): m/z=696 (MH$^+$).

Step K: Preparation of (Z)-(4R,6S,15S,17S)-17-[5,7-dimethoxy-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid ethyl ester 54e. Compound 54e was synthesized from compound 53 and compound 43e in 89% yield, following the procedure as described for compound 54c.

MS (ESI, EI$^+$): m/z=693 (MH$^+$).

Step L: Preparation of (Z)-(4R,6S,15S,17S)-17-[6-methoxy-8-methyl-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid ethyl ester 54f. Compound 54f was synthesized from compound 53 and compound 43f as a beige solid in 60% yield, following the procedure as described for compound 54c.

MS (ESI, EI$^+$): m/z=676 (MH$^+$).

Step M: Preparation of (Z)-(4R,6S,15S,17S)-17-[7-chloro-6-methoxy-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid ethyl ester 54g. Compound 54g was synthesized from compound 53 and compound 43g as a white solid in 57% yield, following the procedure as described for compound 54c.

MS (ESI, EI$^+$): m/z=696 (MH$^+$).

Step N: Preparation of (Z)-(4R,6S,15S,17S)-17-[8-bromo-7-methoxy-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid ethyl ester 54h. Compound 54h was synthesized from compound 53 and compound 43h as a beige solid in 80% yield, following the procedure as described for compound 54c.

MS (ESI, EI$^+$): m/z=740 (MH$^+$).

Step O: Preparation of (Z)-(4R,6S,15S,17S)-17-[8-fluoro-7-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55c. A solution of compound 54c (453 mg, 1 eq.) and LiOH (75.8 mg, 5 eq.) in water/THF was stirred overnight at room temperature. THF was evaporated and the aqueous layer was acidified to pH=6 with 1M aqueous hydrochloric acid. The product was extracted three times with EtOAc. The combined organic layers were washed with brine, dried on sodium sulfate, and concentrated under reduced pressure. The residue was purified by chromatography on silica gel to yield compound 55c as a white powder in 44% yield.

MS (ESI, EI$^+$): m/z=652 (MH$^+$).

Step P: Preparation of (Z)-(4R,6S,15S,17S)-17-[7-methoxy-2-(4-isopropylthiazol-2-yl)quinolin-4-yloxy]-13-N-methyl-2,14-dioxo-1,3,13-triazatricyclo-[13.3.0.0]octadec-7-ene-4-carboxylic acid 55a. Compound 55a was synthesized from compound 54a as a white solid in 22% yield, following the procedure as described for compound 55c.

$^1$H NMR (CDCl$_3$, 400 MHz): δ 1.20-1.26 (m, 2H), 1.28-1.34 (m, 2H), 1.08 (d, J=6.77 Hz, 6H), 1.55-1.62 (m, 2H), 1.81-1.86 (t, J=7.20 Hz, 1H), 1.90-1.93 (m, 1H), 2.23-2.37

(m, 2H), 2.63 (d, J=13.90 Hz, 1H), 2.82-2.90 (m, 1H), 2.96-3.02 (m, 1H), 3.05 (s, 3H), 3.18-3.25 (m, 1H), 3.79-3.83 (t, J=7.79 Hz, 1H), 3.97 (s, 3H), 4.01-4.05 (t, J=7.75 Hz, 1H), 4.59-4.65 (td, J=14.00 and 2.70 Hz, 1H), 4.89-4.92 (t, J=10.50 Hz, 1H), 4.97-5.00 (m, 1H), 5.14 (s, 1H), 5.48-5.55 (m, 1H), 5.63-5.69 (td, J=11.00 and 4.47 Hz, 1H), 7.07 (s, 1H), 7.11-7.14 (dd, J=9.20 and 2.40 Hz, 1H), 7.37 (dd, J=2.40 Hz, 1H), 7.55 (s, 1H), 8.01 (d, J=9.20 Hz, 1H);

MS (ESI, EI$^+$): m/z=634 (MH$^+$).

Step Q: Preparation of (Z)-(4R,6S,15S,17S)-17-[7-methoxy-8-methyl-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55b. Compound 55b was synthesized from compound 54b as a white solid in 25% yield, following the procedure as described for compound 55c.

$^1$H NMR (CDCl$_3$, 400 MHz): δ 0.84-0.89 (m, 2H), 1.20-1.23 (t, J=6.90 Hz, 2H), 1.28-1.34 (m, 2H), 1.40 (d, J=6.93 Hz, 6H), 1.56-1.58 (m, 2H), 1.81-1.85 (t, J=7.00 Hz, 1H), 1.86-1.93 (m, 1H), 2.21-2.27 (m, 1H), 2.62 (d, J=13.20 Hz, 1H), 2.70 (s, 3H), 2.82-2.90 (m, 1H), 3.04 (s, 3H), 3.17-3.24 (m, 1H), 3.46-3.51 (q, J=6.85 Hz, 1H), 3.78-3.82 (t, J=7.60 Hz, 1H), 3.99 (s, 3H), 4.59-4.65 (t, J=13.29 Hz, 1H), 4.89-4.99 (m, 2H), 5.11 (s, 1H), 5.47-5.54 (m, 1H), 5.63-5.69 (td, J=5.54 and 4.45 Hz, 1H), 7.05 (s, 1H), 7.23 (d, J=9.20 Hz, 1H), 7.50 (s, 1H), 7.98 (d, J=9.20 Hz, 1H); MS (ESI, EI$^+$): m/z=648 (MH$^+$).

Step R: Preparation of (Z)-(4R,6S,15S,17S)-17-[8-chloro-7-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55d. Compound 55d was synthesized from compound 54d as a white solid in 15% yield, following the procedure as described for compound 55c.

$^1$H NMR (CDCl$_3$, 400 MHz): δ 1.26-1.34 (m, 2H), 1.39-1.41 (d, J=6.40 Hz, 6H), 1.55-1.61 (m, 6H), 1.82-1.90 (m, 2H), 2.23-2.36 (m, 1H), 2.63 (d, J=14.03 Hz, 1H), 2.81-2.90 (m, 1H), 3.05 (s, 3H), 3.18-3.26 (m, 1H), 3.81-3.86 (t, J=7.68 Hz, 1H), 4.03-4.05 (m, 1H), 4.08 (s, 3H), 4.58-4.64 (td, J=13.40 and 2.34 Hz, 1H), 4.89-4.95 (t, J=10.69 Hz, 1H), 4.97-5.01 (dd, J=5.01 and 4.01 Hz, 1H), 5.15 (s, 1H), 5.50-5.57 (m, 1H), 5.63-5.70 (td, J=10.81 and 4.47 Hz, 1H), 7.10 (s, 1H), 7.27 (d, J=9.20 Hz, 1H), 7.59 (s, 1H), 8.06 (d, J=9.20 Hz, 1H); MS (ESI, EI$^+$): m/z=668 (MH$^+$).

Step S: Preparation of (Z)-(4R,6S,15S,17S)-17-[5,7-dimethoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55e. Compound 55e was synthesized from compound 54e as a white solid in 36% yield, following the procedure as described for compound 55c.

MS (ESI, EI$^+$): m/z=664 (MH$^+$).

Step T: Preparation of (Z)-(4R,6S,15S,17S)-17-[6-methoxy-8-methyl-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55f. Compound 55f was synthesized from compound 54f as a white solid in 10% yield, following the procedure as described for compound 55c.

MS (ESI, EI$^+$): m/z=648 (MH$^+$).

Step U: Preparation of (Z)-(4R,6S,15S,17S)-17-[7-chloro-6-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55g. Compound 55g was synthesized from compound 54g as a white solid in 40% yield, following the procedure as described for compound 55c.

MS (ESI, EI$^+$): m/z=668 (MH$^+$).

Step V: Preparation of (Z)-(4R,6S,15S,17S)-17-[8-bromo-7-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 55h. Compound 55h was synthesized from compound 54h as a beige solid in 90% yield, following the procedure as described for compound 55c.

MS (ESI, EI$^+$): m/z=713 (MH$^+$).

Step W: Preparation of (Z)-(4R,6S,15S,17S)-[17-[8-fluoro-7-methoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56c. Under nitrogen, a solution of compound 55c (76 mg, 1 eq.) and CDI (37.6 mg, 2 eq.) in THF (6 mL) was heated under microwaves radiations to 80° C. for 50 min. 1-Methyl-cyclopropylsulfonamide (31.32 mg, 4 eq.) and DBU (35.3 mg, 2 eq.) were then added under nitrogen. The reaction mixture was heated under microwaves radiations to 80° C. for additional 90 min. The solvent was removed under reduced pressure and the residue was purified by chromatography on silica gel to yield compound 56c as a white solid in 22% yield.

$^1$H NMR (DMSO-d$_6$, 400 MHz): δ 0.86 (m, 2H), 1.09-1.12 (m, 1H), 1.21-1.23 (m, 1H), 1.34 (d, J=6.54 Hz, 6H), 1.39 (s, 3H), 1.45-1.58 (m, 5H), 1.83-1.85 (m, 1H), 2.00-2.03 (m, 1H), 2.20-2.25 (m, 2H), 2.55-2.59 (m, 1H), 2.71 (s, 1H), 2.75-2.80 (m, 1H), 2.87 (s, 1H), 2.90-2.95 (m, 1H), 2.97 (s, 3H), 3.12-3.18 (m, J=6.87 Hz, 1H), 3.49-3.53 (m, 1H), 4.00 (s, 3H), 4.08-4.12 (t, J=8.20 Hz, 1H), 4.39-4.45 (t, J=12.97 Hz, 1H), 4.78-4.83 (t, J=10.45 Hz, 1H), 4.91-4.95 (m, 1H), 5.52-5.54 (m, 1H), 5.65 (brs, 1H), 7.57-7.60 (m, 3H), 7.86-7.89 (d, J=9.52 Hz, 1H), 11.70 (s, 1H); MS (ESI, EI$^+$): m/z=769 (MH$^+$).

Step X: Preparation of (Z)-(4R,6S,15S,17S)-[17-[7-methoxy-2-(4-isopropylthiazol-2-yl)quinolin-4-yloxy]-13-N-methyl-2,14-dioxo-1,3,13-triazatricyclo-[13.3.0.0]octadec-7-en-4-yl]carbonyl(1-methyl-cyclopropyl)sulfonamide 56a. Compound 56a was synthesized from compound 55a as a white solid in 20% yield, following the procedure as described for compound 56c.

$^1$H NMR (CDCl$_3$, 400 MHz): δ 0.74 (m, 2H), 1.10-1.22 (m, 3H), 1.32 (d, J=6.51 Hz, 6H), 1.53 (s, 3H), 1.50-1.64 (m, 6H), 1.73-1.85 (m, 2H), 2.14-2.19 (m, 1H), 2.36-2.37 (m, 1H), 2.51-2.54 (m, 1H), 2.77-2.81 (m, 1H), 2.97 (s, 3H), 3.13-3.15 (m, 1H), 3.69-3.71 (m, 1H), 3.89 (s, 3H), 3.92-3.97 (m, 1H), 4.51-4.58 (t, J=13.51 Hz, 1H), 4.81-4.88 (m, 2H), 4.98 (s, 1H), 5.42-5.45 (m, 1H), 5.55-5.60 (m, 1H), 6.98 (s, 1H), 7.03-7.06 (d, J=8.64 Hz, 1H), 7.19 (s, 1H), 7.49 (s, 1H), 7.93 (d, J=8.64 Hz, 1H), 11.08 (s, 1H); MS (ESI, EI$^+$): m/z=751 (MH$^+$).

Step Y: Preparation of (Z)-(4R,6S,15S,17S)-[17-[7-methoxy-8-methyl-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56b. Compound 56b was synthesized from compound 55b as a white solid in 14% yield, following the procedure as described for compound 56c.

¹H NMR (CDCl₃, 400 MHz): δ 0.82-0.89 (m, 6H), 1.40 (d, J=6.60 Hz, 6H), 1.53 (s, 3H), 1.65-1.76 (m, 2H), 1.81-1.84 (m, 1H), 1.91-1.95 (m, 2H), 2.19-2.25 (m, 1H), 2.41-2.49 (m, 1H), 2.21-2.25 (m, 1H), 2.59-2.63 (d, J=13.63 Hz, 1H) 2.70 (s, 3H), 2.86 (d, J=5.52 Hz, 1H), 2.90-3.03 (m, 2H), 3.06 (s, 3H), 3.21-3.24 (m, 1H), 3.75-3.79 (t, J=7.60 Hz, 1H), 4.00 (s, 3H), 4.60-4.66 (t, J=13.30 Hz, 1H), 4.89-4.98 (m, 2H), 5.04 (s, 1H), 5.49-5.53 (m, 1H), 5.61-5.68 (m, 1H), 7.05 (s, 1H), 7.21-7.24 (d, J=9.09 Hz, 1H), 7.54 (s, 1H), 7.97-8.00 (d, J=9.07 Hz, 1H), 11.16 (s, 1H); MS (ESI, EI⁺): m/z=765 (MH⁺).

Step Z: Preparation of (Z)-(4R,6S,15S,17S)-[17-[8-chloro-7-methoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56d. Compound 56d was synthesized from compound 55d as a white solid in 15% yield, following the procedure as described for compound 56c.

¹H NMR (CDCl₃, 400 Hz): δ 0.82 (m, 2H), 1.28 (s, 2H), 1.40 (d, J=6.93 Hz, 6H), 1.57 (m, 8H), 1.87-1.93 (m, 2H), 2.22-2.24 (m, 1H), 2.43-2.46 (m, 1H), 2.60 (d, J=13.85 Hz, 1H), 2.84-2.90 (m, 1H), 2.97-3.00 (m, 1H), 3.06 (s, 3H), 3.20-3.23 (m, 1H), 3.79-3.81 (m, 1H), 4.04-4.06 (m, 1H), 4.07 (s, 3H), 4.37 (d, J=6.93 Hz, 1H), 4.58-4.66 (t, J=13.85 Hz, 1H), 4.89-4.95 (m, 2H), 5.06 (s, 1H), 5.52-5.54 (m, 1H), 5.64-5.66 (m, 1H), 7.10 (s, 1H), 7.21-7.24 (d, J=9.70 Hz, 1H), 7.59 (s, 1H), 8.05 (d, J=9.70 Hz, 1H), 11.13 (s, 1H); MS (ESI, EI⁺): m/z=785 (MH⁺).

Step AA: Preparation of (Z)-(4R,6S,15S,17S)-[17-[5,7-dimethoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56e. Compound 56e was synthesized from compound 55e as a white solid in 48% yield, following the procedure as described for compound 56c.

MS (ESI, EI⁺): m/z=781 (MH⁺).

Step AB: Preparation of (Z)-(4R,6S,15S,17S)-[17-[6-methoxy-8-methyl-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56f. Compound 56f was synthesized from compound 55f as a white solid in 23% yield, following the procedure as described for compound 56c.

MS (ESI, EI⁺): m/z=765 (MH⁺).

Step AC: Preparation of (Z)-(4R,6S,15S,17S)-[17-[7-chloro-6-methoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56g. Compound 56g was synthesized from compound 55g as a white solid in 20% yield, following the procedure as described for compound 56c.

MS (ESI, EI⁺): m/z=785 (MH⁺).

Step AD: Preparation of (Z)-(4R,6S,15S,17S)-[17-[8-bromo-7-methoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 56h. Compound 56h was synthesized from compound 55h as a white solid in 18% yield, following the procedure as described for compound 56c.

MS (ESI, EI⁺): m/z=831 (MH⁺).

Example 5

Preparation of Macrocyclic Compounds 61

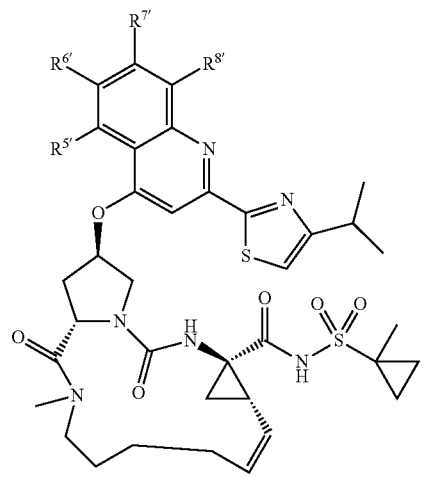

61a: $R^{5'}$ = H, $R^{6'}$ = H, $R^{7'}$ = OCH₃, $R^{8'}$ = H
61b: $R^{5'}$ = H, $R^{6'}$ = H, $R^{7'}$ = OCH₃, $R^{8'}$ = CH₃
61c: $R^{5'}$ = H, $R^{6'}$ = H, $R^{7'}$ = OCH₃, $R^{8'}$ = F
61d: $R^{5'}$ = H, $R^{6'}$ = H, $R^{7'}$ = OCH₃, $R^{8'}$ = Cl
61e: $R^{5'}$ = OCH₃, $R^{6'}$ = H, $R^{7'}$ = OCH₃, $R^{8'}$ = H
61f: $R^{5'}$ = H, $R^{6'}$ = OCH₃, $R^{7'}$ = H, $R^{8'}$ = CH₃
61g: $R^{5'}$ = H, $R^{6'}$ = OCH₃, $R^{7'}$ = Cl, $R^{8'}$ = H
61h: $R^{5'}$ = H, $R^{6'}$ = H, $R^{7'}$ = OCH₃, $R^{8'}$ = Br

The syntheses of macrocyclic compounds 61 are illustrated with compound 61d as shown in Scheme 11, where $R^{5'}$, $R^{6'}$, $R^{7'}$, and $R^{8'}$ in compounds 59 and 60 are the same as defined for compounds 61. The same procedures are also applicable to other compounds 61.

Scheme 11

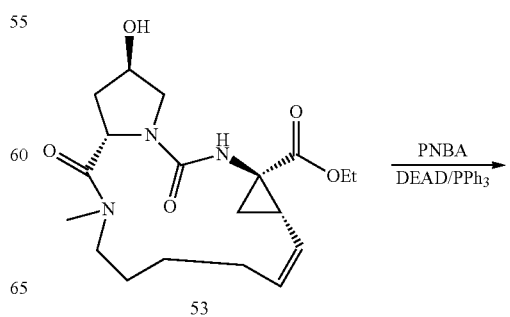

53

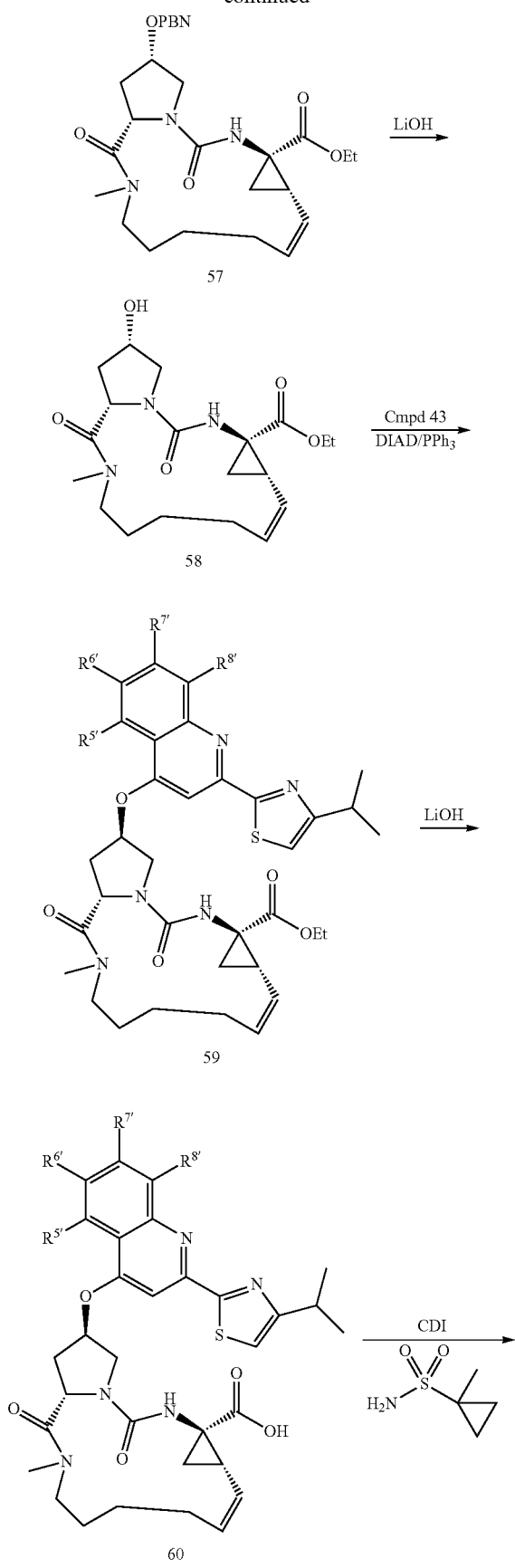

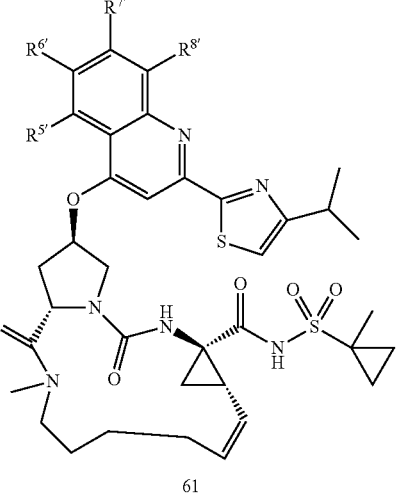

Step A: Preparation of (Z)-(4R,6S,15S,17S)-2,14-dioxo-13-N-methyl-17-(4-nitrobenzoyloxy)-1,3,13-triazatricyclo[13.3.0.0]octadec-7-ene-4-carboxylic acid ethyl ester 57. To a stirred solution of compound 52 (500 mg, 1 eq.), 4-nitrobenzoic acid (290 mg, 1.2 eq.), and triphenylphosphine (450 mg, 1.2 eq.) in dry THF (10 mL) was added DEAD (300 mg, 1.2 eq.) under nitrogen at 0° C. The reaction mixture was stirred for 3 hrs at room temperature and concentrated under reduced pressure. The crude material was purified by flash chromatography on silica gel to yield compound 57 in 16% yield.

MS (ESI, EI$^+$): m/z=529 (MH$^+$).

Step B: Preparation of (Z)-(4R,6S,15S,17S)-2,14-dioxo-17-hydroxy-13-N-methyl-1,3,13-triazatricyclo[13.3.0.0]octadec-7-ene-4-carboxylic acid ethyl ester 58. A solution of compound 57 (700 mg, 1 eq.) and LiOH (75.8 mg, 5 eq.) in water/THF was stirred at room temperature until the reaction was complete. THF was evaporated and the aqueous layer acidified to pH=6 with 1M aqueous hydrochloric acid. The product was extracted three times with ethyl acetate. The combined organic layers were washed with brine and dried over sodium sulfate. The solvent was removed under reduced pressure and the residue was purified by chromatography on silica gel to give compound 58 in 70% yield.

MS (ESI, EI$^+$): m/z=380 (MH$^+$).

Step C: Preparation of (Z)-(4R,6S,15S,17R)-17-[8-chloro-7-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid ethyl ester 59d. Compound 59d was synthesized from compound 58 and compound 43d in 50% yield, following the procedure as described for compound 54c.

MS (ESI, EI$^+$): m/z=696 (MH$^+$).

Step D: Preparation of (Z)-(4R,6S,15S,17R)-17-[8-chloro-7-methoxy-2-(4-isopropylthiazol-2-yl)quinolin-4-yloxy]-13-N-methyl-2,14-dioxo-1,3,13-triazatricyclo[13.3.0.0]octadec-7-ene-4-carboxylic acid 60d. Compound 60d was synthesized from compound 59d as a white solid in 40% yield, following the procedure as described for compound 55c.

$^1$H NMR (DMSO-d$_6$, 400 MHz): δ 1.26-1.34 (m, 4H), 1.33 (d, J=6.40 Hz, 6H), 1.41-1.50 (m, 3H), 1.82-1.90 (m, 2H), 1.97-2.01 (m, 1H), 2.23-2.36 (m, 2H), 2.63 (d, J=14.03 Hz, 2H), 2.96 (s, 3H), 3.12-3.15 (m, 1H), 3.62-3.65 (d, J=11.30 Hz, 1H), 3.77-3.81 (m, 1H), 4.02 (s, 3H), 4.58-4.64 (td,

J=13.40 and 2.34 Hz, 1H), 4.89-4.95 (t, J=10.69 Hz, 1H), 5.25 (s, 1H), 5.44 (m, 1H), 5.65 (s, 1H), 7.51 (s, 1H), 7.54 (s, 1H), 7.56 (d, J=9.78, 1H), 8.17 (d, J=9.78 Hz, 1H); MS (ESI, EI$^+$): m/z=668 (MH$^+$).

Step E: Preparation of (Z)-(4R,6S,15S,17R)-[17-[8-chloro-7-methoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-methyl-cyclopropyl)sulfonamide 61d. Compound 61d was synthesized from compound 60d as a white solid in 15% yield, following the procedure as described for compound 56c.

$^1$H NMR (DMSO-d$_6$, 400 MHz): δ 0.82 (m, 2H), 1.06-1.09 (t, J=7.50 Hz, 2H), 1.21-1.26 (m, 2H), 1.34 (d, J=6.93 Hz, 6H), 1.37 (s, 3H), 1.44-1.59 (m, 5H), 1.85-1.88 (t, J=13.26 Hz, 1H), 2.16-2.20 (q, J=9.36 Hz, 1H), 2.22-2.24 (m, 1H), 2.56-2.60 (d, J=13.26 Hz, 2H), 2.66-2.77 (m, 3H), 3.00 (s, 3H), 3.12-3.18 (m, 1H), 3.34-3.39 (q, J=7.02 Hz, 1H), 3.67-3.70 (d, J=10.94 Hz, 1H), 3.81-3.85 (dd, J=5.53 and 4.57 Hz, 1H), 4.02 (s, 3H), 4.39-4.45 (t, J=13.46 Hz, 1H), 4.78-4.84 (t, J=9.80 Hz, 1H), 5.08-506 (t, J=7.04 Hz, 1H), 5.52-5.54 (m, 1H), 5.66-5.68 (m, 1H), 7.52 (s, 1H), 7.55-7.57 (d, J=9.53 Hz, 1H), 7.59 (s, 1H), 8.18 (d, J=9.53 Hz, 1H), 11.66 (s, 1H); MS (ESI, EI$^+$): m/z=785 (MH$^+$).

Example 6

Preparation of Macrocyclic Compounds 62

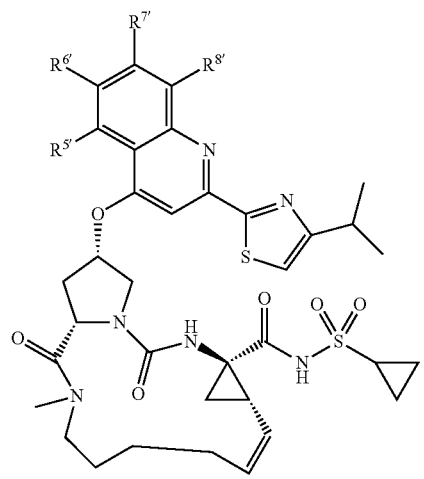

62a: R$^{5'}$ = H, R$^{6'}$ = H, R$^{7'}$ = OCH$_3$, R$^{8'}$ = H
62b: R$^{5'}$ = H, R$^{6'}$ = H, R$^{7'}$ = OCH$_3$, R$^{8'}$ = CH$_3$
62c: R$^{5'}$ = H, R$^{6'}$ = H, R$^{7'}$ = OCH$_3$, R$^{8'}$ = F
62d: R$^{5'}$ = H, R$^{6'}$ = H, R$^{7'}$ = OCH$_3$, R$^{8'}$ = Cl
62e: R$^{5'}$ = OCH$_3$, R$^{6'}$ = H, R$^{7'}$ = OCH$_3$, R$^{8'}$ = H
62f: R$^{5'}$ = H, R$^{6'}$ = OCH$_3$, R$^{7'}$ = H, R$^{8'}$ = CH$_3$
62g: R$^{5'}$ = H, R$^{6'}$ = OCH$_3$, R$^{7'}$ = Cl, R$^{8'}$ = H
62h: R$^{5'}$ = H, R$^{6'}$ = H, R$^{7'}$ = OCH$_3$, R$^{8'}$ = Br

The syntheses of macrocyclic compounds 62 are illustrated with compounds 62b, 62d, and 62f. The same procedures are also applicable to other compounds 62.

Step A: Preparation of (Z)-(4R,6S,15S,17S)-[17-[7-methoxy-8-methyl-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(cyclopropyl)sulfonamide 62b. Compound 62b was synthesized from compound 55b and cyclopropylsulfonamide as a beige solid in 52% yield, following the procedure as described for compound 56c.

MS (ESI, EI$^+$): m/z=751 (MH$^+$).

Step B: Preparation of (Z)-(4R,6S,15S,17S)-[17-[8-chloro-7-methoxy-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(cyclopropyl)sulfonamide 62d. Compound 62d was synthesized from compound 55d and cyclopropylsulfonamide as a white solid in 15% yield, following the procedure as described for compound 56c.

MS (ESI, EI$^+$): m/z=771 (MH$^+$).

Step C: Preparation of (Z)-(4R,6S,15S,17S)-[17-[6-methoxy-8-methyl-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(cyclopropyl)sulfonamide 62f. Compound 62f was synthesized from compound 55f and cyclopropylsulfonamide as a white solid in 37% yield, following the procedure as described for compound 56c.

MS (ESI, EI$^+$): m/z=751 (MH$^+$).

Example 7

Preparation of Macrocyclic Compound 63

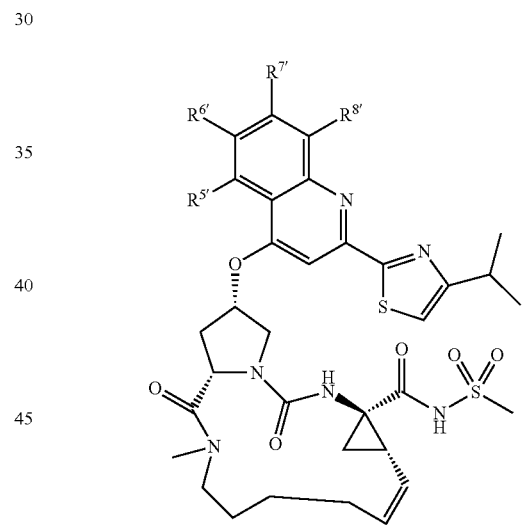

63a: R$^{5'}$ = H, R$^{6'}$ = H, R$^{7'}$ = OCH$_3$, R$^{8'}$ = H
63b: R$^{5'}$ = H, R$^{6'}$ = H, R$^{7'}$ = OCH$_3$, R$^{8'}$ = CH$_3$
63c: R$^{5'}$ = H, R$^{6'}$ = H, R$^{7'}$ = OCH$_3$, R$^{8'}$ = F
63d: R$^{5'}$ = H, R$^{6'}$ = H, R$^{7'}$ = OCH$_3$, R$^{8'}$ = Cl
63e: R$^{5'}$ = OCH$_3$, R$^{6'}$ = H, R$^{7'}$ = OCH$_3$, R$^{8'}$ = H
63f: R$^{5'}$ = H, R$^{6'}$ = OCH$_3$, R$^{7'}$ = H, R$^{8'}$ = CH$_3$
63g: R$^{5'}$ = H, R$^{6'}$ = OCH$_3$, R$^{7'}$ = Cl, R$^{8'}$ = H
63h: R$^{5'}$ = H, R$^{6'}$ = H, R$^{7'}$ = OCH$_3$, R$^{8'}$ = Br

The syntheses of macrocyclic compounds 63 are illustrated with compound 63b. The same procedures are also applicable to other compounds 63.

Preparation of (Z)-(4R,6S,15S,17S)-17-[7-methoxy-8-methyl-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl-methylsulfonamide 63b. Compound 63b was synthesized from compound 55b and methanesulfonamide as a white solid in 24% yield, following the procedure as described for compound 56c.

MS (ESI, EI+): m/z=725 (MH+).

Example 8

Preparation of Substituted Quinolines 65

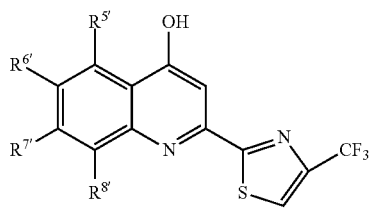

65a: R$^{5'}$ = H, R$^{6'}$ = H, R$^{7'}$ = OCH$_3$, R$^{8'}$ = H
65b: R$^{5'}$ = H, R$^{6'}$ = H, R$^{7'}$ = OCH$_3$, R$^{8'}$ = CH$_3$
65c: R$^{5'}$ = H, R$^{6'}$ = H, R$^{7'}$ = OCH$_3$, R$^{8'}$ = F
65d: R$^{5'}$ = H, R$^{6'}$ = H, R$^{7'}$ = OCH$_3$, R$^{8'}$ = Cl
65e: R$^{5'}$ = OCH$_3$, R$^{6'}$ = H, R$^{7'}$ = OCH$_3$, R$^{8'}$ = H
65f: R$^{5'}$ = H, R$^{6'}$ = OCH$_3$, R$^{7'}$ = H, R$^{8'}$ = CH$_3$
65g: R$^{5'}$ = H, R$^{6'}$ = OCH$_3$, R$^{7'}$ = Cl, R$^{8'}$ = H
65h: R$^{5'}$ = H, R$^{6'}$ = H, R$^{7'}$ = OCH$_3$, R$^{8'}$ = Br

The synthesis of substituted quinolines 65 are illustrated below with compounds 65b and 65d. The same procedures are also applicable to other compounds 65. The substituents in intermediates 64 are the same as compounds 65.

Preparation of N-(6-acetyl-3-methoxy-2-methylphenyl)-4-trifluoromethylthiazole-2-carboxamide 64b. Compound 64b was synthesized from 4-(trifluoromethyl)-1,3-thiazole-2-carboxylic acid and 1-(2-amino-4-methoxy-3-methylphenyl)-ethanone as a beige solid in 74% yield, following the procedure as described for compound 42a.

$^1$H NMR (CDCl$_3$, 400 MHz) δ 2.15 (s, 3H), 2.58 (s, 3H), 3.94 (s, 3H), 6.82 (d, J=8.55 Hz, 1H), 7.78 (d, J=8.55 Hz, 1H), 8.01 (s, 1H), 11.25 (s, 1H).

Preparation of N-(6-acetyl-2-chloro-3-methoxyphenyl)-4-trifluoromethylthiazole-2-carboxamide 64d. Compound 64d was synthesized from 4-(trifluoromethyl)-1,3-thiazole-2-carboxylic acid and 1-(2-amino-3-chloro-4-methoxyphenyl)-ethanone as a beige solid in 65% yield, following the procedure as described for compound 42a.

Preparation of 7-methoxy-8-methyl-2-(4-trifluoromethyl-thiazol-2-yl)-quinolin-4-ol 65b. Compound 65b was synthesized from compound 64b as a yellow powder in 73% yield, following the procedure as described for compound 43a.

MS (ESI, EI+) m/z=341 (MH+).

Preparation of 8-chloro-7-methoxy-2-(4-trifluoromethyl-thiazol-2-yl)-quinolin-4-ol 65d. Compound 65d was synthesized from compound 64d as a yellow powder in 70% yield, following the procedure as described for compound 43a.

MS (ESI, EI+) m/z=361 (MH+).

Example 9

Preparation of Macrocyclic Compound 68

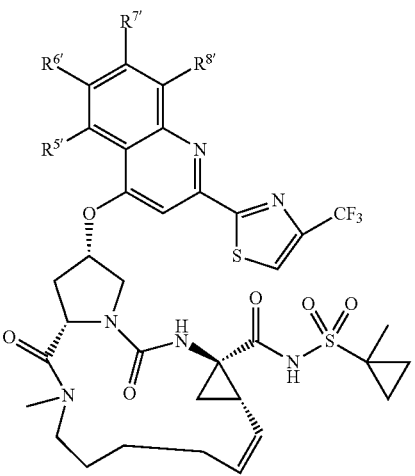

68a: R$^{5'}$ = H, R$^{6'}$ = H, R$^{7'}$ = OCH$_3$, R$^{8'}$ = H
68b: R$^{5'}$ = H, R$^{6'}$ = H, R$^{7'}$ = OCH$_3$, R$^{8'}$ = CH$_3$
68c: R$^{5'}$ = H, R$^{6'}$ = H, R$^{7'}$ = OCH$_3$, R$^{8'}$ = F
68d: R$^{5'}$ = H, R$^{6'}$ = H, R$^{7'}$ = OCH$_3$, R$^{8'}$ = Cl
68e: R$^{5'}$ = OCH$_3$, R$^{6'}$ = H, R$^{7'}$ = OCH$_3$, R$^{8'}$ = H
68f: R$^{5'}$ = H, R$^{6'}$ = OCH$_3$, R$^{7'}$ = H, R$^{8'}$ = CH$_3$
68g: R$^{5'}$ = H, R$^{6'}$ = OCH$_3$, R$^{7'}$ = Cl, R$^{8'}$ = H
68h: R$^{5'}$ = H, R$^{6'}$ = H, R$^{7'}$ = OCH$_3$, R$^{8'}$ = Br

The synthesis of macrocyclic compounds 68 are illustrated below with compounds 68b and 68d, as shown in Scheme 12. The same procedures are also applicable to other macrocyclic compounds 68. The substituents in intermediates 66 and 67 are the same as compounds 68. The same procedures are also applicable to other compounds 68.

Step A: Preparation of (Z)-(4R,6S,15S,17S)-[17-[7-methoxy-8-methyl-2-(4-trifluoromethythiazol-2-yl)quinolin-4-yloxy]-13-N-methyl-2,14-dioxo-1,3,13-triazatricyclo [13.3.0.0]octadec-7-en-4-yl]carboxylic acid ethyl ester 66b. Compound 66b was synthesized from compounds 53 and 65b as a white solid in 60% yield, following the procedure as described for compound 54c.

MS (ESI, EI+) m/z=702 (MH+).

Scheme 12

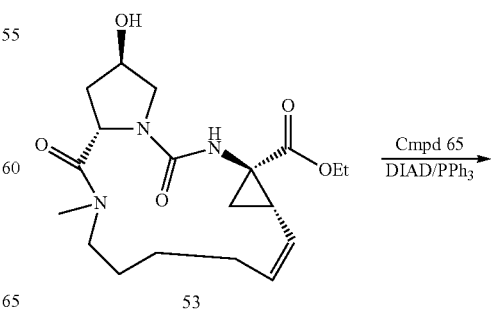

53

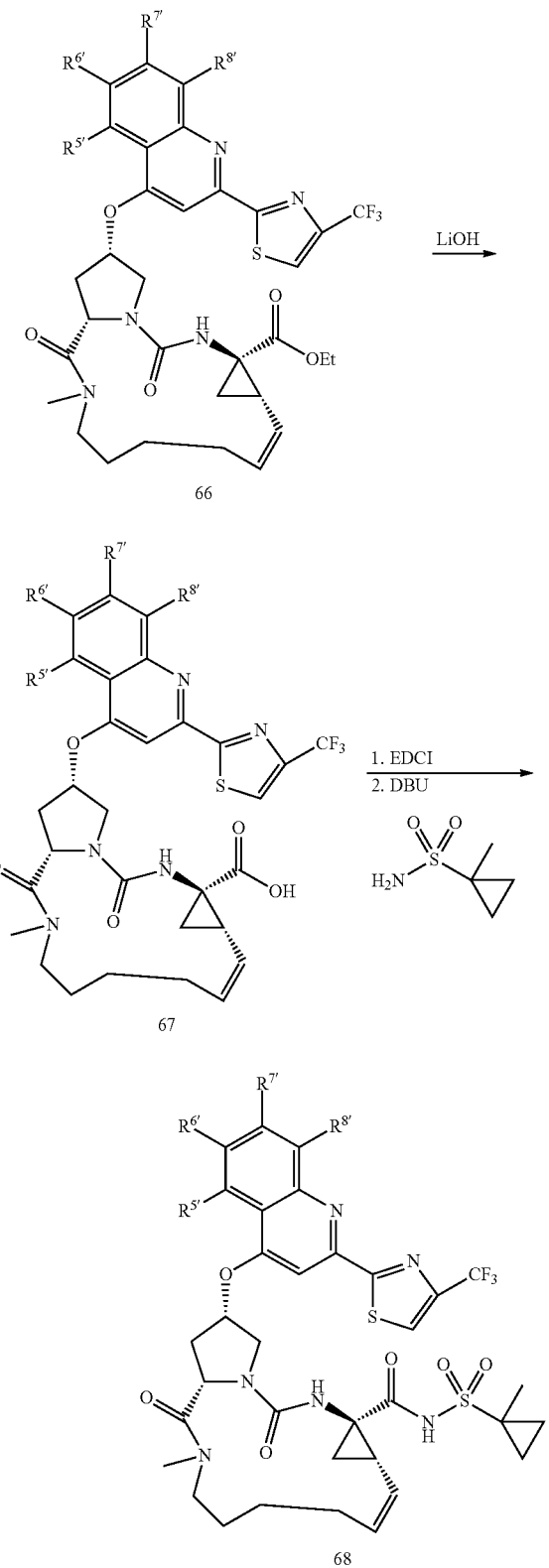

Compound 66d was synthesized from compounds 53 and 65d as a pink solid in 90% yield, following the procedure as described for compound 54c.

MS (ESI, EI⁺) m/z=724 (MH⁺).

Step C: Preparation of (Z)-(4R,6S,15S,17S)-[17-[7-methoxy-8-methyl-2-(4-trifluoromethythiazol-2-yl)quinolin-4-yloxy]-13-N-methyl-2,14-dioxo-1,3,13-triazatricyclo[13.3.0.0]octadec-7-en-4-yl]carboxylic acid 67b. Compound 67b was synthesized from compound 66b as a white solid in 38% yield, following the procedure as described for compound 55c.

MS (ESI, EI⁺) m/z=674 (MH⁺).

Step D: Preparation of (Z)-(4R,6S,15S,17S)-[17-[8-chloro-7-methoxy-2-(4-trifluoromethythiazol-2-yl)quinolin-4-yloxy]-13-N-methyl-2,14-dioxo-1,3,13-triazatricyclo[13.3.0.0]octadec-7-en-4-yl]carboxylic acid 67d. Compound 67d was synthesized from compound 66d as a white solid in 16% yield, following the procedure as described for compound 55c.

MS (ESI, EI⁺) m/z=694 (MH⁺).

Step E: Preparation of (Z)-(4R,6S,15S,17S)-[17-[7-methoxy-8-methyl-2-(4-trifluoromethythiazol-2-yl)quinolin-4-yloxy]-13-N-methyl-2,14-dioxo-1,3,13-triazatricyclo[13.3.0.0]octadec-7-en-4-yl]carbonyl(1-methylcyclopropyl)sulfonamide 68b. Compound 68b was synthesized from compound 67b and 1-methylcyclopropylsulfonamide as a white solid in 40% yield, following the procedure as described for compound 56c. $^1$H NMR (CDCl$_3$, 400 MHz): δ 0.737 (m, 2H), 1.10-1.21 (m, 2H), 1.26-1.33 (m, 2H), 1.44 (s, 3H), 1.41-1.53 (m, 1H), 1.56-1.65 (m, 1H), 1.71-1.76 (m, 1H), 1.84 (dd, J=6.2 and 8.1 Hz, 2H), 2.11 (dt, J=5.7 and 13.5 Hz, 1H), 2.36 (dd, J=9.3 and 18.9 Hz, 1H), 2.53 (dd, J=3.0 and 13.5 Hz, 1H), 2.61 (s, 3H), 2.81 (ddd, J=4.7, 12.4 and 17.1 Hz, 1H), 2.90-2.96 (m, 1H), 2.98 (s, 3H), 3.73 (dd, J=7.0 and 8.3 Hz, 1H), 3.92 (s, 3H), 3.96 (t, J=7.7, 1H), 4.54 (dd, J=2.6 and 13.7 Hz, 1H), 4.84 (t, J=10.7 Hz, 1H), 4.89 (dd, J=5.3 and 8.9 Hz, 1H), 5.10 (s, 1H), 5.41 (q, J=7.0 Hz, 1H), 5.56 (td, J=5.8 and 10.8 Hz, 1H), 7.18 (d, J=9.2 Hz, 1H), 7.42 (s, 1H), 7.80 (s, 1H), 7.94 (d, J=9.2 Hz, 1H), 11.12 (s, 1H); MS (ESI, EI⁺) m/z=791 (MH⁺).

MS (ESI, EI⁺) m/z=791 (MH⁺).

Step F: Preparation of (Z)-(4R,6S,15S,17S)-[17-[8-chloro-7-methoxy-2-(4-trifluoromethythiazol-2-yl)quinolin-4-yloxy]-13-N-methyl-2,14-dioxo-1,3,13-triazatricyclo[13.3.0.0]octadec-7-en-4-yl]carbonyl(1-methylcyclopropyl)sulfonamide 68d. A solution of compound 67d (502 mg, 1 eq.) and EDCI (200 mg, 1.4 eq.) in dry DCM (10 mL) was stirred at room temperature for 16 hrs. DBU (445 mg, 4 eq.) and 1-methylcyclopropylsulfonamide (402 mg, 4 eq.) were then added and the mixture was resumed for 16 hours. The crude material was purified by chromatography on silica gel to yield compound 68d as a white solid in 37% yield.

$^1$H NMR (CDCl$_3$, 400 MHz): δ 0.73-0.81 (m, 2H), 1.10-1.21 (m, 2H), 1.26-1.34 (m, 2H), 1.45 (s, 3H), 1.42-1.46 (m, 1H), 1.57-1.65 (m, 1H), 1.72-1.76 (m, 1H), 1.86 (dd, J=8.45 and 6.07 Hz, 2H), 2.13 (dt, J=13.65 and 5.38 Hz, 1H), 2.36 (dd, J=19.27 and 9.31 Hz, 1H), 2.51-2.55 (m, 1H), 2.76-2.88 (m, 1H), 2.91-2.98 (m, 1H), 2.99 (s, 3H), 3.76 (dd, J=8.41 and 6.72 Hz, 1H), 3.97 (t, J=7.80, 1H), 4.02 (s, 3H), 4.54 (dd, J=13.75 and 2.63 Hz, 1H), 4.85 (t, J=10.7 Hz, 1H), 4.91 (dd, J=8.91 and 5 Hz, 1H), 5.04 (s, 1H), 5.42-5.49 (m, 1H), 5.57 (td, J=10.72 and 5.79 Hz, 1H), 7.24 (d, J=9.2 Hz, 1H), 7.50 (s, 1H), 7.85 (s, 1H), 8.02 (d, J=9.25 Hz, 1H), 11.05 (s, 1H); MS (ESI, EI⁺) m/z=811 (MH⁺).

MS (ESI, EI⁺) m/z=811 (MH⁺).

Step B: Preparation of (Z)-(4R,6S,15S,17S)-[17-[8-chloro-7-methoxy-2-(4-trifluoromethythiazol-2-yl)quinolin-4-yloxy]-13-N-methyl-2,14-dioxo-1,3,13-triazatricyclo[13.3.0.0]octadec-7-en-4-yl]carboxylic acid ethyl ester 66d.

Example 10

Preparation of Macrocyclic Compound 69

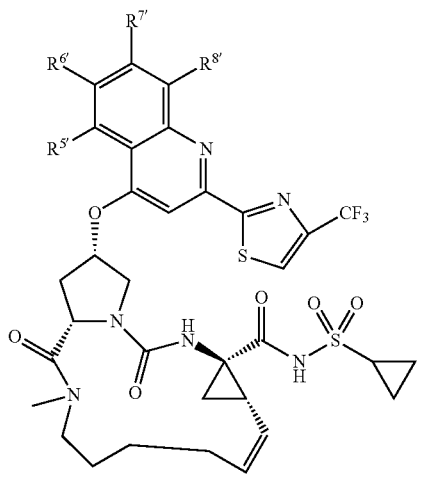

69a: R⁵' = H, R⁶' = H, R⁷' = OCH₃, R⁸' = H
69b: R⁵' = H, R⁶' = H, R⁷' = OCH₃, R⁸' = CH₃
69c: R⁵' = H, R⁶' = H, R⁷' = OCH₃, R⁸' = F
69d: R⁵' = H, R⁶' = H, R⁷' = OCH₃, R⁸' = Cl
69e: R⁵' = OCH₃, R⁶' = H, R⁷' = OCH₃, R⁸' = H
69f: R⁵' = H, R⁶' = OCH₃, R⁷' = H, R⁸' = CH₃
69g: R⁵' = H, R⁶' = OCH₃, R⁷' = Cl, R⁸' = H
69h: R⁵' = H, R⁶' = H, R⁷' = OCH₃, R⁸' = Br

The synthesis of macrocyclic compounds 69 are illustrated below with compound 69b. The same procedure is also applicable to other macrocyclic compounds 69.

Preparation of (Z)-(4R,6S,15S,17S)-[17-[7-methoxy-8-methyl-2-(4-trifluoromethythiazol-2-yl)quinolin-4-yloxy]-13-N-methyl-2,14-dioxo-1,3,13-triazatricyclo[13.3.0.0]octadec-7-en-4-yl]carbonyl(cyclopropyl)sulfonamide 69b. Compound 69b was synthesized from compound 67b and cyclopropylsulfonamide as a white solid in 49% yield, following the procedure as described for compound 68d. $^1$H NMR (CDCl$_3$, 400 MHz): δ 0.78-0.90 (m, 2H), 0.99-1.12 (m, 3H), 1.17-1.24 (m, 3H), 1.26-1.62 (m, 4H), 1.87 (dd, J=6.1 and 8.5 Hz, 2H), 2.12 (dt, J=5.8 and 13.5 Hz, 1H), 2.36 (dd, J=9.3 and 19.2 Hz, 1H), 2.49-2.55 (m, 1H), 2.77-2.95 (m, 3H), 2.98 (s, 3H), 3.73 (m, 1H), 3.92 (s, 3H), 3.96-4.01 (m, 1H), 4.54 (dd, J=2.8 and 13.9 Hz, 2H), 4.81-4.89 (m, 2H), 5.02 (s, 1H), 5.42 (qt, J=7.0 Hz, 1H), 5.57 (td, J=5.7 and 10.7 Hz, 1H), 7.19 (d, J=9.3 Hz, 1H), 7.42 (s, 1H), 7.80 (s, 1H), 7.94 (d, J=9.3 Hz, 1H), 11.13 (s, 1H); MS (ESI, EI⁺) m/z=777 (MH⁺).

MS (ESI, EI⁺) m/z=777 (MH⁺).

Preparation of (Z)-(4R,6S,15S,17S)-[17-[8-chloro-7-methoxy-2-(4-trifluoromethythiazol-2-yl)quinolin-4-yloxy]-13-N-methyl-2,14-dioxo-1,3,13-triazatricyclo[13.3.0.0]octadec-7-en-4-yl]carbonyl(cyclopropyl)sulfonamide 69d. Compound 69d was synthesized from compound 67d and cyclopropylsulfonamide, following the procedure as described for compound 68d. $^1$H NMR (CDCl$_3$, 400 MHz): δ 0.90-0.98 (m, 1H), 1.06-1.19 (m, 2H), 1.23-1.31 (m, 3H), 1.35-1.54 (m, 4H), 1.87-1.94 (m, 1H), 1.95 (dd, J=8.48 and 6.05 Hz, 2H), 2.21 (dt, J=13.54 and 5.50 Hz, 1H), 2.58-2.63 (m, 1H), 2.89-2.96 (m, 1H), 2.98-3.04 (m, 1H), 3.05 (s, 3H), 3.83 (dd, J=8.31 and 6.76 Hz, 1H), 4-4.05 (m, 1H), 4.09 (s, 3H), 4.57-4.65 (m, 1H), 4.89-4.94 (m, 1H), 4.95-4.98 (m, 1H), 5.05 (s, 1H), 5.53 (qt, J=6.86 Hz, 1H), 5.65 (td, J=10.75 and 5.65 Hz, 1H), 7.31 (d, J=9.27 Hz, 1H), 7.57 (s, 1H), 7.92 (s, 1H), 8.09 (d, J=9.27 Hz, 1H), 11.14 (s, 1H).

Example 11

Preparation of Macrocyclic Compounds 76

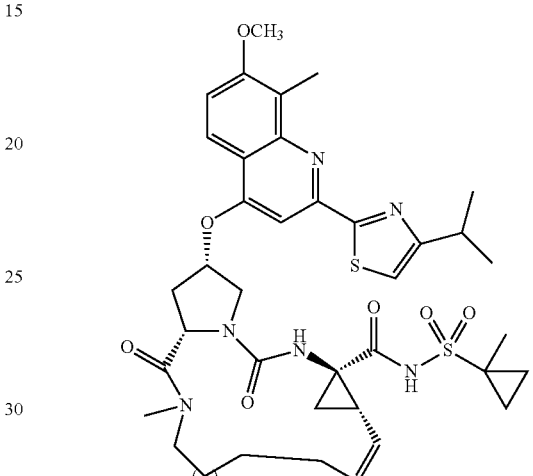

76a: n = 2;
76b: n = 3.

The syntheses of macrocyclic compounds 76 are shown in Scheme 13, where R⁵', R⁶', R⁷', and R⁸' in compounds 74 and 75 are the same as defined in compounds 76.

Scheme 13

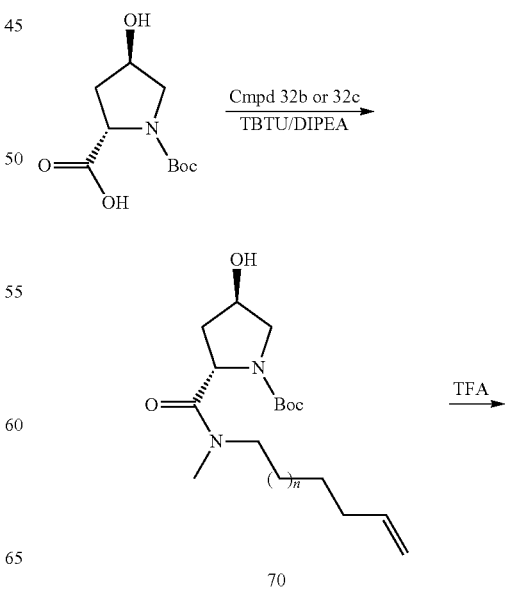

70

-continued

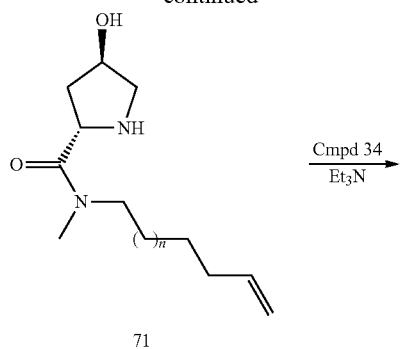
71

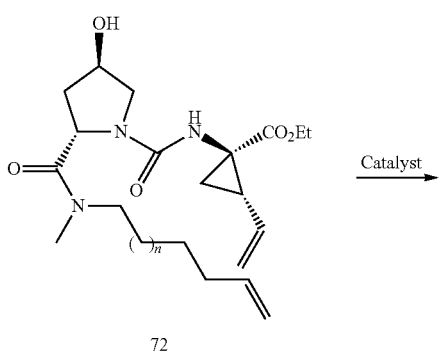
72

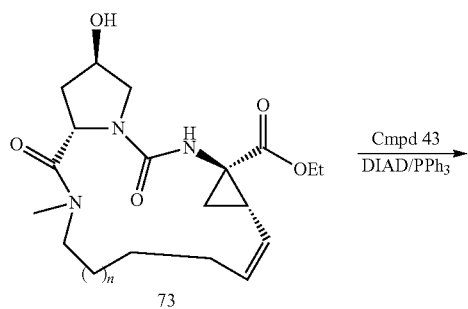
73

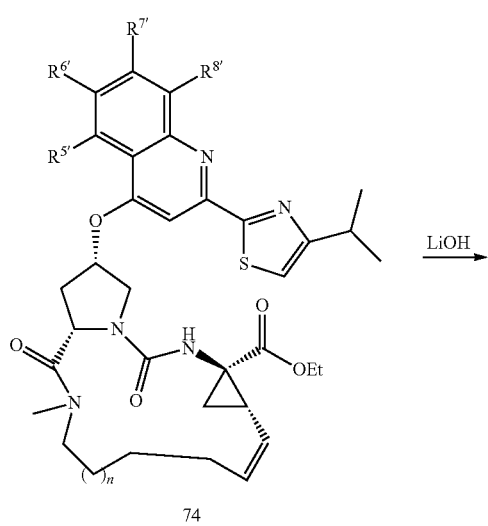
74

-continued

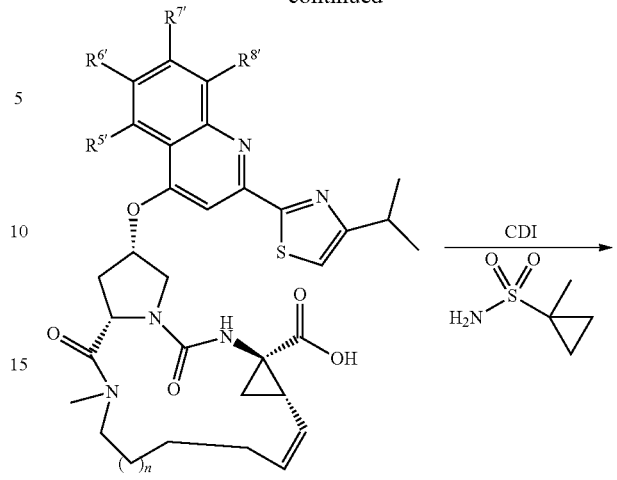
75

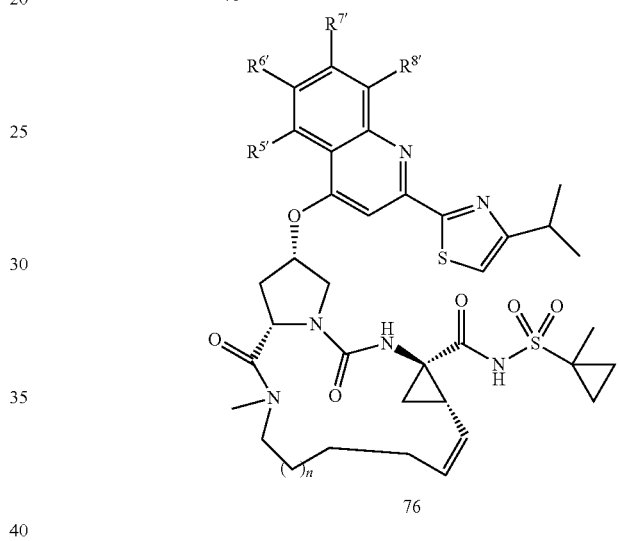
76

Step A: Preparation of (2S,4R)-tert-butyl 2-(N-(hept-6-enyl)-N-methylcarbamoyl)-4-hydroxypyrrolidine-1-carboxylate 70a. Compound 70a was synthesized from compound 32b and cis-N-Boc-4-hydroxy-L-proline as orange oil in quantitative yield, following the procedure as described for compound 48.

$^1$H NMR (DMSO-d$_6$, 400 MHz) δ 1.29-1.3 (m, 9H), 1.33-1.55 (m, 4H), 1.70-1.80 (m, 1H), 1.97-2.12 (m, 4H), 2.77-2.97 (m, 4H), 3.15-3.40 (m, 4H), 4.22 (br s, 1H), 4.50-4.62 (m, 1H), 4.90-5.04 (m, 3H), 5.71-5.83 (m, 1H).

Step B: Preparation of (2S,4R)-tert-butyl 2-(N-(oct-6-enyl)-N-methylcarbamoyl)-4-hydroxypyrrolidine-1-carboxylate 70b. Compound 70b was synthesized from compound 32c and cis-N-Boc-4-hydroxy-L-proline as yellow oil in quantitative yield, following the procedure as described for compound 48.

$^1$H NMR (DMSO-d$_6$, 400 MHz) δ 1.29-1.3 (m, 9H), 1.33-1.55 (m, 4H), 1.70-1.80 (m, 1H), 1.97-2.12 (m, 4H), 2.77-2.97 (m, 4H), 3.01-3.10 (m, 2H), 3.15-3.40 (m, 4H), 4.22 (br s, 1H), 4.50-4.62 (m, 1H), 4.90-5.04 (m, 3H), 5.71-5.83 (m, 1H).

Step C: Preparation of (2S,4R)-2-N-(hept-6-enyl)-4-hydroxy-N-methylpyrrolidine-2-carboxamide 71a. Compound 71a was synthesized from compound 70a as yellow oil in 35% yield, following the procedure as described for compound 49.

MS (ESI, EI$^+$) m/z=241 (MH$^+$).

Step D: Preparation of (2S,4R)-2-N-(oct-6-enyl)-4-hydroxy-N-methylpyrrolidine-2-carboxamide 71b. Compound 71b was synthesized from compound 70b as yellow oil in 51% yield, following the procedure as described for compound 49.

MS (ESI, EI+) m/z=255 (MH+).

Step E: Preparation of (1R)-1-{[2(S)-(hept-5-enyl-methylcarbamoyl)-4(R)-hydroxy-pyrrolidine-N-carbonyl]amino}-2(R)-vinyl-cyclopropanecarboxylic acid ethyl ester 72a. Compound 72a was synthesized from compounds 34 and 71a as a beige solid in 38% yield, following the procedure as described for compound 50.

MS (ESI, EI+) m/z=422 (MH+).

Step F: Preparation of (1R)-1-{[2(S)-(oct-5-enyl-methylcarbamoyl)-4(R)-hydroxy-pyrrolidine-N-carbonyl]amino}-2(R)-vinyl-cyclopropanecarboxylic acid ethyl ester 72b. Compound 72b was synthesized from compounds 34 and 71b as a beige solid in 48% yield, following the procedure as described for compound 50.

MS (ESI, EI+) m/z=436 (MH+).

Step G: Preparation of (Z)-(4R,6S,16S,18R)-2,15-dioxo-18-hydroxy-14-N-methyl-1,3,14-triazatricyclo[14.3.0.0] nonadec-7-ene-4-carboxylic acid ethyl ester 73a. Compound 73a was synthesized from compound 72a as a white solid in 42% yield, following the procedure as described for compound 52.

MS (ESI, EI+) m/z=394 (MH+).

Step H: Preparation of (Z)-(4R,6S,17S,19R)-2,16-dioxo-19-hydroxy-15-N-methyl-1,3,15-triazatricyclo[15.3.0.0] eicos-7-ene-4-carboxylic acid ethyl ester 73b. Compound 73b was synthesized from compound 72b as a white solid in 71% yield, following the procedure as described for compound 52.

MS (ESI, EI+) m/z=408 (MH+).

Step I: Preparation of (Z)-(4R,6S,16S,18R)-2,15-dioxo-18-[7-methoxy-8-methyl-2-(4-isopropylthiazol-2-yl)quinolin-4-yloxy]-14-N-methyl-1,3,14-triazatricyclo[14.3.0.0] nonadec-7-ene-4-carboxylic acid ethyl ester 74a. Compound 74a was synthesized from compounds 43b and 73a as a beige solid in 89% yield, following the procedure as described for compound 54c.

MS (ESI, EI+) m/z=690 (MH+).

Step J: Preparation of (Z)-(4R,6S,17S,19R)-2,16-dioxo-19-[7-methoxy-8-methyl-2-(4-isopropylthiazol-2-yl)quinolin-4-yloxy]-15-N-methyl-1,3,15-triazatricyclo[15.3.0.0] eicos-7-ene-4-carboxylic acid ethyl ester 74b. Compound 74b was synthesized from compounds 43b and 73b as a white solid in 93% yield, following the procedure as described for compound 54c.

MS (ESI, EI+) m/z=704 (MH+).

Step K: Preparation of (Z)-(4R,6S,16S,18R)-2,15-dioxo-18-[7-methoxy-8-methyl-2-(4-isopropylthiazol-2-yl)quinolin-4-yloxy]-14-N-methyl-1,3,14-triazatricyclo[14.3.0.0] nonadec-7-ene-4-carboxylic acid 75a. Compound 75a was synthesized from compound 74a as a white solid in 32% yield, following the procedure as described for compound 55c.

MS (ESI, EI+) m/z=662 (MH+).

Step L: Preparation of (Z)-(4R,6S,17S,19R)-2,16-dioxo-19-[7-methoxy-8-methyl-2-(4-isopropylthiazol-2-yl)quinolin-4-yloxy]-15-N-methyl-1,3,15-triazatricyclo[15.3.0.0] eicos-7-ene-4-carboxylic acid 75b. Compound 75b was synthesized from compound 74b as a white solid in 36% yield, following the procedure as described for compound 55c.

MS (ESI, EI+) m/z=676 (MH+).

Step M: Preparation of (Z)-(4R,6S,16S,18R)-[2,15-dioxo-18-[7-methoxy-8-methyl-2-(4-isopropylthiazol-2-yl)quinolin-4-yloxy]-14-N-methyl-1,3,14-triazatricyclo[14.3.0.0] nonadec-7-en-4-yl]carbonyl(1-methyl-cyclopropyl) sulfonamide 76a. Compound 76a was synthesized from compound 75a and 1-methyl-cyclopropylsulfonamide as a white solid in 12% yield, following the procedure as described for compound 56c.

MS (ESI, EI+) m/z=779 (MH+).

Step N: Preparation of (Z)-(4R,6S,17S,19R)-[2,16-dioxo-19-17-methoxy-8-methyl-2-(4-isopropylthiazol-2-yl)quinolin-4-yloxy-15-N-methyl-1,3,15-triazatricyclo[15.3.0.0] eicos-7-en-4-yl]carbonyl(1-methyl-cyclopropyl) sulfonamide 76b. Compound 76b was synthesized from compound 75b and 1-methyl-cyclopropylsulfonamide as a white solid in 27% yield, following the procedure as described for compound 56c.

MS (ESI, EI+) m/z=793 (MH+).

Example 12

Preparation of Cyclopropanesulfonamide 82

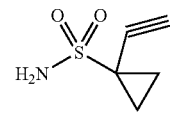

82

The synthesis of cyclopropanesulfonamide 82 is illustrated in Scheme 14.

Step A: Preparation of N-Boc-cyclopropanesulfonamide 77. To a stirred solution of cyclopropanesulfonamide (10.72 g, 88.6 mmol), TEA (13.9 mL, 100.4 mmol), and (4-dimethylamino)pyridine (1.11 g, 9.07 mmol) in DCM (160 mL) was added dropwise a solution of Boc₂O (21.88 g, 100.4 mmol) in DCM (100 mL) at 0° C. over 30 min. The mixture was allowed to warm up to room temperature and stirred for 3 hrs. The mixture was then washed with 1N HCl, water, and brine. Organics were dried over Na₂SO₄, filtered, concentrated under reduced pressure, and triturated with hexane to yield compound 77 as a white powder in 87% yield.

¹H NMR (CDCl₃, 400 MHz) δ 0.92 (td, J=1.72 Hz and J=6.40 Hz, 2H), 1.49 (s, 9H), 1.59 (td, J=1.72 and 6.40 Hz, 2H), 1.95 (m, 2H).

Scheme 14

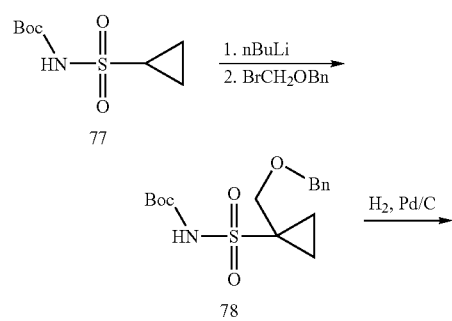

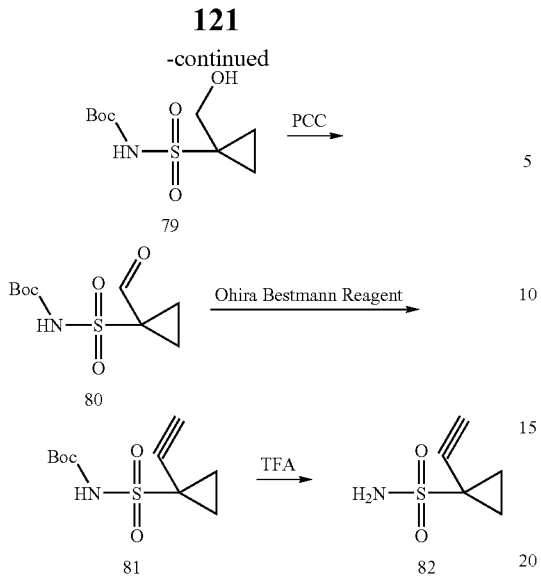

Step B: Preparation of N-Boc-1-benzyloxy-cyclopropanesulfonamide 78. To a stirred solution of compound 77 (500 mg, 2.26 mmol) in anhydrous THF (5 mL) at −80° C. was added nBuLi (2.26 mL, 5.65 mmol) dropwise. The mixture was stirred at −80° C. for 10 min and bromomethylbenzene (271 µL, 3.39 mmol) was added dropwise at −80° C. The mixture was then allowed to warm up to −30° C. Water was then slowly added followed by EtOAc. Organics were dried over $Na_2SO_4$, filtered, concentrated under reduced pressure, and purified by chromatography on silica gel (EtOAc/DCM) to yield compound 78 as a white powder in 30% yield.

$^1$H NMR ($CDCl_3$, 400 MHz) δ 1.04 (td, J=1.72 Hz and J=6.40 Hz, 2H), 1.49 (s, 9H), 1.73 (td, J=1.72 and 6.40 Hz, 2H), 3.78 (s, 2H), 4.56 (s, 2H), 7.07 (brs, 1H), 7.30-7.38 (m, 5H).

Step C: Preparation of N-Boc-1-hydroxymethyl-cyclopropanesulfonamide 79. Compound 78 (2 g, 5.87 mmol) was reacted in a H-Cube® (Thales Technology) with a Pd/C 10% cartridge at 20 bars and 50° C. The crude material was purified by chromatography on silica gel (EtOAc/DCM) to yield compound 79 in 70% yield.

$^1$H NMR ($CDCl_3$, 400 MHz) δ 1.09 (t, J=6.32 Hz, 2H), 1.49 (s, 9H), 1.61 (t, J=6.32 Hz, 2H), 3.72 (s, 1H), 3.89 (s, 2H), 8.23 (brs, 1H).

Step D: Preparation of N-Boc-1-formyl-cyclopropanesulfonamide 80. To a stirred solution of compound 79 (100 mg, 0.39 mmol) in DCM (2 mL) was added pyridinium chlorochromate (130 mg, 0.60 mmol). The mixture was stirred at room temperature for 16 hrs and was filtered through a silica gel column with DCM, and the organic solution was concentrated under reduced pressure to yield compound 80 in 66% yield.

$^1$H NMR ($CDCl_3$, 400 MHz) δ 1.49 (s, 9H), 1.76 (m, 2H), 2.01 (m, 2H), 9.91 (s, 1H).

Step E: Preparation of N-Boc-1-ethynyl-cyclopropanesulfonamide 81. To a stirred solution of compound 80 (230 mg, 0.92 mmol) in MeOH (5 mL) at 0° C. was added $K_2CO_3$ (255 mg, 1.84 mmol), and Ohira-Bestmann reagent (215 g, 1.10 mmol) (*Tetr. Lett.* 2008, 49, 4454). The mixture was stirred at room temperature for 16 hrs and was concentrated under reduced pressure. Water, EtOAc, and citric acid were added to bring pH to 4-5. Organics were dried over $Na_2SO_4$, filtered, and concentrated under reduced pressure to yield compound 81 in 85% yield.

$^1$H NMR ($CDCl_3$, 400 MHz) δ 1.50 (m, 2H), 1.53 (s, 9H), 1.92 (m, 2H), 2.37 (s, 1H), 7.15 (brs, 1H).

Step F: Preparation of 1-ethynyl-cyclopropanesulfonamide 82. A mixture of compound 81 (200 mg, 0.81 mmol) and TFA (0.3 mL) in DCM (5 mL) was stirred at room temperature for 16 hrs. The reaction mixture was concentrated under reduced pressure and the crude material was purified by chromatography on silica gel (MeOH/DCM) to yield compound 82 in 70% yield.

$^1$H NMR ($CDCl_3$, 400 MHz) δ 1.43 (td, J=2.90 and 4.80 Hz, 2H), 1.70 (td, J=2.90 and 4.80 Hz, 2H), 2.38 (s, 1H), 4.79 (s, 2H).

Example 13

Preparation of Macrocyclic Compounds 83

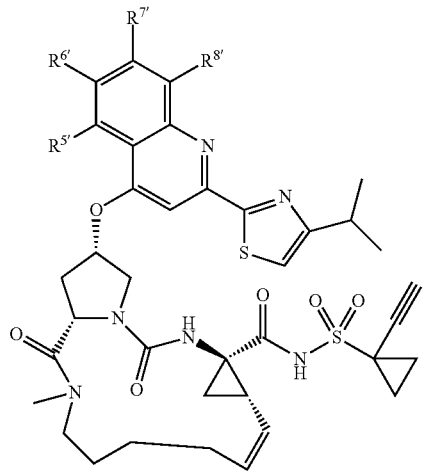

83a: $R^{5'}$ = H, $R^{6'}$ = H, $R^{7'}$ = $OCH_3$, $R^{8'}$ = H
83b: $R^{5'}$ = H, $R^{6'}$ = H, $R^{7'}$ = $OCH_3$, $R^{8'}$ = $CH_3$
83c: $R^{5'}$ = H, $R^{6'}$ = H, $R^{7'}$ = $OCH_3$, $R^{8'}$ = F
83d: $R^{5'}$ = H, $R^{6'}$ = H, $R^{7'}$ = $OCH_3$, $R^{8'}$ = Cl
83e: $R^{5'}$ = $OCH_3$, $R^{6'}$ = H, $R^{7'}$ = $OCH_3$, $R^{8'}$ = H
83f: $R^{5'}$ = H, $R^{6'}$ = $OCH_3$, $R^{7'}$ = H, $R^{8'}$ = $CH_3$
83g: $R^{5'}$ = H, $R^{6'}$ = $OCH_3$, $R^{7'}$ = Cl, $R^{8'}$ = H
83h: $R^{5'}$ = H, $R^{6'}$ = H, $R^{7'}$ = $OCH_3$, $R^{8'}$ = Br

The syntheses of macrocyclic compounds 83 are illustrated with compound 83b as shown in Scheme 15, where $R^{5'}$, $R^{6'}$, $R^{7'}$, and $R^{8'}$ in compounds 83 are the same as defined in compounds 56. The same procedures are also applicable to other compounds 83.

Preparation of (Z)-(4R,6S,15S,17S)-[17-[7-methoxy-8-methyl-2-(4-isopropylthiazol-2-yl)quinolin-4-yloxy]-13-N-methyl-2,14-dioxo-1,3,13-triazatricyclo[13.3.0.0]octadec-7-en-4-yl]carbonyl(1-ethynylcyclopropyl)sulfonamide 83b. Compound 83b was synthesized from compounds 55b and 82 as a white solid in 30% yield, following the procedure as described for compound 56c.

MS (ESI, EI$^+$) m/z=775 (MH$^+$).

Scheme 15

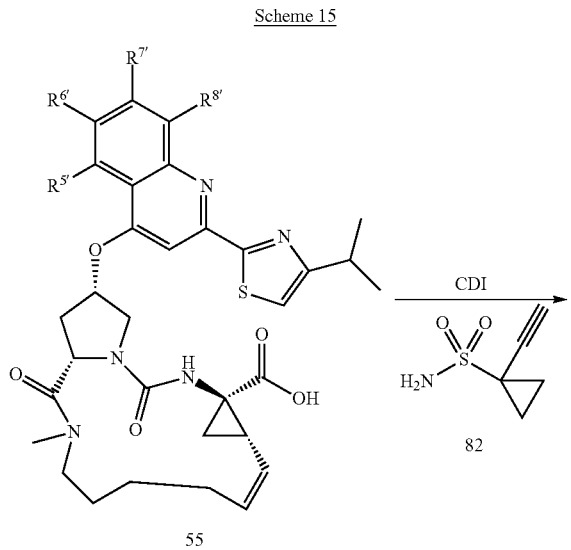

Example 14

Preparation of Substituted Quinolines 88

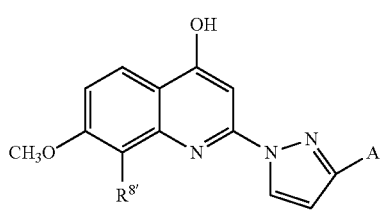

88a: R$^{8'}$ = Cl, A = CF$_3$
88b: R$^{8'}$ = CH$_3$, A = iPr
88c: R$^{8'}$ = CH$_3$, A = CF$_3$
88d: R$^{8'}$ = Cl, A = iPr

The syntheses of substituted quinolines are illustrated in Scheme 16, where R$^{8'}$ and A in compound 87 are the same as defined in compounds 88.

Step A: Preparation of 4-ethoxy-trifluoro-but-3-en-2-one 84. Ethylvinylether (5 g, 1 eq.) was added dropwise at −10° C. and under nitrogen to a stirred solution of trifluoroacetic anhydride (10 mL, 1.05 eq.) and 4-dimethylaminopyridine (80 mg, 0.06 eq.) in DCM (90 mL). The reaction mixture was stirred at 0° C. for 8 hrs and allowed to warm up at room temperature overnight. The mixture was then poured into cold aqueous NaHCO$_3$ solution. The organic layer was separated, washed with water and brine, dried over Na$_2$SO$_4$, filtered, and concentrated under reduced pressure to yield compound 84 as brown oil in 87% yield.

$^1$H NMR (CDCl$_3$, 400 MHz) δ 1.39-1.43 (t, J=7.04 Hz, 3H), 4.08-4.13 (q, J=7.04 Hz, 2H), 5.86 (d, J=12.40 Hz, 1H), 7.90 (d, J=12.40 Hz, 1H).

Scheme 16

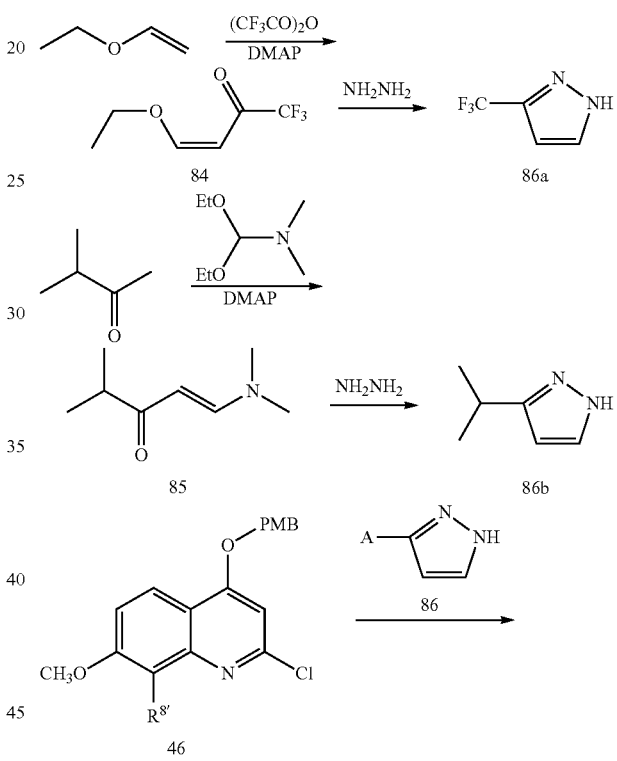

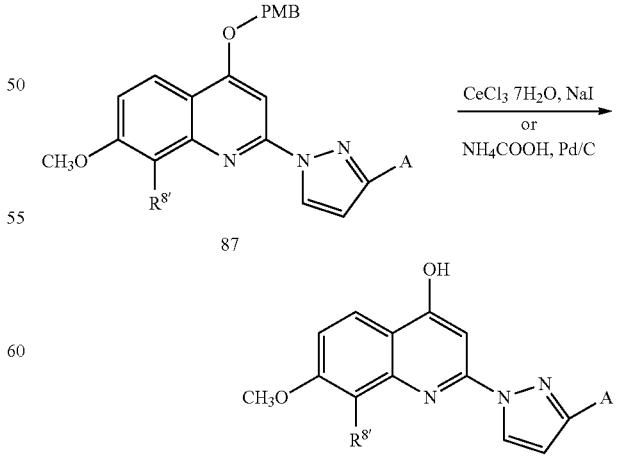

Step B: Preparation of 3-trifluoromethyl-1H-pyrazole 86a. To a stirred solution of hydrazine monochloride (6.62 g, 1.6 eq.) in EtOH (300 mL) was added dropwise compound 84 (10.16 g, 1 eq.) in EtOH (200 mL). The reaction mixture was refluxed for 6 hrs and evaporated to dryness. Water and EtOAc were added to the residue. The organic layer was washed with water and brine, dried over $Na_2SO_4$, filtered, and concentrated under reduced pressure to yield compound 86a as a brown solid in 86% yield.

$^1$H NMR ($CDCl_3$, 376 MHz) δ 6.66 (d, J=2.30 Hz, 1H), 7.72 (d, J=2.30 Hz, 1H); $^{19}$F NMR ($CDCl_3$, MHz) δ 61.41 (s, 3F).

Step C: Preparation of 1-dimethylamino-4-methyl-pent-1-en-3-one 85. 3-Methylbutan-2-one (2.5 g, 1 eq.) and dimethylformamide diethylacetal (7.46 mL, 1.5 eq.) were heated at 100° C. for 4 days to give compound 85 as yellow viscous oil in 80% yield, which was used directly without further purification in the next step.

$^1$H NMR (DMSO-$d_6$, 400 MHz) δ 0.94 (s, 3H), 0.95 (s, 3H), 2.52 (s, 1H), 2.74 (brs, 3H), 3.01 (brs, 3H), 4.96 (d, J=12.97 Hz, 1H), 7.45 (d, J=12.97 Hz, 1H).

Step D: Preparation of 3-isopropyl-1H-pyrazole 86b. Compound 85 (6.6 g, 1 eq.) was added dropwise to a stirred solution of hydrazine monochloride (3.2 g, 1 eq.), sulfuric acid (1.13 mL) and $H_2O$ (6 mL). The reaction mixture was stirred at 68° C. for 2 hrs. The mixture was then neutralized with 1N NaOH and extracted with diethyl ether. The organic layer was dried over $Na_2SO_4$, filtered, and concentrated under reduced pressure to yield compound 86b as a beige solid in 94% yield.

$^1$H NMR (DMSO-$d_6$, 400 MHz) δ 1.17 (s, 3H), 1.19 (s, 3H), 2.87-2.93 (m, 1H), 5.99 (s, 1H), 7.40 (s, 1H). 1.39-1.43 (t, J=7.04 Hz, 3H), 4.08-4.13 (q, J=7.04 Hz, 2H), 5.86 (d, J=12.40 Hz, 1H), 7.90 (d, J=12.40 Hz, 1H).

Step E: Preparation of 8-chloro-7-methoxy-4-(4-methoxy-benzyloxy)-2-(3-trifluoromethyl-1H-pyrazol-1-yl)-quinoline 87a. To a stirred solution of compound 86a (821 mg, 1.1 eq.) in anhydrous DMF (20 mL) at 0° C. was added NaH (241 mg, 1.1 eq.) portionwise. After the reaction mixture was stirred for 1 hr at room temperature, compound 46d (2 g, 1 eq) was added and the mixture was stirred at 90° C. for 16 hrs. After the reaction mixture was cooled to room temperature, EtOAc was added. The organic phase was washed with HCl (2.5 N), dried over $Na_2SO_4$, filtered, and concentrated under reduced pressure. The crude material was purified by chromatography on silica gel (petroleum ether/DCM, 50/50) to give compound 65a as a white solid in 51% yield.

MS (ESI, EI$^-$) m/z=461.9 (MH$^-$).

Step F: Preparation of 7-methoxy-4-(4-methoxy-benzyloxy)-8-methyl-2-(3-trifluoromethyl-1H-pyrazol-1-yl)-quinoline 87c. Compound 87c was synthesized from compounds 46b and 86a following the procedure as described for compound 86a, as a white solid in 19% yield.

$^1$H NMR ($CDCl_3$, 400 MHz) δ 2.64 (s, 3H), 3.86 (s, 3H), 3.99 (s, 3H), 5.33 (s, 2H), 6.75 (d, J=2.58 Hz, 1H), 6.98 (d, J=8.78 Hz, 2H), 7.20 (d, J=9.22 Hz, 1H), 7.48 (d, J=8.78 Hz, 2H), 7.57 (s, 1H), 8.07 (d, J=9.08 Hz, 1H), 8.88 (s, 1H).

Step G: Preparation of 8-chloro-4-hydroxy-7-methoxy-2-(3-trifluoromethyl-1H-pyrazol-1-yl)-quinoline 88a. Compound 87(800 mg, 1 eq.), $CeCl_3.7H_2O$ (965 mg, 1.5 eq.) and NaI (258 mg, 1 eq.) in ACN (10 mL) were stirred at 85° C. for 1 hr under microwave irradiation. Water was added and the mixture was acidified with 1N HCl to pH 5. The reaction mixture was extracted with diethyl ether. The organic layer was dried over $Na_2SO_4$, filtered, and concentrated under reduced pressure. The crude material was purified by chromatography on silica gel (MeOH/DCM) to give compound 86 as a beige solid in 96% yield.

$^1$H NMR (DMSO-$d_6$, 400 MHz) δ 4.02 (s, 3H), 7.07 (s, 1H), 7.43 (s, 1H), 7.51 (d, J=9.11 Hz, 1H), 8.11 (d, J=9.11 Hz, 1H), 8.88 (s, 1H); MS (ESI, EI$^+$) m/z=343.9 (MH$^+$).

Step H: Preparation of 4-hydroxy-7-methoxy-8-methyl-2-(3-isopropyl-pyrazol-1-yl)-quinoline 88b. A solution of compound 86b (350 mg, 1 eq.) and compound 46b (480 mg, 6 eq.) in N-methylpyrrolidone (5 mL) was heated at 200° C. for 30 min. After the reaction mixture was cooled to room temperature, water was added. The mixture was extracted with EtOAc, dried over $Na_2SO_4$, filtered, and concentrated under reduced pressure. The crude material was purified by chromatography on silica gel (EtOAc/DCM). Recrystallisation in diethylether gave compound 88b as a white solid in 49% yield.

$^1$H NMR ($CDCl_3$, 376 MHz) δ 1.35 (s, 3H), 1.36 (s, 3H), 2.85 (s, 3H), 3.97 (s, 3H), 6.40 (d, J=2.65 Hz, 2H), 7.01 (d, J=9.00 Hz, 1H), 8.00 (brs, 1H), 8.23 (d, J=9.00 Hz, 1H), 9.81 (brs, 1H); MS (ESI, EI$^+$) m/z=298 (MH$^+$).

Step I: Preparation of 4-hydroxy-7-methoxy-8-methyl-2-(3-trifluoromethyl-1H-pyrazol-1-yl)-quinoline 88c. A mixture of compound 87c (885 mg, 1.99 mmol), ammonium formate (629 mg, 9.98 mmol), and Pd/C (89 mg, 10% w) in EtOH (16 mL) was refluxed for 1 hr. The reaction was then filtered though celite and concentrated under reduced pressure. The residue was diluted with DCM and washed with water. Organics were dried over $Na_2SO_4$, filtered, concentrated under reduced pressure, and purified by chromatography on silica gel (petroleum ether/EtOAc) to yield compound 88c as a white solid in 93% yield.

$^1$H NMR (DMSO-$d_6$, 400 MHz) δ 2.54 (s, 3H), 3.94 (s, 3H), 7.06 (d, J=2.48 Hz, 1H), 7.37-7.40 (m, 2H), 8.02 (d, J=9.18 Hz, 1H), 8.97 (s, 1H), 11.89 (s, 1H).

Step J: Preparation of 8-chloro-4-hydroxy-7-methoxy-2-(3-isopropyl-1H-pyrazol-1-yl)-quinoline 88d. A mixture of compound 46a (500 mg, 1.37 mmol) and compound 86b (452 mg, 4.11 mmol) in N-methylpyrrolidone (2 mL) was stirred at 200° C. for 30 min under microwave radiation. After the reaction mixture was cooled to room temperature, water was added. The reaction mixture was then extracted with EtOAc, dried over $Na_2SO_4$, filtered, concentrated under reduced pressure, and purified by chromatography on silica gel (DCM/EtOAc) to yield compound 88d as a white solid in 35% yield.

$^1$H NMR (DMSO-$d_6$, 400 MHz) δ 1.26 (s, 3H), 1.28 (s, 3H), 2.98-3.01 (m, 1H), 4.00 (s, 3H), 6.46 (m, 1H), 7.16 (d, 9.32 Hz, 1H), 7.89 (d, J=9.32 Hz, 1H), 8.05 (d, J=10.85 Hz, 1H), 8.60 (m, 1H), 10.69 (s, 1H).

Example 15

Preparation of Macrocyclic Compounds 91

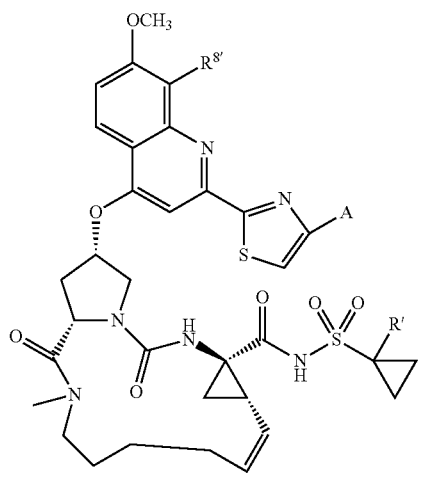

91a: R⁸' = Cl, A = CF₃, R' = CH₃
91b: R⁸' = CH₃, A = iPr, R' = CH₃
91c: R⁸' = CH₃, A = CF₃, R' = CH₃
91d: R⁸' = Cl, A = iPr, R' = CH₃
91e: R⁸' = Cl, A = CF₃, R' = H
91f: R⁸' = CH₃, A = iPr, R' = H
91g: R⁸' = CH₃, A = CF₃, R' = H

The syntheses of macrocyclic compounds 91 are illustrated in Scheme 17, where R⁸' and A in compounds 89 and 90 are the same as defined in compounds 91.

Step A: Preparation of (Z)-(4R,6S,15S,17S)-17-[8-chloro-7-methoxy-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-carboxylic acid ethyl ester 89a. Compound 89a was synthesized from compounds 53 and 88a as a beige solid in 40% yield, following the procedure as described for compound 54c.

MS (ESI, EI⁺) m/z=705 (MH⁺).

Scheme 17

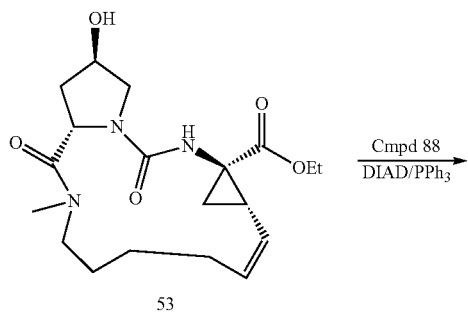

53

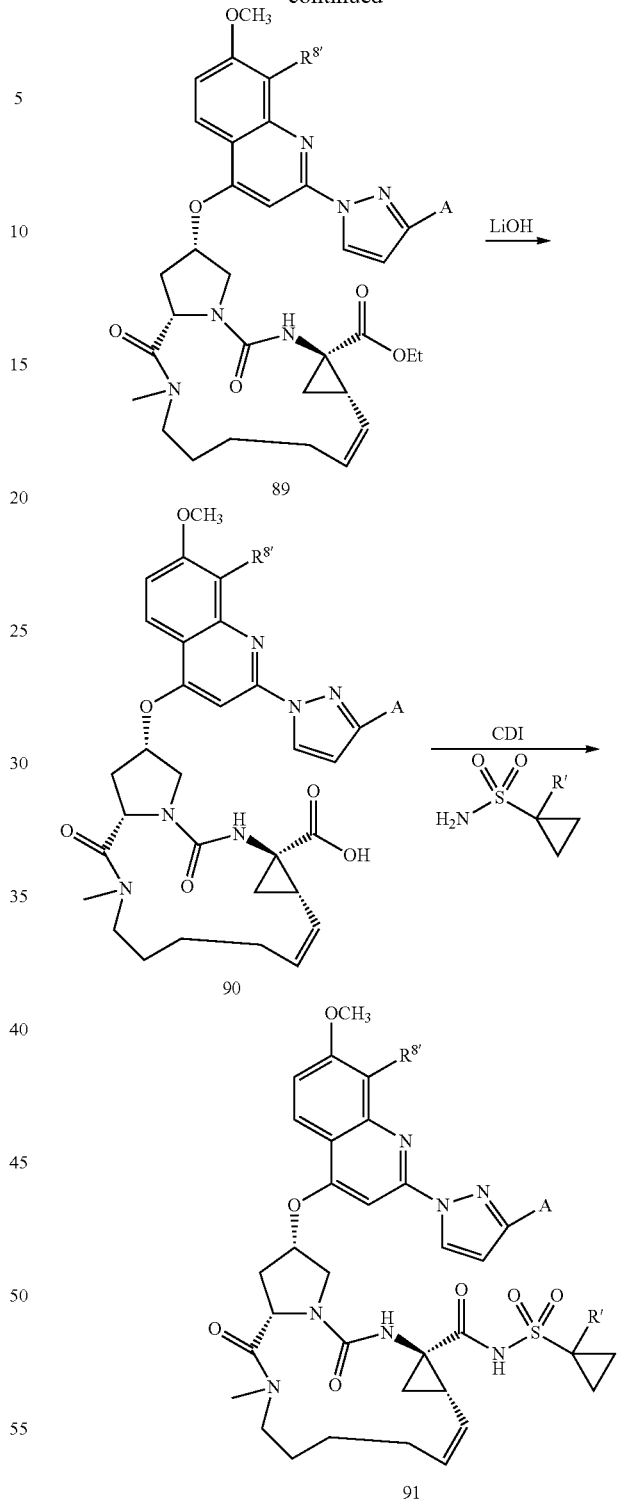

Step B: Preparation of (Z)-(4R,6S,15S,17S)-17-[8-methyl-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-carboxylic acid ethyl ester 89b. Compound 89b was synthesized from compounds 53 and 88b as white foam in 50% yield, following the procedure as described for compound 54c.

MS (ESI, EI⁺) m/z=659 (MH⁺).

Step C: Preparation of (Z)-(4R,6S,15S,17S)-17-[7-methoxy-8 methyl-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-carboxylic acid ethyl ester 89c. Compound 89c was synthesized from compounds 53 and 88c as brown foam in 80% yield, following the procedure as described for compound 54c.

MS (ESI, EI$^+$) m/z=685 (MH$^+$).

Step D: Preparation of (Z)-(4R,6S,15S,17S)-17-[8-chloro-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-carboxylic acid ethyl ester 89d. Compound 89d was synthesized from compounds 53 and 88d as brown foam in 90% yield, following the procedure as described for compound 54c.

MS (ESI, EI$^+$) m/z=679 (MH$^+$).

Step E: Preparation of (Z)-(4R,6S,15S,17S)-17-[8-chloro-7-methoxy-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-carboxylic acid 90a. Compound 90a was synthesized from compound 89a as a white solid in 77% yield, following the procedure as described for compound 55c.

MS (ESI, EI$^+$) m/z=677 (MH$^+$).

Step F: Preparation of (Z)-(4R,6S,15S,17S)-17-[8-methyl-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-carboxylic acid 90b. Compound 90b was synthesized from compound 89b as a yellow solid in 50% yield, following the procedure as described for compound 55c.

MS (ESI, EI$^+$) m/z=631 (MH$^+$).

Step G: Preparation of (Z)-(4R,6S,15S,17S)-17-[7-methoxy-8 methyl-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-carboxylic acid 90c. Compound 90c was synthesized from compound 89c as a pale yellow solid in 18% yield, following the procedure as described for compound 55c.

MS (ESI, EI$^+$) m/z=657 (MH$^+$).

Step H: Preparation of (Z)-(4R,6S,15S,17S)-17-[8-chloro-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-carboxylic acid 90d. Compound 90d was synthesized from compound 89d as a pale yellow solid in 36% yield, following the procedure as described for compound 55c.

MS (ESI, EI$^+$) m/z=650 (MH$^+$).

Step I: Preparation of (Z)-(4R,6S,15S,17S)-[17-[8-chloro-7-methoxy-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-yl]carbonyl(1-methylcyclopropyl)sulfonamide 91a. Compound 91a was synthesized from compound 90a and 1-methylcyclopropylsulfonamide as a white solid in 12% yield, following the procedure as described for compound 56c.

MS (ESI, EI$^+$) m/z=794 (MH$^+$).

Step J: Preparation of (Z)-(4R,6S,15S,17S)-[17-[8-methyl-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-yl]carbonyl(1-methylcyclopropyl)sulfonamide 91b. Compound 91b was synthesized from compound 90b and 1-methylcyclopropylsulfonamide as a white solid in 30% yield, following the procedure as described for compound 56c.

MS (ESI, EI$^+$) m/z=748 (MH$^+$).

Step K: Preparation of (Z)-(4R,6S,15S,17S)-[17-[7-methoxy-8-methyl-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-yl]carbonyl(1-methylcyclopropyl)sulfonamide 91c. Compound 91c was synthesized from compound 90c and 1-methylcyclopropylsulfonamide as a white solid in 9% yield, following the procedure as described for compound 56c.

MS (ESI, EI$^+$) m/z=774 (MH$^+$).

Step L: Preparation of (Z)-(4R,6S,15S,17S)-[17-[8-chloro-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-yl]carbonyl(1-methylcyclopropyl)sulfonamide 91d. Compound 91d was synthesized from compound 90d and 1-methylcyclopropylsulfonamide as a white solid in 28% yield, following the procedure as described for compound 56c.

MS (ESI, EI$^+$) m/z=768 (MH$^+$).

Step M: Preparation of (Z)-(4R,6S,15S,17S)-[17-[8-chloro-7-methoxy-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-yl]carbonyl(cyclopropyl)sulfonamide 91e. Compound 91e was synthesized from compound 90a and cyclopropylsulfonamide as a beige solid in 46% yield, following the procedure as described for compound 56c.

MS (ESI, EI$^+$) m/z=780 (MH$^+$).

Step N: Preparation of (Z)-(4R,6S,15S,17S)-[17-[8-methyl-7-methoxy-2-(3-isopropyl-1H-pyrazol-1-yl)quinolin-4-yloxy]-13-N-methyl-2,14-dioxo-1,3,13-triazatricyclo[13.3.0.0]octadec-7-ene-4-yl]carbonyl(cyclopropyl)sulfonamide 91f. Compound 91f was synthesized from compound 90b and cyclopropylsulfonamide as a white solid in 30% yield, following the procedure as described for compound 56c.

MS (ESI, EI$^+$) m/z=734 (MH$^+$).

Step O: Preparation of (Z)-(4R,6S,15S,17S)-[17-[7-methoxy-8-methyl-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-yl]carbonyl(cyclopropyl)sulfonamide 91g. Compound 91g was synthesized from compound 90c and cyclopropylsulfonamide as a white solid in 46% yield, following the procedure as described for compound 56c.

MS (ESI, EI$^+$) m/z=760 (MH$^+$).

Example 16

Preparation of Macrocyclic Compounds 96

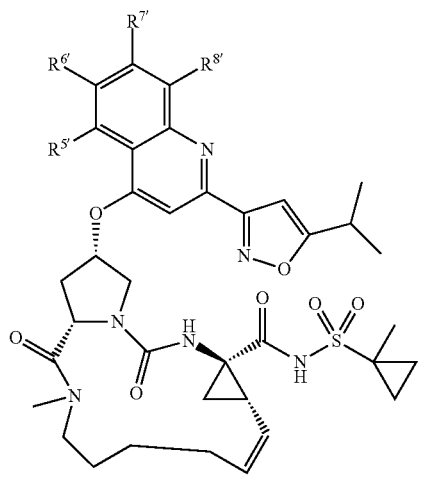

96a: R⁵' = H, R⁶' = H, R⁷' = OCH₃, R⁸' = H
96b: R⁵' = H, R⁶' = H, R⁷' = OCH₃, R⁸' = CH₃
96c: R⁵' = H, R⁶' = H, R⁷' = OCH₃, R⁸' = F
96d: R⁵' = H, R⁶' = H, R⁷' = OCH₃, R⁸' = Cl
96e: R⁵' = OCH₃, R⁶' = H, R⁷' = OCH₃, R⁸' = H
96f: R⁵' = H, R⁶' = OCH₃, R⁷' = H, R⁸' = CH₃
96g: R⁵' = H, R⁶' = OCH₃, R⁷' = Cl, R⁸' = H
96h: R⁵' = H, R⁶' = H, R⁷' = OCH₃, R⁸' = Br

The syntheses of macrocyclic compounds 96 are illustrated with compound 96d as shown in Scheme 18, where $R^{5'}$, $R^{6'}$, $R^{7'}$, and $R^{8'}$ in compounds 92 to 96 are the same as defined in compounds 56. The same procedures are also applicable to other compounds 96.

Step A: Preparation of N-(6-acetyl-2-chloro-3-methoxyphenyl)-5-isopropylisoxazole-3-carboxamide 92d. To a stirred solution of 5-isopropylisoxazole-3-carboxylic acid (3.5 g, 22.6 mmol) in DCM (35 mL) was added anhydrous DMF (few drops) and oxalyl chloride (3.82 mL, 43.2 mmol) at 0° C. under nitrogen. At the end of the gas escape, the reaction mixture was allowed to warm up to room temperature. The mixture was stirred at room temperature for 2 hrs and was evaporated. Dioxane (70 mL) was added under nitrogen, followed by a solution of 1-(2-amino-3-chloro-4-methoxy-phenyl)-ethanone 40d (4.10 g, 20.6 mmol) in dioxane (15 mL). The reaction mixture was stirred at room temperature for 16 hrs. NaHCO₃ was then added. The mixture was extracted with EtOAc. Organics were dried over Na₂SO₄, filtered, and concentrated under reduced pressure. The crude material was triturated in Et₂O to yield compound 92d as a brown solid in 60% yield.

¹H NMR (CDCl₃, 400 MHz) δ 1.47 (s, 3H), 1.48 (s, 3H), 1.76 (brs, 1H), 2.57 (s, 3H), 3.34-3.40 (m, 1H), 3.98 (s, 3H), 6.86 (d, J=8.53 Hz, 1H), 7.64 (d, J=8.53 Hz, 1H), 8.07 (s, 1H).

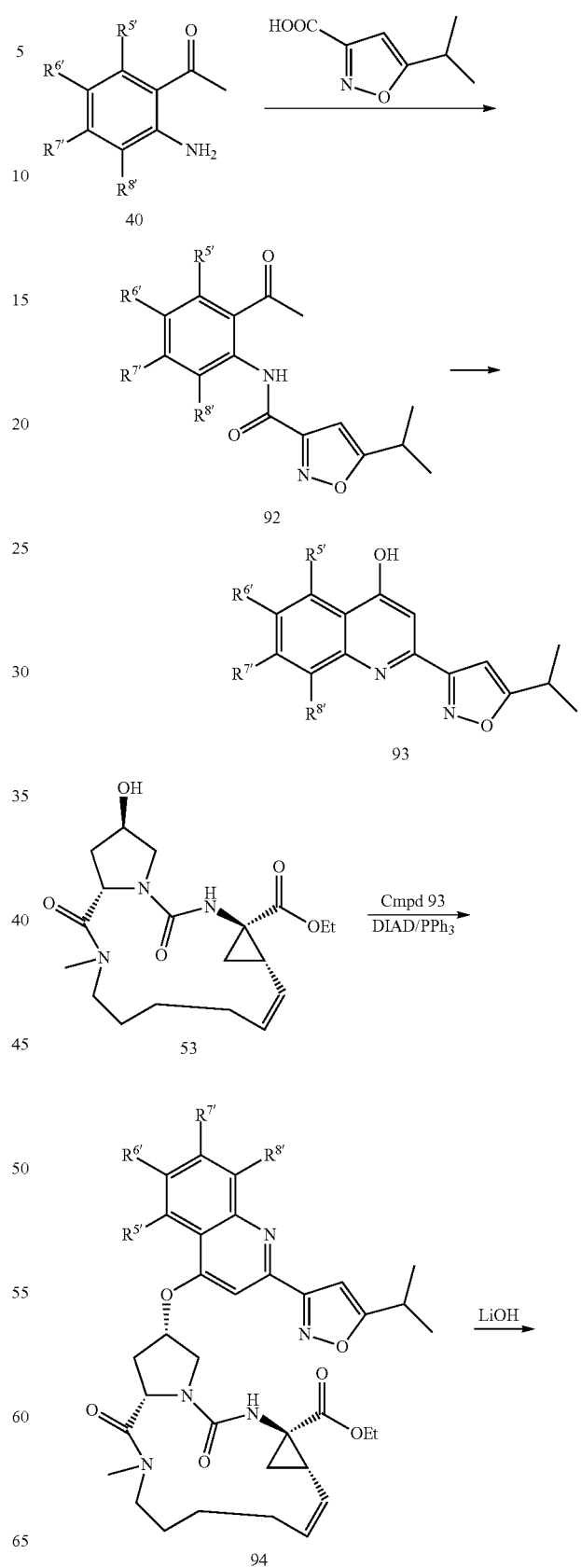

Scheme 18

-continued

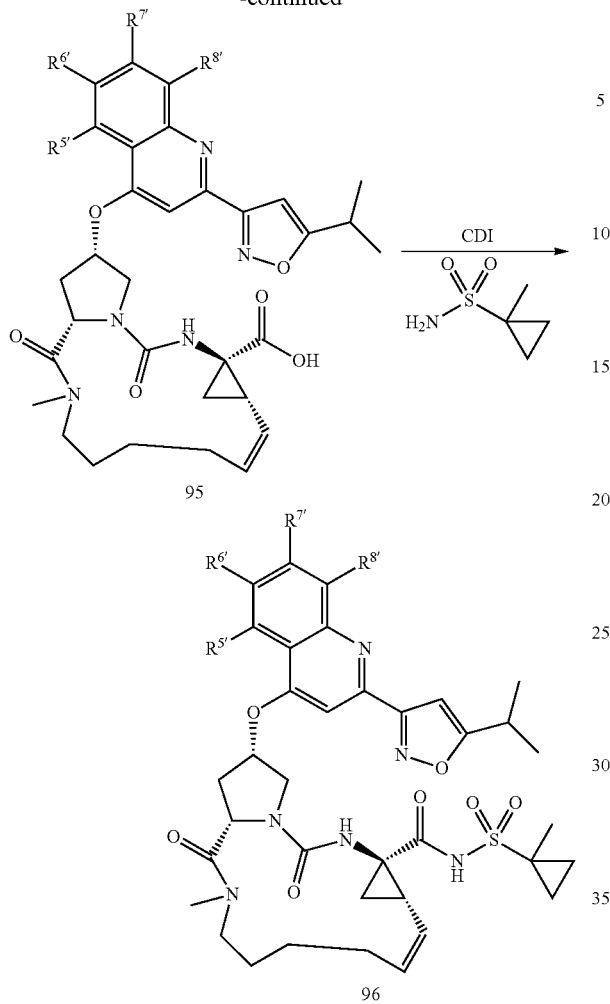

Step B: Preparation of 8-chloro-2(5-isopropyl-isoxazol-3-yl)-7-methoxy-quinolin-4-ol 93d. Compound 93d was synthesized from compound 92d as a white solid in quantitative yield, following the procedure as described for compound 43a.

$^1$H NMR (CDCl$_3$, 400 MHz) δ 1.39 (s, 3H), 1.41 (s, 3H), 3.17-3.31 (m, 1H), 4.06 (s, 3H), 6.36 (s, 1H), 6.59 (s, 1H), 7.06 (d, J=8.48 Hz, 1H), 8.28 (d, J=8.48 Hz, 1H), 9.42 (s, 1H).

Step C: Preparation of (Z)-(4R,6S,15S,17S)-17-[8-chloro-7-methoxy-2-(5-isopropylisoxazol-3-yl)quinolin-4-yloxy]-13-N-methyl-2,14-dioxo-1,3,13-triazatricyclo[13.3.0.0]octadec-7-ene-4-carboxylic acid ethyl ester 94d. Compound 94d was synthesized from compounds 53 and 93d as a beige solid in 56% yield, following the procedure as described for compound 54c.

MS (ESI, EI$^+$) m/z=680 (MH$^+$).

Step D: Preparation of (Z)-(4R,6S,15S,17S)-17-[8-chloro-7-methoxy-2-(5-isopropylisoxazol-3-yl)quinolin-4-yloxy]-13-N-methyl-2,14-dioxo-1,3,13-triazatricyclo[13.3.0.0]octadec-7-ene-4-carboxylic acid 95d. Compound 95d was synthesized from compound 94d as a white solid in 10% yield, following the procedure as described for compound 55c.

MS (ESI, EI$^+$) m/z=652 (MH$^+$).

Step E: Preparation of (Z)-(4R,6S,15S,17S)-[17-[8-chloro-7-methoxy-2-(5-isopropylisoxazol-3-yl)quinolin-4-yloxy]-13-N-methyl-2,14-dioxo-1,3,13-triazatricyclo[13.3.0.0]octadec-7-ene-4-yl]carbonyl(1-methylcyclopropyl)sulfonamide 96d. Compound 96d was synthesized from compound 95d as a white solid in 16% yield, following the procedure as described for compound 56c.

MS (ESI, EI$^+$) m/z=769 (MH$^+$).

Example 17

Preparation of Macrocyclic Compounds 101

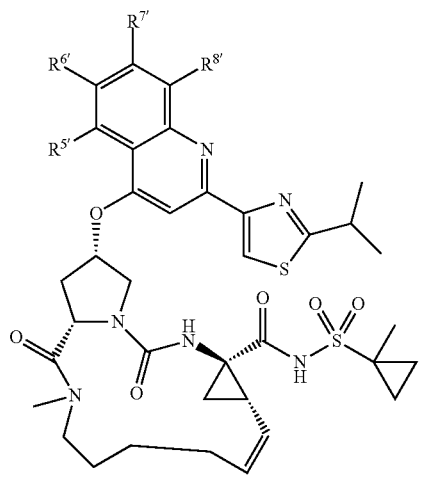

101a: R$^{5'}$ = H, R$^{6'}$ = H, R$^{7'}$ = OCH$_3$, R$^{8'}$ = H
101b: R$^{5'}$ = H, R$^{6'}$ = H, R$^{7'}$ = OCH$_3$, R$^{8'}$ = CH$_3$
101c: R$^{5'}$ = H, R$^{6'}$ = H, R$^{7'}$ = OCH$_3$, R$^{8'}$ = F
101d: R$^{5'}$ = H, R$^{6'}$ = H, R$^{7'}$ = OCH$_3$, R$^{8'}$ = Cl
101e: R$^{5'}$ = OCH$_3$, R$^{6'}$ = H, R$^{7'}$ = OCH$_3$, R$^{8'}$ = H
101f: R$^{5'}$ = H, R$^{6'}$ = OCH$_3$, R$^{7'}$ = H, R$^{8'}$ = CH$_3$
101g: R$^{5'}$ = H, R$^{6'}$ = OCH$_3$, R$^{7'}$ = Cl, R$^{8'}$ = H
101h: R$^{5'}$ = H, R$^{6'}$ = H, R$^{7'}$ = OCH$_3$, R$^{8'}$ = Br

The syntheses of macrocyclic compounds 101 are illustrated with compound 101d as shown in Scheme 19, where R$^{5'}$, R$^{6'}$, R$^{7'}$, and R$^{8'}$ in compounds 92 to 96 are the same as defined in compounds 56. The same procedures are also applicable to other compounds 101.

Step A: Preparation of N-(6-acetyl-2-chloro-3-methoxyphenyl)-2-isopropylthiazole-4-carboxamide 97d. To a stirred solution of 2-isopropyl-1,3-thiazol-4-carboxylic acid (3.5 g, 20.4 mmol) in DCM (35 mL) was added oxalyl chloride (3.46 mL, 40.9 mmol) with a few drop of anhydrous DMF at 0° C. At the end of gas escape, the mixture was allowed to warm up at room temperature and then stirred for 2 hrs. The reaction mixture was concentrated under reduced pressure and solubilized in dioxane (70 mL). A solution of 1-(2-amino-3-chloro-4-methoxy-phenyl)-ethanone 40d (3.71 g, 18.6 mmol) in dioxane (15 mL) was then slowly added. The mixture was stirred at room temperature for 16 hrs. NaHCO$_3$ was added. The mixture was extracted with EtOAc, dried over Na$_2$SO$_4$, filtered, and concentrated under reduced pressure. The crude material was triturated in diethyl ether to yield compound 97b in 60% yield.

$^1$H NMR (CDCl$_3$, 400 MHz) δ 1.47 (s, 3H), 1.48 (s, 3H), 2.57 (s, 3H), 3.34-3.41 (quint, J=6.90 Hz, 1H), 3.98 (s, 3H), 6.86 (d, J=8.48 Hz, 1H), 7.64 (d, J=8.48 Hz, 1H), 8.07 (s, 1H);

MS (ESI, EI$^-$) m/z=351 (MH$^-$).

Scheme 19

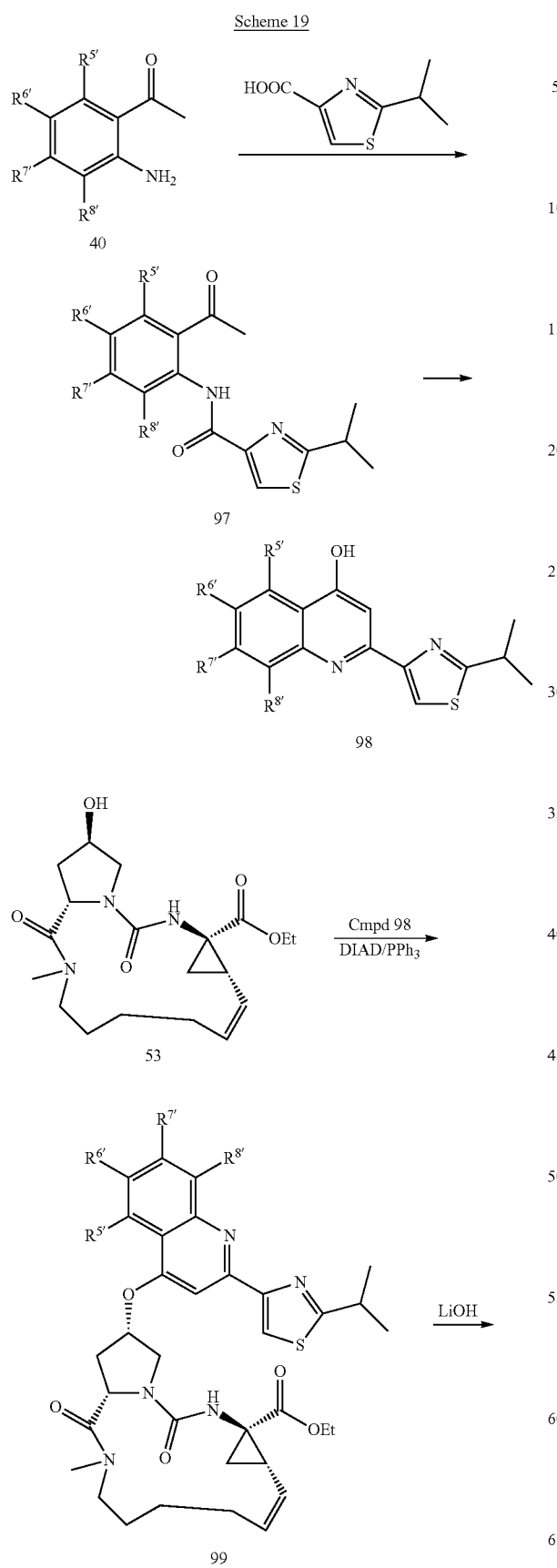

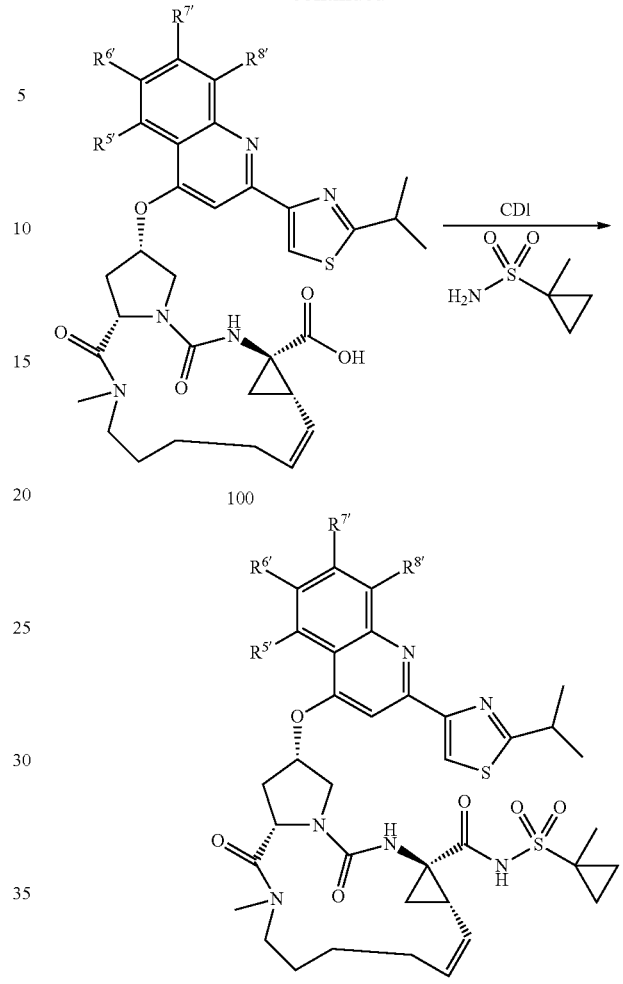

Step B: Preparation of 8-chloro-2-(2-isopropyl-thiazol-4-yl)-7-methoxy-quinolin-4-ol 98d. Compound 97d (352 mg, 1 mmol) and potassium tert-butoxide (236 mg, 2.1 mmol) in tert-butyl alcohol (10 mL) were stirred in a sealed vessel at 120° C. for 1 hr under microwave radiations. The mixture was then poured into diethyl ether, acidified with 2.5N HCl to pH 5 and extracted with ethyl acetate, and concentrated under reduced pressure to yield compound 98b in 82% yield.

$^1$H NMR (CDCl$_3$, 400 MHz) δ 1.49 (s, 3H), 1.51 (s, 3H), 3.38-3.45 (quint, J=6.90 Hz, 1H), 4.06 (s, 3H), 6.70 (brs, 1H), 7.05 (d, J=9.35 Hz, 1H), 7.76 (s, 1H).

Step C: Preparation of (Z)-(4R,6S,15S,17S)-17-[8-chloro-7-methoxy-2-(2-isopropythiazol-4-yl)quinolin-4-yloxy]-13-N-methyl-2,14-dioxo-1,3,13-triazatricyclo[13.3.0.0]octadec-7-ene-4-carboxylic acid ethyl ester 99d. Compound 99d was synthesized from compounds 53 and 98d as a white solid in 31% yield, following the procedure as described for compound 54c.

MS (ESI, EI$^+$) m/z=696 (MH$^+$).

Step D: Preparation of (Z)-(4R,6S,15S,17S)-17-[8-chloro-7-methoxy-2-(2-isopropythiazol-4-yl)quinolin-4-yloxy]-13-N-methyl-2,14-dioxo-1,3,13-triazatricyclo[13.3.0.0]octadec-7-ene-4-carboxylic acid 10d. Compound 100d was synthesized from compound 99d as a white solid in 47% yield, following the procedure as described for compound 55c.

MS (ESI, EI$^+$) m/z=668 (MH$^+$).

Step E: Preparation of (Z)-(4R,6S,15S,17S)-[17-[8-chloro-7-methoxy-2-(2-isopropythiazol-4-yl)quinolin-4-yloxy]-13-N-methyl-2,14-dioxo-1,3,13-triazatricyclo[13.3.0.0]octadec-7-ene-4-yl]carbonyl(1-methylcyclopropyl)sulfonamide 101d. Compound 110d was synthesized from compound 100d as a white solid in 38% yield, following the procedure as described for compound 56c.

MS (ESI, EI⁺) m/z=785 (MH⁺).

Example 18

Preparation of Macrocyclic Compounds 110

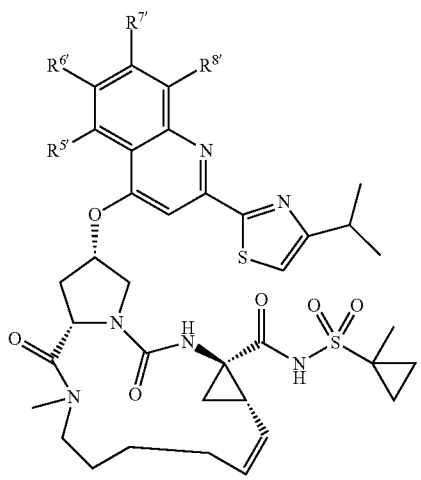

110a: $R^{5'}$ = H, $R^{6'}$ = H, $R^{7'}$ = OCH₃, $R^{8'}$ = H
110b: $R^{5'}$ = H, $R^{6'}$ = H, $R^{7'}$ = OCH₃, $R^{8'}$ = CH₃
110c: $R^{5'}$ = H, $R^{6'}$ = H, $R^{7'}$ = OCH₃, $R^{8'}$ = F
110d: $R^{5'}$ = H, $R^{6'}$ = H, $R^{7'}$ = OCH₃, $R^{8'}$ = Cl
110e: $R^{5'}$ = OCH₃, $R^{6'}$ = H, $R^{7'}$ = OCH₃, $R^{8'}$ = H
110f: $R^{5'}$ = H, $R^{6'}$ = OCH₃, $R^{7'}$ = H, $R^{8'}$ = CH₃
110g: $R^{5'}$ = H, $R^{6'}$ = OCH₃, $R^{7'}$ = Cl, $R^{8'}$ = H
110h: $R^{5'}$ = H, $R^{6'}$ = H, $R^{7'}$ = OCH₃, $R^{8'}$ = Br

The syntheses of macrocyclic compounds 110 are illustrated with compound 110d as shown in Schemes 20 and 21 where $R^{5'}$, $R^{6'}$, $R^{7'}$, and $R^{8'}$ in compounds 102 to 110 are the same as defined in compounds 56. The same procedures are also applicable to other compounds 110.

Step A: Preparation of N-(2-chloro-3-methoxyphenyl)-2-hydroxyimino-acetamide 102d. To a stirred solution of sodium sulfate (58.5 g, 412 mmol) in water (100 mL) was added a solution of chloralhydrate (9.36 g, 56.6 mmol) in water (120 mL). Chloroanisidine 39d (10 g, 51.5 mmol) was added followed by 37% HCl (20 mL). A solution of hydroxylamine (50% in water, 4.7 mL, 154.5 mmol) in 50 mL was then added and the reaction mixture was refluxed for 90 min. The suspended solid was filtered off, and washed with water and ether. Organics were dried over Na₂SO₄, filtered, and concentrated under reduced pressure to yield compound 102d as a brown solid.

¹H NMR (DMSO-d₆, 400 MHz) δ 3.86 (s, 3H), 6.98 (d, J=8.07 Hz, 1H), 7.31 (t, J=8.07 Hz, 1H), 7.61 (d, J=8.07 Hz, 1H), 7.66 (s, 1H), 9.43 (s, 1H), 12.43 (s, 1H).

Scheme 20

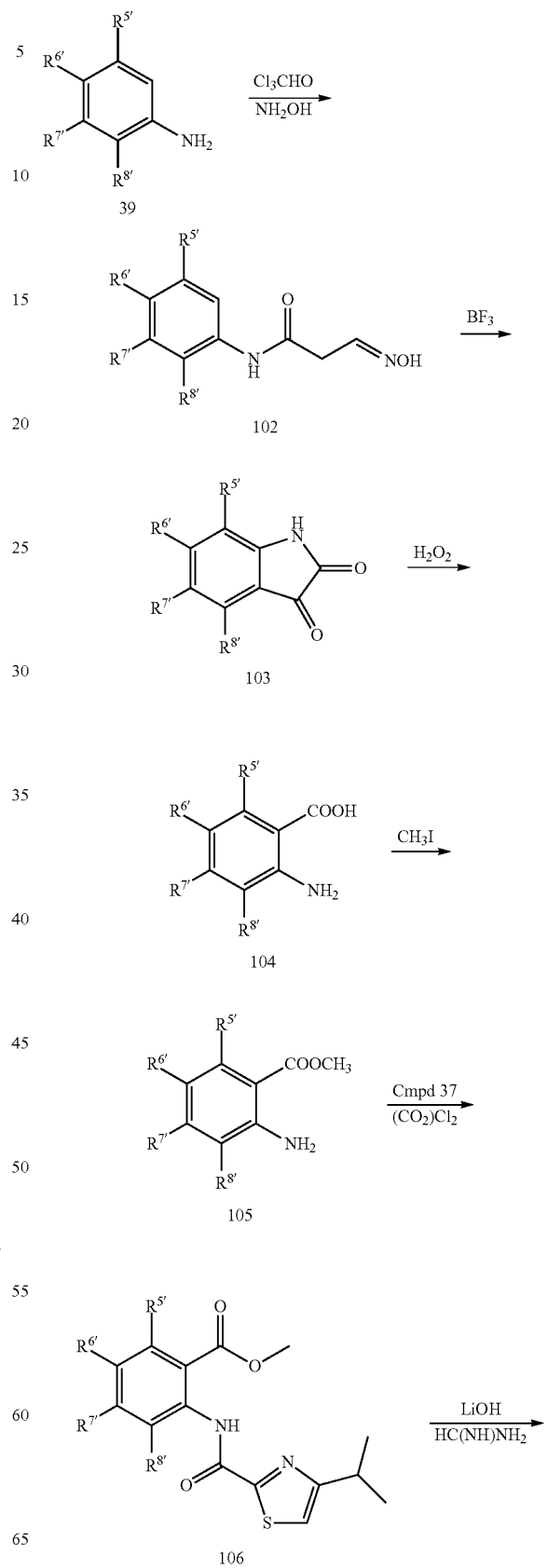

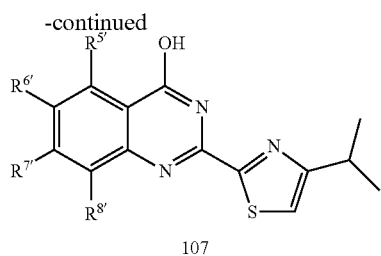

107

Step B: Preparation of 7-chloro-6-methoxy-1H-indole-2,3-dione 103d. Compound 102d (10.46 g, 45.74 mmol) was added portionwise to BF$_3$.Et$_2$O at 40° C. The mixture was then heated at 90° C. for 3 hrs. After cooling down to room temperature, the reaction mixture was poured into crushed ice and extracted with EtOAc. Organics were dried over Na$_2$SO$_4$, filtered, concentrated under reduced pressure, and purified by chromatography on silica gel (petroleum ether/EtOAc). The compound obtained was recrystallised from EtOH to yield compound 103d as a brown solid in 63% yield.

$^1$H NMR (DMSO-d$_6$, 400 MHz) δ 3.96 (s, 3H), 6.79 (d, J=9.10 Hz, 1H), 7.52 (d, J=9.10 Hz, 1H), 11.40 (s, 1H).

Step C: Preparation of 2-amino-3-chloro-4-methoxy benzoic acid 104d. A suspension of compound 103d (6.03 g, 28.52 mmol), NaOH (1.25 g, 31.37 mmol), and NaCl (3.49 g, 59.89 mmol) in water (60 mL) was stirred at room temperature for 30 min and was then ice-cooled. H$_2$O$_2$ was added dropwise. The mixture was stirred at 0° C. for 20 min and at room temperature for 3 hrs. The reaction mixture was quenched with glacial AcOH, filtered, and washed with water. The solid obtained was dissolved in DCM, dried over Na$_2$SO$_4$, filtered, and concentrated under reduced pressure. The crude material was purified by chromatography on silica gel (DCM/MeOH) to yield compound 104d as an orange solid in 36% yield.

$^1$H NMR (DMSO-d$_6$, 400 MHz) δ 3.85 (s, 3H), 6.41 (d, J=9.05 Hz, 1H), 6.77 (brs, 2H), 7.74 (d, J=9.05 Hz, 1H), 12.7 (brs, 1H).

Step D: Preparation of 2-amino-3-chloro-4-methoxy benzoic acid methyl ester 105d. To a stirred solution of compound 104d (1.9 g, 9.6 mmol) in dry DMF (25 mL) was added K$_2$CO$_3$ (1.32 g, 9.6 mmol) at room temperature. The reaction mixture was stirred for 30 min and methyl iodide (0.77 mL, 12.4 mmol) was added. After 2 hrs at room temperature, 5% aqueous citric acid was added. The mixture was extracted with EtOAc. Organics were washed with water, dried over Na$_2$SO$_4$, filtered, concentrated under reduced pressure, and purified by chromatography on silica gel (petroleum ether/EtOAc) to yield compound 105d as beige solid in 50% yield.

$^1$H NMR (CDCl$_3$, 400 MHz) δ (ppm) 3.79 (s, 3H), 3.86 (s, 3H), 6.23 (d, J=9.03 Hz, 1H), 7.75 (d, J=9.03 Hz, 1H).

Step E: Preparation of methyl 3-chloro-2-(4-isopropylthiazole-2-carboxamido)-4-methoxybenzoate 106d. To a stirred solution of compound 37 (758 mg, 4.28 mmol) in dry DCM was added oxalyl chloride (720 μL, 8.56 mmol) and few drops of DMF at 0° C. The reaction mixture was stirred at 0° C. for 30 min and at room temperature for 2 hrs. The mixture was filtered, concentrated under reduced pressure, and dissolved in dioxane (3 mL). Compound 105d (770 mg, 3.56 mmol) in dioxane (6 mL) was then added. The reaction mixture was stirred at room temperature for 16 hrs. Solvent was evaporated. Water was added to the mixture. The reaction mixture was extracted with EtOAc. Organics were dried over Na$_2$SO$_4$, filtered, concentrated under reduced pressure, and purified by chromatography on silica gel (petroleum ether/EtOAc) to yield compound 106d as a pale yellow solid in 92% yield.

$^1$H NMR (CDCl$_3$, 400 MHz) δ 1.19 (d, J=6.63 Hz, 6H), 3.09-3.16 (m, 1H), 3.79 (s, 3H), 3.91 (s, 3H), 6.82 (d, J=9.02 Hz, 1H), 7.19 (s, 1H), 7.82 (d, J=9.02 Hz, 1H), 9.97 (s, 1H).

Step F: Preparation of 8-chloro-2-(4-isopropyl-thiazol-2-yl)-7-methoxy-quinazolin-4-ol 107d. To a stirred solution of compound 106d (1.32 g, 3.58 mmol) in EtOH/H$_2$O (1/1, 10 mL) was added LiOH (10.3 mg, 4.29 mmol). The reaction mixture was stirred at 60° C. for 2 hrs. An aqueous solution of citric acid (5%) was added and the mixture was extracted with EtOAc. Organic were dried over Na$_2$SO$_4$, filtered, and concentrated under reduced pressure. The residue was stirred with formamidine (26 mL) at 150° C. for 4 hrs, and the mixture was allowed to cool down to room temperature overnight. The mixture was poured into water, and extracted with DCM. Organics were dried over Na$_2$SO$_4$, filtered, concentrated under reduced pressure, and purified by chromatography on silica gel (petroleum ether/EtOAc) to yield compound 107d as beige solid in 58% yield.

$^1$H NMR (DMSO-d$_6$, 400 MHz) δ 1.32 (d, J=6.71 Hz, 6H), 3.09-3.15 (m, 1H), 4.01 (s, 3H), 7.42 (d, J=9.03 Hz, 1H), 7.67 (s, 1H), 8.11 (d, J=9.03 Hz, 1H), 12.42 (s, 1H).

Step G: Preparation of (Z)-(4R,6S,15S,17S)-17-[8-chloro-7-methoxy-2-(4-isopropylthiazol-2-yl)quinazolin-4-yloxy]-13-N-methyl-2,14-dioxo-1,3,13-triazatricyclo[13.3.0.0]octadec-7-ene-4-carboxylic acid ethyl ester 108d. Compound 108d was synthesized from compounds 53 and 107d as yellow oil in 16% yield, following the procedure as described for compound 54c.

MS (ESI, EI$^+$) m/z=697 (MH$^+$).

Step H: Preparation of (Z)-(4R,6S,15S,17S)-17-[8-chloro-7-methoxy-2-(4-isopropylthiazol-2-yl)quinazolin-4-yloxy]-13-N-methyl-2,14-dioxo-1,3,13-triazatricyclo[13.3.0.0]octadec-7-ene-4-carboxylic acid 109d. Compound 109d was synthesized from compound 108d as a white solid in 16% yield, following the procedure as described for compound 55c.

MS (ESI, EI$^+$) m/z=669 (MH$^+$).

Step I: Preparation of (Z)-(4R,6S,15S,17S)-[17-[8-chloro-7-methoxy-2-(4-isopropylthiazol-2-yl)quinazolin-4-yloxy]-13-N-methyl-2,14-dioxo-1,3,13-triazatricyclo[13.3.0.0]octadec-7-ene-4-yl]carbonyl(1-methylcyclopropyl)sulfonamide 110d. Compound 110d was synthesized from compound 109d as a white solid in 16% yield, following the procedure as described for compound 56c.

MS (ESI, EI$^+$) m/z=786 (MH$^+$).

Scheme 21

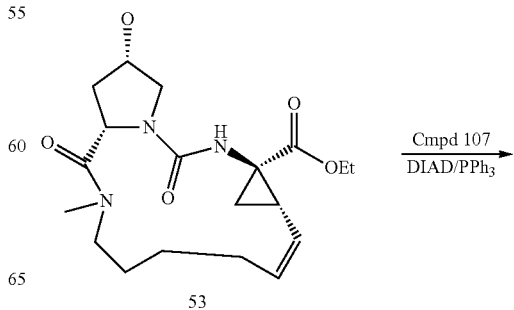

53

141
-continued

142

Example 19

Preparation of Macrocyclic Compound 91e

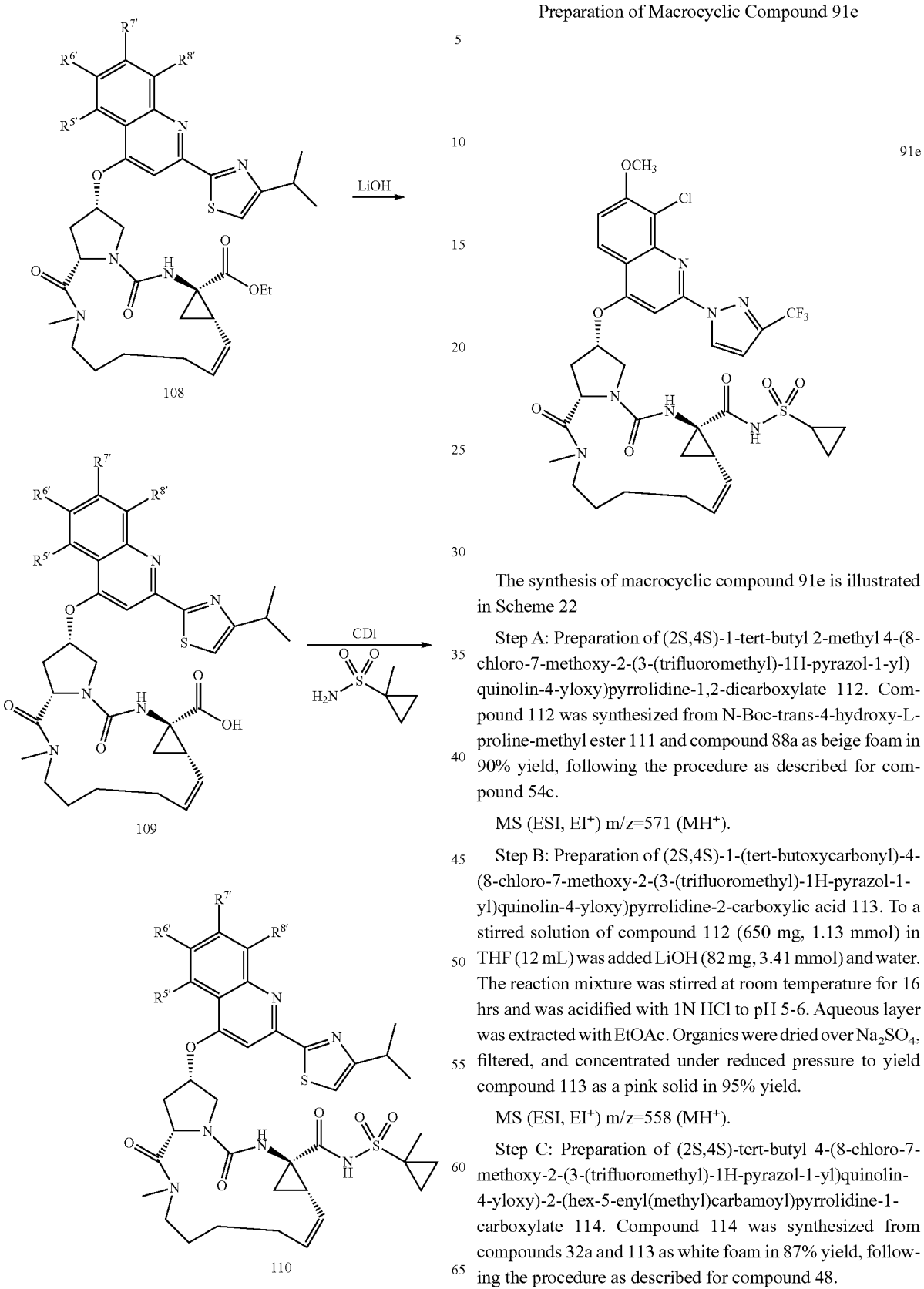

The synthesis of macrocyclic compound 91e is illustrated in Scheme 22

Step A: Preparation of (2S,4S)-1-tert-butyl 2-methyl 4-(8-chloro-7-methoxy-2-(3-(trifluoromethyl)-1H-pyrazol-1-yl)quinolin-4-yloxy)pyrrolidine-1,2-dicarboxylate 112. Compound 112 was synthesized from N-Boc-trans-4-hydroxy-L-proline-methyl ester 111 and compound 88a as beige foam in 90% yield, following the procedure as described for compound 54c.

MS (ESI, EI$^+$) m/z=571 (MH$^+$).

Step B: Preparation of (2S,4S)-1-(tert-butoxycarbonyl)-4-(8-chloro-7-methoxy-2-(3-(trifluoromethyl)-1H-pyrazol-1-yl)quinolin-4-yloxy)pyrrolidine-2-carboxylic acid 113. To a stirred solution of compound 112 (650 mg, 1.13 mmol) in THF (12 mL) was added LiOH (82 mg, 3.41 mmol) and water. The reaction mixture was stirred at room temperature for 16 hrs and was acidified with 1N HCl to pH 5-6. Aqueous layer was extracted with EtOAc. Organics were dried over Na$_2$SO$_4$, filtered, and concentrated under reduced pressure to yield compound 113 as a pink solid in 95% yield.

MS (ESI, EI$^+$) m/z=558 (MH$^+$).

Step C: Preparation of (2S,4S)-tert-butyl 4-(8-chloro-7-methoxy-2-(3-(trifluoromethyl)-1H-pyrazol-1-yl)quinolin-4-yloxy)-2-(hex-5-enyl(methyl)carbamoyl)pyrrolidine-1-carboxylate 114. Compound 114 was synthesized from compounds 32a and 113 as white foam in 87% yield, following the procedure as described for compound 48.

MS (ESI, EI$^+$) m/z=653 (MH$^+$).

Scheme 22
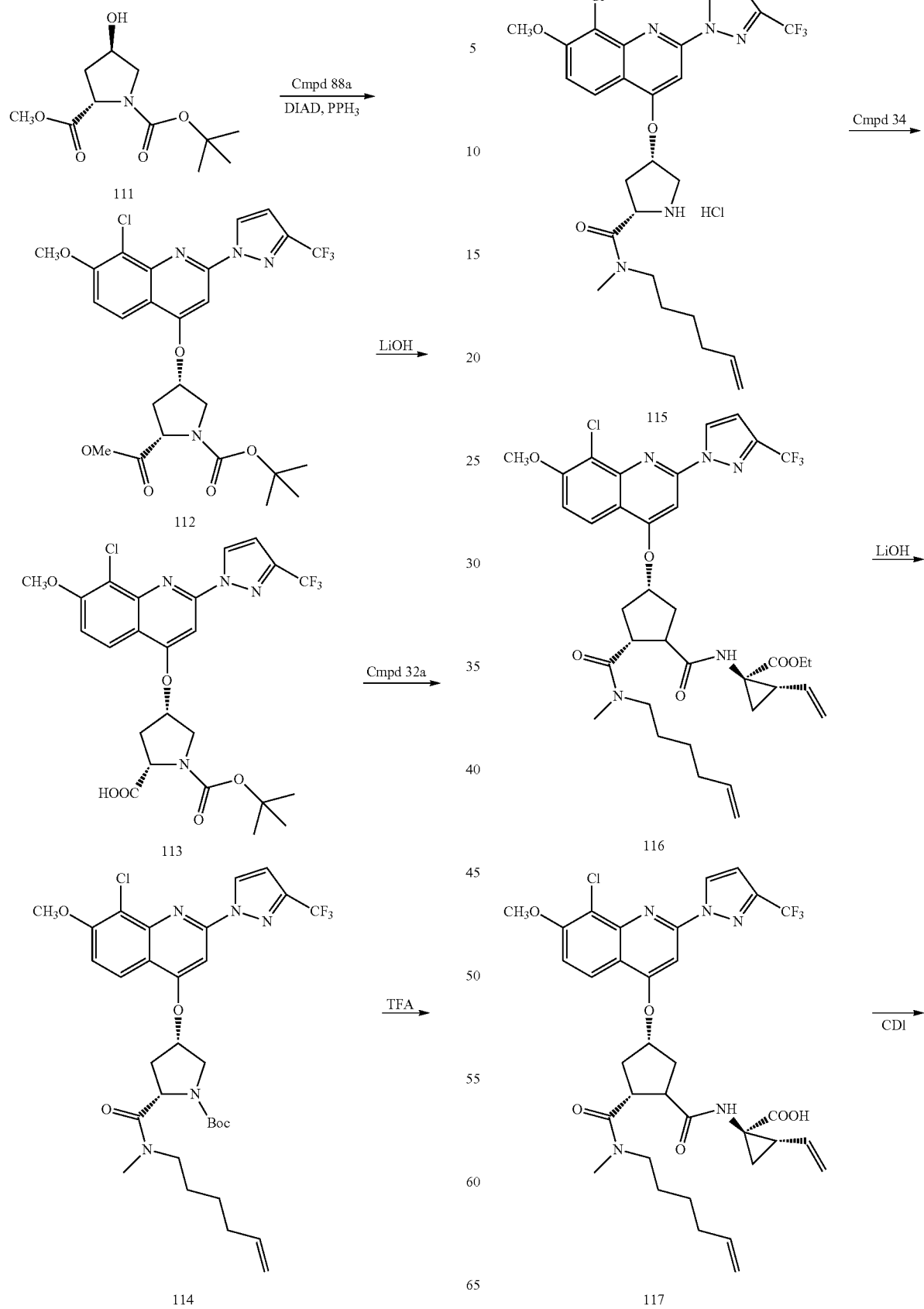

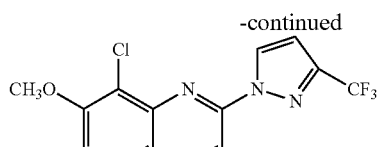

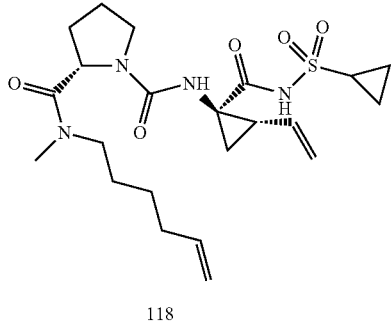

118

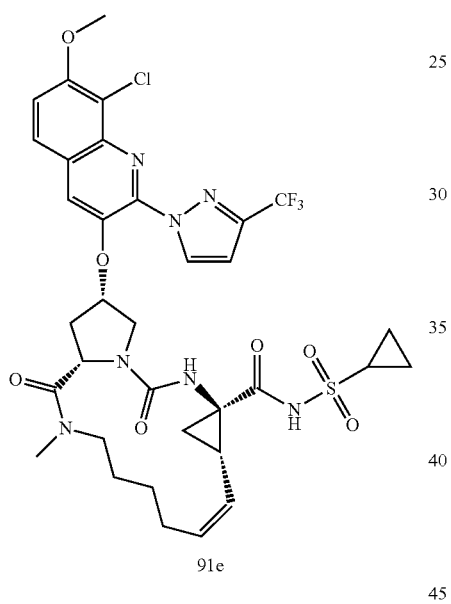

91e

Step D: Preparation of (2S,4S)-4-(8-chloro-7-methoxy-2-(3-(trifluoromethyl)-1H-pyrazol-1-yl)quinolin-4-yloxy)-N-(hex-5-enyl)-N-methylpyrrolidine-2-carboxamide 115. Compound 115 was synthesized from compound 114 as a white solid in quantitative yield, following the procedure as described for compound 82.

MS (ESI, EI$^+$) m/z=553 (MH$^+$).

Step E: Preparation of (1R,2S)-ethyl 1-((2S,4S)-4-(8-chloro-7-methoxy-2-(3-(trifluoromethyl)-1H-pyrazol-1-yl)quinolin-4-yloxy)-2-(hex-5-enyl(methyl)carbamoyl)pyrrolidine-1-carboxamido)-2-vinylcyclopropanecarboxylate 116. Compound 116 was synthesized from compounds 33 and 115 as a white solid in 75% yield, following the procedure as described for compound 50.

MS (ESI, EI$^+$) m/z=734 (MH$^+$).

Step F: Preparation of (1R,2S)-1-((2S,4S)-4-(8-chloro-7-methoxy-2-(3-(trifluoromethyl)-1H-pyrazol-1-yl)quinolin-4-yloxy)-2-(hex-5-enyl(methyl)carbamoyl)pyrrolidine-1-carboxamido)-2-vinylcyclopropanecarboxylic acid 117.

Compound 117 was synthesized from compound 116 as a white solid in 60% yield, following the procedure as described for compound 55c.

MS (ESI, EI$^+$) m/z=706 (MH$^+$).

Step G: Preparation of (2S,4S)-4-(8-chloro-7-methoxy-2-(3-(trifluoromethyl)-1H-pyrazol-1-yl)quinolin-4-yloxy)-N1-((1R,2S)-1-(cyclopropylsulfonylcarbamoyl)-2-vinylcyclopropyl)-N2-(hex-5-enyl)-N2-methylpyrrolidine-1,2-dicarboxamide 118. Compound 118 was synthesized from compound 117 and cyclopropylamine as a white solid in 40% yield, following the procedure as described for compound 56c.

MS (ESI, EI$^+$) m/z=809 (MH$^+$).

Step H: Preparation of (Z)-(4R,6S,15S,17S)-[17-[8-chloro-7-methoxy-2-(3-trifluoromethyl-1H-pyrazol-1-yl)quinolin-4-yloxy]-13-N-methyl-2,14-dioxo-1,3,13-triazatricyclo[13.3.0.0]octadec-7-ene-4-yl]carbonyl(cyclopropyl)sulfonamide 91e. To a stirred solution of compound 118 (55 mg, 0.07 mmol) in degassed DCE (68 ml) at 40° C. was added Zhan IB catalyst (1 mg, 2% mol). After the reaction mixture was stirred for 1 hr at 40° C., a second batch of Zhan IB catalyst (0.5 mg) was added. After the reaction mixture was stirred for 1 hr at 60° C., a third batch of Zhan IB catalyst (0.5 mg) was added. The reaction mixture was stirred at 60° C. for 16 hrs. The mixture was concentrated under reduced pressure and purified by chromatography on silica gel (petroleum ether/EtOAc) to yield compound 91e as a beige solid in 40% yield.

MS (ESI, EI$^+$) m/z=780 (MH$^+$)

Example 20

Preparation of Substituted Quinolines 88

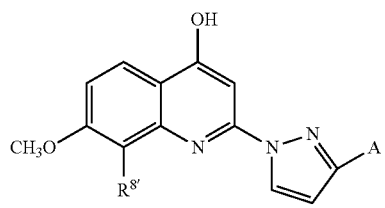

88a: R$^{8'}$ = CH$_3$, A = CF$_3$
88b: R$^{8'}$ = Cl$_3$, A = CF$_3$
88c: R$^{8'}$ = Cl$_3$, A = iPr
88d: R$^{8'}$ = CH$_3$, A = iPr

The syntheses of substituted quinolines are illustrated in Scheme 23 where R$^{8'}$ and A in compound 119 are the same as defined in compound 88.

Scheme 23

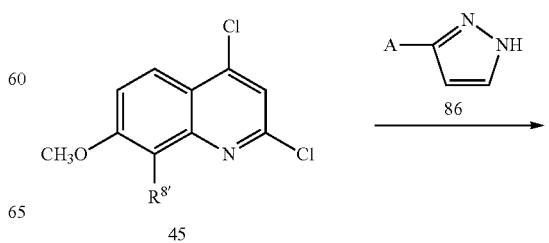

45

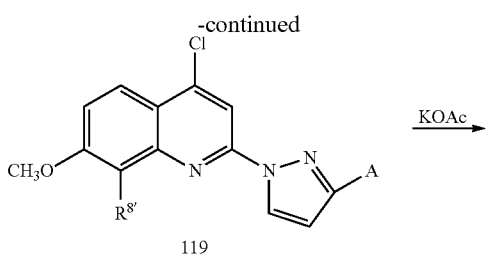

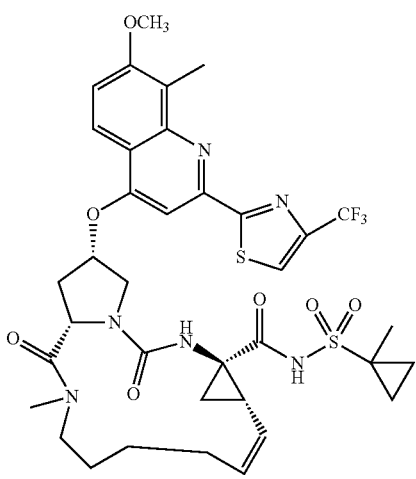

pound 120 (51 g) was dissolved in THF (170 mL) at room temperature. Sodium hydroxide in water (1.47 eq. in 170 mL) was added. The reaction mixture was stirred at room temperature for 15 hrs, warmed to 50° C. for 1.5 hrs, and then cooled before neutralizing with 5M HCl. After neutralizing with 5M HCl, the reaction mixture was extracted with DCM. The organic layer was washed with water and brine, dried over sodium sulfate, and concentrated under vacuum to yield compound 121 (47.7 g) as a thick, yellow oil in 99% yield.

Scheme 24

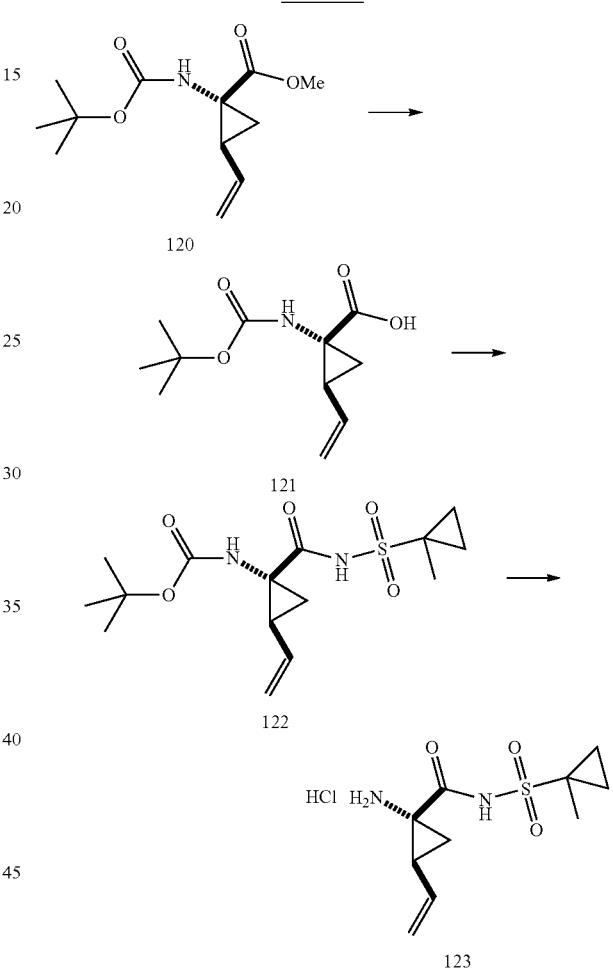

Step A: Synthesis of 4,8-dichloro-7-methoxy-2-(3-(trifluoromethyl)-1H-pyrazol-1-yl)quinoline 119b. A mixture of compound 45d (5 g, 19 mmol) and 3-trifluoromethylpyrazole 86a (7.76 g, 57 mmol) was heated at 120° C. for 4-6 hrs and the reaction was followed by LCMS and TLC. The reaction mixture was purified by silica gel column (mono and dipyrazole were separated) using DCM and heptane as mobile phase to yield compound 119b (3.5 g) in 51% yield.

Step B: Synthesis of 8-chloro-7-methoxy-2-(3-(trifluoromethyl)-1H-pyrazol-1-yl)quinolin-4-ol 88b. To a solution of compound 119b (250 mg) in DMSO (2.5 mL) was added CH$_3$COOK (3 eq.), water (2 eq.). The reaction mixture was heated to 140° C. for 4 hrs. After cooled to RT, water (1 mL) was added to the reaction mixture slowly under stirring. Solid was filtered and washed with water to yield compound 88b in >80% yield. In a separate reaction, when 5 eq. of CH$_3$COOK was used, the reaction was completed in 1 hr.

Example 21

Preparation of Macrocyclic Compound 68b

The synthesis of macrocyclic compound 68b is illustrated in Schemes 24 and 25.

Step A: Synthesis of (1R,2S)-1-(tert-butoxycarbonylamino)-2-vinylcyclopropanecarboxylic acid 121. Compound 120 (51 g) was dissolved in THF (170 mL) at room temperature.

Step B: Synthesis of tert-butyl (1R,2S)-1-(1-methylcyclopropylsulfonyl-carbamoyl)-2-vinylcyclopropylcarbamate 122. Compound 121 (104.6 g) was dissolved in THF (1.0 L) at room temperature under argon. CDI (1.5 eq.) was added and the reaction mixture was refluxed for 20 min. After the reaction mixture was cooled to 4-6° C., sulfonamide (1.5 eq.) was added, followed by the addition of DBU (2 eq.). After stirring at room temperature for 64 hrs, the reaction mixture was diluted with DCM, neutralized with 1M HCl, and washed with saturated brine to pH 7. The organics were dried over sodium sulfate and concentrated to give an off-white solid in 106.4 g. Crystallization from methanol/water gave compound 122 (91 g) as a white solid in 77% yield.

Step C: Synthesis of (1R,2S)-1-amino-N-(1-methylcyclopropylsulfonyl)-2-vinylcyclopropanecarboxamide hydrochloride 123. Compound 122 (51.5 g) was suspended in methanol (150 mL). A solution of acetyl chloride (3 eq.) in methanol was added to the suspension. The reaction mixture was heated at 50° C. for 3 hrs. The reaction mixture was concentrated at 45-50° C. and co-evaporated with DCM to give compound 123 (42.4 g) as a white powder in 102% yield due to DCM.
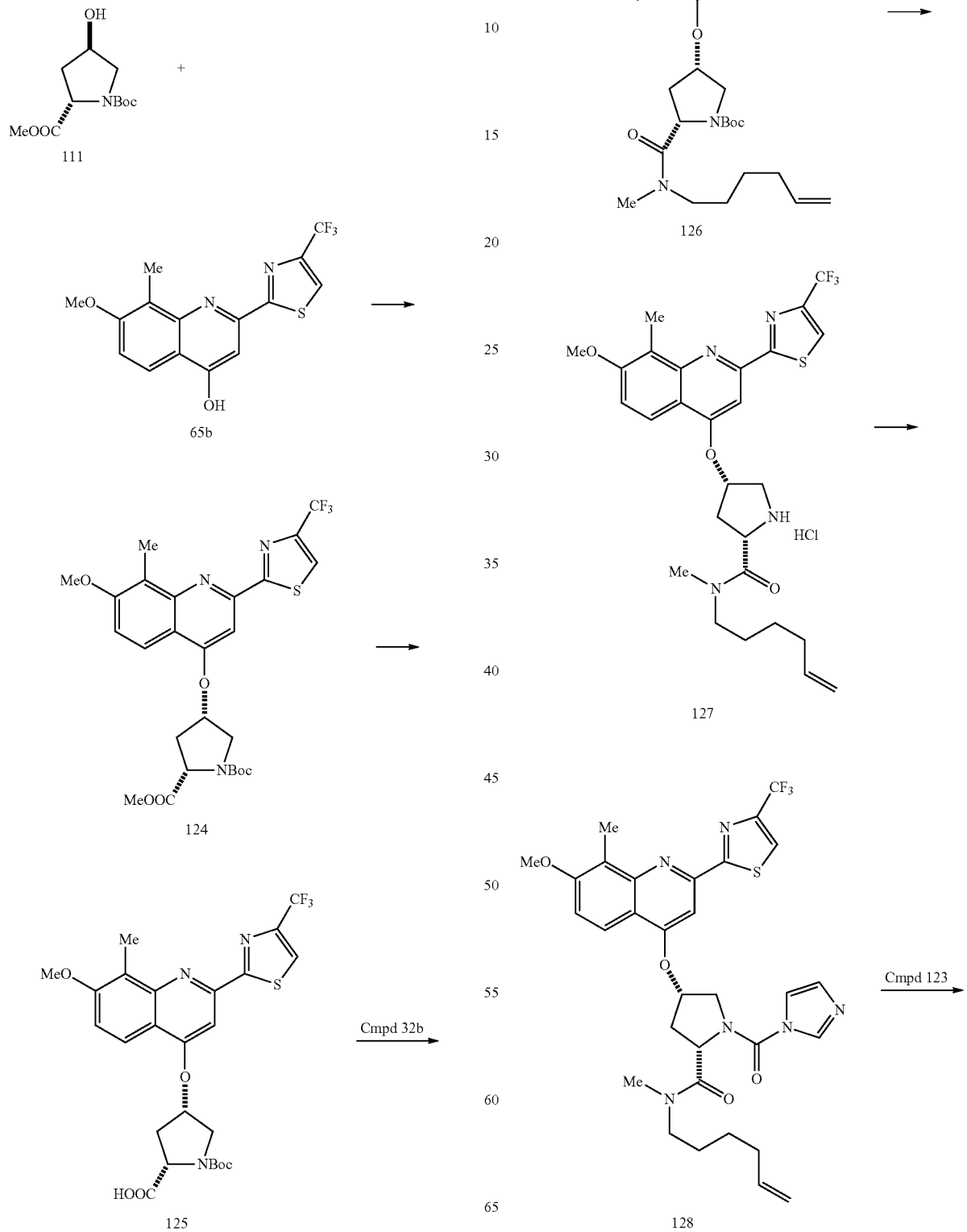

-continued

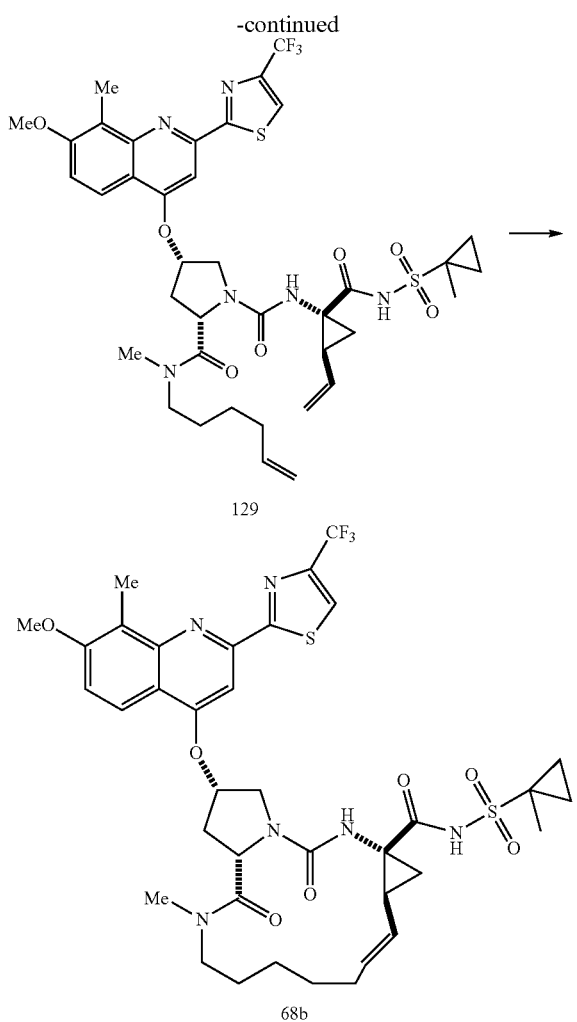

Step D: Synthesis of (2S,4S)-1-tert-butyl 2-methyl 4-(7-methoxy-8-methyl-2-(4-(trifluoromethyl)thiazol-2-yl)quinolin-4-yloxy)pyrrolidine-1,2-dicarboxylate 124. Triphenylphosphine (1.5 eq.) was dissolved in 180 mL of tetrahydrofuran under argon. The solution was cooled down to 0-5° C. DIAD (1.5 eq.) was slowly added over a period of 15-20 min. Compound 65b (20 g, 1 eq.) was added over 5-10 min at the temperature of 0-5° C. Compound III (17.6 g, 1.2 eq.) was added, and the reaction mixture was warmed to room temperature. One hour later, the reaction mixture was concentrated under vacuum at 40-45° C. and the crude was triturated with MeOH, TBME, and heptane to yield compound 124 (22.24 g) as a white powder in 67% yield and 98.7% purity.

MS: m/z (ESI$^+$)=568.27 [M+H]$^+$, 100%; m/z (ESI$^-$)=626.50 [M+OAc]$^-$, 100%.

Step E: Synthesis of (2S,4S)-1-(tert-butoxycarbonyl)-4-(7-methoxy-8-methyl-2-(4-(trifluoromethyl)thiazol-2-yl)quinolin-4-yloxy)pyrrolidine-2-carboxylic acid 125. Compound 124 (22.24 g) was dissolved in THF (66 mL) at room temperature. Water (66 mL) was added, followed by lithium hydroxide (5 eq.) in one portion. The reaction mixture was heated at 40° C. for 3 hrs, cooled, acidified with 5M HCl, and extracted with DCM. The organic phase was dried over Na$_2$SO$_4$ and concentrated under vacuum to give compound 125 (21.33 g) as an off-white powder in 92% yield (7.5 w % of THF) and 99% purity.

MS: m/z (ESI$^+$)=554.24 [M+H]$^+$, 100%; m/z (ESI$^-$)=552.37 [M−H]$^-$, 100%.

Step F: Synthesis of (2S,4S)-tert-butyl 2-(hex-5-enyl(methyl)carbamoyl)-4-(7-methoxy-8-methyl-2-(4-(trifluoromethyl)thiazol-2-yl)quinolin-4-yloxy)pyrrolidine-1-carboxylate 126. Compound 125 (21.33 g) was dissolved in anhydrous DMF (48 mL) at room temperature. O-(Benzotriazol-1-yl)-N,N,N',N'-tetramethyluronium tetrafluoroborate (1.25 eq.) was added at room temperature and the reaction mixture was stirred for 10 min. Compound 32b (1.1 eq.) was added and the reaction mixture was stirred for additional 10-15 min. After cooling to 5° C., diisopropylethylamine (3 eq.) was added. After warming to room temperature for 1 hr, the reaction mixture was diluted with ethyl acetate, washed with brine and ammonium chloride, dried over Na$_2$SO$_4$, and concentrated under vacuum to give crude 126 (22.09 g) as an orange foam. The crude product was crystallized from ethyl acetate and heptane to give compound 126 (20.8 g) as an off-white powder in 90% yield and 99% purity.

MS: m/z (ESI$^+$)=649.43 [M+H]$^+$, 100%; m/z (ESI$^-$)=707.57 [M+OAc]$^-$, 100%.

Step G: Synthesis of (2S,4S)—N-(hex-5-enyl)-4-(7-methoxy-8-methyl-2-(4-(trifluoromethyl)thiazol-2-yl)quinolin-4-yloxy)-N-methylpyrrolidine-2-carboxamide 127. Compound 126 (19.92 g) was suspended in anhydrous methanol (120 mL) under argon at room temperature. Separately acetyl chloride (3 eq.) was added to anhydrous methanol (60 mL) at 10-20° C. This solution was added to the compound 126 solution at 5° C. The reaction mixture was heated at 40° C. for 3-4 hrs. After the completion of the reaction, the reaction mixture was concentrated under vacuum and then co-evaporated with 200 mL of anhydrous dichloromethane. The product was then dried in a vacuum oven at 40-45° C. Compound 127 (18.35 g) was recovered as a yellow foam in quantitative yield and 100% purity (HPLC).

MS: m/z (ESI$^+$)=549.31 [M+H]$^+$, 100%; m/z (ESI$^-$)=607.50 [M+OAc]$^-$, 100%.

Step H: Synthesis of (2S,4S)—N-(hex-5-enyl)-1-(1H-imidazole-1-carbonyl)-4-(7-methoxy-8-methyl-2-(4-(trifluoromethyl)thiazol-2-yl)quinolin-4-yloxy)-N-methylpyrrolidine-2-carboxamide 128. Compound 127 (18.35 g) was dissolved in anhydrous dichloromethane (37 mL) under argon. 1,1'-Carbonyldiimidazole (2 eq.) was added at room temperature. The reaction mixture was stirred for 40 min. The mixture was diluted with DCM, washed with water, dried over Na$_2$SO$_4$, and concentrated under vacuum. Compound 128 (19.39 g) was recovered as a pale yellow foam in 99% yield over two steps and in 98% purity (HPLC).

MS: m/z (ESI$^-$): 701.63 [M+OAc]$^-$, 100%.

Step I: Synthesis of (2S,4S)—N$^2$-(hex-5-enyl)-4-(7-methoxy-8-methyl-2-(4-(trifluoromethyl)thiazol-2-yl)quinolin-4-yloxy)-N$^2$-methyl-N$^1$-((1R,2S)-1-(1-methylcyclopropylsulfonylcarbamoyl)-2-vinylcyclopropyl)pyrrolidine-1,2-dicarboxamide 129. Compounds 128 (18.89 g) and 123 were mixed at room temperature in anhydrous acetonitrile (76 mL) and heated at 65° C. until the reaction was complete. The reaction mixture was then concentrated under vacuum to yield a first orange foam (36.21 g). The first foam was dissolved in DCM and repeatedly washed with brine, dried over Na$_2$SO$_4$, and concentrated under vacuum to give a second orange foam (25.08 g). Compound 129 (12.2 g) was crystallized from a solution of the second orange foam in DCM, ethyl acetate, and heptane as a white solid in 50.8% yield and 98% purity.

MS: m/z (ESI$^+$)=819.54 [M+H]$^+$, 100%; m/z (ESI$^-$)=817.60 [M−H]$^-$, 100%.

Step J: Synthesis of 1-methyl-cyclopropanesulfonic acid {(Z)-(4R,6S,15S,17S)-17-[7-methoxy-8-methyl-2-(4-trifluoromethyl-thiazol-2-yl)-quinolin-4-yloxy]-13-methyl-2,14-dioxo-1,3,13-triaza-tricyclo[13.3.0.0*4,6*]octadec-7-ene-4-carbonyl}-amide 68b. Compound 129 (3.91 g) was dissolved in dichloroethane (980 mL) under Ar at room temperature. The solution was degassed with argon and then heated at 73-77° C. Zhan 1B catalyst (1%) in dichloroethane was slowly added to the reaction solution. At 25 min, another 1% of the catalyst in DCE was added. In total, 8% of the catalyst was added over 4 hrs and 20 min. The reaction mixture was treated with 2-mercaptonicotinic acid ("MNA") (1 g). The reaction mixture was cooled down to room temperature, concentrated under vacuum to ~100 mL, and then washed with 0.5M aqueous NaHCO$_3$. To the separated organic phase was added MNA (1 g) and the mixture was stirred at room temperature for 55-65 min. The mixture was washed twice with aqueous 0.5M NaHCO$_3$, dried over Na$_2$SO$_4$, and filtered. Charcoal (11 g) was added to the organic solution and the mixture was stirred at room temperature for 15 hrs. The mixture was concentrated under vacuum to ~10-15 mL and filtered through a silica plug. The crude solid was triturated in warm methanol to give compound 68b (1.1 g) as an off-white solid in 30% yield and 98% purity.

MS: m/z (ESI$^+$)=791.47 [M+H]$^+$, 100%; m/z (ESI$^-$)=789.57 [M−H]$^-$, 100%.

Example 22

Preparation of Macrocyclic Compound 62d

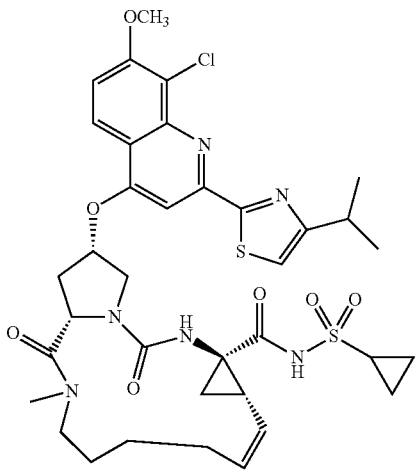

The synthesis of macrocyclic compound 62d is illustrated in Schemes 26 and 27.

Step A: Synthesis of tert-butyl (1R,2S)-1-(cyclopropylsulfonyl-carbamoyl)-2-vinylcyclopropylcarbamate 130. Compound 121 (47.75 g) was dissolved in THF (480 mL) at room temperature. CDI (1.3 eq.) was added and the reaction mixture was refluxed for 30 min. After the reaction mixture was cooled to 20° C., sulfonamide (1.5 eq.) was added, followed by the addition of DBU (2 eq.). After stirring at room temperature for 15 hrs, the reaction mixture was diluted with DCM, neutralized with 5M HCl, and washed with saturated brine to pH 7. The organics were dried over sodium sulfate and concentrated to give an off-white solid in 65 g. Crystallization from methanol/water gave compound 130 (60.17 g) as a white solid in 87% yield.

Step B: Synthesis of (1R,2S)-1-amino-N-(cyclopropylsulfonyl)-2-vinylcyclopropanecarboxamide hydrochloride 131. Compound 130 (1 g) was suspended in methanol (2.5 mL). A solution of acetyl chloride (3 eq.) in methanol was added to the suspension. The reaction mixture was heated at 50° C. for 3 hrs. The reaction mixture was concentrated at 45-50° C. and co-evaporated with DCM to give compound 131 (833 mg) as a white foam in 103% yield due to DCM.

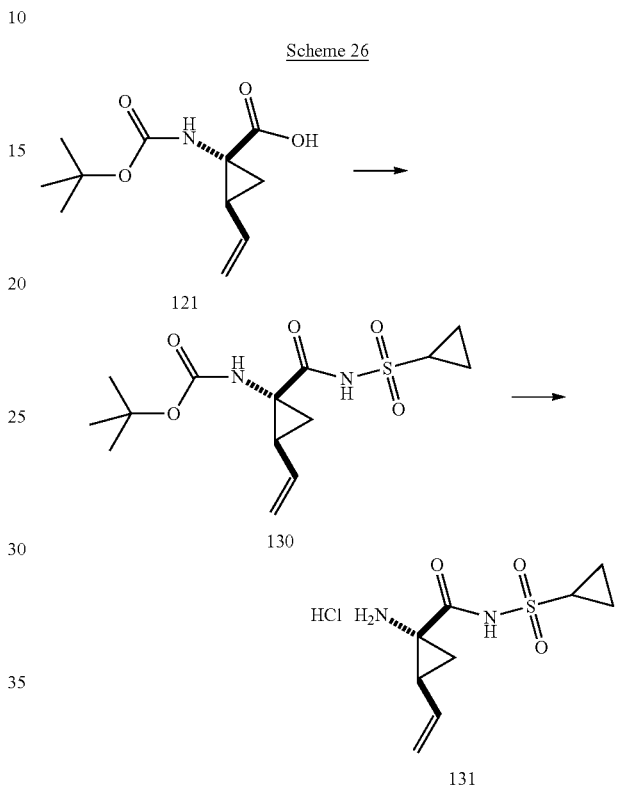

Scheme 26

Step C: Synthesis of (2S,4S)-1-tert-butyl 2-methyl 4-(8-chloro-2-(4-isopropylthiazol-2-yl)-7-methoxyquinolin-4-yloxy)pyrrolidine-1,2-dicarboxylate 132. Triphenylphosphine (1.5 eq.) was dissolved in 250 mL of tetrahydrofuran under argon. The solution was cooled down to 0-5° C. DIAD (1.5 eq.) was slowly added over a period of 15-20 min. Compound 56d (25 g, 1 eq.) was added over 5-10 min at the temperature of 0-5° C. Compound III (22.48 g, 1.2 eq.) was added, and the reaction mixture was warmed to room temperature. Three hours later, the reaction mixture was concentrated under vacuum at 40-45° C. and the crude was triturated with MeOH, TBME, and heptane to yield compound 132 (30 g) as a white powder in 70% yield and 98.7% purity.

MS: m/z (ESI$^+$)=562.35 [M+H]$^+$, 100%, 564.31, [M+H]$^+$, 35%; m/z (ESI$^-$)=620.55 [M+OAc]$^-$, 100%, 622.55 [M+OAc]$^-$, 35%.

Step D: Synthesis of (2S,4S)-1-(tert-butoxycarbonyl)-4-(8-chloro-2-(4-isopropylthiazol-2-yl)-7-methoxyquinolin-4-yloxy)pyrrolidine-2-carboxylic acid 133. Compound 132 (20 g) was dissolved in THF (66 mL) at room temperature. Water (66 mL) was added, followed by lithium hydroxide (5 eq.) in one portion. The reaction mixture was heated at 40° C. for 3 hrs, cooled, acidified with 5M HCl, and extracted with DCM. The organic phase was dried over Na$_2$SO$_4$ and concentrated under vacuum to give compound 133 (20.57 g) as a yellow form in 99% yield and 96-97% purity.

155
MS: m/z (ESI⁺)=548.37 [M+H]⁺, 100%, 550.33, [M+H]⁺, 35%; m/z (ESI⁻)=546.49 [M−H]⁻, 100%, 548.52 [M−H]⁻, 35%.
Scheme 27
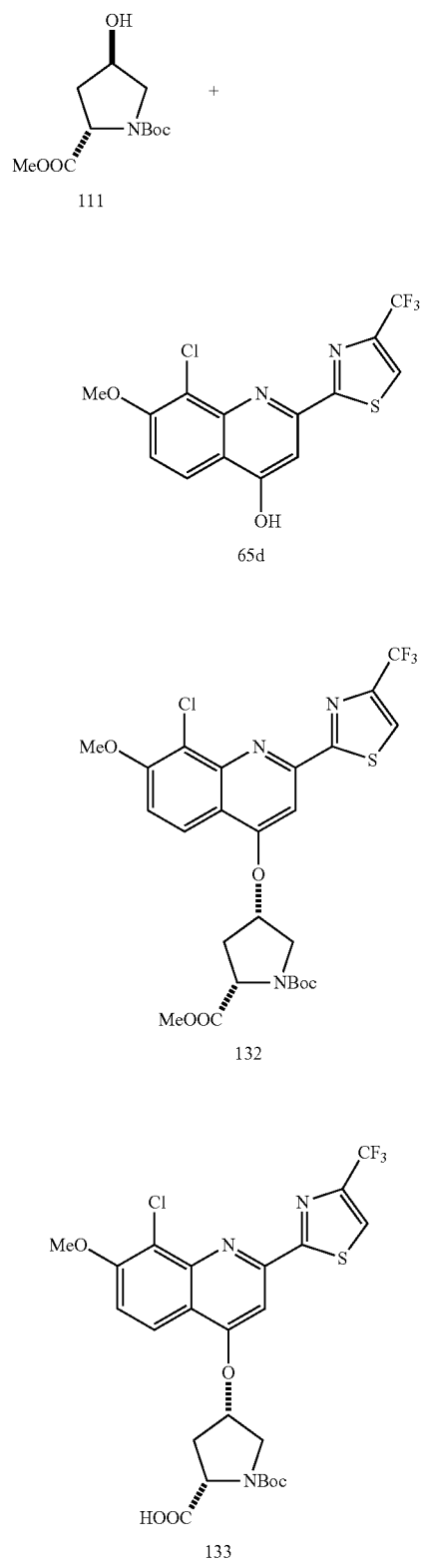
156
-continued
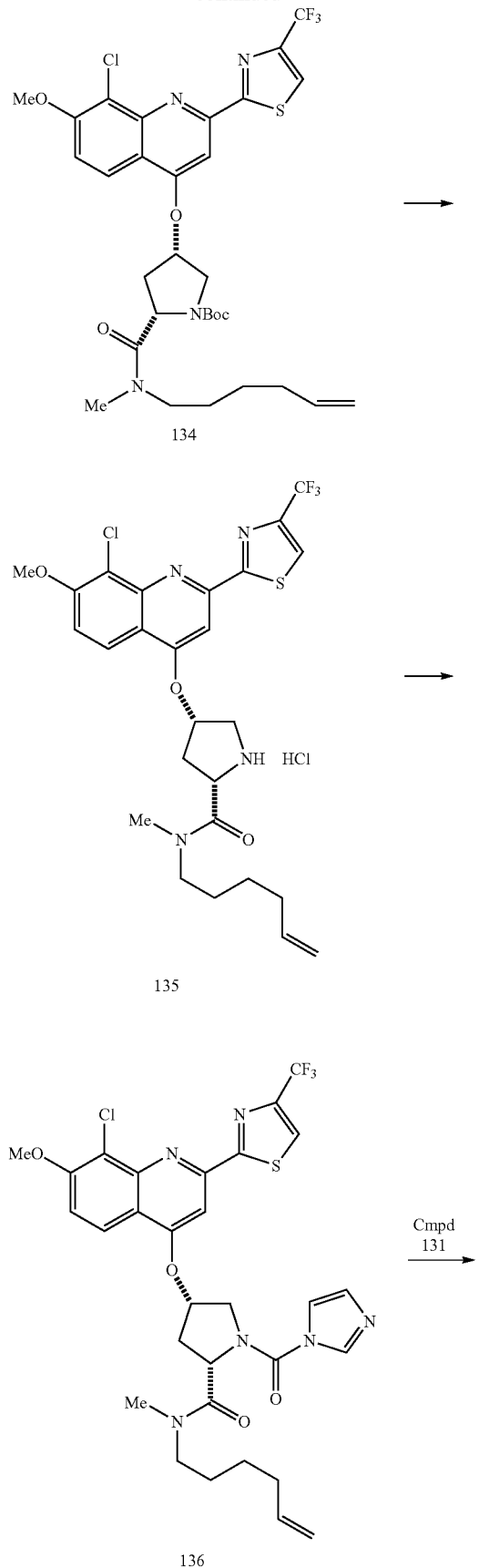

-continued

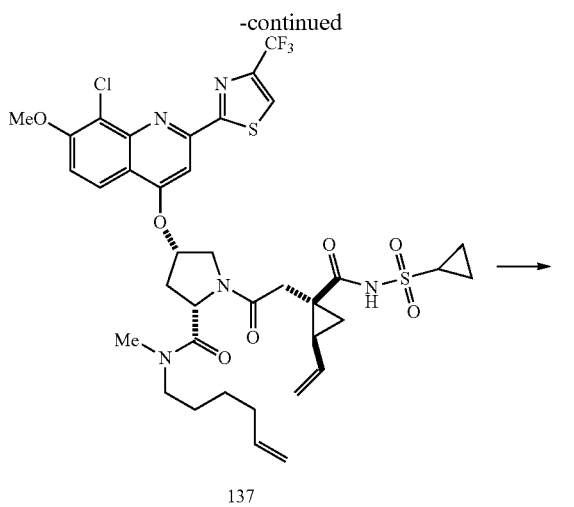

137

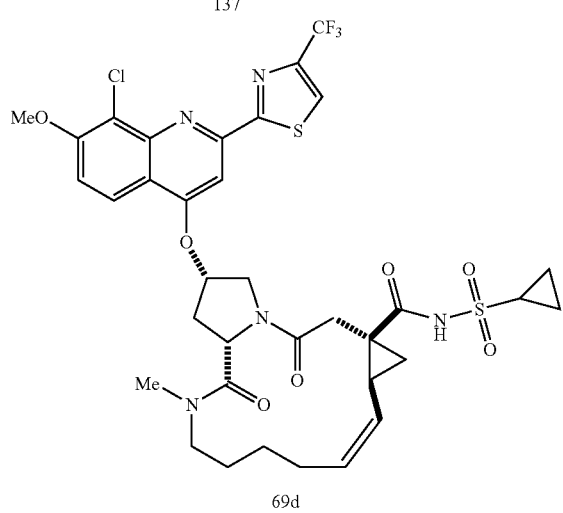

69d

Step E: Synthesis of (2S,4S)-tert-butyl 4-(8-chloro-2-(4-isopropylthiazol-2-yl)-7-methoxyquinolin-4-yloxy)-2-(hex-5-enyl(methyl)carbamoyl)pyrrolidine-1-carboxylate 134. Compound 133 (20.5 g) was dissolved in anhydrous DMF (48 mL) at room temperature. O-(Benzotriazol-1-yl)-N,N,N',N'-tetramethyluronium tetrafluoroborate (1.25 eq.) was added at room temperature and the reaction mixture was stirred for 10 min. Compound 32a (1.1 eq.) was added and the reaction mixture was stirred for additional 10-15 min. After cooling to 5° C., diisopropylethylamine (3 eq.) was added. After warming to room temperature for 1 hr, the reaction mixture was diluted with ethyl acetate, washed with brine and ammonium chloride, dried over $Na_2SO_4$, and concentrated under vacuum to give crude 134 (22.09 g) as an orange foam. The crude product was crystallized from ethyl acetate and heptane to give compound 134 (20.55 g) as a white powder in 92% yield and 98% purity.

MS: m/z (ESI$^+$)=643.48 [M+H]$^+$, 100%, 645.48, [M+H]$^+$, 35%; m/z (ESI$^-$)=701.74 [M+OAc]$^-$, 100%, 703.71 [M+OAc]$^-$, 35%.

Step F: Synthesis of (2S,4S)-4-(8-chloro-2-(4-isopropylthiazol-2-yl)-7-methoxyquinolin-4-yloxy)-N-(hex-5-enyl)-N-methylpyrrolidine-2-carboxamide hydrochloride 135. Compound 134 (20.37 g) was suspended in anhydrous methanol (120 mL) under argon at room temperature. Separately acetyl chloride (3 eq.) was added to anhydrous methanol (70 mL) at 10-20° C. This solution was added to the compound 134 solution at 5° C. The reaction mixture was heated at 40° C. for 3-4 hrs. After the completion of the reaction, the reaction mixture was concentrated under vacuum and then co-evaporated with 100 mL of anhydrous dichloromethane. The product was then dried in a vacuum oven at 40-45° C. Compound 135 (19.81 g) was recovered as a yellow foam in quantitative yield and 100% purity (HPLC).

MS: m/z (ESI$^+$)=543.36 [M+H]$^+$, 100%, 545.33, [M+H]$^+$, 35%; m/z (ESI$^-$)=601.59 [M+OAc]$^-$, 100%, 603.57 [M+OAc]$^-$, 35%.

Step G: Synthesis of (2S,4S)-4-(8-chloro-2-(4-isopropylthiazol-2-yl)-7-methoxyquinolin-4-yloxy)-N-(hex-5-enyl)-1-(1H-imidazole-1-carbonyl)-N-methylpyrrolidine-2-carboxamide 136. Compound 135 (10 g) was dissolved in anhydrous dichloromethane (20 mL) under argon. 1,1'-Carbonyldiimidazole (2 eq.) was added at room temperature. The reaction mixture was stirred for 45 min. The mixture was diluted with DCM, washed with water, dried over $Na_2SO_4$, and concentrated under vacuum. Compound 136 (9.9 g) was recovered as an off-white foam in 99% yield and in 98% purity (HPLC).

MS: m/z (ESI$^+$)=637.54 [M+H]$^+$, 100%, 639.56, [M+H]$^+$, 35%.

Step H: Synthesis of (2S,4S)-4-(8-chloro-2-(4-isopropylthiazol-2-yl)-7-methoxyquinolin-4-yloxy)-N$^1$-((1R,2S)-1-(cyclopropylsulfonylcarbamoyl)-2-vinylcyclopropyl)-N$^2$-(hex-5-enyl)-N$^2$-methylpyrrolidine-1,2-dicarboxamide 137. Compounds 136 (7.2 g) and 131 were mixed at room temperature in anhydrous acetonitrile (29 mL) and heated at 65° C. until the reaction was complete. The reaction mixture was then concentrated under vacuum to yield a first orange foam (14.0 g). The first foam was dissolved in DCM and repeatedly washed with brine, dried over $Na_2SO_4$, and concentrated under vacuum to give a second orange foam (9.63 g). Compound 137 (4.48 g) was crystallized from a solution of the second orange foam in acetone and TBME as a white solid in 49% yield and 98% purity. A second crop gave an additional 554 mg compound 137, thus the total yield was 55%.

MS: m/z (ESI$^+$)=799.61 [M+H]$^+$, 100%, 801.57, [M+H]$^+$, 35%; m/z (ESI$^-$)=797.72 [M+OAc]$^-$, 100%, 799.71 [M+OAc]$^-$, 35%.

Step I: Synthesis of Cyclopropanesulfonic acid {(Z)-(4R,6S,15S,17S)-17-[8-chloro-2-(4-isopropyl-thiazol-2-yl)-7-methoxy-quinolin-4-yloxy]-13-methyl-2,14-dioxo-1,3,13-triaza-tricyclo[13.3.0.0*4,6*]octadec-7-ene-4-carbonyl}-amide 62d. Compound 137 (5.5 g) was dissolved in dichloroethane (1.375 mL) under Ar at room temperature. The solution was degassed with argon and then heated at 73-77° C. Zhan 1B catalyst (1%) in dichloroethane was slowly added to the reaction solution. At 25 min, another 1% of the catalyst in DCE was added. At 45 min, 2-mercaptonicotinic acid (0.5 eq.) was added. The reaction mixture was cooled down to room temperature, concentrated under vacuum to ~130 mL, and then washed with 0.5M aqueous NaHCO$_3$. To the separated organic phase was added MNA (0.5 eq.) and the mixture was stirred at room temperature for 55-65 min. The mixture was washed twice with aqueous 0.5M NaHCO$_3$, dried over $Na_2SO_4$, and filtered. Charcoal (5.5 g) was added to the organic solution and the mixture was stirred at room temperature for 15 hrs. The mixture was concentrated under vacuum to ~10-15 mL and filtered through a silica plug. The crude solid was crystallized from hot methanol and DCE to give compound 62d (2.87 g) as a white solid in 54% yield and 98% purity. More product was obtained similarly from the filtrate to give 487 mg of a white solid. Thus, the total yield was 63%.

MS: m/z (ESI⁺)=771.54 [M+H]⁺, 100%, 773.79, [M+H]⁺, 35%; m/z (ESI⁻)=769.54 [M+OAc]⁻, 100%, 771.61 [M+OAc]⁻, 35%.

Example 23

Preparation of Macrocyclic Compounds $G_1$, $G_2$, $G_3$, and $G_4$

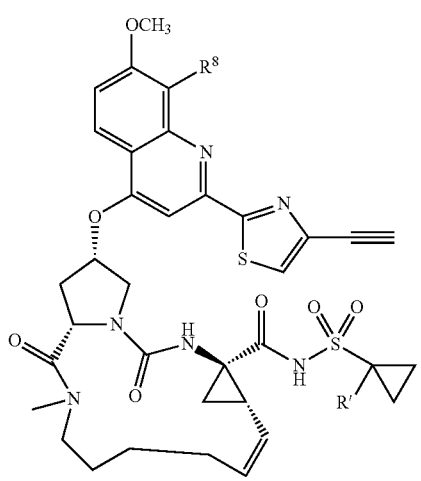

$G_1$: $R^8$ = Cl, R' = H
$G_2$: $R^8$ = Cl, R' = CH$_3$
$G_3$: $R^8$ = CH$_3$, R' = H
$G_4$: $R^8$ = CH$_3$, R' = CH$_3$

The synthesis of macrocyclic compounds $G_1$, $G_2$, $G_3$, and $G_4$ is shown in Schemes 28 and 29.

Step A: Synthesis of N-(6-acetyl-2-chloro-3-methoxyphenyl)-4-bromothiazole-2-carboxamide $A_1$. Oxalyl chloride (6.77 g, 1.4 eq.) was added dropwise under nitrogen at 0° C. to a suspension of 4-bromothiazole-2-carboxylic acid (9.52 g, 1.2 eq.) in DCM (310 mL) and DMF (315 µL). The reaction mixture was stirred at 0° C. for 30 min and then at room temperature for additional 90 min. The solvent was then removed under reduced pressure to give acid chloride used directly in the next step without further purification. Under nitrogen, a solution of 6-acetyl-2-chloro-3-methoxy aniline (7.6 g, 1 eq.) in 1,4-dioxane (310 mL) was added at 0° C. to a solution of acid chloride in 1,4-dioxane. The reaction mixture was stirred at room temperature for 2.5 hrs and the solvent was removed under reduced pressure. The residue was triturated in ether and then in isopropylacetate to yield compound $A_1$ in 14% yield.

¹H NMR (CDCl₃, 400 MHz): δ (ppm) 2.59 (s, 3H), 4 (s, 3H), 6.91 (d, J=8.78 Hz, 1H), 7.54 (s, 1H), 7.72 (d, J=8.78 Hz, 1H), 10.28 (s, 1H).

Scheme 28

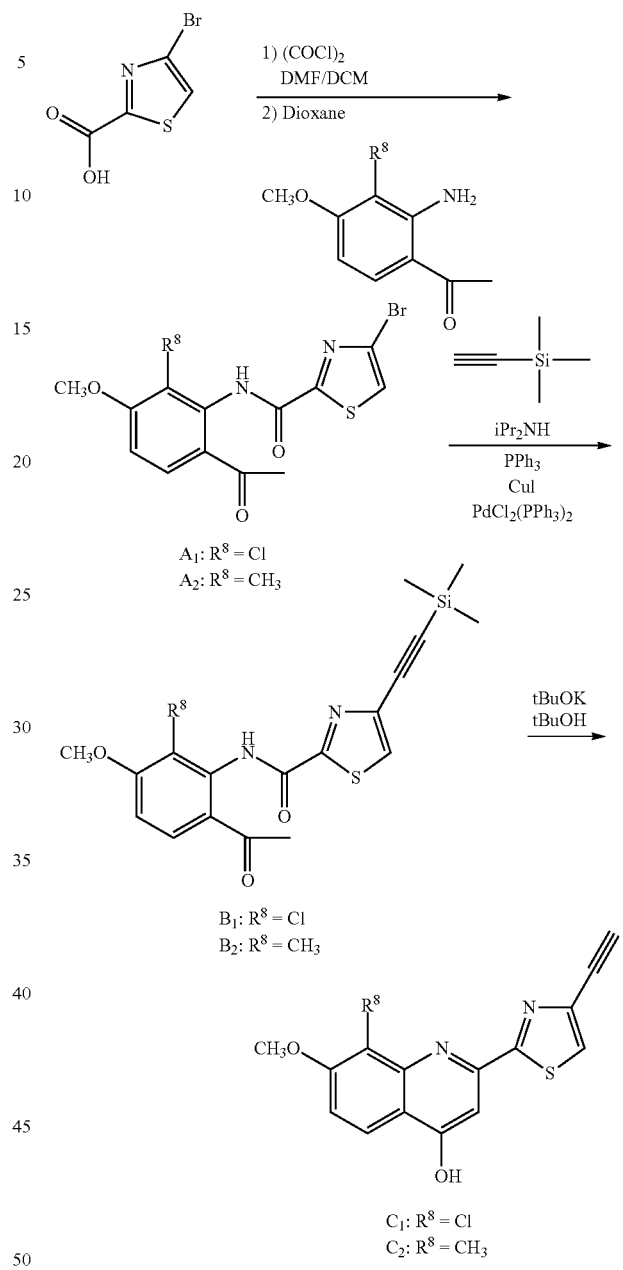

$A_1$: $R^8$ = Cl
$A_2$: $R^8$ = CH$_3$ $B_1$: $R^8$ = Cl
$B_2$: $R^8$ = CH$_3$ $C_1$: $R^8$ = Cl
$C_2$: $R^8$ = CH$_3$

Step B: Synthesis of N-(6-acetyl-2-chloro-3-methoxyphenyl)-4-(2-trimethylsilyl)ethynyl)thiazole-2-carboxamide $B_1$. Compound $A_1$ (3 g, 1 eq.), ethynyltrimethylsilane (1.6 mL, 1.5 eq.), diisopropylamine (12 mL), triphenylphosphine (0.081 g, 4%), copper(I) iodide (0.059 mg, 4%), Cl₂Pd (PPh₃)₂ (0.113 g, 2%) were mixed together and stirred at 90° C. overnight. After cooled down to room temperature, diisopropyl ether was added. The precipitate was collected by filtration, washed with diisopropyl ether and pentane. The solid was solubilized in dichloromethane and washed with water. The organic layer was dried over Na₂SO₄, filtered, and concentrated under diminished pressure to give compound $B_1$ as a brown solid in 93% yield.

¹H NMR (CDCl₃, 400 MHz) δ 0.29 (s, 9H), 2.57 (s, 3H), 4 (s, 3H), 6.91 (d, J=8.91 Hz, 1H), (d, J=8.65 Hz, 1H), 7.73 (s, 1H); MS (ESI, EI⁺) m/z=407 (MH⁺).

Scheme 29

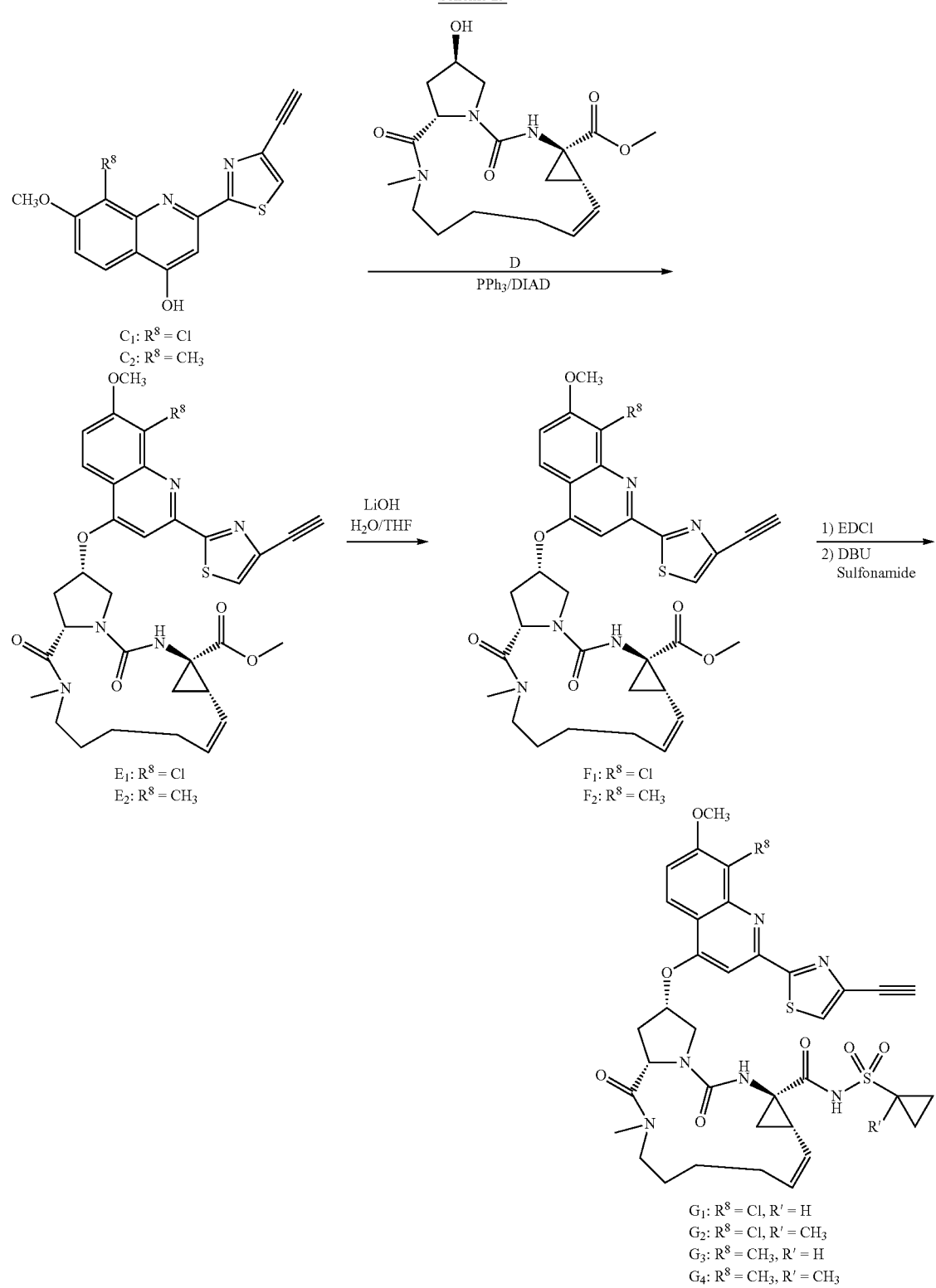

Step C: Synthesis of 8-chloro-7-methoxy-2-(4-ethynylthiazol-2-yl)quinolin-4-ol $C_1$. To a solution of compound $B_1$ (2.94 g, 1 eq.) in tert-butanol (15 mL) was added potassium tert-butoxide (1.7 g, 2.1 eq.) and the mixture was stirred at 90° C. for 2 hrs. Tert-butanol was evaporated in vacuo and water added before acidification to pH 5 by addition of 1N HCl. The product was extracted with dichloromethane. The organic layer was dried over $Na_2SO_4$, filtered, and concentrated under diminished pressure. The residue was triturated in diisopropyl ether and filtered off. The filtrate was purified by chromatography on silica gel column (methanol/dichloromethane) to yield compound $B_1$ as an orange solid in 48% yield.

$^1$H NMR (CDCl$_3$, 400 MHz) δ 3.26 (s, 1H), 4.06 (s, 3H), 6.75 (s, 1H), 7.07 (d, J=9.15 Hz, 1H), 7.72 (s, 1H), 8.27 (d, J=9.15 Hz, 1H), 9.84 (brs, 1H); MS (ESI, EI$^+$) m/z=316.92 (MH$^+$).

Step D: Synthesis of (Z)-(4R,6S,15S,17R)-2,14-dioxo-17-hydroxy-13-N-methyl-1,3,13-triazatricyclo[13.3.0.0]octadec-7-ene-4-carboxylic acid methyl ester D. Compound D (beige powder) was synthesized following the procedure as described for compound 53.

$^1$H NMR (CDCl$_3$, 400 MHz) δ 1.23 (t, J=7.02 Hz, 1H), 1.29-1.38 (m, 1H), 1.49-1.56 (m, 2H), 1.64 (dd, J=8.81 and 5.02 Hz, 1H), 1.69-1.77 (m, 1H), 1.85-1.97 (m, 2H), 2.14-2.20 (m, 1H), 2.34-2.42 (m, 1H), 2.51-2.56 (m, 1H), 2.73-2.84 (m, 1H), 3.01 (s, 3H), 3.54 (s, 2H), 3.71 (s, 3H), 4.10 (br s, 1H), 4.51-4.61 (m, 2H), 4.97 (t, J=7.49 Hz, 1H), 5.45 (t, J=10.69 Hz, 1H), 5.63 (td, J=10.76 and 5.64 Hz, 1H), 6.32 (s, 1H).

Step E: Synthesis of (Z)-(4R,6S,15S,17S)-17[8-chloro-7-methoxy-2-(4-ethynylthiazol-2-yl)quinolin-4-yloxy]-13-N-methyl-2,14-dioxo-1,3,13-triazatricyclo[13.3.0.0]octadec-7-ene-4-carboxylic acid methyl ester $E_1$. Compound $E_1$, a mixture of diastereoisomers (brown oil), was synthesized from compound $C_1$ (740 mg, 1 eq.) and compound D (850 mg, 1 eq.) following the procedure as described for compound 54c.

MS (ESI, EI$^+$) m/z=664.13 (MH$^+$).

Step F: Synthesis of (Z)-(4R,6S,15S,17S)-17[8-chloro-7-methoxy-2-(4-ethynylthiazol-2-yl)quinolin-4-yloxy]-13-N-methyl-2,14-dioxo-1,3,13-triazatricyclo[13.3.0.0]octadec-7-ene-4-carboxylic acid $F_1$. Compound $F_1$ (white solid) was synthesized from crude compound $E_1$ in 16% yield over two steps, following the procedure as described for compound 55c (purification by HPLC).

$^1$H NMR (CDCl$_3$, 400 MHz) δ 1.26-1.33 (m, 2H), 1.43-1.47 (m, 2H), 1.54-1.56 (m, 2H), 1.79-1.83 (m, 1H), 1.87-1.93 (m, 1H), 2.2-2.32 (m, 2H), 2.62 (d, J=13.64 Hz, 1H), 2.79-2.87 (m, 1H), 2.99-3.04 (m, 1H), 3.05 (s, 3H), 3.23 (s, 1H), 3.81-3.85 (m, 1H), 4.05-4.08 (m, 1H), 4.09 (s, 3H), 4.60 (td, J=13.56 Hz and J=2.38 Hz, 1H), 4.91 (t, J=10.69 Hz, 1H), 4.94-4.98 (m, 1H), 5.39-5.45 (m, 1H), 5.46 (s, 1H), 5.64 (td, J=10.77 Hz and J=4.68 Hz, 1H), 7.29 (d, J=9.30 Hz, 1H), 7.55 (s, 1H), 7.68 (s, 1H), 8.05 (d, J=9.30 Hz, 1H).

Step G: Synthesis of (Z)-(4R,6S,15S,17S)-[17-[8-chloro-7-methoxy-2-(4-ethynylthiazol-2-yl)quinolin-4-yloxy]-13-N-methyl-2,14-dioxo-1,3,13-triazatricyclo-[13.3.0.0]octadec-7-en-4-yl]carbonyl(1-methyl-cyclopropyl)sulfonamide $G_2$. Under nitrogen, a solution of compound $F_1$ (140 mg, 1 eq.) and EDCI (82 mg, 2 eq.) in dry dichloromethane (5 mL) was stirred at room temperature for 2 hrs. 1-Methyl-cyclopropylsulfonamide (116 mg, 4 eq.) and DBU (130 mg, 2 eq.) were then added under nitrogen and the reaction mixture was stirred for additional 20 hrs. Dichloromethane and water were added and the two layers separated. The organic layer was washed with water (three times) and brine, then dried over Na$_2$SO$_4$, filtered, and concentrated under reduced pressure. The residue was purified by chromatography on silica gel to yield compound $G_2$ as a beige solid in 33% yield.

$^1$H NMR (CDCl$_3$, 400 MHz): δ 0.80-0.84 (m, 2H), 0.86-0.90 (m, 1H), 1.24-1.33 (m, 1H), 1.37-1.42 (m, 2H), 1.50-1.55 (m, 5H), 1.79-1.84 (m, 1H), 1.90-1.94 (m, 2H), 2.15-2.22 (m, 1H), 2.40-2.46 (m, 1H), 2.57-2.63 (m, 1H), 2.82-2.92 (m, 1H), 2.99-3.06 (m, 1H), 3.05 (s, 3H), 3.24 (s, 1H), 3.80-3.84 (m, 1H), 4.03-4.07 (m, 1H), 4.08 (s, 3H), 4.61 (td, J=13.77 and 2.56 Hz, 1H), 4.89-4.97 (m, 2H), 5.19 (s, 1H), 5.43-5.49 (m, 1H), 5.64 (td, J=10.73 and 5.78 Hz, 1H), 7.29 (dd, J=9.24 Hz, 1H), 7.60 (s, 1H), 7.69 (s, 1H), 8.05 (dd, J=9.24 Hz, 1H), 11.14 (br s, 1H); MS (ESI, EI$^+$): m/z=766.97 (MH$^+$).

Step H: Synthesis of N-(6-acetyl-3-methoxy-2-methylphenyl)-4-bromothiazole-2-carboxamide $A_2$. Compound $A_2$ (beige solid) was synthesized from 4-bromothiazole-2-carboxylic acid (5 g, 1 eq.) and 6-acetyl-3-methoxy-2-methyl aniline (3.58 g, 1 eq.) in 61% yield, following the procedure as described for compound $A_1$.

$^1$H NMR (CDCl$_3$, 400 MHz): δ 2.13 (s, 3H), 2.59 (s, 3H), 3.93 (s, 3H), 6.81 (d, J=8.73 Hz, 1H), 7.50 (s, 1H), 7.77 (d, J=8.73 Hz, 1H), 11.18 (br s, 1H); MS (ESI, EI$^+$): m/z=392 (MNa$^+$).

Step I: Synthesis of N-(6-acetyl-3-methoxy-2-methylphenyl)-4-(2-trimethylsilyl)ethynyl)thiazole-2-carboxamide $B_2$. Compound $B_2$ (yellow solid) was synthesized from compound $A_2$ (3.9 g, 1 eq.) and ethynyltrimethylsilane (2.2 mL, 1.5 eq.) in 98% yield, following the procedure as described for compound $B_1$.

$^1$H NMR (CDCl$_3$, 400 MHz): δ 0.29 (s, 9H), 2.13 (s, 3H), 2.58 (s, 3H), 3.93 (s, 3H), 6.81 (d, J=8.73 Hz, 1H), 7.69 (s, 1H), 7.76 (d, J=8.73 Hz, 1H), 11.05 (br s, 1H); MS (ESI, EI$^+$): m/z=409 (MNa$^+$).

Step J: Synthesis of 7-methoxy-8-methyl-2-(4-ethynylthiazol-2-yl)quinolin-4-ol $C_2$. Compound $C_2$ (white solid) was synthesized from compound $B_2$ (3.81 g, 1 eq.) in 21% yield, following the procedure as described for compound $C_1$.

$^1$H NMR (CDCl$_3$, 400 MHz): δ 2.44 (s, 3H), 3.25 (s, 1H), 3.98 (s, 3H), 6.77 (s, 1H), 7.03 (d, J=9.05 Hz, 1H), 7.70 (s, 1H), 8.25 (d, J=9.05 Hz, 1H), 9.39 (br s, 1H); MS (ESI, EI$^+$): m/z 297 (MH$^+$).

Step K: Synthesis of (Z)-(4R,6S,15S,17S)-17[7-methoxy-8-methyl-2-(4-ethynylthiazol-2-yl)quinolin-4-yloxy]-13-N-methyl-2,14-dioxo-1,3,13-triazatricyclo[13.3.0.0]octadec-7-ene-4-carboxylic acid methyl ester $E_2$. Compound $E_2$, mixture of diastereoisomers (yellow foam) was synthesized from compound $C_2$ (600 mg, 1 eq.) and compound D (768 mg, 1 eq.) following the procedure as described for compound 54c.

MS (ESI, EI$^+$): m/z=644 (MH$^+$).

Step L: Synthesis of (Z)-(4R,6S,15S,17S)-17[7-methoxy-8-methyl-2-(4-ethynylthiazol-2-yl)quinolin-4-yloxy]-13-N-methyl-2,14-dioxo-1,3,13-triazatricyclo[13.3.0.0]octadec-7-ene-4-carboxylic acid $F_2$. Compound $F_2$ (white solid) was synthesized from compound $E_2$ (2.08 g, 1 eq.) following the procedure as described for compound 55c.

$^1$H NMR (CDCl$_3$, 400 MHz): δ 1.27-1.92 (m, 8H), 2.19-2.25 (m, 1H), 2.28-2.35 (m, 1H), 2.54-2.64 (m, 2H), 2.68 (s, 3H), 2.83-2.89 (m, 1H), 2.94-3.04 (m, 1H), 3.05 (s, 1H), 3.79-3.83 (m, 1H), 3.99 (s, 3H), 4-4.09 (m, 1H), 4.57-4.65 (m, 1H), 4.89-4.98 (m, 2H), 5.21 (s, 1H), 5.39-5.46 (m, 1H), 5.62-5.69 (m, 1H), 6.99 (s, 1H), 7.25 (d, J=Hz, 1H), 7.50 (s, 1H), 7.66 (s, 1H), 7.98 (d, J=9.25 Hz, 1H); MS (ESI, EI$^+$): m/z=630 (MH$^+$).

Step M: Synthesis of (Z)-(4R,6S,15S,17S)-[17-[8-chloro-7-methoxy-2-(4-ethynylthiazol-2-yl)quinolin-4-yloxy]-13-N-methyl-2,14-dioxo-1,3,13-triazatricyclo-[13.3.0.0]octadec-7-en-4-yl]carbonyl (cyclopropyl)sulfonamide $G_1$. Compound $G_1$ (cream solid) was synthesized from compound $F_2$ (63 mg, 1 eq.) and cyclopropylsulfonamide (47 mg, 4 eq.) in 75% yield, following the procedure as described for compound $G_2$ (purification of the desired compound by HPLC).

$^1$H NMR (CDCl$_3$, 400 MHz): δ 0.90-0.97 (m, 1H), 1.06-1.20 (m, 2H), 1.21-1.35 (m, 1H), 1.37-1.43 (m, 1H), 1.46-1.53 (m, 1H), 1.53-1.73 (m, 4H), 1.86-1.93 (m, 1H), 1.94 (dd, J=8.48 and 6.05 Hz, 1H), 2.15-2.21 (m, 1H), 2.37-2.45 (m, 1H), 2.57-2.62 (m, 1H), 2.90-2.97 (m, 1H), 3-3.03 (m, 1H), 3.04 (s, 3H), 3.23 (s, 1H), 3.78-3.82 (m, 1H), 4.02-4.06 (m, 1H), 4.08 (s, 3H), 4.60 (td, J=13.68 and 2.60 Hz, 1H), 4.89-4.94 (m, 2H), 5.22 (s, 1H), 5.40-5.47 (m, 1H), 5.64 (td, J=10.79 and 5.70 Hz, 1H), 7.28 (dd, J=9.25 Hz, 1H), 7.57 (s, 1H), 7.70 (s, 1H), 8.05 (dd, J=9.25 Hz, 1H), 11.21 (br s, 1H); MS (ESI, EI$^+$): m/z=753 (MH$^+$).

Step N: Synthesis of (Z)-(4R,6S,15S,17S)-[17-[7-methoxy-8-methyl-2-(4-ethynylthiazol-2-yl)quinolin-4-yloxy]-13-N-methyl-2,14-dioxo-1,3,13-triazatricyclo-[13.3.0.0]octadec-7-en-4-yl]carbonyl (cyclopropyl)sulfonamide $G_3$. Compound $G_3$ (beige solid) was synthesized from compound $F_2$ (120 mg, 1 eq.) and cyclopropylsulfonamide (91 mg, 4 eq.) in 35% yield, following the procedure as described for compound $G_2$.

$^1$H NMR (CDCl$_3$, 400 MHz): δ 0.76-1.72 (m, 10H), 1.94 (dd, J=8.45 and 6.04 Hz, 2H), 2.15-2.22 (m, 1H), 2.39-2.46 (m, 1H), 2.57-2.63 (m, 1H), 2.68 (s, 3H), 2.84-3.04 (m, 2H), 3.05 (s, 3H), 3.22 (s, 1H), 3.76-3.80 (m, 1H), 3.99 (s, 3H), 3.99-4.04 (m, 1H), 4.61 (td, J=13.45 and 2.65 Hz, 1H), 4.89-4.94 (m, 2H), 5.06 (s, 1H), 5.39-5.46 (m, 1H), 5.64 (td, J=10.78 and 5.77 Hz, 1H), 7.24 (d, J=9.25 Hz, 1H), 7.51 (s, 1H), 7.66 (s, 1H), 7.98 (d, J=9.25 Hz, 1H), 11.17 (br s, 1H); MS (ESI, EI$^+$): m/z=733 (MH$^+$).

Step O: Synthesis of (Z)-(4R,6S,15S,17S)-[17-[7-methoxy-8-methyl-2-(4-ethynylthiazol-2-yl)quinolin-4-yloxy]-13-N-methyl-2,14-dioxo-1,3,13-triazatricyclo-[13.3.0.0]octadec-7-en-4-yl]carbonyl (1-methylcyclopropyl)sulfonamide $G_4$. Compound $G_4$ (white solid) was synthesized from compound $F_2$ (150 mg, 1 eq.) and 1-methylcyclopropylsulfonamide (138 mg, 4 eq.) in 8% yield, following the procedure as described for compound $G_2$.

$^1$H NMR (CDCl$_3$, 400 MHz): δ 0.82-1.38 (m, 4H), 1.53 (s, 3H), 1.55-1.84 (m, 5H), 1.90-1.95 (m, 2H), 2.15-2.21 (m, 1H), 2.41-2.48 (m, 1H), 2.57-2.63 (m, 1H), 2.68 (s, 3H), 2.83-2.93 (m, 1H), 2.99-3.04 (m, 1H), 3.05 (s, 3H), 3.22 (s, 1H), 3.77-3.81 (m, 1H), 3.99 (s, 3H), 4-4.04 (m, 1H), 4.58-4.65 (m, 1H), 4.89-4.96 (m, 2H), 5.07 (s, 1H), 5.39-5.46 (m, 1H), 5.61-5.68 (m, 1H), 7.24 (d, J=9.17 Hz, 1H), 7.52 (s, 1H), 7.66 (s, 1H), 7.99 (d, J=9.17 Hz, 1H), 11.12 (br s, 1H); MS (ESI, EI$^+$): m/z=747.21 (MH$^+$).

Example 24

Preparation of Macrocyclic Compounds $O_1$, $O_2$, $O_3$, and $O_4$

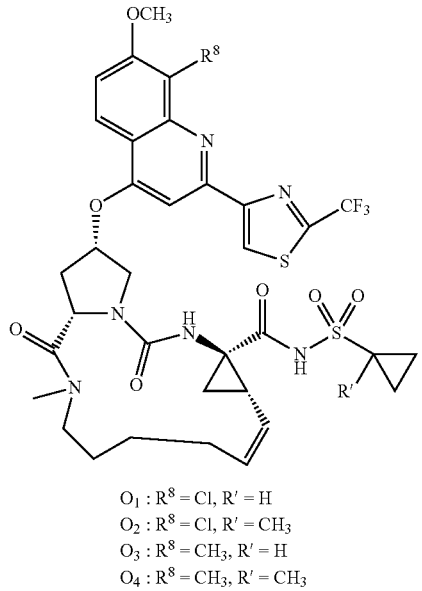

$O_1$ : $R^8$ = Cl, R' = H
$O_2$ : $R^8$ = Cl, R' = CH$_3$
$O_3$ : $R^8$ = CH$_3$, R' = H
$O_4$ : $R^8$ = CH$_3$, R' = CH$_3$

The synthesis of macrocyclic compounds $O_1$, $O_2$, $O_3$, and $O_4$ is shown in Schemes 30 and 31.

Step A: Synthesis of 2-(trifluoromethylthiazole)-4-carboxylic acid ethyl ester H. A solution of 2,2,2-trifluoroacetamide (14.24 g, 1 eq.) and Lawesson's reagent (30.6 g, 0.6 eq.) in THF (120 mL) was stirred at reflux for 18 hrs. The mixture was cooled, ethyl bromopyruvate (16 mL, 1 eq.) was added and the reaction refluxed for weekend. The reaction was cooled, evaporated in vacuum, and the resulting crude material extracted with dichloromethane and washed with water. The organic layer was dried over Na$_2$SO$_4$, filtered, and concentrated to give an orange oil. The oil was purified by chromatography on a silica gel (petroleum ether/dichloromethane) to yield compound H in 40% yield.

$^1$H NMR (DMSO-d$_6$, 400 MHz): δ 1.32 (t, J=7.10 Hz, 3H), 4.34 (q, J=7.10 Hz, 2H), 8.9 (s, 1H); $^{19}$F NMR (DMSO-d$_6$, 376 MHz): δ −60.29 (s, 3F); MS (ESI, EI$^+$): m/z=225.9 (MH$^+$).

Step B: Synthesis of lithium 2-(trifluoromethyl)thiazole-4-carboxylate I. Compound I (pink solid) was synthesized from compound H (12.14 g, 1 eq.) in 75% yield, following the procedure as described for compound 37.

MS (ESI, EI$^+$): m/z=198 (MH$^+$).

Scheme 30

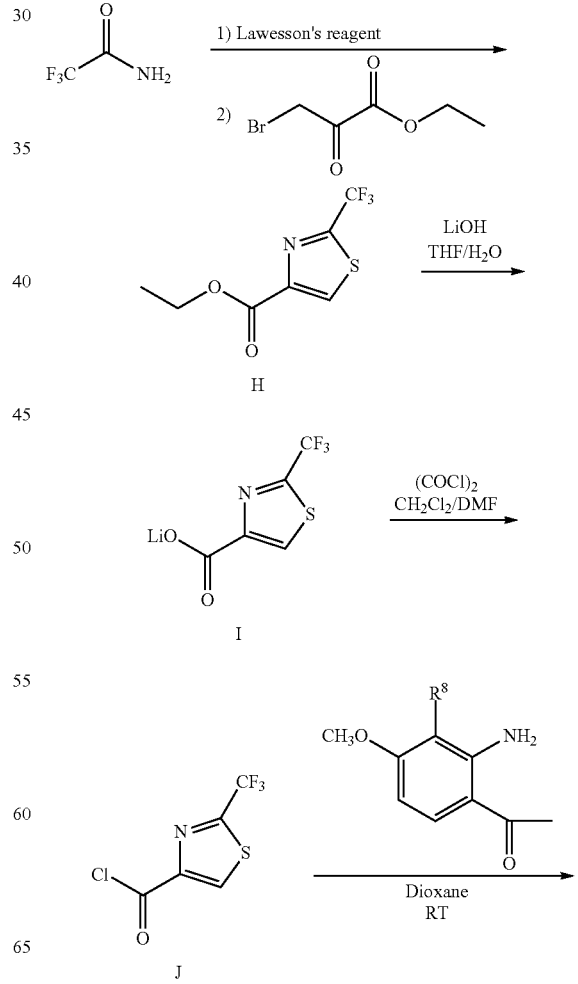

-continued

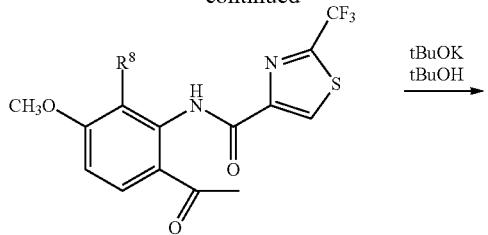

K₁: R⁸ = Cl
K₂: R⁸ = CH₃

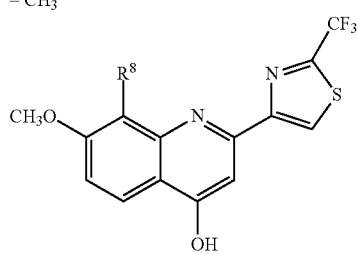

L₁: R⁸ = Cl
L₂: R⁸ = CH₃

Step C: Synthesis of N-(6-acetyl-2-chloro-3-methoxyphenyl)-2-(trifluoromethyl)thiazole-4-carboxamide K₁. Oxalyl chloride (1.9 mL, 1.4 eq.) was added dropwise under nitrogen at 0° C. to a suspension of compound 1 (4 g, 1.2 eq.) in DCM (120 mL) and DMF (few drops). The reaction mixture was stirred at 0° C. for 30 min and then at room temperature for additional 3 hrs. The solid was removed by filtration under nitrogen and the filtrate was evaporated to give a yellow oil. This oil was solubilised in dioxane (30 mL) and added under nitrogen to a solution of 6-acetyl-2-chloro-3-methoxy aniline (3.26 g, 1 eq.) in 1,4-dioxane (60 mL). The reaction mixture was stirred at room temperature for 3 days. The solvent was removed under reduced pressure, the residue was solubilised in dichloromethane, washed with water, dried over Na₂SO₄ and concentrated in vacuum. The crude oil was triturated in MeOH/Et₂O mixture to give the compound K₁ as a white solid in 69% yield.

$^1$H NMR (CDCl$_3$, 400 MHz): δ 2.59 (s, 3H), 4 (s, 3H), 6.90 (d, J=8.75 Hz, 1H), 7.70 (d, J=8.75 Hz, 1H), 8.44 (s, 1H), 10.28 (s, 1H); $^{19}$F NMR (CDCl$_3$, 376 MHz): δ −61.08 (s, 3F).

Scheme 31

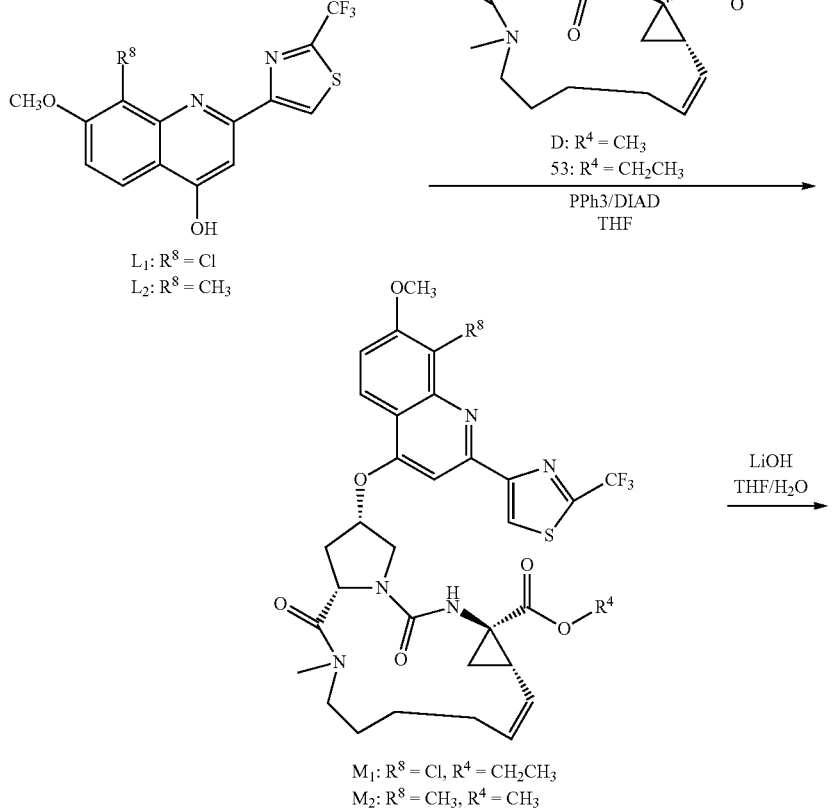

M₁: R⁸ = Cl, R⁴ = CH₂CH₃
M₂: R⁸ = CH₃, R⁴ = CH₃

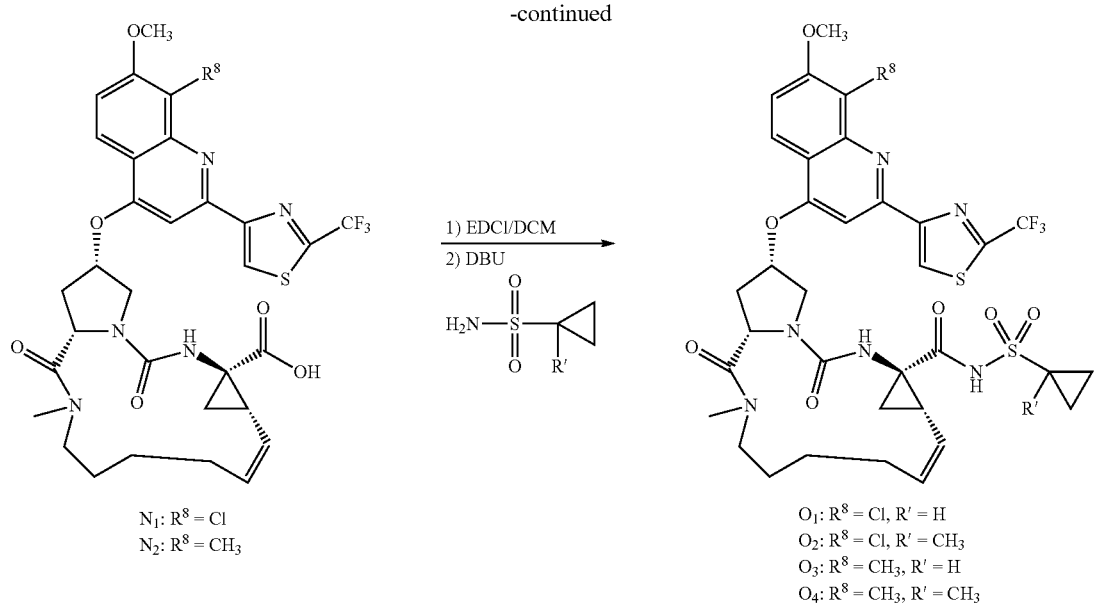

N₁: R⁸ = Cl
N₂: R⁸ = CH₃

O₁: R⁸ = Cl, R' = H
O₂: R⁸ = Cl, R' = CH₃
O₃: R⁸ = CH₃, R' = H
O₄: R⁸ = CH₃, R' = CH₃

Step D: Synthesis of 8-chloro-2-(2-(trifluoromethyl)thiazol-4-yl)-7-methoxyquinolin-4-ol $L_1$. Compound $L_1$ (white solid) was synthesized from compound $K_1$, (1 g, 1 eq.) in 26% yield, following the procedure as described for compound $C_1$.

$^1$H NMR (CDCl$_3$, 400 MHz): δ (ppm) 4.07 (s, 3H), 6.78 (s, 1H), 7.09 (d, J=9.13 Hz, 1H), 8.14 (s, 1H), 8.30 (d, J=9.13 Hz, 1H), 9.93 (s, 1H); $^{19}$F NMR (CDCl$_3$, 376 MHz): δ −61.14 (s, 3F); MS (ESI, EI⁺): m/z=360.91 (MH⁺).

Step E: Synthesis of (Z)-(4R,6S,15S,17S)-17[8-chloro-7-methoxy-2-(2-trifluoromethylthiazol-4-yl)quinolin-4-yloxy]-13-N-methyl-2,14-dioxo-1,3,13-triazatricyclo[13.3.0.0]octadec-7-ene-4-carboxylic acid ethyl ester $M_1$. Compound $M_1$, a mixture of diastereoisomers, was synthesized from compound $L_1$ (570 mg, 1 eq.) and compound 53 (600 mg, 1 eq.), following the procedure as described for compound 54c.

MS (ESI, EI⁺): m/z=722.04 (MH⁺).

Step F: Synthesis of (Z)-(4R,6S,15S,17S)-17[8-chloro-7-methoxy-2-(2-trifluoromethylthiazol-4-yl)quinolin-4-yloxy]-13-N-methyl-2,14-dioxo-1,3,13-triazatricyclo[13.3.0.0]octadec-7-ene-4-carboxylic acid $N_1$. Compound $N_1$ was synthesized from compound $M_1$ (1 eq.), following the procedure as described for compound 55c.

$^1$H NMR (CDCl$_3$, 400 MHz): δ 1.27-1.60 (m, 6H), 1.81-1.93 (m, 1H), 2.21-2.26 (m, 1H), 2.28-2.35 (m, 1H), 2.59-2.64 (m, 1H), 2.81-2.88 (m, 1H), 3-3.07 (m, 1H), 3.05 (s, 3H), 3.83-3.87 (m, 1H), 4.02-4.07 (m, 1H), 4.09 (s, 3H), 4.57-4.64 (m, 1H), 4.89-4.94 (m, 1H), 4.99-5.02 (m, 1H), 5.22 (s, 1H), 5.50-5.57 (m, 1H), 5.65 (td, J=10.75 and 4.70 Hz, 1H), 7.29 (d, J=9.25 Hz, 1H), 7.60 (br s, 1H), 8.09 (d, J=9.25 Hz, 1H), 8.73 (br s, 1H); $^{19}$F NMR (CDCl$_3$, 376 MHz): δ −60.90 (s, 3F); MS (ESI, EI⁺): m/z=693.98 (MH⁺).

Step G: Synthesis of (Z)-(4R,6S,15S,17S)-[17-[8-chloro-7-methoxy-2-(2-trifluoromethylthiazol-4-yl)quinolin-4-yloxy]-13-N-methyl-2,14-dioxo-1,3,13-triazatricyclo[13.3.0.0]octadec-7-en-4-yl]carbonyl-(cyclopropyl)sulfonamide $O_1$. Compound $O_1$ (white solid) was synthesized from compound $N_1$ (115 mg, 1 eq.) in 21% yield, following the procedure as described for compound $G_2$.

$^1$H NMR (CDCl$_3$, 400 MHz): δ 0.89-0.96 (m, 1H), 1.06-1.17 (m, 1H), 1.22-1.29 (m, 2H), 1.38-1.43 (m, 2H), 1.45-1.52 (m, 1H), 1.55-1.69 (m, 1H), 1.88-1.96 (m, 2H), 2.17-2.23 (m, 1H), 2.39-2.46 (m, 1H), 2.57-2.63 (m, 1H), 2.80-2.89 (m, 1H), 2.89-2.95 (m, 1H), 2.97-3.03 (m, 1H), 3.05 (s, 3H), 3.60-3.69 (m, 1H), 3.80-3.84 (m, 1H), 4-4.04 (m, 1H), 4.08 (s, 3H), 4.58-4.64 (m, 1H), 4.91 (t, J=10.69 Hz, 1H), 4.96 (dd, J=8.75 and 5.10 Hz, 1H), 5.15 (s, 1H), 5.49-5.55 (m, 1H), 5.64 (td, J=10.71 and 5.65 Hz, 1H), 7.28 (d, J=9.20 Hz, 1H), 7.59 (s, 1H), 8.08 (d, J=9.20 Hz, 1H), 8.72 (s, 1H), 11.18 (br s, 1H); $^{19}$F NMR (CDCl$_3$, 376 MHz): δ −60.89 (s, 3F); MS (ESI, EI⁺): m/z=797.02 (MH⁺).

Step H: Synthesis of (Z)-(4R,6S,15S,17S)-[17-[8-chloro-7-methoxy-2-(2-trifluoromethylthiazol-4-yl)quinolin-4-yloxy]-13-N-methyl-2,14-dioxo-1,3,13-triazatricyclo-[13.3.0.0]octadec-7-en-4-yl]carbonyl-(1-methylcyclopropyl)sulfonamide $O_2$. Compound $O_2$ (white solid) was synthesized from compound $N_1$ (80 mg, 1 eq.) in 19% yield, following the procedure as described for compound $G_2$.

$^1$H NMR (CDCl$_3$, 400 MHz): δ 0.77-0.84 (m, 2H), 1.18-1.26 (m, 2H), 1.33-1.43 (m, 2H), 1.49-1.56 (m, 1H), 1.52 (s, 3H), 1.64-1.74 (m, 1H), 1.79-1.83 (m, 1H), 1.86-1.94 (m, 2H), 2.17-2.24 (m, 1H), 2.41-2.48 (m, 1H), 2.58-2.63 (m, 1H), 2.83-2.92 (m, 1H), 2.96-3.04 (m, 1H), 3.05 (s, 3H), 3.80-3.84 (m, 1H), 4-4.04 (m, 1H), 4.08 (s, 3H), 4.58-4.65 (m, 1H), 4.91 (t, J=10.71 Hz, 1H), 4.98 (dd, J=8.86 and 5.07 Hz, 1H), 5.10 (s, 1H), 5.50-5.56 (m, 1H), 5.64 (td, J=10.77 and 5.68 Hz, 1H), 7.28 (d, J=9.20 Hz, 1H), 7.60 (s, 1H), 8.09 (d, J=9.20 Hz, 1H), 8.72 (s, 1H), 11.16 (br s, 1H); MS (ESI, EI⁺): m/z=811.03 (MH⁺).

Step I: Synthesis of N-(6-acetyl-3-methoxy-2-methylphenyl)-4-(2-trifluoromethyl)thiazole-4-carboxamide $K_2$. Compound $K_2$ (white solid) was synthesized from compound J (5.2 g, 1.2 eq.) and 6-acetyl-3-methoxy-2-methyl aniline (3.6 g, 1 eq.) in 52% yield, following the procedure as described for compound $K_1$.

$^1$H NMR (DMSO-d$_6$, 400 MHz): δ 2.01 (s, 3H), 3.90 (s, 3H), 7.02 (d, J=8.81 Hz, 1H), 7.81 (d, J=8.81 Hz, 1H), 8.82 (s, 1H); MS (ESI, EI⁺): m/z=381 (MNa⁺).

Step J: Synthesis of 7-methoxy-8-methyl-2-(2-trifluoromethyl-thiazol-4-yl)quinolin-4-ol $L_2$. Compound $L_2$ (brown solid) was synthesized from compound K₂ (3.76 g, 1 eq.) in 52% yield, following the procedure as described for compound C₁ (80° C. overnight).

¹H NMR (CDCl₃, 400 MHz): δ 2.42 (s, 3H), 3.98 (s, 3H), 6.72 (s, 1H), 7.04 (d, J=9.02 Hz, 1H), 8.10 (s, 1H), 8.25 (d, J=9.02 Hz, 1H), 9.45 (br s, 1H); MS (ESI, EI⁺): m/z=341.06 (MH⁺).

Step K: Synthesis of (Z)-(4R,6S,15S,17S)-17[7-methoxy-8-methyl-2-(2-trifluoromethylthiazol-4-yl)quinolin-4-yloxy]-13-N-methyl-2,14-dioxo-1,3,13-triazatricyclo [13.3.0.0]octadec-7-ene-4-carboxylic acid methyl ester M₂. Compound M₂, a mixture of diastereoisomers, was synthesized from compound L₂ (359 mg, 1 eq.) and compound D (400 mg, 1 eq.) in 64% yield, following the procedure as described for compound 54c.

MS (ESI, EI⁺): m/z=688 (MH⁺).

Step L: Synthesis of (Z)-(4R,6S,15S,17S)-17[7-methoxy-8-methyl-2-(2-trifluoromethylthiazol-4-yl)quinolin-4-yloxy]-13-N-methyl-2,14-dioxo-1,3,13-triazatricyclo [13.3.0.0]octadec-7-ene-4-carboxylic acid N₂. Compound N₂ was synthesized from compound M₂ (460 mg, 1 eq.) in 40% yield, following the procedure as described for compound 55c (purification by chromatography on a silica gel).

¹H NMR (CDCl₃, 400 MHz): δ 1.26-1.34 (m, 1H), 1.38-1.43 (m, 2H), 1.52-1.69 (m, 2H), 1.82 (dd, J=8.12 and 6.26 Hz, 1H), 1.84-1.94 (m, 1H), 2.23 (td, J=13.52 and 5.65 Hz, 1H), 2.29-2.36 (m, 1H), 2.61 (td, J=13.52 and 3.32 Hz, 1H), 2.70 (s, 3H), 2.82-2.89 (m, 1H), 2.97-3.04 (m, 1H), 3.04 (s, 3H), 3.80-3.84 (m, 1H), 3.98-4.02 (m, 1H), 3.99 (s, 3H), 4.61 (td, J=13.63 and 2.73 Hz, 1H), 4.91 (t, J=10.70 Hz, 1H), 4.98 (dd, J=8.97 and 5.22 Hz, 1H), 5.14 (s, 1H), 5.47-5.53 (m, 1H), 5.65 (td, J=10.85 and 4.81 Hz, 1H), 7.24 (d, J=9.25 Hz, 1H), 7.52 (s, 1H), 8 (d, J=9.25 Hz, 1H), 8.59 (s, 1H); MS (ESI, EI⁺): m/z=674 (MH⁺).

Step M: Synthesis of (Z)-(4R,6S,15S,17S)-[17-[7-methoxy-8-methyl-2-(2-trifluoromethylthiazol-4-yl)quinolin-4-yloxy]-13-N-methyl-2,14-dioxo-1,3,13-triazatricyclo-[13.3.0.0]octadec-7-en-4-yl]carbonyl-(cyclopropyl) sulfonamide O₃. Compound O₃ (white solid) was synthesized from compound N₂ (100 mg, 1 eq.) and cyclopropylsulfonamide (72 mg, 4 eq.) in 27% yield, following the procedure as described for compound G₂.

¹H NMR (CDCl₃, 400 MHz): δ 0.88-0.94 (m, 1H), 1.07-1.15 (m, 2H), 1.21-1.29 (m, 2H), 1.33-1.41 (m, 2H), 1.44-1.51 (m, 1H), 1.53-1.72 (m, 2H), 1.87-1.95 (m, 2H), 2.15-2.20 (m, 1H), 2.38-2.46 (m, 1H), 2.56-2.62 (m, 1H), 2.69 (s, 3H), 2.82-3.03 (m, 2H), 2.97 (s, 3H), 3.74-3.81 (m, 1H), 3.95-4.02 (m, 4H), 4.58-4.64 (m, 1H), 4.88-4.95 (m, 2H), 5.10-5.13 (m, 1H), 5.44-5.52 (m, 1H), 5.59-5.67 (m, 1H), 7.20-7.24 (m, 1H), 7.49-7.54 (m, 1H), 7.98-8.02 (m, 1H), 8.55-8.59 (m, 1H), 11.16 (br s, 1H); ¹⁹F NMR (CDCl₃, 376 MHz): δ −60.88 (s, 3F);

MS (ESI, EI⁺): m/z=777 (MH⁺).

Step N: Synthesis of (Z)-(4R,6S,15S,17S)-[17-[7-methoxy-8-methyl-2-(2-trifluoromethylthiazol-4-yl)quinolin-4-yloxy]-13-N-methyl-2,14-dioxo-1,3,13-triazatricyclo-[13.3.0.0]octadec-7-en-4-yl]carbonyl-(1-methylcyclopropyl)sulfonamide O₄. Compound O₄ (white solid) was synthesized from compound N₂ (80 mg, 1 eq.) and (1-methylcyclopropyl)-sulfonamide (64 mg, 4 eq.) in 24% yield, following the procedure as described for compound G₂.

¹H NMR (CDCl₃, 400 MHz): δ 0.79-0.84 (m, 1H), 0.86-0.90 (m, 1H), 1.20-1.43 (m, 4H), 1.52 (s, 3H), 1.65-1.73 (m, 2H), 1.78-1.83 (m, 1H), 1.90-1.93 (m, 2H), 2.17-2.22 (m, 1H), 2.40-2.48 (m, 1H), 2.57-2.62 (m, 1H), 2.70 (s, 3H), 2.84-2.94 (m, 2H), 2.95-3.02 (m, 1H), 3.05 (s, 3H), 3.77-3.81 (m, 1H), 3.99 (s, 3H), 3.98-4.01 (m, 1H), 4.58-4.66 (m, 1H), 4.91 (t, J=10.82 Hz, 1H), 4.96 (dd, J=8.86 and 5.44 Hz, 1H), 5.07 (s, 1H), 5.47-5.54 (m, 1H), 5.63 (td, J=10.67 and 5.85 Hz, 1H), 7.23 (d, J=9.24 Hz, 1H), 7.53 (s, 1H), 8.01 (d, J=9.24 Hz, 1H), 8.59 (s, 1H), 11.16 (br s, 1H); ¹⁹F NMR (CDCl₃, 376 MHz): δ −60.88 (s, 3F); MS (ESI, EI⁺): m/z=791 (MH⁺).

Example 25

Preparation of Macrocyclic Compounds T₁ and T₂

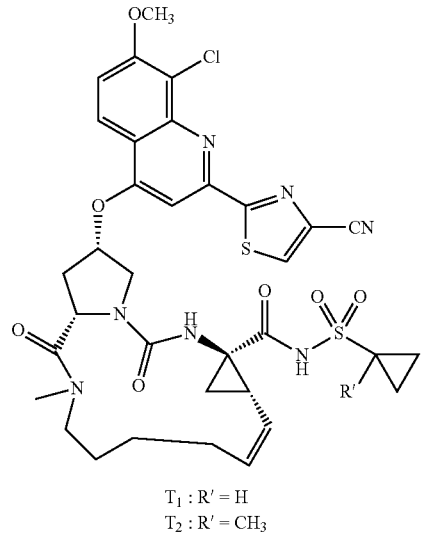

T₁ : R' = H
T₂ : R' = CH₃

The synthesis of macrocyclic compounds T₁ and T₂ is shown in Scheme 32.

Step A: Synthesis of 2-(4-bromothiazol-2-yl)-8-chloro-7-methoxy-quinolin-4-ol P. Compound P (yellow solid) was synthesized from compound A₁ (2 g, 1 eq.) in 92% yield, following the procedure as described for compound AE (80° C. overnight).

¹H NMR (CDCl₃, 400 MHz) δ 4.06 (s, 3H), 6.73 (s, 1H), 7.07 (d, J=9.10 Hz, 1H), 7.46 (s, 1H), 8.27 (d, J=9.10 Hz, 1H), 9.74 (br s, 1H); MS (ESI, EI⁺): m/z=372.90 (MH⁺).

Step B: Synthesis of 8-chloro-2-(4-cyanothiazol-2-yl)-7-methoxy-quinolin-4-ol Q. The compound P (286 mg, 1 eq.) in degazed dimethylacetamide (10 mL), and Zn (4.5 mg, 0.09 eq.), Zn(CN)₂ (84 mg, 0.6 eq.), Pd₂dba₃ (21 mg, 0.03 eq.), and dppf (26 mg, 0.06 eq.) were heated at 110° C. under microwaves for 30 min. Then, water was added, the precipitate filtered and dissolved in ethyl acetate, dried, and concentrated under vacuum. The residue was purified by chromatography on a silica gel to give compound Q as a yellow solid in 81% yield.

¹H NMR (CDCl₃, 400 MHz) δ 4.07 (s, 3H), 6.79 (br s, 1H), 7.08 (d, J=9.11 Hz, 1H), 8.19 (s, 1H), 8.28 (d, J=9.11 Hz, 1H), 9.74 (br s, 1H); MS (ESI, EI⁺): m/z=318.15 (MH⁺).

Step C: Synthesis of (Z)-(4R,6S,15S,17S)-17[8-chloro-7-methoxy-2-(4-cyanothiazol-2-yl)quinolin-4-yloxy]-13-N-methyl-2,14-dioxo-1,3,13-triazatricyclo-[13.3.0.0]octadec-7-ene-4-carboxylic acid methyl ester R. Compound R, a mixture of diastereoisomers (beige solid), was synthesized from compound Q (250 mg, 1 eq.) and compound D (299 mg, 1 eq.), following the procedure as described for compound 54c.

MS (ESI, EI⁺): m/z=665 (MH⁺).

Scheme 32
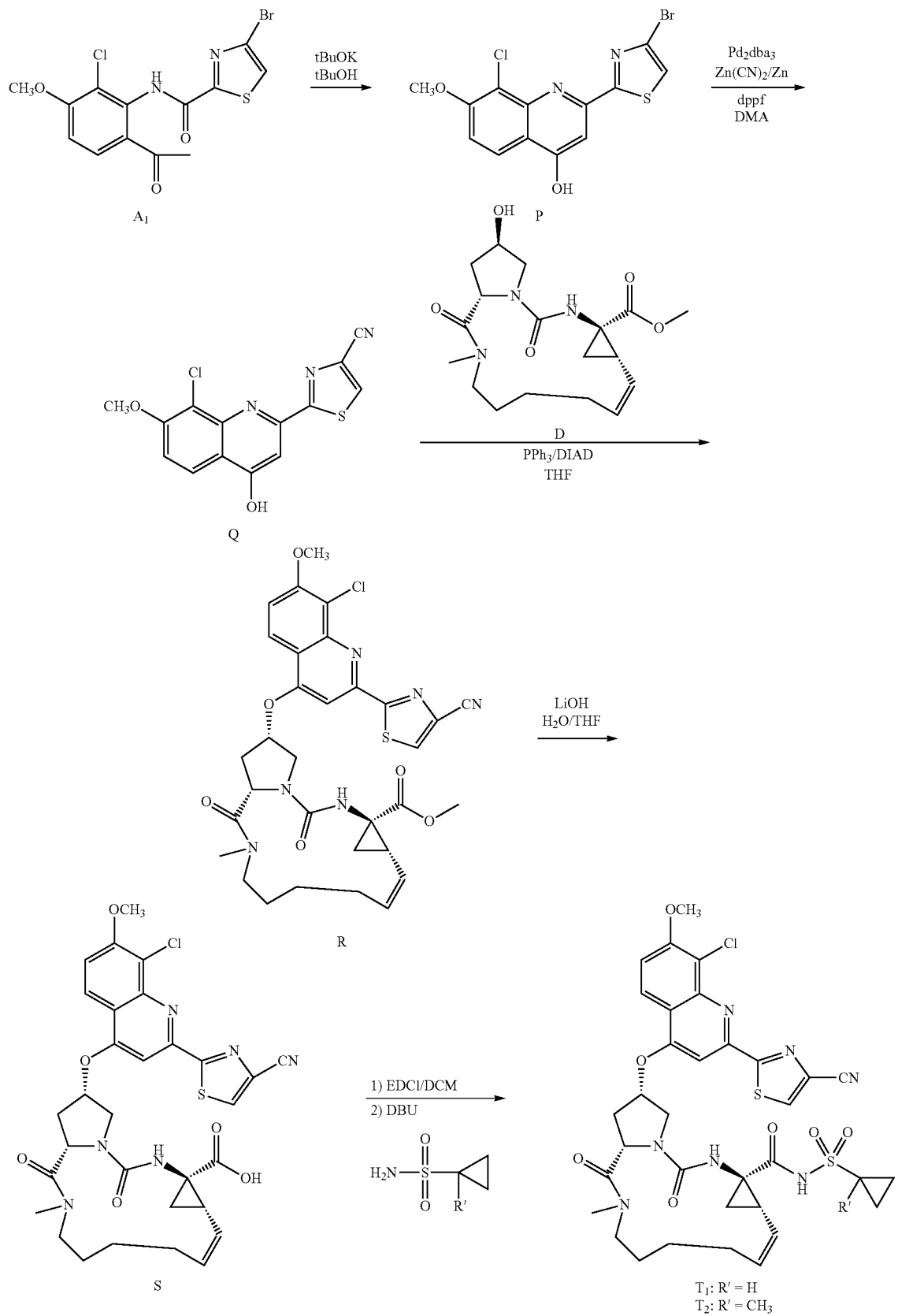
T₁: R' = H
T₂: R' = CH₃

Step D: Synthesis of (Z)-(4R,6S,15S,17S)-17[8-chloro-7-methoxy-2-(4-cyanothiazol-2-yl)quinolin-4-yloxy]-13-N-methyl-2,14-dioxo-1,3,13-triazatricyclo[13.3.0.0]octadec-7-ene-4-carboxylic acid S. Compound S (white solid) was synthesized from crude compound R following the procedure as described for compound 55c.

$^1$H NMR (CDCl$_3$, 400 MHz) δ 0.83-1.60 (m, 8H), 2.21-2.27 (m, 1H), 2.29-2.36 (m, 1H), 2.58-2.64 (m, 1H), 2.80-2.88 (m, 1H), 3.02-3.10 (m, 1H), 3.06 (s, 3H), 3.87-3.91 (m, 1H), 4.02-4.09 (m, 1H), 4.09 (s, 3H), 4.56-4.64 (m, 1H), 4.92 (t, J=10.80 Hz, 1H), 5.02 (dd, J=8.95 and 4.79 Hz, 1H), 5.17 (s, 1H), 5.46-5.52 (m, 1H), 5.66 (td, J=10.81 and 4.38 Hz, 1H), 7.33 (d, J=9.26 Hz, 1H), 7.53 (s, 1H), 8.09 (d, J=9.26 Hz, 1H), 8.14 (s, 1H); MS (ESI, EI$^+$): m/z 651.29 (MH$^+$).

Step E: Synthesis of (Z)-(4R,6S,15S,17S)-[17-[8-chloro-7-methoxy-2-(2-cyanothiazol-4-yl)quinolin-4-yloxy]-13-N-methyl-2,14-dioxo-1,3,13-triazatricyclo-[13.3.0.0]octadec-7-en-4-yl]carbonyl-(cyclopropyl)sulfonamide T$_1$. Compound T$_1$ (yellow solid) was synthesized from compound S (80 mg, 1 eq.) in 17% yield, following the procedure as described for compound G$_2$.

$^1$H NMR (Acetone-d$_6$, 400 MHz) δ 0.83-1.74 (m, 16H), 2.59-2.66 (m, 2H), 3.13 (s, 3H), 3.13-3.24 (m, 2H), 3.84-3.94 (m, 1H), 4.15 (s, 3H), 4.20-4.30 (m, 1H), 4.61-4.69 (m, 1H), 5.03-5.09 (m, 1H), 5.51-5.62 (m, 1H), 5.73-5.83 (m, 1H), 7.65 (d, J=9.35 Hz, 1H), 7.74 (s, 1H), 8.27 (d, J=9.35 Hz, 1H), 8.80 (s, 1H); MS (ESI, EI$^+$): m/z=754.39 (MH$^+$).

Step F: Synthesis of (Z)-(4R,6S,15S,17S)-[17-[8-chloro-7-methoxy-2-(2-cyanothiazol-4-yl)quinolin-4-yloxy]-13-N-methyl-2,14-dioxo-1,3,13-triazatricyclo-[13.3.0.0]octadec-7-en-4-yl]carbonyl-(1-methylcyclopropyl)sulfonamide T$_2$. Compound T$_2$ (white solid) was synthesized from compound S (40 m g, 1 eq.) in 11% yield, following the procedure as described for compound G$_2$.

$^1$H NMR (CDCl$_3$, 400 MHz) δ 0.81-1.96 (m, 9H), 2.17-2.24 (m, 3H), 2.41-2.48 (m, 2H), 2.57-2.63 (m, 2H), 2.85-2.90 (m, 1H), 3.01-3.09 (m, 2H), 3.06 (s, 3H), 3.85-3.89 (m, 1H), 4-4.04 (m, 1H), 4.09 (s, 3H), 4.57-4.65 (m, 1H), 4.90-4.95 (m, 1H), 4.98-5.02 (m, 1H), 5.03 (s, 1H), 5.46-5.53 (m, 1H), 5.61-5.68 (m, 1H), 7.33 (d, J=9.27 Hz, 1H), 7.55 (s, 1H), 8.10 (d, J=9.27 Hz, 1H), 8.14 (s, 1H), 11.05 (br s, 1H); MS (ESI, EI$^+$): m/z=768.06 (MH$^+$).

Example 26

Preparation of Macrocyclic Compounds AC$_1$, AC$_2$, and AC$_3$

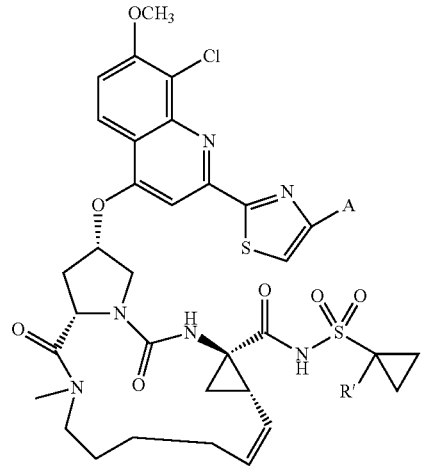

AC$_1$ : A = cPr, R' = H
AC$_2$ : A = cBu, R' = H
AC$_3$ : A = cBu, R' = CH$_3$

The synthesis of macrocyclic compounds AC$_1$, AC$_2$, and AC$_3$ is shown in Scheme 33.

Step A: Synthesis of 2-bromo-1-cyclopropylethanone U$_1$. To a stirred ice-cooled solution of cyclopropyl methyl ketone (21 g, 1 eq.) in methanol (150 mL) was added dropwise bromine (12.9 ml, 1 eq.). The reaction was allowed to proceed (decolorization) below 10° C. Stirring was continued at room temperature for 1 hr before adding water (75 mL). After an additional 15 min, the mixture was diluted with water (225 mL) and extracted with ethyl ether (two times). Ether layers were washed with 10% Na$_2$CO$_3$ solution and brine. Dried organic layers were evaporated in vacuo to yield a crude orange oil, purified by distillation to yield compound U$_1$ as a colorless oil in 52% yield.

$^1$H NMR (CDCl$_3$, 400 MHz): δ 0.98-1.02 (m, 2H), 1.09-1.13 (m, 2H), 2.15-2.22 (m, 1H), 4 (s, 2H).

Step B: Synthesis of 4-cyclopropylthiazole-2-carboxylic acid ethyl ester V$_1$. Compound V$_1$ (brown oil) was synthesized from compound U$_1$ (10 g, 1.25 eq.) in 73% yield, following the procedure as described for compound 36.

$^1$H NMR (DMSO-d$_6$, 400 MHz): δ 0.80-0.84 (m, 2H), 0.92-0.97 (m, 2H), 1.30 (t, J=7.10 Hz, 3H), 2.13-2.20 (m, 1H), 4.34 (q, J=7.10 Hz, 2H), 7.70 (s, 1H); MS (ESI, EI$^+$): m/z=198 (MH$^+$).

Scheme 33

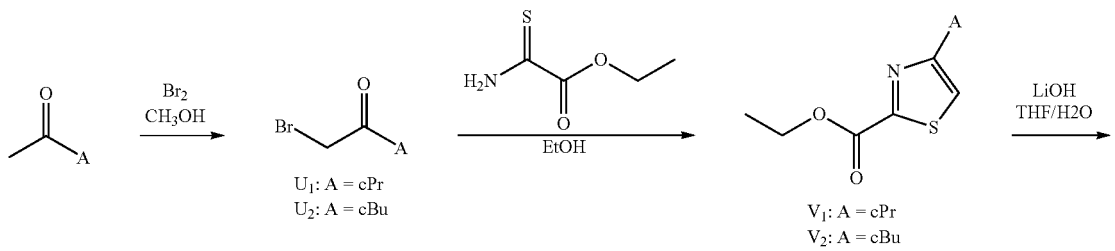

U$_1$: A = cPr
U$_2$: A = cBu

V$_1$: A = cPr
V$_2$: A = cBu

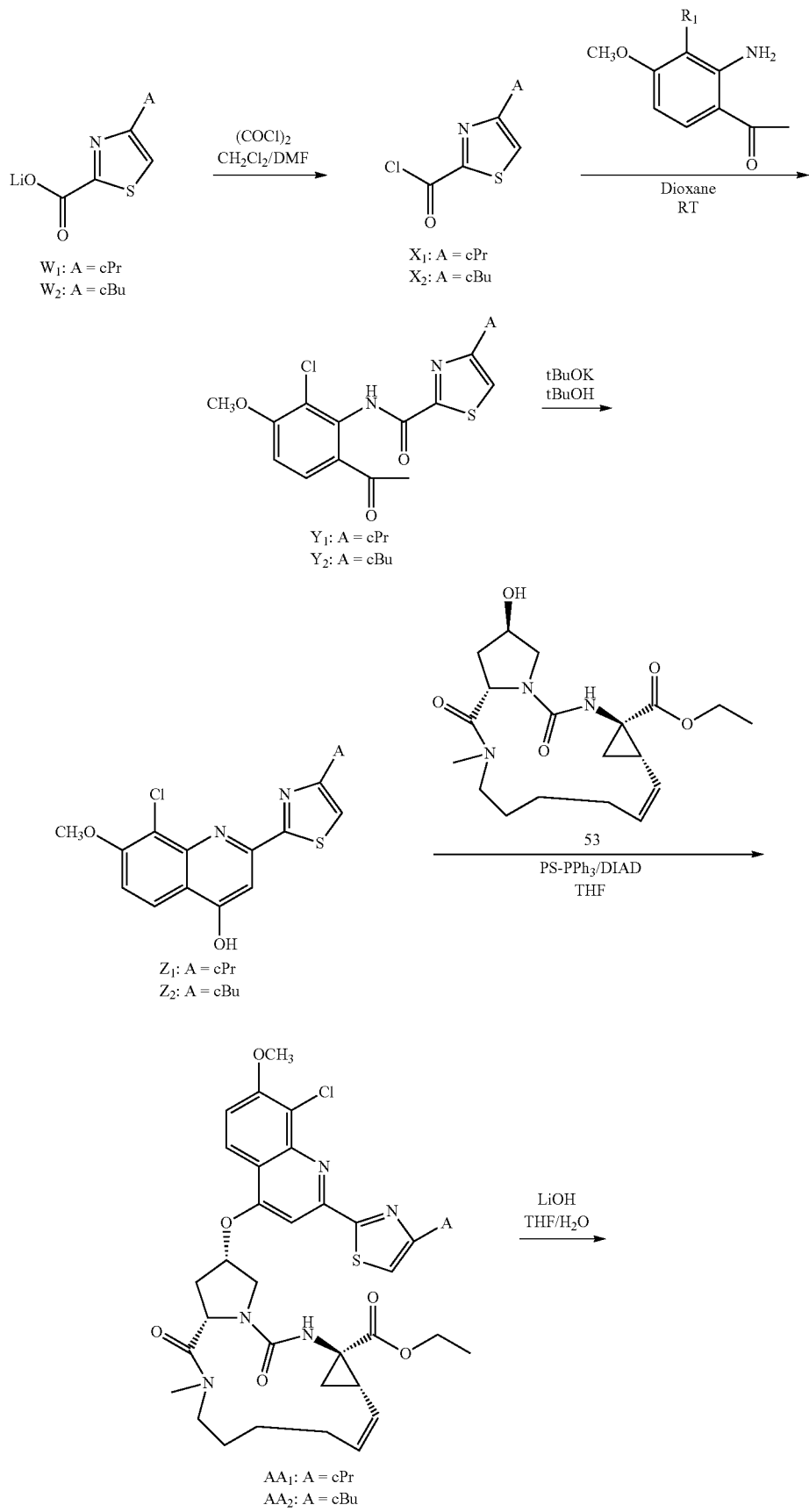

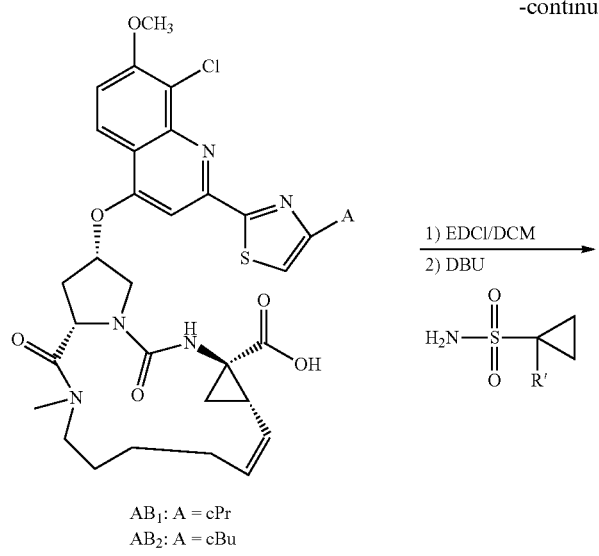

AB₁: A = cPr
AB₂: A = cBu

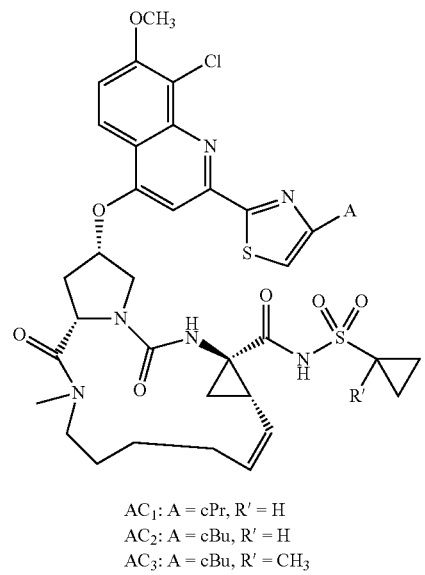

AC₁: A = cPr, R' = H
AC₂: A = cBu, R' = H
AC₃: A = cBu, R' = CH₃

Step C: Synthesis of Lithium 4-cyclopropylthiazole-2-carboxylate $W_1$. Compound $W_1$ (brown solid) was synthesized from compound $V_1$ (6 g, 1 eq.) in 91% yield, following the procedure as described for compound 37.

$^1$H NMR (DMSO-d₆, 400 MHz): δ 0.780-0.80 (m, 2H), 0.81-0.84 (m, 2H), 1.95-2.01 (m, 1H), 7.11 (s, 1H).

Step D: Synthesis of 4-cyclopropylthiazole-2-carbonyl chloride $X_1$. Compound $X_1$ (brown solid) was synthesized from compound $W_1$ (3 g, 1 eq.) in quantitative yield, following the procedure as described for compound 38.

MS (ESI, EI⁺): m/z=170 (MH⁺).

Step E: Synthesis of N-(6-acetyl-2-chloro-3-methoxyphenyl)-4-cyclopropylthiazole-2-carboxamide $Y_1$. To a solution of compound $X_1$ (3.4 g, 1.2 eq.) in dioxane (60 mL) was added 6-acetyl-2-chloro-3-methoxy aniline (3.01 g, 1 eq.) in dioxane. The mixture was stirred at room temperature overnight. Water was added and the mixture was extracted with ethyl acetate. The organic layer was dried over Na₂SO₄, filtered, and concentrated under vacuum. The residue was purified by chromatography on silica gel (petroleum ether/ethyl acetate) to yield compound $Y_1$ as a brown solid in 66% yield.

$^1$H NMR (CDCl₃, 400 MHz): δ 1-1.06 (m, 4H), 2.08-2.15 (m, 1H), 2.58 (s, 3H), 3.99 (s, 3H), 6.87 (d, J=8.78 Hz, 1H), 7.16 (s, 1H), 7.67 (d, J=8.78 Hz, 1H), 10.27 (br s, 1H); MS (ESI, EI⁺): m/z 351 (MH⁺).

Step F: Synthesis of 8-chloro-7-methoxy-2-(4-cyclopropylthiazol-2-yl)quinolin-4-ol $Z_1$. Compound $Z_1$ (orange solid) was synthesized from compound $Y_1$ (3.50 g, 1 eq) in 84% yield, following the procedure as described for compound AE (80° C. overnight).

$^1$H NMR (CDCl₃, 400 MHz): δ 1.04-1.07 (m, 4H), 2.13-2.18 (m, 1H), 4.06 (s, 3H), 6.75 (s, 1H), 7.06 (d, J=9.10 Hz, 1H), 7.09 (s, 1H), 8.27 (d, J=9.10 Hz, 1H), 9.92 (br s, 1H); MS (ESI, EI⁺): m/z 333.13 (MH⁺).

Step G: Synthesis of (Z)-(4R,6S,15S,17S)-17[8-chloro-7-methoxy-2-(4-cyclopropylthiazol-2-yl)quinolin-4-yloxy]-13-N-methyl-2,14-dioxo-1,3,13-triazatricyclo[13.3.0.0]octadec-7-ene-4-carboxylic acid ethyl ester $AA_1$. Compound $AA_1$, a mixture of diastereoisomers (cream solid), was synthesized from compound 53 (342 mg, 1 eq.), compound $Z_1$ (300 mg, 1 eq.), and supported triphenylphosphine (1.08 g, 2.2 eq.) in 95% yield, following the procedure as described for compound 54c.

MS (ESI, EI⁺): m/z=694 (MH⁺).

Step H: Synthesis of (Z)-(4R,6S,15S,17S)-17[8-chloro-7-methoxy-2-(4-cyclopropylthiazol-2-yl)quinolin-4-yloxy]-13-N-methyl-2,14-dioxo-1,3,13-triazatricyclo[13.3.0.0]octadec-7-ene-4-carboxylic acid $AB_1$. Compound $AB_1$ (white solid) was synthesized from compound $AA_1$ (599 mg, 1 eq.) in 15% yield, following the procedure as described for compound 55c. In this case, the pure diastereoisomer was purified by chromatography (DCM/MeOH).

MS (ESI, EI⁺): m/z=666 (MH⁺).

Step I: Synthesis of (Z)-(4R,6S,15S,17S)-[17-[8-chloro-7-methoxy-2-(4-cyclopropylthiazol-2-yl)quinolin-4-yloxy]-13-N-methyl-2,14-dioxo-1,3,13-triazatricyclo-[13.3.0.0]octadec-7-ene-4-yl]carbonyl-(cyclopropyl)sulfonamide $AC_1$. Compound $AC_1$ (yellow solid) was synthesized from compound $AB_1$ (88 mg, 1 eq.) and cyclopropylsulfonamide (64 mg, 4 eq.) in 51% yield, following the procedure as described for compound $G_2$ (purification by HPLC).

$^1$H NMR (CDCl₃, 400 MHz): δ 0.93-0.97 (m, 2H), 1-1.04 (m, 2H), 1.08-1.17 (m, 2H), 1.37-1.41 (m, 2H), 1.46-1.53 (m, 1H), 1.55-1.69 (m, 4H), 1.87-1.96 (m, 2H), 2.14-2.59 (m, 2H), 2.38-2.45 (m, 1H), 2.58-2.63 (m, 1H), 2.90-3.01 (m, 2H), 3.04 (s, 3H), 3.78 (dd, J=8.26 and 7.03 Hz, 1H), 4.01-4.05 (m, 2H), 4.07 (s, 3H), 4.61 (td, J=13.74 and 2.79 Hz, 1H), 4.88-4.95 (m, 2H), 5.14 (s, 1H), 5.45-5.51 (m, 1H), 5.64 (td, J=10.78 and 5.78 Hz, 1H), 7 (s, 1H), 7.25 (d, J=9.30 Hz, 1H), 7.53 (s, 1H), 8.04 (d, J=9.30 Hz, 1H), 11.22 (br s, 1H); MS (ESI, EI⁺): m/z=769 (MH⁺).

Step J: Synthesis of 2-bromo-1-cyclobutylylethanone $U_2$. Compound $U_2$ (yellow oil) was synthesized from cyclobutyl methyl ketone (22 g, 1 eq.) and bromine (11.5 mL, 1 eq.) in 60% yield, following the procedure as described for compound $U_1$.

$^1$H NMR (CDCl₃, 400 MHz): δ 1.75-1.84 (m, 1H), 1.89-2 (m, 1H), 2.10-2.27 (m, 4H), 3.49-3.57 (m, 1H), 3.82 (s, 2H).

Step K: Synthesis of 4-cyclobutylthiazole-2-carboxylic acid ethyl ester $V_2$. Compound $V_2$ (yellow oil) was synthesized from compound $U_2$ (23.87 g, 1 eq.) and ethyl thiooxamate (21.41 g, 1 eq.) in 64% yield, following the procedure as described for compound 36.

$^1$H NMR (DMSO-d₆, 400 MHz): δ 1.32 (t, J=7.12 Hz, 3H), 1.82-1.89 (m, 1H), 1.92-2.02 (m, 1H), 2.15-2.33 (m, 4H), 3.65-3.74 (m, 1H), 4.36 (q, J=7.12 Hz, 2H), 7.76 (d, J=0.64 Hz, 1H); MS (ESI, EI$^+$): m/z=212 (MH$^+$).

Step L: Synthesis of Lithium 4-cyclobutylthiazole-2-carboxylate $W_2$. Compound $W_2$ (beige solid) was synthesized from compound $V_2$ (17.5 g, 1 eq.) in 97% yield, following the procedure as described for compound 37.

$^1$H NMR (DMSO-d$_6$, 400 MHz): δ 1.73-1.85 (m, 1H), 1.88-2 (m, 1H), 2.18-2.24 (m, 4H), 3.50-3.61 (m, 1H), 7.14 (s, 1H); MS (ESI, EI$^+$): m/z=184 (MH$^+$).

Step M: Synthesis of 4-cyclobutylthiazole-2-carbonyl chloride $X_2$. Compound $X_2$ was synthesized from compound $W_2$ (5 g, 1 eq.), following the procedure as described for compound 38.

MS (ESI, EI$^+$): m/z=198 (MH$^+$).

Step N: Synthesis of N-(6-acetyl-2-chloro-3-methoxyphenyl)-4-cyclobutylthiazole-2-carboxamide $Y_2$. Compound $Y_2$ (white solid) was synthesized from compound $X_2$ (5.48 g, 1.2 eq.) in 70% yield, following the procedure as described for compound $Y_1$.

$^1$H NMR (CDCl$_3$, 400 MHz): δ 1.96-2.12 (m, 2H), 2.34-2.44 (m, 4H), 2.59 (s, 3H), 3.70-3.78 (m, 1H), 3.99 (s, 3H), 6.88 (d, J=8.82 Hz, 1H), 7.20 (s, 1H), 7.68 (d, J=8.76 Hz, 1H), 10.33 (br s, 1H); MS (ESI, EI$^+$): m/z=365 (MH$^+$).

Step O: Synthesis of 8-chloro-7-methoxy-2-(4-cyclobutylthiazol-2-yl)quinolin-4-ol $Z_2$. Compound $Z_2$ (beige solid) was synthesized from compound $Y_2$ (5.68 g, 1 eq.) in 84% yield, following the procedure as described for compound AE (80° C. overnight).

$^1$H NMR (DMSO-d$_6$, 400 MHz): δ 1.87-1.95 (m, 1H), 1.96-2.07 (m, 1H), 2.23-2.35 (m, 4H), 3.67-3.76 (m, 1H), 4.02 (s, 3H), 7.51 (s, 1H), 7.53 (d, J=9.30 Hz, 1H), 7.63 (s, 1H), 8.11 (d, J=9.30 Hz, 1H), 11.89 (br s, 1H); MS (ESI, EI$^+$): m/z=347 (MH$^+$).

Step P: Synthesis of (Z)-(4R,6S,15S,17S)-17[8-chloro-7-methoxy-2-(4-cyclobutylthiazol-2-yl)quinolin-4-yloxy]-13-N-methyl-2,14-dioxo-1,3,13-triazatricyclo[13.3.0.0]octadec-7-ene-4-carboxylic acid ethyl ester $AA_2$. Compound $AA_2$, a mixture of diastereoisomers, was synthesized from compound Z (365 mg, 1 eq.) and compound 53 (400 mg, 1 eq.) in 34% yield, following the procedure as described for compound 54c.

MS (ESI, EI$^+$): m/z=708 (MH$^+$).

Step Q: Synthesis of (Z)-(4R,6S,15S,17S)-17[8-chloro-7-methoxy-2-(4-cyclobutylthiazol-2-yl)quinolin-4-yloxy]-13-N-methyl-2,14-dioxo-1,3,13-triazatricyclo[13.3.0.0]octadec-7-ene-4-carboxylic acid $AB_2$. Compound $AB_2$ (off-white solid) was synthesized from compound $AA_2$ in 35% yield, following the procedure as described for compound 55c.

$^1$H NMR (CDCl$_3$, 400 MHz): δ 1.22-1.33 (m, 2H), 1.38-1.42 (m, 2H), 1.52-1.63 (m, 2H), 1.81-1.84 (m, 1H), 1.88-2 (m, 2H), 2.03-2.14 (m, 1H), 2.22-2.36 (m, 4H), 2.40-2.48 (m, 2H), 2.59-2.64 (m, 1H), 2.80-2.88 (m, 1H), 2.97-3.04 (m, 1H), 3.04 (s, 3H), 3.72-3.83 (m, 2H), 4.03-4.07 (m, 1H), 4.07 (s, 3H), 4.61 (td, J=13.46 and 2.20 Hz, 1H), 4.91 (t, J=10.65 Hz, 1H), 4.98 (dd, J=8.96 and 4.96 Hz, 1H), 5.19 (s, 1H), 5.49-5.55 (m, 1H), 5.65 (td, J=10.65 and 4.55 Hz, 1H), 7.14 (s, 1H), 7.26 (d, J=9.25 Hz, 1H), 7.58 (s, 1H), 8.05 (d, J=9.25 Hz, 1H); MS (ESI, EI$^+$): m/z=680.23 (MH$^+$).

Step R: Synthesis of (Z)-(4R,6S,15S,17S)-[17-[8-chloro-7-methoxy-2-(4-cyclobutylthiazol-2-yl)quinolin-4-yloxy]-13-N-methyl-2,14-dioxo-1,3,13-triazatricyclo-[13.3.0.0]octadec-7-en-4-yl]carbonyl-(cyclopropyl)sulfonamide $AC_2$. Compound $AC_2$ (off-white solid) was synthesized from compound $AB_2$ (120 mg, 1 eq.) in 24% yield, following the procedure as described for compound $G_2$.

$^1$H NMR (CDCl$_3$, 400 MHz): δ 0.86-0.90 (m, 2H), 0.91-0.97 (m, 1H), 1.06-1.19 (m, 2H), 1.22-1.43 (m, 3H), 1.46-1.69 (m, 3H), 1.88-2 (m, 2H), 2.03-2.15 (m, 1H), 2.19-2.25 (m, 1H), 2.29-2.35 (m, 2H), 2.41-2.46 (m, 3H), 2.58-2.64 (m, 1H), 2.80-2.90 (m, 1H), 2.91-3.02 (m, 1H), 3.05 (s, 3H), 3.74-3.82 (m, 2H), 4.02-4.07 (m, 1H), 4.07 (s, 3H), 4.58-4.65 (m, 1H), 4.91 (t, J=10.79 Hz, 1H), 4.94 (dd, J=8.95 and 5.40 Hz, 1H), 5.08 (s, 1H), 5.48-5.55 (m, 1H), 5.64 (td, J=10.74 and 5.66 Hz, 1H), 7.14 (s, 1H), 7.26 (d, J=9.24 Hz, 1H), 7.59 (s, 1H), 8.05 (d, J=9.24 Hz, 1H), 11.19 (br s, 1H); MS (ESI, EI$^+$): m/z=783.24 (MH$^+$).

Step S: Synthesis of (Z)-(4R,6S,15S,17S)-[17-[8-chloro-7-methoxy-2-(4-cyclobutylthiazol-2-yl)quinolin-4-yloxy]-13-N-methyl-2,14-dioxo-1,3,13-triazatricyclo-[13.3.0.0]octadec-7-en-4-yl]carbonyl-(1-methylcyclopropyl) sulfonamide $AC_3$. Compound $AC_3$ (off-white solid) was synthesized from compound $AB_2$ (95 mg, 1 eq.) in 27% yield, following the procedure as described for compound $G_2$.

$^1$H NMR (CDCl$_3$, 400 MHz): δ 0.79-0.84 (m, 2H), 0.86-0.90 (m, 1H), 1.22-1.41 (m, 3H), 1.52 (s, 3H), 1.49-1.75 (m, 3H), 1.80-1.83 (m, 1H), 1.89-2.01 (m, 2H), 2.05-2.15 (m, 1H), 2.17-2.24 (m, 1H), 2.29-2.34 (m, 2H), 2.39-2.48 (m, 3H), 2.58-2.63 (m, 1H), 2.82-2.92 (m, 1H), 2.95-3.04 (m, 1H), 3.05 (s, 3H), 3.73-3.82 (m, 2H), 4.03-4.06 (m, 1H), 4.07 (s, 3H), 4.61 (td, J=13.71 and 2.41 Hz, 1H), 4.91 (t, J=10.72 Hz, 1H), 4.96 (dd, J=8.85 and 5.24 Hz, 1H), 5.14 (s, 1H), 5.47-5.54 (m, 1H), 5.64 (td, J=10.80 and 5.79 Hz, 1H), 7.14 (s, 1H), 7.25 (d, J=9.25 Hz, 1H), 7.59 (s, 1H), 8.05 (d, J=9.25 Hz, 1H), 11.16 (br s, 1H); MS (ESI, EI$^+$): m/z=797.48 (MH$^+$).

Example 27

Preparation of Macrocyclic Compound AH

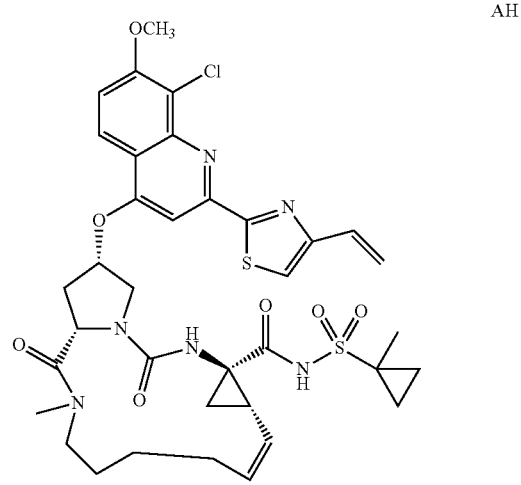

AH

The synthesis of macrocyclic compound AH is shown in Scheme 34.

Step A: Synthesis of N-(6-acetyl-2-chloro-3-methoxyphenyl)-4-vinylthiazole-2-carboxamide AD. A solution of compound $A_1$ (2.10 g, 1 eq.) and tributylvinyl tin (2.06 g, 1.2 eq.) in toluene (55 mL) was degazed by bubbling nitrogen during 15 min. Then, triphenylphosphine (250 mg, 4%) was added under nitrogen and the reaction mixture was heated to 100° C. overnight. After cooling, the solvent was concentrated under diminished pressure and the residue was triturated with diethyl ether to yield compound G as a beige powder in 88% yield.

$^1$H NMR (CDCl$_3$, 400 MHz): δ 2.60 (s, 3H), 4 (s, 3H), 5.5 (dd, J=10.85 and 1.24 Hz, 1H), 6.24 (dd, J=17.26 and 1.24 Hz, 1H), 6.79 (dd, J=17.34 and 10.78 Hz, 1H), 6.90 (d, J=8.74 Hz, 1H), 7.40 (s, 1H), 7.71 (d, J=8.74 Hz, 1H), 10.45 (br s, 1H).

Step B: Synthesis of 8-chloro-7-methoxy-2-(4-vinylthiazol-2-yl)quinolin-4-ol AE. Potassium tert-butoxide (2.13 g, 2.2 eq.) was added to a suspension of compound AD (2.91 g, 1 eq.) in tert-butanol (30 mL). The reaction mixture was heated to 100° C. for 5 hrs. After one night at room temperature, the mixture was diluted with diethyl ether and the precipitate filtered, washed with diethyl ether, and solubilized in water. The pH was adjusted to 6-7 by addition of 1N HCl and the precipitate was filtered, washed with water, and triturated with diethyl ether to yield compound AE in 73% yield.

$^1$H NMR (CDCl$_3$, 400 MHz): δ 4.06 (s, 3H), 5.54 (d, J=10.82 Hz, 1H), 6.25 (d, J=17.31 Hz, 1H), 6.74 (s, 1H), 6.79 (dd, J=17.31 and 10.82 Hz, 1H), 7.06 (d, J=9.10 Hz, 1H), 7.32 (s, 1H), 8.28 (d, J=9.10 Hz, 1H), 9.97 (br s, 1H).

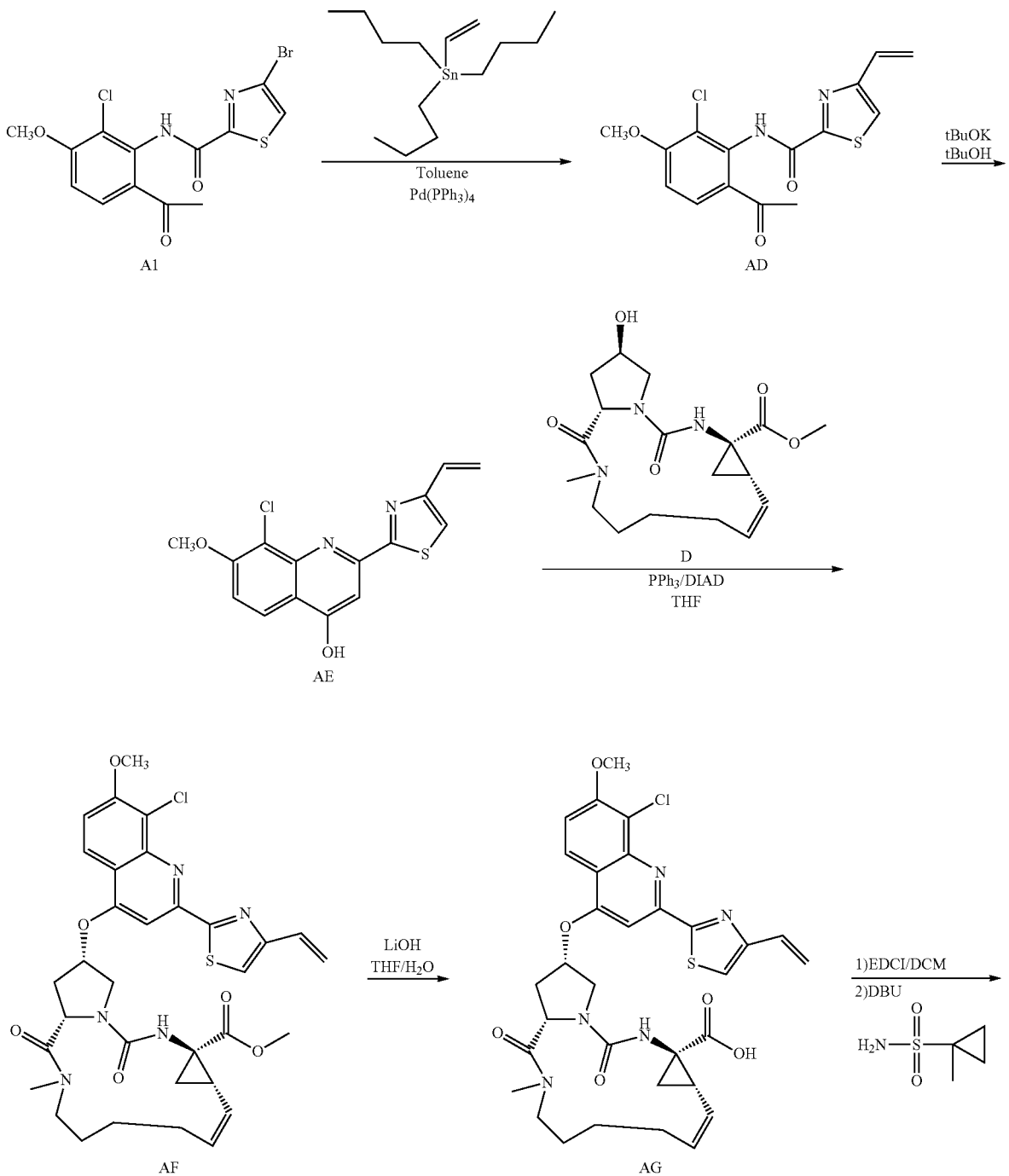

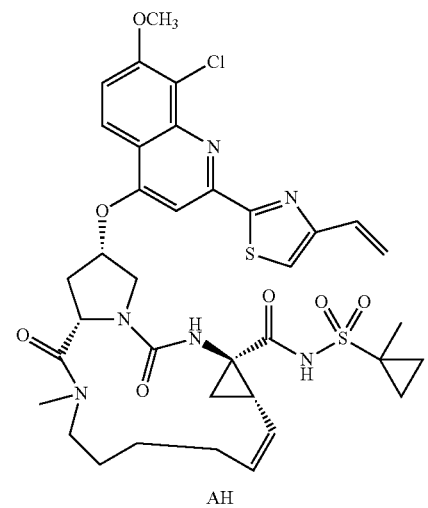

AH

Step C: Synthesis of (Z)-(4R,6S,15S,17S)-17[8-chloro-7-methoxy-2-(4-vinylthiazol-2-yl)quinolin-4-yloxy]-13-N-methyl-2,14-dioxo-1,3,13-triazatricyclo[13.3.0.0]octadec-7-ene-4-carboxylic acid methyl ester AF. Compound AF, a mixture of diastereoisomers (white powder), was synthesized from compound D (2.80 g, 1.2 eq.) and compound AE (2 g, 1 eq.) in 43% yield, following the procedure as described for compound 54c.

MS (ESI, EI$^+$): m/z=666.37 (MH$^+$).

Step D: Synthesis of (Z)-(4R,6S,15S,17S)-17[8-chloro-7-methoxy-2-(4-vinylthiazol-2-yl)quinolin-4-yloxy]-13-N-methyl-2,14-dioxo-1,3,13-triazatricyclo[13.3.0.0]octadec-7-ene-4-carboxylic acid AG. Compound AG was synthesized from compound AF (1.62 g, 1 eq.) in 45% yield, following the procedure as described for compound 55c.

$^1$H NMR (CDCl$_3$, 400 MHz): δ 1.24-1.32 (m, 2H), 1.40-1.44 (m, 2H), 1.51-1.58 (m, 2H), 1.80 (dd, J=8.16 and 6.33 Hz, 1H), 1.83-1.91 (m, 1H), 2.2-2.32 (m, 2H), 2.58-2.63 (m, 1H), 2.95-3.01 (m, 1H), 3.03 (s, 3H), 3.81 (dd, J=8.53 and 6.88 Hz, 1H), 4.02-4.06 (m, 1H), 4.07 (s, 3H), 4.59 (td, J=13.50 and 2.70 Hz, 1H), 4.89-4.96 (m, 2H), 5.33 (s, 1H), 5.44 (dd, J=10.82 and 1.44 Hz, 1H), 5.45-5.51 (m, 1H), 5.63 (td, J=10.82 and 4.72 Hz, 1H), 6.16 (dd, J=17.34 and 1.31 Hz, 1H), 6.81 (dd, J=17.34 and 10.90 Hz, 1H), 7.26 (d, J=9.29 Hz, 1H), 7.33 (s, 1H), 7.61 (s, 1H), 8.04 (d, J=9.29 Hz, 1H); MS (ESI, EI$^+$): m/z=652.14 (MH$^+$).

Step E: Synthesis of (Z)-(4R,6S,15S,17S)-[17-[8-chloro-7-methoxy-2-(4-vinylthiazol-2-yl)quinolin-4-yloxy]-13-N-methyl-2,14-dioxo-1,3,13-triazatricyclo-[13.3.0.0]octadec-7-en-4-yl]carbonyl(1-methyl-cyclopropyl)sulfonamide AH. Compound AH (white powder) was synthesized from compound AG (160 mg, 1 eq.) and 1-methyl-cyclopropylsulfonamide (133 mg, 4 eq.) in 13% yield, following the procedure as described for compound G$_2$.

$^1$H NMR (CDCl$_3$, 400 MHz): δ 0.79-0.85 (m, 2H), 1.19-1.26 (m, 1H), 1.33-1.41 (m, 2H), 1.53-1.60 (m, 5H), 1.62-1.72 (m, 2H), 1.81-1.85 (m, 1H), 1.92-1.95 (m, 1H), 2.19-2.25 (m, 1H), 2.40-2.47 (m, 1H), 2.58-2.63 (m, 1H), 2.82-2.93 (m, 1H), 2.96-3.04 (m, 1H), 3.05 (s, 3H), 3.79-3.83 (m, 1H), 4.01-4.05 (m, 1H), 4.08 (s, 3H), 4.58-4.65 (m, 1H), 4.92 (t, J=10.77 Hz, 1H), 4.97 (dd, J=8.93 and 5.12 Hz, 1H), 5.06 (s, 1H), 5.46 (dd, J=10.80 and 1.21 Hz, 1H), 5.47-5.54 (m, 1H), 5.61-5.68 (m, 1H), 6.19 (dd, J=17.36 and 1.24 Hz, 1H), 6.83 (dd, J=17.36 and 10.87 Hz, 1H), 7.28 (d, J=9 Hz, 1H), 7.34 (s, 1H), 7.64 (s, 1H), 8.06 (d, J=9.25 Hz, 1H), 11.12 (brs, 1H); MS (ESI, EI$^+$): m/z=769.26 (MH$^+$).

Example 28

Preparation of Macrocyclic Compound AN

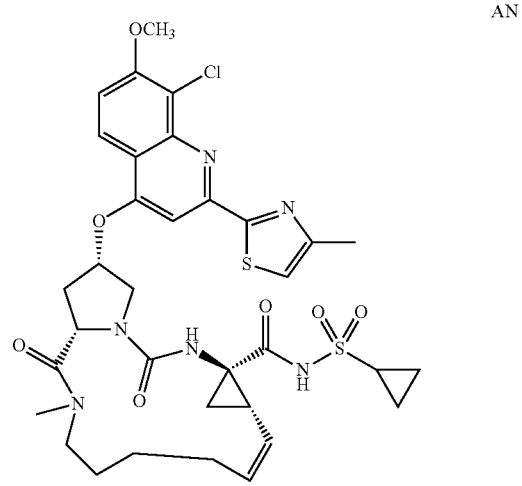

AN

The synthesis of macrocyclic compound AN is shown in Scheme 35.

Scheme 35

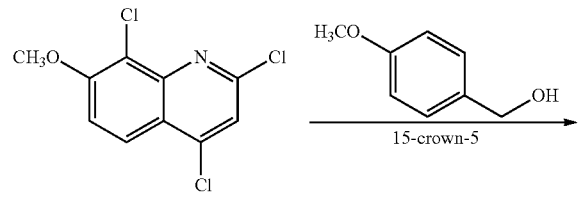

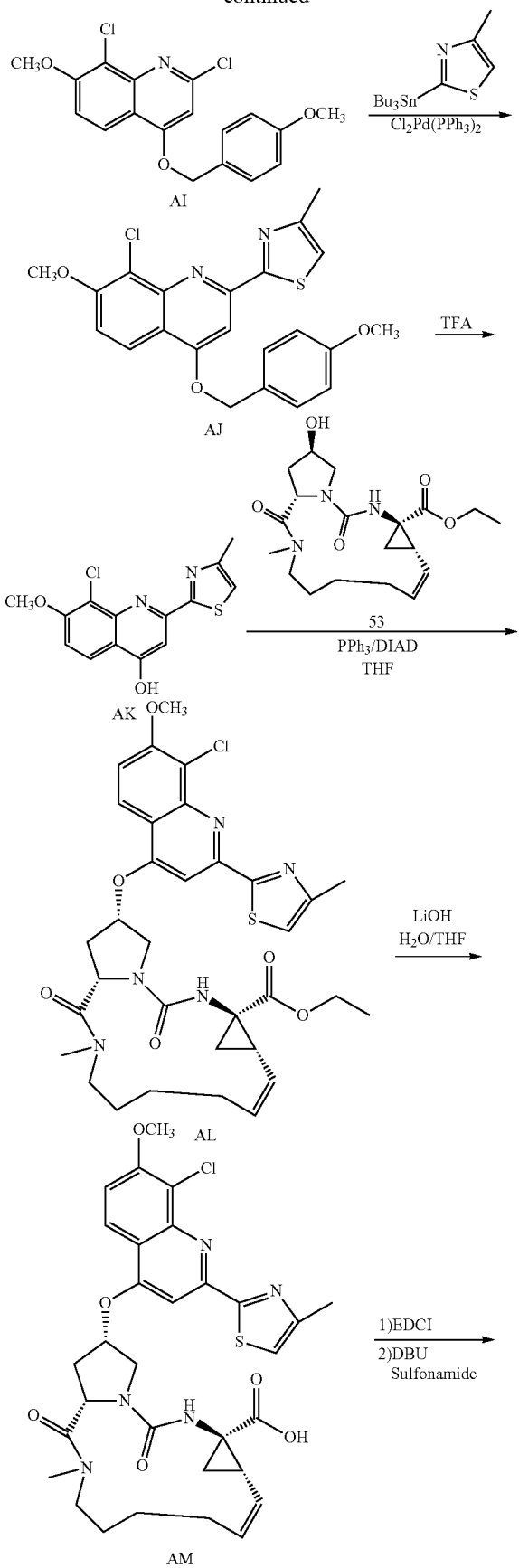

Step A: Synthesis of 4-(4-methoxybenzyloxy)-2,8-dichloro-7-methoxyquinoline AI. Sodium hydride (2.74 g, 1.2 eq.) was added portionwise to a solution of p-methoxybenzyl alcohol (8.55 mL, 1.2 eq.) and 15-crown-5 (13.6 mL, 1.2 eq.) in 35 mL of DMF. The mixture was allowed to stir at room temperature for 30 min, and then added to a solution of 2,4,8-trichloro-7-methoxyquinoline (15 g, 1 eq.) in DMF (75 mL) via canula. After 18 hrs of stirring at room temperature, the mixture was poured on 500 mL of water and NH$_4$Cl aqueous. Ethyl acetate (200 mL) was added and the precipitate was filtered. The filtrate was purified by chromatography on silica gel to yield compound AI in 56% yield.

$^1$H NMR (CDCl$_3$, 400 MHz) δ 3.85 (s, 3H), 4.05 (s, 3H), 5.19 (s, 2H), 6.77 (s, 1H), 6.97 (d, J=8.64 Hz, 2H), 7.23 (d, J=9.25 Hz, 1H), 7.41 (d, J=8.64 Hz, 2H), 8.08 (d, J=9.25 Hz, 1H); MS (ESI, EI$^+$): m/z=386.1 (MNa$^+$).

Step B: Synthesis of 4-(4-methoxybenzyloxy)-8-chloro-7-methoxy-2-(4-methylthiazol-2-yl)quinoline AJ. To a solution of compound AI (1 g, 1 eq.) and 2-(tributylstannyl)-4-methylthiazole (1.28 g, 1.2 eq.) in DMF (14 mL) were added PdCl$_2$(PPh$_3$)$_2$ (193 mg, 10%) and potassium carbonate (455 mg, 1.2 eq.) and the resulting mixture was stirred at 90° C. overnight. DMF was concentrated under vacuum and water and dichloromethane were added. The aqueous layer was extracted with dichloromethane and the combined organic layers washed with water and brine, dried over Na$_2$SO$_4$, filtered, and concentrated. The residue was purified by chromatography on a silica gel to yield compound AJ as a white solid in 65% yield.

$^1$H NMR (CDCl$_3$, 400 MHz) δ 2.57 (s, 3H), 3.86 (s, 3H), 4.06 (s, 3H), 5.33 (s, 2H), 6.98 (d, J=8.64 Hz, 2H), 7.08 (s, 1H), 7.25 (d, J=9.25 Hz, 1H), 7.46 (d, J=8.64 Hz, 2H), 7.74 (s, 1H), 8.12 (d, J=9.25 Hz, 1H); MS (ESI, EI$^+$): m/z=427.1 (MH$^+$).

Step C: Synthesis of 8-chloro-7-methoxy-2-(4-methylthiazol-2-yl)quinolin-4-ol AK. Compound AJ (750 mg, 1 eq.) in trifluoroacetic acid (5 mL) was stirred at room temperature for 10 min. Then, the acid was evaporated, ethyl acetate added and concentrated again in diminished pressure. The residue was triturated in diethyl ether to give the compound AK as a white solid in quantitative yield.

$^1$H NMR (CDCl$_3$, 400 MHz) δ 2.59 (d, J=0.81 Hz, 3H), 4.10 (s, 3H), 7.19 (d, J=9.25 Hz, 1H), 7.22 (d, J=0.81 Hz, 1H), 7.25 (s, 1H), 8.36 (d, J=9.25 Hz, 1H), 10.51 (br s, 1H); MS (ESI, EI$^+$): m/z 306.93 (MH$^+$).

Step D: Synthesis of (Z)-(4R,6S,15S,17S)-17[8-chloro-7-methoxy-2-(4-methylthiazol-2-yl)quinolin-4-yloxy]-13-N-methyl-2,14-dioxo-1,3,13-triazatricyclo[13.3.0.0]octadec-7-ene-4-carboxylic acid ethyl ester AL. Compound AL, a mixture of diatereoisomers, was synthesized from compound AK (365 mg, 1 eq.) and compound 53 (450 mg, 1 eq.) in 40% yield, following the procedure as described for compound 54c.

MS (ESI, EI⁺): m/z=668.08 (MH⁺).

Step E: Synthesis of (Z)-(4R,6S,15S,17S)-17[8-chloro-7-methoxy-2-(4-methylthiazol-2-yl)quinolin-4-yloxy]-13-N-methyl-2,14-dioxo-1,3,13-triazatricyclo[13.3.0.0]octadec-7-ene-4-carboxylic acid AM. Compound AM was synthesized from compound AL (320 mg, 1 eq.) in 11% yield, following the procedure as described for compound 55c.

$^1$H NMR (CDCl$_3$, 400 MHz) δ 1.20-1.55 (m, 6H), 1.75-1.79 (m, 1H), 1.84-1.91 (m, 1H), 2.17-2.28 (m, 2H), 2.53 (s, 3H), 2.56-2.63 (m, 1H), 2.76-2.84 (m, 1H), 2.97-3.05 (m, 1H), 3.02 (s, 3H), 3.76-3.80 (m, 1H), 4.06 (s, 3H), 4.08-4.11 (m, 1H), 4.54-4.62 (m, 1H), 4.91-4.98 (m, 2H), 5.41-5.47 (m, 1H), 5.56-5.62 (m, 1H), 7.08 (s, 1H), 7.25 (d, J=9.25 Hz, 1H), 7.55 (s, 1H), 8.05 (d, J=9.25 Hz, 1H); MS (ESI, EI⁺): m/z=640.06 (MH⁺).

Step F: Synthesis of (Z)-(4R,6S,15S,17S)-[17-[8-chloro-7-methoxy-2-(4-methylthiazol-4-yl)quinolin-4-yloxy]-13-N-methyl-2,14-dioxo-1,3,13-triazatricyclo-[13.3.0.0]octadec-7-en-4-yl]carbonyl-(cyclopropyl)sulfonamide AN. Compound AN (white solid) was synthesized from compound AM (34 mg, 1 eq.) and cyclopropylsulfonamide (26 mg, 4 eq.) in 9% yield, following the procedure as described for compound G2.

$^1$H NMR (CDCl$_3$, 400 MHz) δ 0.85-0.96 (m, 1H), 1.07-1.17 (m, 2H), 1.2-1.79 (m, 6H), 1.87-1.95 (m, 2H), 2.17-2.24 (m, 1H), 2.36-2.44 (m, 1H), 2.53-2.57 (m, 3H), 2.57-2.62 (m, 1H), 2.81-3 (m, 3H), 3.02-3.05 (m, 3H), 3.75-3.80 (m, 1H), 4.05-4.12 (m, 4H), 4.56-4.64 (m, 1H), 4.87-4.94 (m, 2H), 5.27 (br s, 1H), 5.43-5.50 (m, 1H), 5.59-5.67 (m, 1H), 7.08-7.09 (m, 1H), 7.24-7.28 (m, 1H), 7.61 (s, 1H), 8.03-8.06 (m, 1H), 11.24 (br s, 1H); MS (ESI, EI⁺): m/z 743.12 (MH⁺).

Example 29

Synthesis of DArPhin Catalysts

The DArPhin catalysts, such as AP, AQ, AR, and AT, were prepared following methods described herein as shown in Scheme 36.

Scheme 36

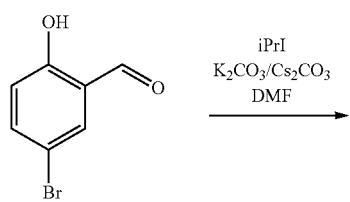

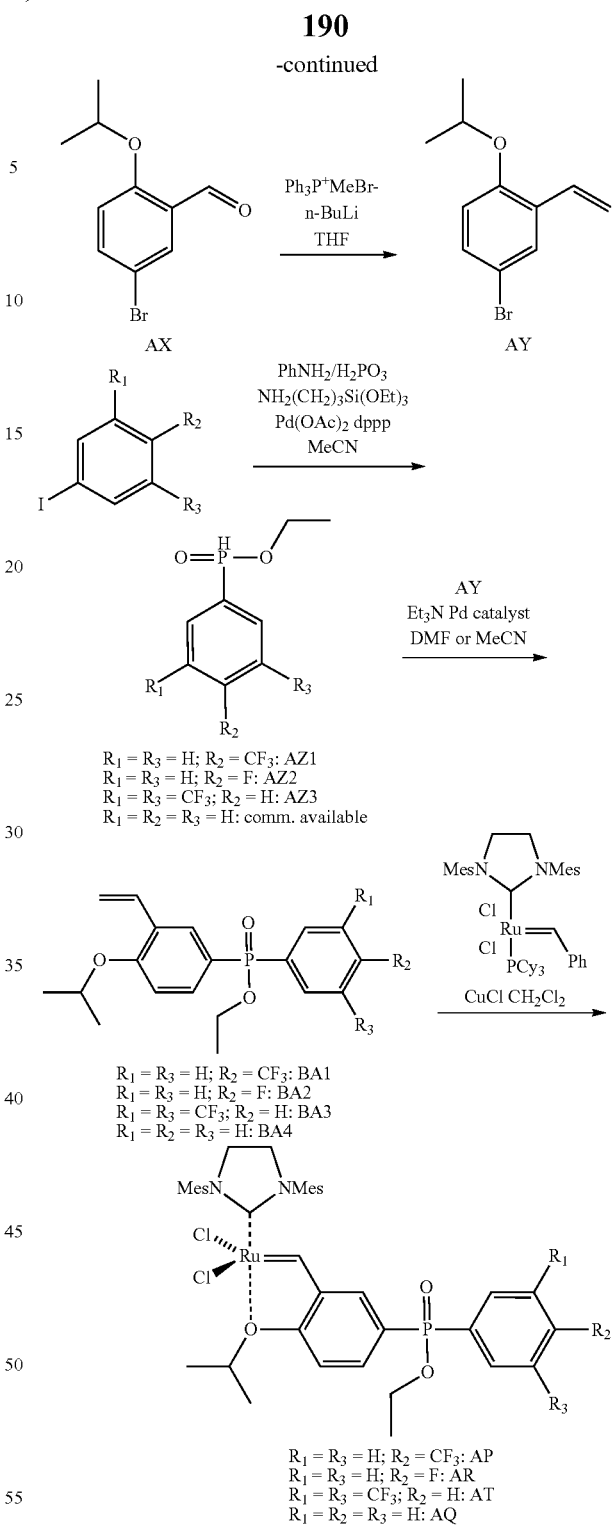

Step A: Synthesis of 5-bromo-2-isopropoxybenzaldehyde AX. To a suspension of potassium carbonate (34.4 g, 249 mmol) and cesium carbonate (16.2 g, 50 mmol) in dimethylformamide were added 5-bromosalicaldehyde (25.0 g, 124 mmol) and 2-iodopropane (25.0 mL, 249 mmol). The suspension was stirred at room temperature overnight, then at 70° C. for 4 hrs. The volatiles were removed, and the residue was partitioned between methyl t-butylether and water. The aqueous layer was extracted with methyl t-butylether and the combined organic phases were washed with water, sodium hydroxide, and brine, and then dried over magnesium sulfate. Concentration to dryness afforded compound AX (30.0 g) as a pale yellow oil in 99% yield.

$^1$H NMR (CDCl$_3$, 400 MHz): δ 1.40 (d, J=6.3 Hz, 6H), 4.65 (sept., J=6.0 Hz, 1H), 6.89 (d, J=9.0 Hz, 1H), 7.59 (dd, J=9.0 and 2.7 Hz, 1H), 7.91 (d, J=2.7 Hz, 1H), 10.39 (s, 1H).

Step B: Synthesis of 4-bromo-1-isopropoxy-2-vinylbenzene AY. To a suspension of methyltriphenylphosphonium bromide (41.1 g, 115 mmol) in THF (1.2 L) cooled to −70° C., was added n-butyllithium (123 mmol, 2.5 M in hexanes). The mixture was stirred for a further 10 min, and then allowed to warm up to 0° C. and stir at this temperature for 10 min. The reaction mixture is then cooled again at −50° C., and 5-bromo-2-isopropoxybenzaldehyde (20.0 g, 82.2 mmol) in solution in THF (5 mL) was added. The mixture was stirred for 10 min, then allowed to warm up to room temperature. An ammonium chloride solution was added and the reaction mixture was diluted with a mixture methyl t-butylether/hexane, filtered through celite, and then dried over magnesium sulfate. The solvent was removed in vacuo to afford compound AY (18.9 g) as a pale yellow oil in 95% yield.

$^1$H NMR (CDCl$_3$, 400 MHz): δ 1.34 (d, J=6.0 Hz, 6H), 4.50 (sept., J=6.0 Hz, 1H), 5.27 (dd, J=11.0 and 1.1 Hz, 1H), 5.71 (dd, J=17.9 and 1.2 Hz, 1H), 6.75 (d, J=8.7 Hz, 1H), 6.97 (dd, J=17.7 and 11.2 Hz, 1H), 7.28 (dd, J=8.7 and 2.5 Hz, 1H), 7.57 (d, J=2.5 Hz, 1H).

Step C: Synthesis of ethyl 4-(trifluoromethyl)phenylphosphinate AZ1. To a degassed solution of 4-iodobenzotrifluoride (4.70 g, 17.2 mmol), anilinium hypophosphite (3.51 g, 22.1 mmol), and 3-aminopropyl triethoxysilane (4.88 g, 22.1 mmol) in anhydrous acetonitrile (110 mL) were added palladium acetate (82.5 mg, 0.367 mmol, 2 mol %) and 1,3-bis(diphenylphosphino)propane (167 mg, 0.404 mol, 2.2 mol %). The mixture was heated under reflux for 32 hrs, then cooled down to room temperature, diluted with ethyl acetate and hydrochloric acid (IM) and partitioned. The aqueous layer was further extracted with ethyl acetate, and the combined extracts were washed with aqueous sodium hydrogen carbonate and brine and dried over magnesium sulfate. The solvent was removed in vacuo and the residue was purified by column chromatography using 25 to 100% ethyl acetate in petroleum ether. Further purification by distillation afforded compound AZ1 (1.14 g) in 28% yield.

$^1$H NMR (CDCl$_3$, 400 MHz): δ 1.35-1.43 (m, 3H), 4.12-4.27 (m, 2H), 7.63 (d, J=570.8 Hz, 1H), 7.75-7.80 (m, 2H), 7.90-7.94 (m, 2H). $^{31}$P NMR (CDCl$_3$, 161.8 MHz): δ 22.6.

Step D: Synthesis of ethyl [4-(trifluoromethyl)phenyl]-{4-(isopropoxy)-3-vinylphenyl}phosphinate BA1. To a degassed solution of ethyl 4-(trifluoromethyl)-phenylphosphinate (1.00 g, 4.20 mmol) and 4-bromo-1-isopropoxy-2-vinylbenzene (921 mg, 3.81 mmol) in DMF (40 mL) were added the triethylamine (1.1 mL, 7.62 mmol) and tris(dibenzylideneacetone)dipalladium (698 mg, 0.762 mmol). The mixture was warmed at 70° C. overnight. The volatiles were removed in vacuo and the residue was purified by column chromatography using 5 to 100% ethyl acetate in petroleum ether to afford compound BA1 (130 mg) as a dark green oil in 8.6% yield.

$^1$H NMR (CDCl$_3$, 400 MHz): δ 1.37 (d, J=6.0 Hz, 6H), 1.38 (t, J=7.1 Hz, 3H), 4.07-4.17 (m, 2H), 4.63 (sept., J=6.1 Hz, 1H), 5.31 (dd, J=11.2 and 1.1 Hz, 1H), 5.79 (dd, J=17.7 and 1.1 Hz, 1H), 6.92 (dd, J=8.6 and 3.1 Hz, 1H), 6.99 (dd, J=17.3 and 10.8 Hz, 1H), 7.59-7.66 (m, 1H), 7.67-7.72 (m, 2H), 7.87-7.96 (m, 3H). $^{31}$P NMR (CDCl$_3$, 161.8 MHz): δ 30.7.

Step E: Synthesis of 1,3-bis(2,4,6-trimethylphenyl)-4,5-dihydroimidazol-2-ylidene[2-(1-propoxy-5-(4-trifluoromethylphenyl ethylphosphite))phenyl]methylene-ruthenium (II) dichloride AP. Grubbs' 2nd generation catalyst (277 mg, 0.326 mmol) and copper (I) chloride were charged in a Schlenk tube and degassed. A degassed solution of ethyl [4-(trifluoromethyl)phenyl]-{4-(isopropoxy)-3-vinylphenyl}phosphinate (130 mg, 0.326 mmol) in anhydrous dichloromethane (17 mL) was transferred via cannula to the solids, and the mixture was heated at 30° C. for 70 min. The solvent was removed in vacuo and the residue was purified by column chromatography using 20 to 66% ethyl acetate in petroleum ether to afford compound AP (115 mg) as a green powder in 41% yield.

$^1$H NMR (CDCl$_3$, 400 MHz): δ 1.26 (d, J=6.0 Hz, 6H), 1.39 (t, J=7.0 Hz, 3H), 2.38 (br s) and 2.45 (br s) (18H), 4.07-4.16 (m, 2H), 4.19 (br s, 4H), 4.93 (sept., J=6.0 Hz, 1H), 6.88 (br dd, J=8.5 and 2.0 Hz, 1H), 7.05 (br s, 4H), 7.27-7.47 (m, 3H), 7.86-7.99 (m, 3H), 16.4 (br s, 1H).

$^{31}$P NMR (CDCl$_3$, 161.8 MHz): δ 29.0.

Step F: Synthesis of ethyl phenyl-{4-(isopropoxy)-3-vinylphenyl}phosphinate BA4. To a degassed mixture of ethyl phenylphosphinate (1.87 g, 11.0 mmol) and 4-bromo-1-isopropoxy-2-vinylbenzene (2.43 g, 10.0 mmol) in acetonitrile (66 mL) were added the triethylamine (3.1 mL, 22.0 mmol), palladium acetate (112 mg, 0.5 mmol), and 1,1'-bis(diphenylphosphino)ferrocene (277 mg, 0.5 mmol). The mixture was further degassed and heated at 68° C. for 24 hrs. The volatiles were removed in vacuo, and the crude was purified by column chromatography using 50 to 80% ethyl acetate in petroleum ether to afford compound BA4 (3.74 g) in 87% yield.

$^1$H NMR (CDCl$_3$, 400 MHz): δ 1.36 (d, J=5.7 Hz, 6H), 1.37 (t, J=6.9 Hz, 3H), 4.15-4.05 (m, 2H), 4.62 (sept., J=6.0 Hz, 1H), 5.28 (dd, J=11.2 and 1.4 Hz, 1H), 5.78 (dd, J=17.7 and 1.4 Hz, 1H), 6.91 (dd, J=8.45 and 3.0 Hz, 1H), 6.99 (dd, J=17.9 and 11.4 Hz, 1H), 7.41-7.47 (m, 2H), 7.47-7.55 (m, 1H), 7.63 (ddd, J=11.7, 8.5 and 2.0 Hz, 1H), 7.79 (dd, J=12.3 and 1.4 Hz, 1H), 7.81 (dt, J=12.3 and 1.4 Hz, 1H), 7.90 (dd, J=12.4 and 2.0 Hz, 1H).

$^{31}$P NMR (CDCl$_3$, 161.8 MHz): δ 32.61.

Step G: Synthesis of 1,3-bis(2,4,6-trimethylphenyl)-4,5-dihydroimidazol-2-ylidene[2-(1-propoxy-5-(phenyl ethylphosphite))phenyl]methyleneruthenium (II) dichloride AQ. Grubbs' second generation catalyst (2.00 g, 2.36 mmol) and copper (I) chloride (233 mg, 2.36 mmol) were charged in a Schlenk tube and degassed. A degassed solution of ethyl phenyl-{4-(isopropoxy)-3-vinylphenyl}phosphinate (778 mg, 2.36 mmol) in anhydrous dichloromethane (120 mL) was transferred via cannula to the solids, and the mixture was heated at 30° C. for 60 min. The solvent was removed in vacuo and the residue was purified by column chromatography using 40 to 100% ethyl acetate in petroleum ether to afford compound AQ (775 mg) in 41% yield.

$^1$H NMR (CDCl$_3$, 400 MHz): δ 1.27 (d, J=6.1 Hz, 6H), 1.37 (t, J=7.0 Hz, 3H), 2.39 (br s) and 2.47 (br s) (18H), 3.98-4.17 (m, 2H), 4.18 (br s, 4H), 4.93 (sept., J=6.0 Hz, 1H), 6.87 (d, J=7.2 Hz, 1H), 7.05 (s, 4H), 7.32 (d, J=11.9 Hz, 1H), 7.42-7.57 (m, 3H), 7.77 (dd, J=12.3 and 7.2 Hz, 2H), 7.94-8.08 (m, 1H), 16.43 (s, 1H). $^{31}$P NMR (CDCl$_3$, 161.8 MHz): δ 30.79.

Step H: Synthesis of ethyl 4-fluorophenylphosphinate AZ2. To a degassed mixture of 4-fluoro-1-iodo-benzene (25.0 g, 112.6 mmol), anilinium hypophosphite (21.5 g, 135.1 mmol) and 3-aminopropyl triethoxysilane (24.9 g, 135.1 mmol) in anhydrous acetonitrile (750 mL) were added palladium acetate (560 mg, 2.48 mmol) and 1,3-bis(diphenylphosphino)propane (1.02 g, 2.48 mmol). The mixture was heated under reflux overnight, then cooled down to room temperature, and the volatiles were removed in vacuo. The residue was diluted with ethyl acetate and hydrochloric acid (1M) and partitioned. The aqueous layer was further extracted with ethyl acetate and the combined extracts were washed with aqueous sodium hydrogen carbonate and brine. The volatiles were removed in vacuo, then the residue was purified by column chromatography using 50 to 100% ethyl acetate in petroleum ether, affording compound AZ2 (10.1 g) as a dark orange oil in 48% yield.

$^1$H NMR (CDCl$_3$, 400 MHz): δ 1.84 (t, J=7.1 Hz, 3H), 4.08-4.24 (m, 2H), 7.20 (td, J=8.7 and 2.5 Hz, 2H), 7.58 (d, J=566.6 Hz, 1H), 7.74-7.85 (m, 2H). $^{31}$P NMR (CDCl$_3$, 161.8 MHz): δ 23.62 (J=566.8 Hz).

Step I: Synthesis of ethyl (4-fluorophenyl)-[4-{isopropoxy}-3-vinylphenyl]-phosphinate BA2. To a degassed mixture of 4-fluoro-phenylphosphinate (2.07 g, 11.0 mmol) and 4-bromo-1-isopropoxy-2-vinylbenzene (2.43 g, 10.0 mmol) in acetonitrile (66 mL) were added triethylamine (3.1 mL, 22.0 mmol), palladium acetate (112 mg, 0.5 mmol), and 1,1'-bis(diphenylphosphino)ferrocene (277 mg, 0.5 mmol). The mixture was heated at 68° C. for 24 hrs. The volatiles were removed in vacuo, and the residue was purified by column chromatography using 40 to 80% ethyl acetate in petroleum ether to afford 2.84 g of compound BA2 in 82% yield.

$^1$H NMR (CDCl$_3$, 400 MHz): δ 1.36 (d, J=6.0 Hz, 6H), 1.38 (t, J=7.1 Hz, 3H), 4.02-4.15 (m, 2H), 4.62 (sept., J=6.0 Hz, 1H), 5.29 (dd, J=11.2 and 1.1 Hz, 1H), 5.78 (dd, J=17.7 and 1.4 Hz, 1H), 6.91 (dd, J=8.7 and 3.0 Hz, 1H), 6.99 (dd, J=17.4 and 10.9 Hz, 1H), 7.12 (td, J=8.8 and 2.5 Hz, 2H), 7.61 (ddd, J=11.7, 8.6 and 1.9 Hz, 1H), 7.75-7.84 (m, 2H), 7.88 (dd, J=12.5 and 1.9 Hz, 1H). $^{31}$P NMR (CDCl$_3$, 161.8 MHz): δ 30.71.

Step J: Synthesis of 1,3-bis(2,4,6-trimethylphenyl)-4,5-dihydroimidazol-2-ylidene[2-(1-propoxy-5-({4-fluorophenyl}ethylphosphite))phenyl]methyleneruthenium (II) dichloride AR. Grubbs' second generation catalyst (2.00 g, 2.36 mmol) and copper (I) chloride (233 mg, 2.36 mmol) were charged in a Schlenk tube and degassed. A degassed solution of ethyl phenyl-{4-(isopropoxy)-3-vinylphenyl}phosphinate (822 mg, 2.36 mmol) in anhydrous dichloromethane (120 mL) was transferred via cannula to the solids, and the mixture was heated at 30° C. for 60 min. The solvent was removed in vacuo and the residue was purified by column chromatography using 30 to 60% ethyl acetate in petroleum ether to afford compound AR (552 mg) in 29% yield.

$^1$H NMR (CDCl$_3$, 400 MHz): δ 1.27 (d, J=6.1 Hz, 6H), 1.37 (t, J=7.0 Hz, 3H), 2.39 (br s) and 2.45 (br s) (18H), 3.98-4.15 (m, 2H), 4.19 (br s, 4H), 4.93 (sept., J=6.0 Hz, 1H), 6.87 (d, J=8.2 Hz, 1H), 7.05 (br s, 4H), 7.15 (dt, J=8.6 and 2.2 Hz, 2H), 7.29 (d, J=11.9 Hz, 1H), 7.72-7.81 (m, 2H), 7.91-7.99 (m, 1H), 16.44 (s, 1H). $^{31}$P NMR (CDCl$_3$, 161.8 MHz): δ 29.94.

Step K: Synthesis of ethyl 3,5-bis(trifluoromethyl)phenylphosphinate AZ3. To a degassed solution of 1-iodo-3,5-bistrifluoromethylbenzene (10.0 g, 29.4 mmol), anilinium hypophosphite (5.62 g, 35.3 mmol) and 3-aminopropyl triethoxysilane (7.81 g, 35.3 mmol) in anhydrous acetonitrile (200 mL) were added palladium acetate (132 mg, 0.588 mmol, 2 mol %) and 1,3-bis(diphenylphosphino)propane (267 mg, 0.647 mol, 2.2 mol %). The mixture was heated under reflux overnight, then cooled down to room temperature, diluted with ethyl acetate and hydrochloric acid (1M), and partitioned. The aqueous layer was further extracted with ethyl acetate and the combined extracts were washed with aqueous sodium hydrogen carbonate and brine, and dried over sodium sulfate. The volatiles were removed in vacuo, and the residue was purified by column chromatography using 30 to 70% ethyl acetate in petroleum ether to afford compound AZ3 (4.65 g) as a cloudy oil in 52% yield.

$^1$H NMR (CDCl$_3$, 400 MHz): δ 1.45 (t, J=7.1 Hz, 3H), 4.18-4.35 (m, 2H), 7.69 (d, J=579.6 Hz, 1H), 8.10 (s, 1H), 8.23 (s, 1H), 8.27 (s, 1H). $^{31}$P NMR (CDCl$_3$, 161.8 MHz): δ 19.59 (J=580.6 Hz).

Step L: Synthesis of ethyl [3,5-bis(trifluoromethyl)phenyl]-{4-(isopropoxy)-3-vinylphenyl}phosphinate BA3. To a degassed solution of ethyl 3,5-bis(trifluoromethyl)-phenylphosphinate (3.33 g, 15.24 mmol) and 4-bromo-1-isopropoxy-2-vinylbenzene (3.33 mg, 13.8 mmol) in DMF (25 mL) were added the triethylamine (3.85 mL, 27.6 mmol) and tris(dibenzylideneacetone)dipalladium (2.53 g, 2.76 mmol). The mixture was heated in an oil bath at 70° C. overnight. The volatiles were removed in vacuo and the mixture was purified by column chromatography with 20 to 70% ethyl acetate in petroleum ether to afford compound BA3 (185 mg) as an oil in 2.8% yield.

$^1$H NMR (CDCl$_3$, 400 MHz): δ 1.38 (dd, J=6.1 and 1.4 Hz, 6H) overlapping 1.41 (t, J=7.1 Hz, 3H), 4.11-4.21 (m, 2H), 4.65 (sept., J=6.1 Hz, 1H), 5.33 (dd, J=11.2 Hz and 1.4 Hz, 1H), 5.80 (dd, J=17.9 and 1.2 Hz, 1H), 6.96 (dd, J=8.6 and 3.0 Hz, 1H) overlapping 7.00 (dd, J=18.0 and 11.4 Hz, 1H), 7.63 (ddd, J=11.9, 11.9 and 2.0 Hz, 1H), 7.90 (dd, J=12.7 and 2.1 Hz, 1H), 7.99 (s, 1H), 8.22 (s, 1H), 8.25 (s, 1H), $^{31}$P NMR (CDCl$_3$, 161.8 MHz): δ 28.59.

Step M: Synthesis of 1,3-bis(2,4,6-trimethylphenyl)-4,5-dihydroimidazol-2-ylidene[2-(1-propoxy-5-(3,5-bis(trifluoromethyl)phenyl ethylphosphite))phenyl]methylene-ruthenium (II) dichloride AT. Grubbs' second generation catalyst (326 mg, 0.384 mmol), and copper (I) chloride (38 mg, 0.384 mmol) were charged in a Schlenk tube and degassed. A degassed solution of ethyl [3,5-bis(trifluoromethyl)phenyl]-{4-(isopropoxy)-3-vinylphenyl}-phosphinate (179 mg, 0.384 mmol) in anhydrous dichloromethane (20 mL) was transferred via cannula to the solids, and the mixture was heated at 30° C. for 70 min. The solvent was removed in vacuo and the residue was purified by column chromatography with 20 to 80% ethyl acetate in petroleum ether to afford compound AT (185 mg) as a green powder in 52% yield.

$^1$H NMR (CDCl$_3$, 400 MHz): δ 1.26 (dd, J=6.0 and 4.0 Hz, 6H), 1.43 (t, J=7.0 Hz, 3H), 2.41 (br s) and 2.44 (br s) (18H), 4.07-4.25 (m, 2H) overlapping 4.20 (br s, 4H), 4.94 (sept., J=6.1 Hz, 1H), 6.91 (dd, J=8.5 and 2.4 Hz, 1H), 7.06 (br s, 4H), 7.29 (dd, J=11.9 and 1.7 Hz, 1H), 8.02 (br s, 1H), 8.03 (m, 1H), 8.20 (s, 1H), 8.23 (s, 1H), 16.40 (s, 1H).

$^{31}$P NMR (CDCl$_3$, 161.8 MHz): δ 26.33.

Example 30

Ring Closure Metathesis

Catalytic activity AP, AQ, AR, and AT, along with AO and AS, as shown in Scheme 37, were evaluated using olefin substrates as shown in Scheme 38.

Scheme 37
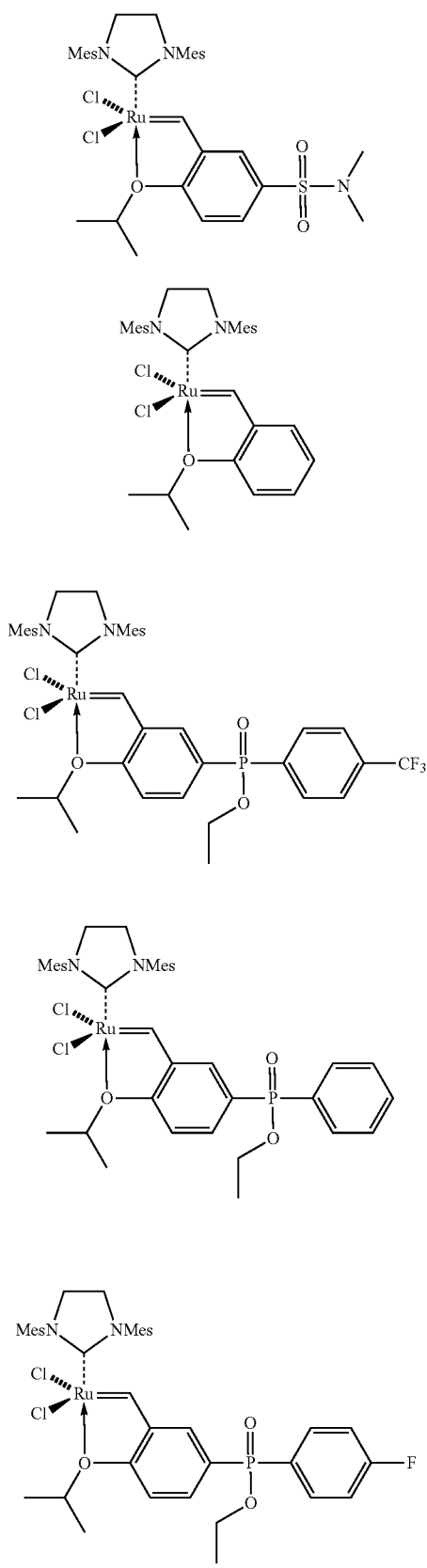
-continued
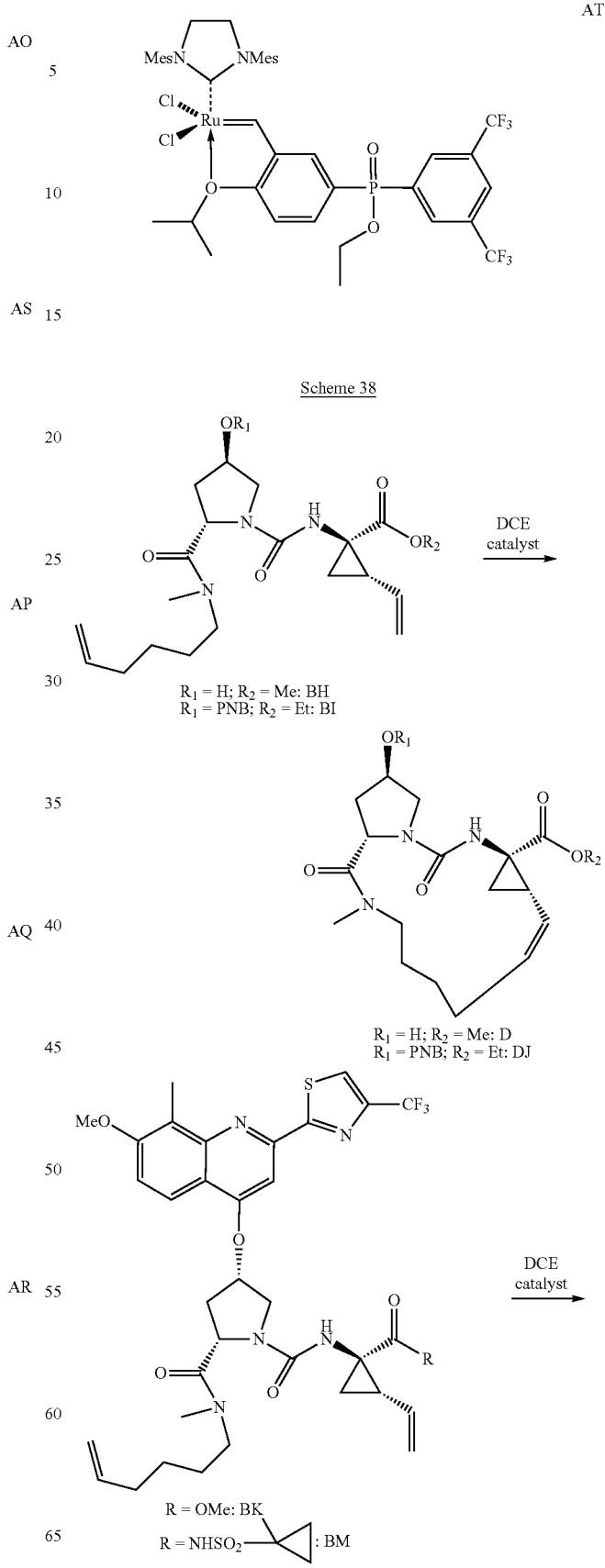

-continued

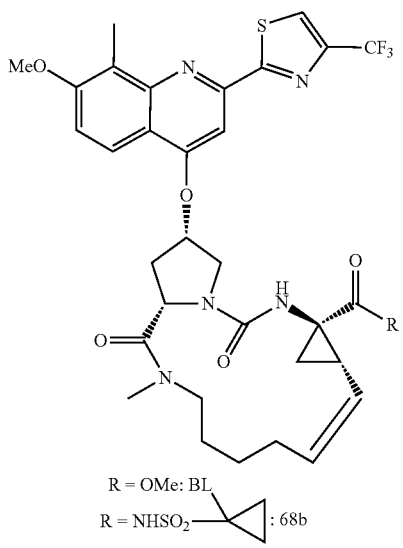

R = OMe: BL
R = NHSO$_2$-△ : 68b

Synthesis of Substrates
Syntheses of Compounds BH and BI
Compound BI was synthesized according to Scheme 39.

Scheme 39

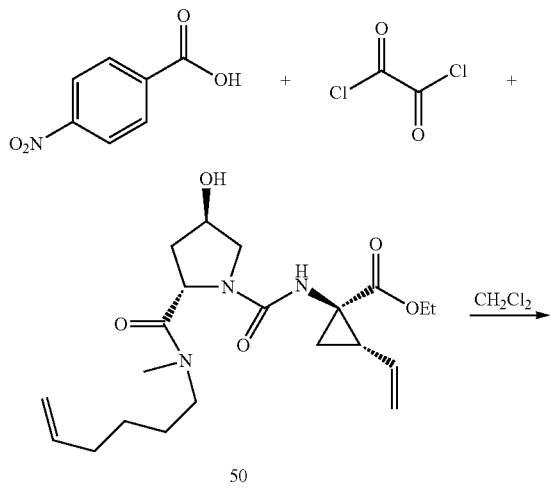

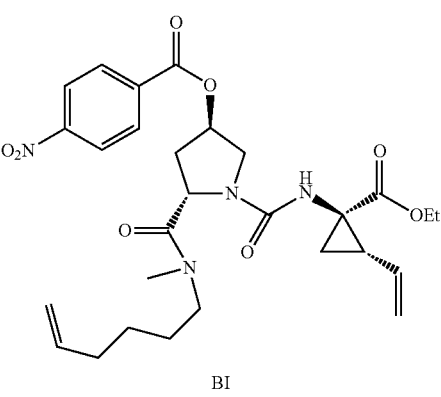

BI

Preparation of (3R,5S)-1-((1R,2S)-1-(ethoxycarbonyl)-2-vinylcyclopropyl-carbamoyl)-5-(hex-5-enyl(methyl)carbamoyl)pyrrolidin-3-yl 4-nitrobenzoate BI. To a solution of 4-nitrobenzoic acid (3.1 g, 1.5 eq) in CH$_2$Cl$_2$ (61 mL) were added dropwise 3.1 mL oxalyl chloride (3 eq), followed by 60 µL DMF. The reaction mixture was stirred at room temperature for 2 hrs and concentrated in vacuo. A solution of the resulting solid in CH$_2$Cl$_2$ (30 mL) was added dropwise to a solution of compound 50 (5.0 g, 1 eq) and triethylamine (3.4 mL, 2 eq) in CH$_2$Cl$_2$ (30 mL). The reaction mixture was stirred at room temperature for 2 hrs, and then washed with water and a saturated aqueous solution of sodium carbonate. The aqueous layer was extracted with CH$_2$Cl$_2$. The combined organic phases were dried on sodium sulphate, filtered, and concentrated to dryness. Recrystallisation with TBME gave compound BI as a yellow powder, and the filtrate was submitted to flash chromatography using CH$_2$Cl$_2$/MeOH as an eluant, affording a total of 6.42 g of compound BI in 93% yield.

$^1$H NMR (CDCl$_3$, 400 MHz) δ 1.23 (m, 3H), 1.36-1.61 (m, 5H), 1.69 (m, 1H), 1.86 (td, J=5.1 and 7.8 Hz, 1H), 2.05-2.19 (m, 3H), 2.35-2.50 (m, 2H), 2.95 and 3.15 (2 s, rotamers, 3H), 3.21 and 3.80 (2 m, rotamers, 1H), 3.38 (m, 1H), 3.61 (m, 1H), 4.09 (m, 2H), 4.21 (m, 1H), 4.94-5.00 (m, 1H), 5.05 (br d, J=10.3 Hz, 2H), 5.10 (dd, J=1.30 and 10.2 Hz, 1H), 5.27 (d, J=17.0 Hz, 1H), 5.68-5.84 (m, 3H), 8.20 (d, J=8.8 Hz, 2H), 8.31 (d, J=8.8 Hz, 2H).

Compound BH (white powder) was synthesized using the same procedure as compound 50.

$^1$H NMR (CDCl$_3$, 400 MHz) δ 1.34-1.46 (m, 2H), 1.49-1.57 (m, 3H), 1.70 (s, 2H), 1.86 (td, J=8.0 and 5.4 Hz, 1H), 2.03-2.28 (m, 6H), 2.92 and 3.11 (2 s, rotamers, 3H), 3.27-3.44 (m, 2H), 3.69 (s, 3H), 3.79 (m, J=5.1 and 4.5 Hz, 1H), 4.71 (br s, 1H), 4.90-4.97 (m, 1H), 4.97-5.05 (m, 1H), 5.09 (dd, J=10.3 and 1.5 Hz, 1H), 5.20 (br s, 1H), 5.27 (dd, J=17.1 and 1.0 Hz, 1H), 5.67-5.85 (m, 2H).

Syntheses of Compounds BK and BM
Compounds BK and BM were prepared according to Scheme 40.

Scheme 40

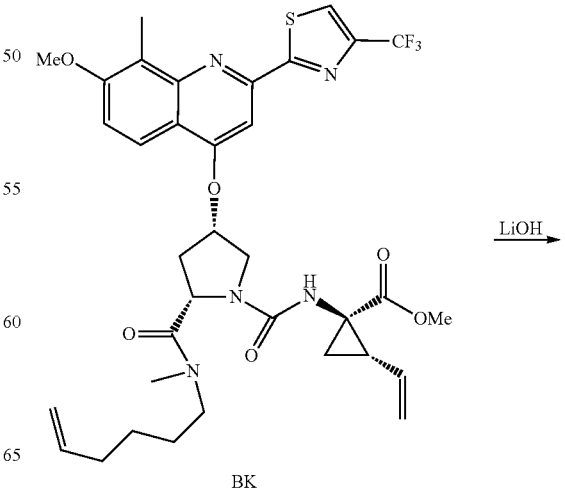

BK

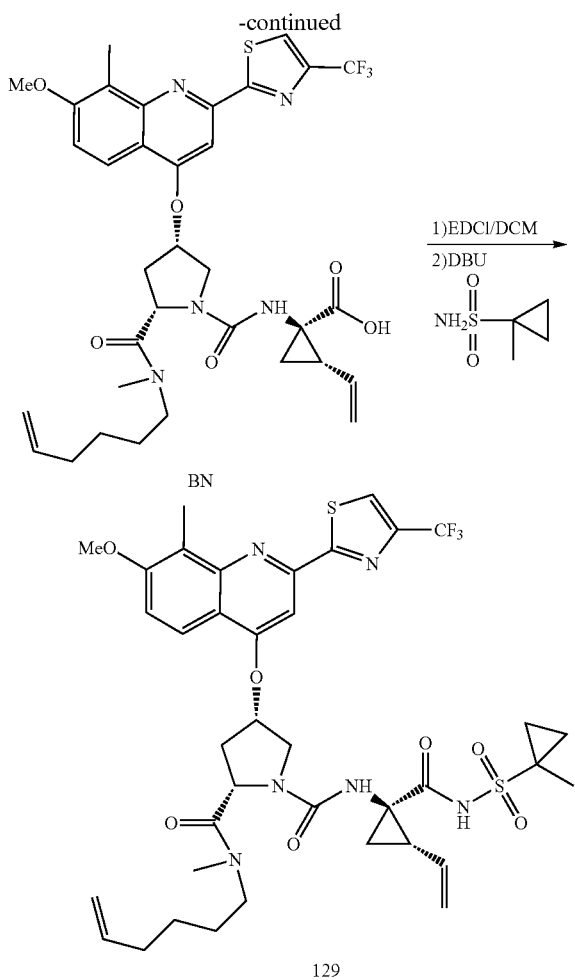

Step A: Preparation of (1R,2S)-methyl 1-((2S,4S)-2-(hex-5-enyl(methyl)carbamoyl)-4-(7-methoxy-8-methyl-2-(4-(trifluoromethyl)thiazol-2-yl)quinolin-4-yloxy)pyrrolidine-1-carboxamido)-2-vinylcyclopropanecarboxylate BK. Compound BK (yellow solid) was synthesized using the same procedure as compound 116, starting from compounds 111 and 65b.

$^1$H NMR (CDCl$_3$, 400 MHz) δ 1.18-1.45 (m, 4H), 1.48-1.58 (m, 1H), 1.81-1.90 (m, 2H), 2.05 (m, J=7.6 Hz, 1H), 2.21 (se, J=7.3 Hz, 1H), 2.27-2.36 (m, 1H), 2.67 (s, 3H), 2.88 and 3.00 (2 s, rotamers, 3H), 3.06-3.14 and 3.20-3.29 (2 m, rotamers, 1H), 3.33-3.42 and 3.49-3.58 (2 m, rotamers, 1H), 3.71 (s, 3H), 3.92 (td, J=10.1 and 3.8 Hz, 1H), 3.98 and 3.99 (2 s, rotamers, 3H), 4.06-4.13 (m, 1H), 4.83-5.03 (m, 3H), 5.10 (d, J=10.5 Hz, 1H), 5.14 (dd, J=10.3 and 1.2 Hz, 1H), 5.21 (s, 1H), 5.26-5.34 (m, 1H), 5.40-5.46 (m, 1H), 5.58-5.80 (m, 2H), 7.24-7.28 (m, 1H), 7.45 (d, J=7.1 Hz, 1H), 7.86 (s, 1H), 8.05 (t, J=8.1 Hz, 1H); MS (ESI, EI$^+$) m/z 716.2 (MH$^+$).

Step B: Preparation of (1R,2S)-1-((2S,4S)-2-(hex-5-enyl(methyl)carbamoyl)-4-(7-methoxy-8-methyl-2-(4-(trifluoromethyl)thiazol-2-yl)quinolin-4-yloxy)pyrrolidine-1-carboxamido)-2-vinylcyclopropanecarboxylic acid BN. Compound BN (yellow solid) was synthesized in quantitative yield from compound BK (4.30 g, 1 eq.) and LiOH (290 mg, 2 eq.), following the procedure as described for compound AC.

MS (ESI, EI$^+$) m/z=702.4 (MH$^+$).

Step C: Preparation of (2S,4S)—N$^2$-(hex-5-enyl)-4-(7-methoxy-8-methyl-2-(4-(trifluoromethyl)thiazol-2-yl)quinolin-4-yloxy)-N$^2$-methyl-N$^1$-((1R,2S)-1-(1-methylcyclopropylsulfonylcarbamoyl)-2-vinylcyclopropyl)pyrrolidine-1,2-dicarboxamide 129. Compound 129 (white solid) was synthesized from compound BN (4.22 g, 1 eq.) and methylcyclopropylsulfonamide (3.25 g, 4 eq.) in 31% yield, following the procedure as described for compound G2.

$^1$H NMR (CDCl$_3$, 400 MHz) δ 0.74-0.86 (m, 2H), 1.11-1.21 (m, 2H), 1.30-1.40 (m, 3H), 1.50 (s, 3H), 1.60-1.68 (m, 3H), 1.78 (q, J=6.0 Hz, 1H), 1.88-1.94 (m, 1H), 2.00-2.08 (m, 1H), 2.22 (q, J=8.7 Hz, 1H), 2.33 (dd, J=14.0 and 2.1 Hz, 1H), 2.67 (s, 3H), 2.78-2.82 (m, 1H), 2.87 and 2.97 (2 s, rotamers, 3H), 3.15-3.36 (m, 1H), 3.58-3.68 (m, 1H), 3.90-4.01 (m, 5H), 4.82-4.91 (m, 1H), 4.92-5.01 (m, 2H), 5.11 (d, J=10.2 Hz, 1H), 5.25-5.35 (m, 2H), 5.46-5.51 (m, 1H), 5.54-5.76 (m, 2H), 7.25-7.30 (m, 1H), 7.46 (d, J=7.0 Hz, 1H), 7.87 (s, 1H), 8.02 (t, J=10.1 Hz, 1H); MS (ESI, EI$^+$) m/z=819.2 (MH$^+$).

Ring Closure Metathesis

All reactions were performed in 1,2-dichloroethane at 0.005 M with N$_2$ bubbling through the reaction mixture. For the substrates depicted in Scheme 38, the typical scale of the reaction was 200-250 mg. The catalyst was added in solution in 0.5 mL of DCE, in the pre-heated reaction mixture. The conversion of the starting material was followed via TLC and/or HPLC. Products are isolated after flash chromatography (note: compound BJ was stirred with charcoal and filtered on celite prior to purification).

The experimental results of catalytic activity for the different catalysts are listed in Tables 1 to 4, respectively.

Synthesis of (1aR,6R,7aS,15aS,Z)-methyl 6-hydroxy-9-methyl-3,8-dioxo-1a,2,3,5,6,7,7a,8,9,10,11,12,13,15a-tetradecahydro-1H-cyclopropa[m]pyrrolo[1,2-c][1,3,6]triazacyclotetradecine-1a-carboxylate D.

TABLE 1

Compound D

| Entry | Catalyst | Temperature | Catalyst loading | Isolated yield | Time (hr) |
|---|---|---|---|---|---|
| 1 | AO | 80° C. | 2% + 1% (1.5 hr) | 51% | 2.5 |
| 2 | AP | 80° C. | 2% + 2% (1.5 hr) | 44% | 3.0 |
| 3 | AQ | 80° C. | 2% + 1% (1.5 hr) | 56% | 2.5 |
| 4 | AR | 80° C. | 2% + 1% (1.5 hr) | 47% | 2.5 |
| 5 | AS | 80° C. | 2% + 1% (1.5 hr) | 50% | 2.5 |
| 6 | AT | 80° C. | 2% + 2% (1.5 hr) | 53% | 3.0 |

Synthesis of (1aR,6R,7aS,15aS,Z)-methyl 9-methyl-6-(4-nitrobenzoyloxy)-3,8-dioxo-1a,2,3,5,6,7,7a,8,9,10,11,12,13,15a-tetradecahydro-1H-cyclopropa[m]pyrrolo[1,2-c][1,3,6]triazacyclotetradecine-1a-carboxylate BJ.

$^1$H NMR (CDCl$_3$, 400 MHz): δ 1.24 (t, J=7.1 Hz, 3H), 1.27-1.35 (m, 1H), 1.37-1.47 (m, 1H), 1.49-1.62 (m, 1H), 1.66-1.79 (m, 3H), 1.87 (br t, J=13.2 Hz, 1H), 2.26-2.47 (m, 2H), 2.60 (br d, J=13.5 Hz, 1H), 3.05 (s, 3H), 3.51 (d, J=9.3 Hz, 1H), 3.94 (dd, J=9.8 and 5.3 Hz, 1H), 4.06-4.16 (m, 1H), 4.18-4.27 (m, 1H), 4.57 (td, J=13.2 and 3.0 Hz, 1H), 5.00 (s, 3H), 5.00-5.05 (m, 1H), 5.48 (t, J=10.3 Hz, 1H), 5.60-5.68 (m, 1H), 5.72 (br s, 1H), 8.20 (d, J=8.8 Hz, 2H), 8.31 (d, J=8.8 Hz, 2H).

TABLE 2

Compound BJ

| Entry | Catalyst | Temperature | Catalyst loading | Isolated yield | Time (hr) |
|---|---|---|---|---|---|
| 1 | AO | 80° C. | 2% + 2% (20 min) | 65% | 0.67 |
| 2 | AP | 80° C. | 2% + 2% (20 min) + 1% (40 min) | 78% | 1.0 |
| 3 | AT | 80° C. | 2% + 2% (20 min) | 75% | 0.67 |

Synthesis of (1aR,6S,7aS,15aS,Z)-methyl 6-(7-methoxy-8-methyl-2-(4-(trifluoromethyl)thiazol-2-yl)quinolin-4-yloxy)-9-methyl-3,8-dioxo-1a,2,3,5,6,7,7a,8,9,10,11,12,13,15a-tetradecahydro-1H-cyclopropa[m]pyrrolo[1,2-c][1,3,6]triazacyclotetradecine-1a-carboxylate BL.

$^1$H NMR (CDCl$_3$, 400 MHz): δ 1.29-1.44 (m, 2H), 1.50-1.62 (m, 2H), 1.66 (s, 1H), 1.68-1.78 (m, 2H), 1.88 (td, J=13.5 and 2.5 Hz, 1H), 2.15-2.23 (m, 1H), 2.40 (dd, J=9.9 and 9.5 Hz, 1H), 2.58 (td, J=13.7 and 3.5 Hz, 1H), 2.68 (s, 3H), 2.97 (td, J=13.3 and 8.4 Hz, 1H), 3.04 (s, 3H), 3.74 (s, 3H), 3.74-3.80 (m, 1H), 3.99 (s, 3H), 4.07 (t, J=7.5 Hz, 1H), 4.62 (td, J=13.4 and 2.9 Hz, 1H), 4.95 (br t, J=6.7 Hz, 1H), 5.07 (s, 1H), 5.41-5.53 (m, 2H), 5.65 (s, J=5.4 Hz, 1H), 7.25 (d, J=9.1 Hz, 1H), 7.51 (s, 1H), 7.87 (s, 1H), 8.02 (d, J=9.1 Hz, 1H).

MS (ESI, EI$^+$): m/z=687.98 (MH$^+$).

TABLE 3

Compound BL

| Entry | Catalyst | Temperature | Catalyst loading | Isolated yield | Time (hr) |
|---|---|---|---|---|---|
| 1 | AO | 80° C. | 2% + 2% (1 hr) + 2% (2 hr) | 51% | 3.5 |
| 2 | AP | 80° C. | 2% + 2% (1 hr) + 2% (2 hr) | 49% | 3.5 |
| 3 | AQ | 80° C. | 2% + 2% (1 hr) + 2% (2 hr) | 49% | 3.5 |
| 4 | AR | 80° C. | 2% + 2% (1 hr) + 2% (2 hr) | 48% | 3.5 |
| 5 | AS | 80° C. | 2% + 2% (1 hr) + 2% (2 hr) | 49% | 3.5 |
| 6 | AT | 80° C. | 2% + 2% (1 hr) + 2% (2 hr) | 49% | 3.5 |

Synthesis of (Z)-(4R,6S,15S,17S)-[17-[7-methoxy-8-methyl-2-(4-trifluoromethythiazol-2-yl)quinolin-4-yloxy]-13-N-methyl-2,14-dioxo-1,3,13-triazatricyclo[13.3.0.0]octadec-7-en-4-yl]carbonyl(1-methylcyclopropyl)sulfonamide 68b.

TABLE 4

Compound 68b

| Entry | Catalyst | Temperature | Catalyst loading | Isolated yield | Time (hr) |
|---|---|---|---|---|---|
| 1 | AO | 60° C. | 2% + 2% (45 m) + 2% (2 h) | 79% | 4.0 |
| 2 | AP | 60° C. | 2% + 2% (45 m) + 2% (2 h) + 2% (3 h) | 45% | 24.0 |
| 3 | AQ | 60° C. | 2% + 2% (45 m) + 2% (2 h) + 2% (3 h) | 63% | 24.0 |
| 4 | AR | 60° C. | 2% + 2% (45 m) + 2% (2 h) + 2% (3 h) | 30% | 24.0 |
| 5 | AS | 60° C. | 2% + 2% (45 m) + 2% (2 h) + 2% (3 h) | 60% | 24.0 |
| 6 | AT | 60° C. | 2% + 2% (45 m) + 2% (2 h) + 2% (3 h) | 53% | 24.0 |

Example 31

HCV Protease Assay

General procedure: Measurement of the inhibitory effect of compounds on HCV protease activity was performed with the SensoLyte™ 620 HCV Protease Assay kit from AnaSpec, Inc. (San Jose, Calif.) under conditions described by the supplier using 1.2 nM HCV NS3-NS4A protease, which was obtained according to Taremi et al. (*Protein Science*, 1998, 7, 2143-2149). The compounds were tested at a variety of concentrations in assay buffer containing a final DMSO concentration of 5%. Reactions were allowed to proceed for 60 min at room temperature and fluorescence measurements were recorded with a Tecan Infinity Spectrofluorimeter. The IC$_{50}$ values were determined from the percent inhibition versus concentration data using a sigmoidal non-linear regression analysis based on four parameters with Tecan Magellan software.

Example 32

HCV Replicon Assay

General procedure: Huh-7 cells containing HCV Con1 subgenomic replicon (GS4.1 cells) were grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin, and 0.5 mg/mL G418 (Invitrogen). For dose-response testing, the cells were seeded in 96-well plates at 7.5×10$^3$ cells/well in a volume of 50 μL, and incubated at 37° C./5% CO$_2$. Three hours after plating, 50 μL of ten 2-fold serial dilutions of compounds (highest concentration, 75 PM) were added, and cell cultures were incubated at 37° C./5% CO$_2$ in the presence of 0.5% DMSO. Alternatively, compounds were tested at a single concentration of 15 μM. In all cases, Huh-7 cells lacking the HCV replicon served as negative control. The cells were incubated in the presence of compounds for 72 hr after which they were monitored for expression of the NS4A protein by enzyme-linked immunosorbent assay (ELISA). For this, the plates were then fixed for 1 min with acetone/methanol (1:1, v/v), washed twice with phosphate-buffered saline (PBS), 0.1% Tween 20, blocked for 1 hr at room temperature with TNE buffer containing 10% FBS and then incubated for 2 hr at 37° C. with the anti-NS4A mouse monoclonal antibody A-236 (ViroGen) diluted in the same buffer. After washing three times with PBS, 0.1% Tween 20, the cells were incubated 1 hr at 37° C. with anti-mouse immunoglobulin G-peroxidase conjugate in TNE, 10% FBS. After washing as described above, the reaction was developed with O-phenylenediamine (Zymed). The reaction was stopped after 30 min with 2 NH$_2$SO$_4$, and absorbance was read at 492 nm using Sunrise Tecan spectrophotometer. EC$_{50}$ values were determined from the % inhibition versus concentration data using a sigmoidal non-linear regression analysis based on four parameters with Tecan Magellan software. When screening at a single concentration, the results were expressed as % inhibition at 15 μM.

For cytotoxicity evaluation, GS4.1 cells were treated with compounds as described above and cellular viability was monitored using the Cell Titer 96 AQ$_{ueous}$ One Solution Cell Proliferation Assay (Promega). CC$_{50}$ values were determined from the % cytotoxicity versus concentration data with Tecan Magellan software as described above.

The biological results are summarized in Table 5, wherein A represents a value smaller than 1 μM, and B represents a value between 1 μM to 10 μM, C represents a value between 10 μM to 75 μM and D represents a value greater than 75 μM.

TABLE 5

| Compound | IC$_{50}$ (μM) | EC$_{50}$ (μM) | CC$_{50}$ (μM) |
|---|---|---|---|
| 56a | A | A | D |
| 56b | A | A | D |
| 56c | A | A | D |
| 56d | A | A | D |
| 56e | A | B | D |
| 56f | A | A | D |
| 56g | A | A | D |
| 56h | A | A | D |
| 62b | A | A | D |

TABLE 5-continued

| Compound | IC$_{50}$ (μM) | EC$_{50}$ (μM) | CC$_{50}$ (μM) |
|---|---|---|---|
| 62d | A | A | D |
| 62f | A | A | D |
| 63b | A | B | D |
| 68b | A | A | D |
| 68d | A | A | D |
| 69b | A | A | D |
| 69d | A | A | C |
| 76a | B | B | D |
| 76b | A | B | D |
| 83b | A | A | D |
| 91a | A | A | D |
| 91b | A | A | C |
| 91c | A | A | D |
| 91d | A | A | D |
| 91e | A | A | D |
| 91f | A | A | D |
| 91g | A | A | D |
| 96d | A | B | D |
| 101d | A | A | D |
| 110d | A | A | D |
| G1 | A | A | C |
| G2 | A | A | C |
| G3 | A | A | C |
| G4 | A | A | C |
| O1 | A | A | C |
| O2 | A | A | C |
| O3 | A | A | C |
| O4 | A | A | D |
| T1 | A | A | C |
| T2 | A | A | D |
| AC1 | A | A | C |
| AC2 | A | A | C |
| AC3 | A | A | D |
| AH | A | A | C |
| AN | A | A | C |

Example 33

Antiviral Activity in a Genotype 1b Replicon Assay

Compounds were tested in a genotype 1b replicon assay as described in Example 32 and the results are summarized in Table 6, wherein A represents a value smaller than 1 μM, and B represents a value between 1 μM to 10 μM, C represents a value between 10 μM to 75 μM and D represents a value greater than 75 μM.

TABLE 6

| Cmpd. No. | EC$_{50}$ | CC$_{50}$ |
|---|---|---|
| 56b | A | C |
| 56d | A | >C |
| 62d | A | C |
| 68b | A | C |
| 69b | A | D |
| 91e | A | C |

Example 34

Antiviral Activity in a HCV Genotype 2a Infectious Virus Assay

Compounds were tested in a HCV genotype 2a infectious virus assay and the results are summarized in Table 7, wherein A represents a value smaller than 1 μM, and B represents a value between 1 μM to 10 μM, C represents a value between 10 μM to 75 μM and D represents a value greater than 75 μM.

TABLE 7

| Cmpd. No. | EC$_{50}$ |
|---|---|
| 56b | B |
| 56d | A |
| 62d | A |
| 68b | A |
| 69b | A |
| 91e | A |

Example 35

Resistance Profile

Compounds were evaluated against three mutant proteases R155Q, A156S, and D168A, as summarized in Table 8, wherein A represents a value smaller than 1, and B represents a value between 1 to 10, and C represents a value greater than 10. The fold of change in inhibitory activity was determined by measuring the ratio of the inhibitory activity of a compound against a mutant enzyme over the inhibitory activity of the same compound against non-mutant enzyme. The inhibitory activity was determined using the procedure as described in Example 31.

TABLE 8

| Cmpd. No. | Fold-Change | | |
|---|---|---|---|
| | R155Q | A156S | D168A |
| 56b | A | A | C |
| 56d | A | A | C |
| 62d | A | A | C |
| 91e | A | A | C |

Example 36

Generation of Recombinant JFH-1 Virus Stocks

The recombinant JFH-1 HCV virus used in the HCV in vitro infection assay was generated by transfection of HPC cells with JFH-1 RNA produced by in vitro transcription. The JFH-1 DNA template was derived synthetically using sequence information derived from NCBI Accession #AB047639 (Wakita, et al., Nat. Med. 2005, 11:791-796). Source: DNA2.0, Menlo Park, Calif.

The cDNA for the JFH-1 HCV clone was synthesized by DNA2.0 and contains a T7 promoter to drive the transcription of the JFH-1 genomic RNA. This plasmid was amplified using the Hi-Speed Plasmid Midi kit (Qiagen) according to the manufacturer's instructions.

Thirty micrograms of purified DNA was digested overnight at 37° C. with 300 U XbaI. The digested DNA served as a template for the in vitro transcription of the JFH-1 genomic RNA using the MEGAScript T7 kit (Ambion) as instructed by the manufacturer. The JFH-1 RNA product was resuspended to 1 μg/μL in RNA storage solution (Ambion). The quality of the JFH-1 RNA was verified by agarose gel electrophoresis (1.2% E-gel) prior to electroporation.

Complete growth media for Huh-7 and HPC cells (Huh-7 media) was prepared as follows: DMEM (containing glucose, L-glutamine and sodium pyruvate), 10% FBS, 100 IU/mL penicillin, 100 μg/mL streptomycin, 2 mM GlutaMAX, 1% MEM non-essential amino acids. Subconfluent HPC cells were treated with trypsin-EDTA, collected with Huh-7 media, and centrifuged at 1,500 rpm for 5 min at 4° C. in an Allegra 6R centrifuge (Beckman Coulter) in a 50 mL conical tube. The cells were then rinsed twice by resuspending the cells in 50 mL of PBS and centrifuging at 1,500 rpm for 5 min at 4° C.

JFH-1 RNA was electroporated into HPC cells using a Thermo Scientific Hybaid OptiBuffer kit (containing buffer A, solution B and compounds C and D). After washing, the HPC cells were resuspended in OptiBuffer buffer A at $1 \times 10^7$ cells/mL, and 400 µL ($4 \times 10^6$ cells) was transferred to a 1.5 mL RNase-free microfuge tube and gently centrifuged at 2,000 rpm in a Microfuge 18 (Beckman Coulter) centrifuge at room temperature for 5 minutes. During this centrifugation step, the electroporation medium was prepared by mixing 2.5 mL of OptiBuffer solution B with 1 vial of OptiBuffer compound C (5.5 mg of ATP), 1 vial of OptiBuffer compound D (7.7 mg of glutathione) and 2.5 mL of autoclaved water. After aspirating the supernatant, the cell pellet was resuspended in 400 µL of electroporation medium. JFH-1 RNA (8 µg) was added to the resuspended cells, whereupon they were transferred to a 0.4 cm cuvette and electroporated in a Bio-Rad GenePulser XCell electroporation module with a single pulse at 960 µf, 270 V and maximum resistance. A mock transfection, without RNA, was electroporated as a negative control. Growth media (600 µL) was immediately added to the cuvette. Cells were then transferred into a 15 mL conical tube containing 3.4 mL of Huh-7 media. Approximately $1.2 \times 10^5$ cells were seeded into each well of a Corning Costar 6-well plate and incubated at 37° C. with 5% $CO_2$.

When confluent, the transfected HPC cells were trypsinized and split 1:5 into new 6-well plates. At day 5 and 14 post transfection, conditioned media was collected from the cultures, cell debris was removed by centrifugation at 2,000 rpm for 10 min in a table-top centrifuge (Beckman Coulter Allegra 6R with GH3.8 rotor) and media was filtered through a 0.2 µm syringe-top filter. The transfected cells were also fixed for immunohistochemistry and lysed for immunoblotting analysis.

The recombinant JFH-1 HCV virus was amplified in a manner described by (Zhong, et al., *Proc. Nat. Acad. Sci. USA.* 2005, 102:9294-9299). HPC cells were split to 10% confluency in 225 cm² flasks and infected with 1 mL of the transfected cell culture media (described above) at 5 hrs post seeding. At 5 days post infection (p.i.), the cultures were split 1:2 into new 225 cm² flasks. One half the initial culture media was carried over into the split cultures to facilitate virus amplification. At 10 day p.i., conditioned media was collected from the 225 cm² flasks, centrifuged at 2,000 rpm for 10 min in a table-top centrifuge and filtered through a MF75 sterilization filter (0.45 µm) bottle-top unit. Two milliliter aliquots of this virus stock were stored at −80° C. for future use.

Example 37

HCV In Vitro Infection Core ELISA Assay

The HCV in vitro infection core ELISA assay measures the ability of a test compound to inhibit replication of an infectious HCV (strain JFH-1; genotype 2a) in cell culture. Recently, an in vitro infection model identified by Wakita et al. (*Nat. Med.* 2005, 11:791-796) was found to replicate in retinoic acid-inducible gene I (RIG-I)-deficient or cluster of differentiation (CD)-81-positive Huh-7 hepatoma cell lines. We have developed this model for determining the efficacy of antiviral compounds against an infectious virus in vitro using HCV producing cells (HPC), a proprietary Huh-7-derived cell sublineage capable of propagating the JFH-1 HCV virus. The readout of the assay is quantification of HCV core protein by ELISA 5 days post infection with JFH-1 virus and treatment with a test compound.

Ninety-six-well Corning Costar plates were seeded with HPC cells at a density of $3.0 \times 10^3$ cells per well in 50 µL of Huh-7 media. Compound stock solutions were made up freshly in Huh-7 media (DMEM (containing glucose, L-glutamine and sodium pyruvate), 10% FBS, 100 IU/mL penicillin, 100 µg/mL streptomycin, 2 mM GlutaMAX, 1% MEM non-essential amino acids) as 2× stock. Seven additional 3-fold drug dilutions were prepared from the 2× stocks in Huh-7 media. At least 4 hours after HPC cells were seeded, the media in the 96-well culture plates was aspirated and 50 µL of each drug dilution and 50 µL of JFH-1 HCV was added to each well.

At 16 hrs post treatment and infection, the virus inoculum was removed by aspiration. The cultures were treated at the same final concentrations of drug diluted to 1× in Huh-7 media to a final volume of 200 µL. Cells were incubated in the presence of drug for 4 additional days at 37° C./5% $CO_2$.

Media was removed from the plates by aspiration. Cells were fixed with 250 µL 1:1 acetone:methanol for 90 seconds, washed once in PBS and then three times with 1× KPL wash solution. The assay plates were then blocked with 150 µL/well 10% FBS-TNE (50 mM Tris-HCl (pH 7.5; Sigma), 100 mM NaCl, 1 mM EDTA with 10% FBS) for 1 hr at room temperature. Cells were washed three times with 1×KPL wash solution and incubated with 100 µL/well anti-hepatitis C core mAb (1 mg/mL stock diluted 1:500 in 10% FBS-TNE) for 2 hours at 37° C. Cells were washed three times with 1×KPL wash solution and incubated with 100 µL/well HRP-goat anti-mouse antibody (diluted 1:2,500 in 10% FBS-TNE) for 1 hr at 37° C.

OPD solution was prepared using 1 OPD tablet+12 mL citrate/phosphate buffer (16 mM citric acid, 27 mM $Na_2HPO_4$) plus 5 µL 30% $H_2O_2$ per plate. Cells were washed three times with 1×KPL wash solution and developed with 100 µL/well OPD solution for 30 minutes in the dark at room temperature. The reaction was stopped with 100 µL/well of 2N $H_2SO_4$, and absorbance measured at $A_{490}$ nm in a Victor³ V 1420 multilabel counter (Perkin Elmer). The $EC_{50}$ values for each compound were calculated from dose response curves from the resulting best-fit equations determined by Microsoft Excel and XLfit 4.1 software. The negative control for inhibition of virus replication was untreated HPC cells infected with the JFH-1 HCV virus strain. The negative ELISA control was untreated, uninfected HPC cells. The positive ELISA control was untreated HPC cells infected the JFH-1 HCV virus strain.

Example 38

MTS Cytotoxicity Assay

The cytotoxicity assay measures the viability of cells after treatment with a test compound for 5 days. The assay readout is the bioreduction of the yellow MTS tetrazolium compound to a purple formazan product. This conversion is mediated by NADPH or NADH and is directly proportional to the number of live cells in a culture.

Ninety-six-well Corning Costar plates were seeded with HPC cells at a density of $3.0 \times 10^3$ cells per well in 50 µL of Huh-7 media. Compound stock solutions were made up freshly in Huh-7 media as 2× stocks. Seven additional 3-fold drug dilutions were prepared from the 2× stocks in Huh-7 media for a total of 8 dilutions.

At least 4 hours after HPC cells were seeded, 50 µL of each drug dilution was added to the cultures. At 16 hrs post treatment, the existing media was removed by aspiration. Cultures were treated at the same final concentrations of drug diluted to 1× in Huh-7 medium to a final volume of 100 µL. Cells were incubated for 4 additional days at 37° C./5% $CO_2$ in the presence of drug.

After 5 days of treatment, the CellTiter 96® Aqueous One Solution cell proliferation assay was performed by adding 20 µL of MTS solution to each well. The plates were then incubated at 37° C./5% $CO_2$ for 3 hours. Plates were read at $A_{490}$ nm in a Victor$^3$ V 1420 multilabel counter (Perkin Elmer) and $CC_{50}$ concentrations were determined using Microsoft Excel and XLfit 4.1 software. The positive control for cell death: culture wells containing only Huh-7 medium. The negative control for cell death: culture wells containing untreated, uninfected HPC cells.

Example 39

HCV In Vitro Infection Western Blotting Assay

This assay measures the ability of a test compound to inhibit replication of the JFH-1 HCV strain in cell culture. The readout of the assay is the quantification of HCV NS3 or core protein by western blotting 5 days post infection with JFH-1 virus and drug treatment. Negative controls: untreated, uninfected HPC cells. Positive controls: untreated HPC cells infected the JFH-1 HCV virus strain.

Twenty-four-well Corning Costar plates were seeded with HPC cells at a density of 1.5×10$^4$ cells per well in 0.8 mL of Huh-7 media (DMEM (containing glucose, L-glutamine and sodium pyruvate), 10% FBS, 100 IU/mL penicillin, 100 µg/mL streptomycin, 2 mM GlutaMAX, 1% MEM non-essential amino acids). Compound stock solutions were made up freshly in Huh-7 media as 10× stocks. Four additional 5-fold drug dilutions were prepared from the 10× stocks in Huh-7 media for a total of 5 dilutions.

At least 3 hrs after HPC cells were seeded, 100 µL of each drug dilution and 100 µL of JFH-1 HCV was added to each well. At 16 hrs post treatment and infection, the virus inoculum was removed by aspiration. The cultures were treated at the same final concentrations of drug diluted to 1× in Huh-7 media to a final volume of 1 mL. Cells were incubated in the presence of drug for 4 additional days at 37° C./5% $CO_2$.

Media was removed from the plates by aspiration and the cells washed with 1 mL of PBS. After removing the PBS, 100 µL/well of SDS sample buffer (50 mM Tris-HCl, pH7.5, 2% ultrapure SDS, 10% glycerol, 0.01% bromophenol blue, 0.1 M DTT) was added. The samples were collected into RNase-free microfuge tubes, incubated at 95° C. for 5-10 minutes and centrifuged at maximum speed for 2 min in an Eppendorf 5415D centrifuge.

To prepare the Western Blot, fifteen microliters of each sample was loaded into each lane of a 4-20% Tris-glycine polyacrylamide gel in an XCell II Blot Module (Invitrogen); 6 µL of the SeeBluePlus2 prestained protein standard was also loaded into one lane. Each gel was run at 125 V for 1.5 hrs in Novex SDS (1× Tris/glycine/SDS) running buffer (Invitrogen). Each gel was transferred onto an iBlot nitrocellulose membrane using the iBlot apparatus (Invitrogen) according to the manufacturer's protocol. The membrane was rinsed in PBST (Sigma) and then blocked with 6 mL of blocking buffer (5% (w/v) nonfat milk in PBST solution) at room temperature for 1 hour with rocking. Each blot was incubated in 6 mL of blocking buffer containing HCV NS3 murine mAb (1:500; ViroGen Corp.) and anti-GAPDH murine IgG Ab (1:1,000,000; Calbiotech) or anti-core mAb (1:500; Affinity BioReagents) overnight at 4° C. with rocking. After 3 ten minute washes in PBST at room temperature with rocking each blot was incubated with 6 mL of blocking buffer (5% (w/v) nonfat milk in PBST solution) containing HRP conjugated donkey anti-mouse Ab (1:5,000) for 1 hour at room temperature with rocking. Each blot was washed as described above and then exposed to 5 mL of substrate from the SuperSignal West Dura substrate kit (Pierce) according to the manufacturer's protocol. The blots were then exposed using the Florochem 5,500 imager (Alpha Innotech).

Virus replication was quantified by determining the band densities of NS3 and core proteins using ImageQuant 5.2 software. Background (the density determined within the NS3 or core region with mock-transfected cells) was subtracted from NS3, core, and GAPDH band densities. Each corrected NS3 or core value was then normalized to the corresponding corrected GAPDH value for the same sample. The $EC_{50}$ value, which is the concentration of a test compound that reduced NS3 or core protein production by 50%, was determined for each compound using Microsoft Excel and XLfit 4.1 software. Each $EC_{50}$ value determination was performed in duplicate.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of preparing compound 129a having a structure of:

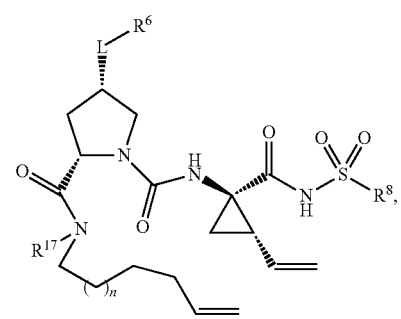

129a which comprises the steps of:

(a) reacting compound 127a having a structure of:

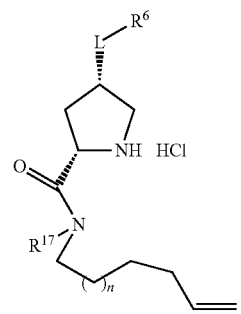

127a with CDI to form compound 128a having a structure of:

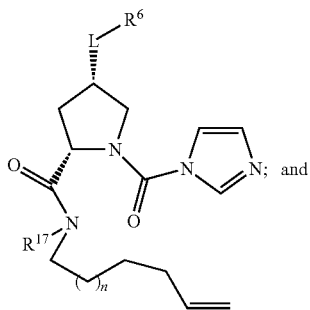

(b) coupling compound 128a with compound 128b having a structure of:

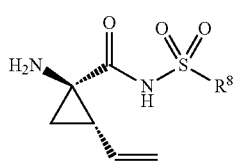

to form compound 129a;
wherein:
$R^6$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
$R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, —$CH_2NR^{8a}R^{8b}$, —$CH(R^{8c})NR^{8a}R^{8b}$, —$CHR^{8c}CHR^{8d}NR^{8a}R^{8b}$, or —$CH_2CR^{8c}R^{8d}NR^{8a}R^{8b}$,
wherein:
each $R^{8a}$, $R^{8c}$, and $R^{8d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, or $C_{6-14}$ aryl-$C_{1-6}$ alkylene; and
each $R^{8b}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —$S(O)_kR^{11}$, —$S(O)_kNR^{11}R^{12}$, —$C(O)R^{11}$, —$C(O)OR^{11}$, —$C(O)NR^{11}R^{12}$, or —$C(=NR^{13})NR^{11}R^{12}$; wherein each $R^{11}$, $R^{12}$, and $R^{13}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{11}$ and $R^{12}$ together with the N atom to which they are attached form heterocyclyl; or
$R^{8a}$ and $R^{8b}$ together with the N atom to which they are attached form heterocyclyl;
$R^{17}$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
L is a bond, $C_{1-6}$ alkylene, $C_{3-7}$ cycloalkylene, $C_{2-6}$ alkenylene, $C_{2-6}$ alkynylene, X, or —$(CR^{6a}R^{6b})_pX$—; wherein p is an integer of 1, 2, or 3; $R^{6a}$ and $R^{6b}$ are each independently hydrogen, halo, cyano, hydroxyl, or alkoxy; and X is —O—, —C(O)—, —C(O)O—, —OC(O)O—, —C(O)NR^{14}—, —NR^{14}—, —NR^{14}C(O)NR^{15}—, —C(=NR^{14})NR^{15}—, —NR^{14}C(=NR^{15})NR^{16}—, —S(O)_k—, —S(O)_kNR^{14}—, —NR^{14}S(O)_kNR^{15}—, —P(O)(OR^{14})—, or —OP(O)(OR^{14})—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and
each k is independently an integer of 1 or 2; and n is an integer of 0, 1, 2, 3, 4, or 5;
wherein each alkyl, alkylene, alkenyl, alkenylene, alkynyl, alkynylene, aryl, cycloalkyl, cycloalkylene, heterocyclyl, and heteroaryl is optionally substituted with one or more groups, each independently selected from cyano, halo, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^b$, —$NR^aC(O)OR^b$, —$NR^aC(O)NR^bR^c$, —$NR^aC(=NR^d)NR^bR^c$, —$NR^aS(O)R^b$, —$NR^aS(O)_2R^b$, —$NR^aS(O)NR^bR^c$, —$NR^aS(O)_2NR^bR^c$, —$SR^a$, —$S(O)R^a$, or —$S(O)_2R^a$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of cyano, halo, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or —$C(O)R^e$, —$C(O)OR^e$, —$C(O)NR^fR^g$, —$C(NR^e)NR^fR^g$, —$OR^e$, —$OC(O)R^e$, —$OC(O)OR^e$, —$OC(O)NR^fR^g$, —$OC(=NR^e)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^f$, —$NR^eC(O)OR^f$, —$NR^eC(O)NR^fR^g$, —$NR^eC(=NR^h)NR^fR^g$, —$NR^eS(O)R^f$, —$NR^eS(O)_2R^f$, —$NR^eS(O)NR^fR^g$, —$NR^eS(O)_2NR^fR^g$, —$SR^e$, —$S(O)R^e$, or —$S(O)_2R^e$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^f$ and $R^g$ together with the N atom to which they are attached form heterocyclyl.

2. The method of claim 1, wherein $R^6$ is selected from the group consisting of:

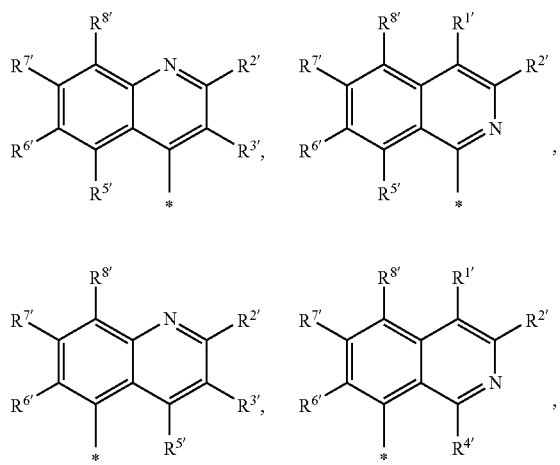

211

-continued

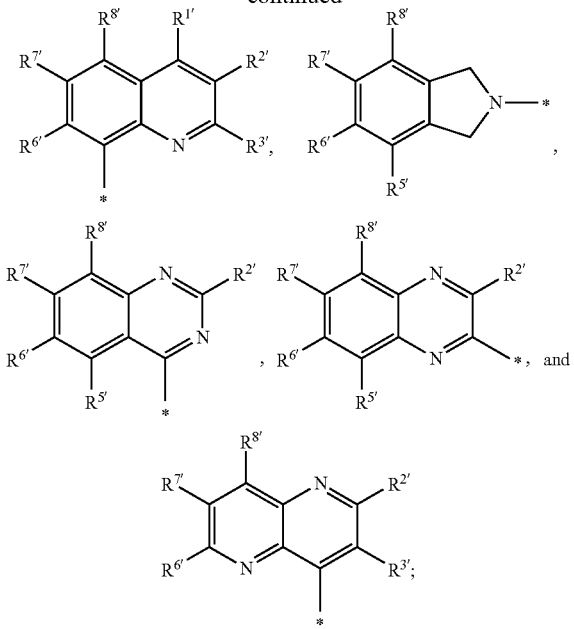

wherein:
each $R^{1'}$, $R^{2'}$, $R^{3'}$, $R^{5'}$, $R^{6'}$, $R^{7'}$, and $R^{8'}$ is independently: hydrogen, halo, cyano, trifluoromethyl, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^b$, —N$R^a$C(O)O$R^b$, —N$R^a$C(O)N$R^bR^c$, —N$R^a$C(=N$R^d$)N$R^bR^c$, —N$R^a$S(O)$R^b$, —N$R^a$S(O)$_2R^b$, —N$R^a$S(O)N$R^bR^c$, —N$R^a$S(O)$_2$N$R^bR^c$, —S$R^a$, —S(O)$R^a$, or —S(O)$_2R^a$;
wherein each $R^a$, $R^b$, $R^c$, and $R^d$ is independently hydrogen; or $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or $R^b$ and $R^c$ together with the N atom to which they are attached form heterocyclyl, optionally substituted with one or more substituents Q.

3. The method of claim 2, wherein $R^2$ is selected from the group consisting of:

212

-continued

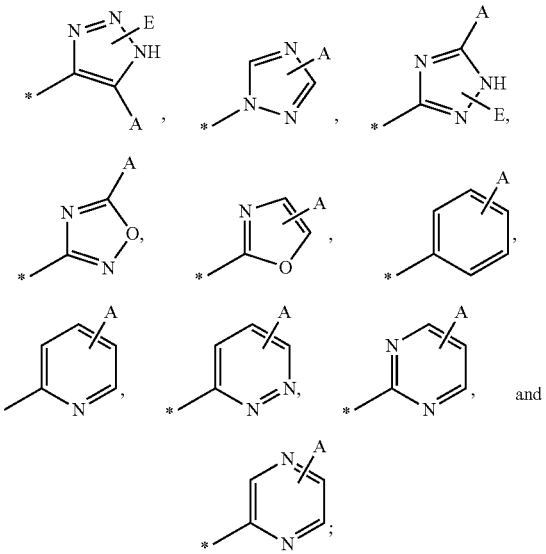

wherein
each A is independently hydrogen, halo, cyano, or nitro; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^b$, —N$R^a$C(O)O$R^b$, —N$R^a$C(O)N$R^bR^c$, —N$R^a$C(=N$R^d$)N$R^bR^c$, —N$R^a$S(O)$R^b$, —N$R^a$S(O)$_2R^b$, —N$R^a$S(O)N$R^bR^c$, —N$R^a$S(O)$_2$N$R^bR^c$, —S$R^a$, —S(O)$R^a$, or —S(O)$_2R^a$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or $R^b$ and $R^c$ together with the N atom to which they are attached form heterocyclyl, optionally substituted with one or more substituents Q; and each E is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^b$, —N$R^a$C(O)O$R^b$, —N$R^a$C(O)N$R^bR^c$, —N$R^a$C(=N$R^d$)N$R^bR^c$, —N$R^a$S(O)$R^b$, —N$R^a$S(O)$_2R^b$, —N$R^a$S(O)N$R^bR^c$, —N$R^a$S(O)$_2$N$R^bR^c$, —S$R^a$, —S(O)$R^a$, or —S(O)$_2R^a$;

wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or $R^b$ and $R^c$ together with the N atom to which they are attached form heterocyclyl, optionally substituted with one or more substituents Q.

4. The method of claim 2, wherein $R^{2'}$ is selected from the group consisting of:

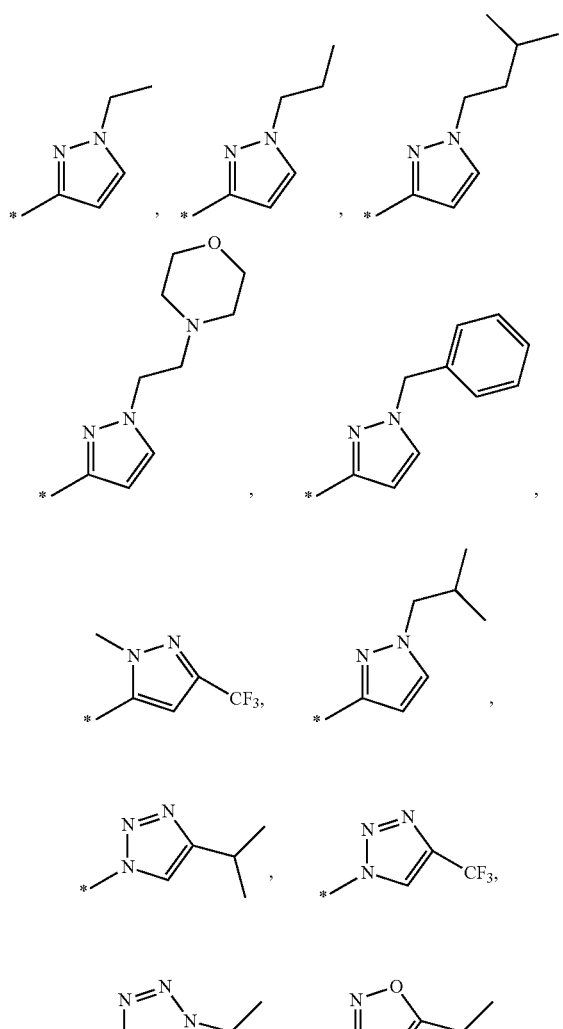
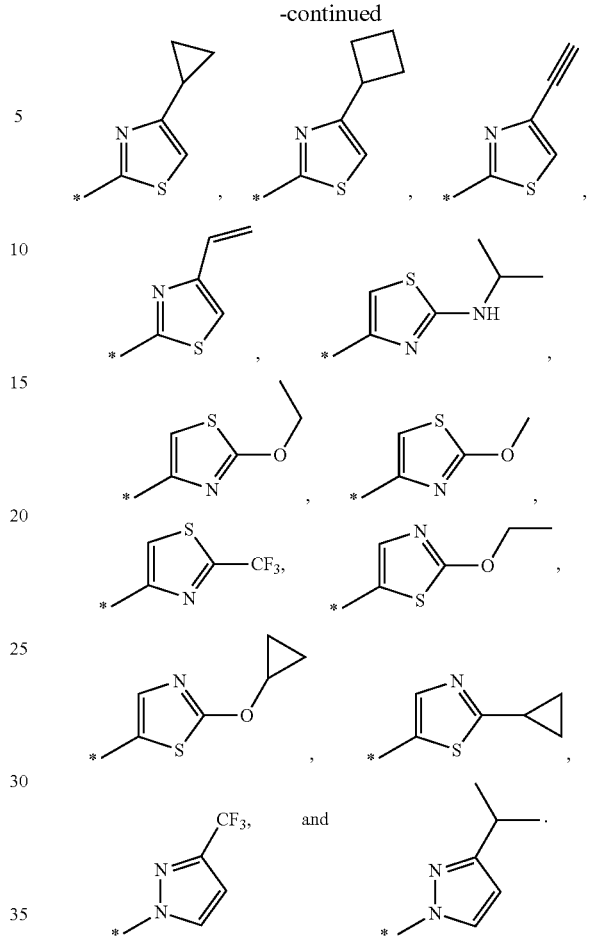
5. The method of claim 1, wherein $R^{17}$ is hydrogen or methyl.
6. The method of claim 1, wherein L is a bond or —O—.
7. The method of claim 1, wherein n is 1, 2, or 3.
8. The method of claim 1, wherein $R^8$ is methyl, cyclopropyl, 1-methylcyclopropyl, cyclobutyl, cyclopentyl, or cyclohexyl.
9. The method of claim 1, wherein the compound 129a is
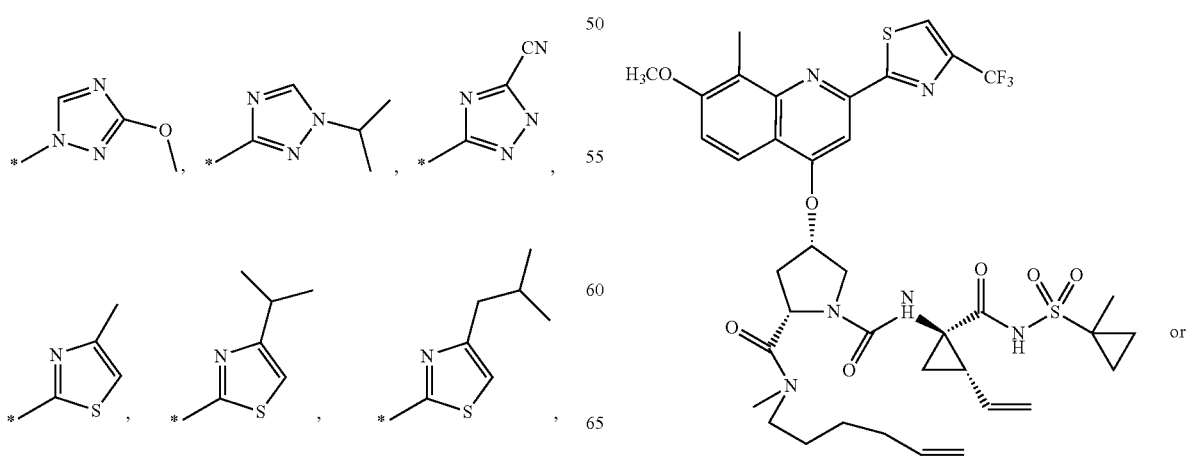
or 10. A method of preparing compound 7 having a structure of:

7 which comprises the step of contacting compound 129a having the structure of:

129a with a ring closure metathesis catalyst;
wherein:
R$^6$ is hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl;
R$^8$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, C$_{1-6}$ alkyl-C$_{3-7}$ cycloalkylene, —CH$_2$NR$^{8a}$R$^{8b}$, —CH(R$^{8c}$)NR$^{8a}$R$^{8b}$, —CHR$^{8c}$CHR$^{8d}$NR$^{8a}$R$^{8b}$, or —CH$_2$CR$^{8c}$R$^{8d}$NR$^{8a}$R$^{8b}$, wherein:
each R$^{8a}$, R$^{8c}$, and R$^{8d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, or C$_{6-14}$ aryl-C$_{1-6}$ alkylene; and
each R$^{8b}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, —S(O)$_k$R$^{11}$, —S(O)$_k$NR$^{11}$R$^{12}$, —C(O)R$^{11}$, —C(O)OR$^{11}$, —C(O)NR$^{11}$R$^{12}$, or —C(=NR$^{13}$)NR$^{11}$R$^{12}$; wherein each R$^{11}$, R$^{12}$, and R$^{13}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^{11}$ and R$^{12}$ together with the N atom to which they are attached form heterocyclyl; or
R$^{8a}$ and R$^{8b}$ together with the N atom to which they are attached form heterocyclyl;
R$^{17}$ is hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl;
L is a bond, C$_{1-6}$ alkylene, C$_{3-7}$ cycloalkylene, C$_{2-6}$ alkenylene, C$_{2-6}$ alkynylene, X, or —(CR$^{6a}$R$^{6b}$)$_p$X—; wherein p is an integer of 1, 2, or 3; R$^{6a}$ and R$^{6b}$ are each independently hydrogen, halo, cyano, hydroxyl, or alkoxy; and X is —O—, —C(O)—, —C(O)O—, —OC(O)O—, —C(O)NR$^{14}$—, —NR$^{14}$—, —NR$^{14}$C(O)NR$^{15}$—, —C(=NR$^{14}$)NR$^{15}$—, —NR$^{14}$C(=NR$^{15}$)NR$^{16}$—, —S(O)$_k$—, —S(O)$_k$NR$^{14}$—, —NR$^{14}$S(O)$_k$NR$^{15}$—, —P(O)(OR$^{14}$)—, or —OP(O)(OR$^{14}$)—, where each R$^{14}$, R$^{15}$, and R$^{16}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; and each k is independently an integer of 1 or 2; and
n is an integer of 0, 1, 2, 3, 4, or 5;
wherein each alkyl, alkylene, alkenyl, alkenylene, alkynyl, alkynylene, aryl, cycloalkyl, cycloalkylene, heterocyclyl, and heteroaryl is optionally substituted with one or more groups, each independently selected from cyano, halo, or nitro; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more, in one embodiment, one, two, three, or four, substituents Q; or —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)$_2$R$^b$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;
wherein each Q is independently selected from the group consisting of cyano, halo, or nitro; C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC (=NR^e)NR^fR^g, —OS(O)R^e, —OS(O)_2R^e, —OS(O)NR^fR^g, —OS(O)_2NR^fR^g, —NR^fR^g, —NR^eC(O)R^f, —NR^eC(O)OR^f, —NR^eC(O)NR^fR^g, —NR^eC(=NR^h)NR^fR^g, —NR^eS(O)R^f, —NR^eS(O)_2R^f, —NR^eS(O)NR^fR^g, —NR^eS(O)_2NR^fR^g, —SR^e, —S(O)R^e, or —S(O)_2R^e; wherein each R^e, R^f, R^g, and R^h is independently hydrogen; C_{1-6} alkyl, C_{2-6} alkenyl, C_{2-6} alkynyl, C_{3-7} cycloalkyl, C_{6-14} aryl, heteroaryl, or heterocyclyl; or R^f and R^g together with the N atom to which they are attached form heterocyclyl.

11. The method of claim 10, wherein R^6 is selected from the group consisting of:

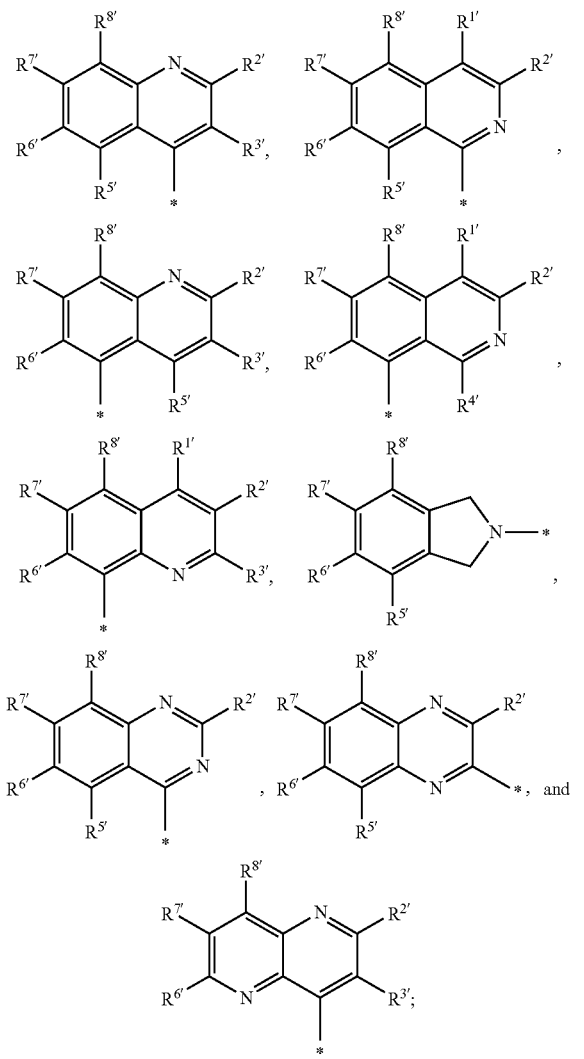

wherein:
each R^{1'}, R^{2'}, R^{3'}, R^{5'}, R^{6'}, R^{7'}, and R^{8'} is independently: hydrogen, halo, cyano, trifluoromethyl, or nitro; C_{1-6} alkyl, C_{2-6} alkenyl, C_{2-6} alkynyl, C_{3-7} cycloalkyl, C_{6-14} aryl, heteroaryl, or heterocyclyl, each optionally substituted with one or more substituents Q; or C(O)R^a, —C(O)OR^a, —C(O)NR^bR^c, —C(NR^a)NR^bR^c, —OR^a, —OC(O)R^a, —OC(O)OR^a, —OC(O)NR^bR^c, —OC(=NR^a)NR^bR^c, —OS(O)R^a, —OS(O)_2R^a, —OS(O)NR^bR^c, —OS(O)_2NR^bR^c, —NR^bR^c, —NR^aC(O)R^b, —NR^aC(O)OR^b, —NR^aC(O)NR^bR^c, —NR^aC(=NR^d)NR^bR^c, —NR^aS(O)R^b, —NR^aS(O)_2R^b, —NR^aS(O)NR^bR^c, —NR^aS(O)_2NR^bR^c, —SR^a, —S(O)R^a, or —S(O)_2R^a; wherein each R^a, R^b, R^c, and R^d is independently hydrogen; or C_{1-6} alkyl, C_{2-6} alkenyl, C_{2-6} alkynyl, C_{3-7} cycloalkyl, C_{6-14} aryl, heteroaryl, or heterocyclyl, each optionally substituted with one or more substituents Q; or R^b and R^c together with the N atom to which they are attached form heterocyclyl, optionally substituted with one or more substituents Q.

12. The method of claim 11, wherein R is selected from the group consisting of:

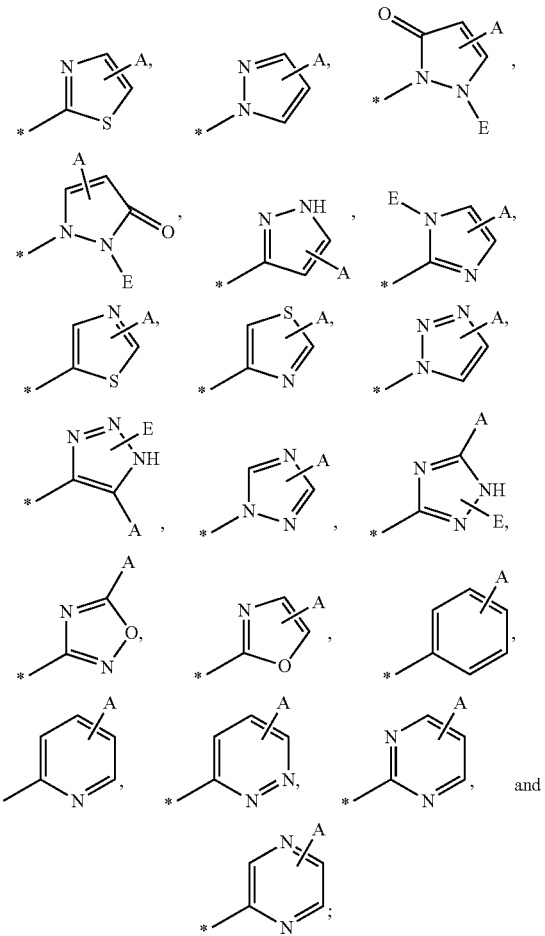

wherein
each A is independently hydrogen, halo, cyano, or nitro; C_{1-6} alkyl, C_{2-6} alkenyl, C_{2-6} alkynyl, C_{3-7} cycloalkyl, C_{6-14} aryl, heteroaryl, or heterocyclyl, each optionally substituted with one or more substituents Q; or —C(O)R^a, —C(O)OR^a, —C(O)NR^bR^c, —C(NR^a)NR^bR^c, —OR^a, —OC(O)R^a, —OC(O)OR^a, —OC(O)NR^bR^c, —OC(=NR^a)NR^bR^c, —OS(O)R^a, —OS(O)_2R^a, —OS(O)NR^bR^c, —OS(O)_2NR^bR^c, —NR^bR^c, —NR^aC(O)R^b, —NR^aC(O)OR^b, —NR^aC(O)NR^bR^c, —NR^aC(=NR^d)NR^bR^c, —NR^aS(O)R^b, —NR^aS(O)_2R^b, —NR^aS(O)NR^bR^c, —NR^aS(O)_2NR^bR^c, —SR^a, —S(O)R^a, or —S(O)_2R^a; wherein each R^a, R^b, R^c, and R^d is independently hydrogen; C_{1-6} alkyl, C_{2-6} alkenyl, C_{2-6} alkynyl, C_{3-7} cycloalkyl, C_{6-14} aryl, heteroaryl, or heterocyclyl, each optionally substituted with one or more substituents Q; or R^b and R^c together with the N atom to which they are attached form heterocyclyl, optionally substituted with one or more substituents Q; and each E is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^d$)NR$^b$R$^c$, —NR$^a$S(O)R$^b$, —NR$^a$S(O)R$^b$, —NR$^a$S(O)NR$^b$R$^c$, —NR$^a$S(O)$_2$NR$^b$R$^c$, —SR$^a$, —S(O)R$^a$, or —S(O)$_2$R$^a$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more substituents Q; or R$^b$ and R$^c$ together with the N atom to which they are attached form heterocyclyl, optionally substituted with one or more substituents Q.

13. The method of claim 11, wherein R$^2$ is selected from the group consisting of:

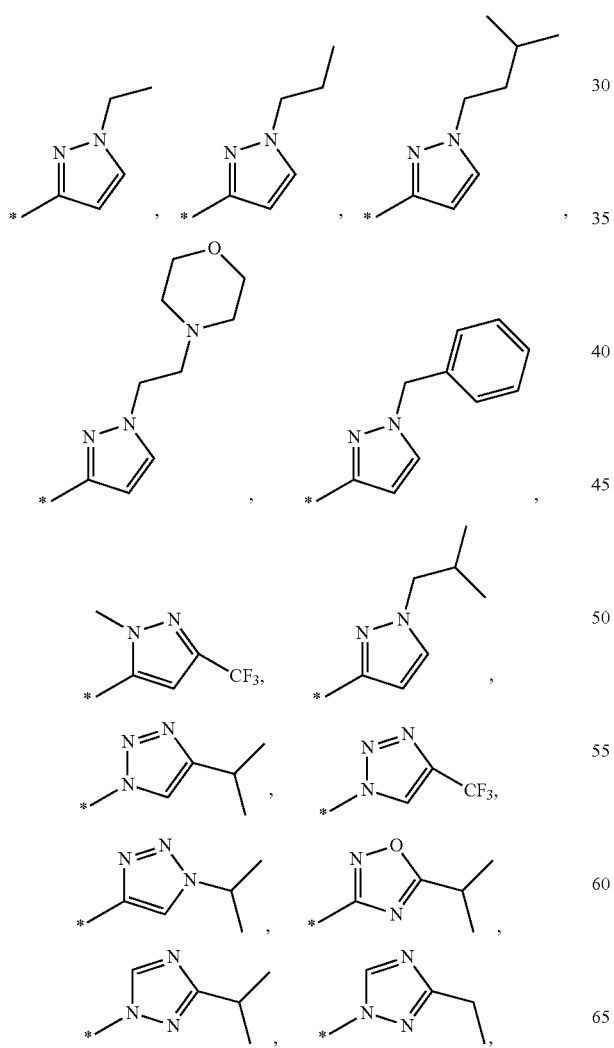

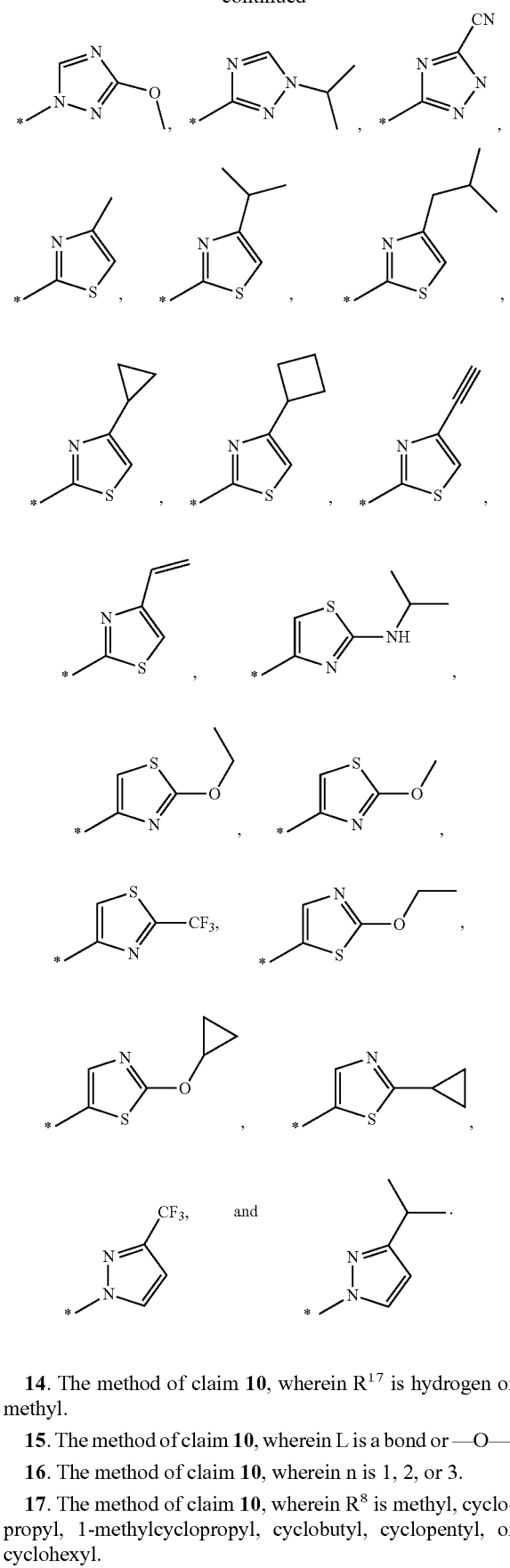

14. The method of claim 10, wherein R$^{17}$ is hydrogen or methyl.

15. The method of claim 10, wherein L is a bond or —O—.

16. The method of claim 10, wherein n is 1, 2, or 3.

17. The method of claim 10, wherein R$^8$ is methyl, cyclopropyl, 1-methylcyclopropyl, cyclobutyl, cyclopentyl, or cyclohexyl.

18. The method of claim 10, wherein the compound 7 is
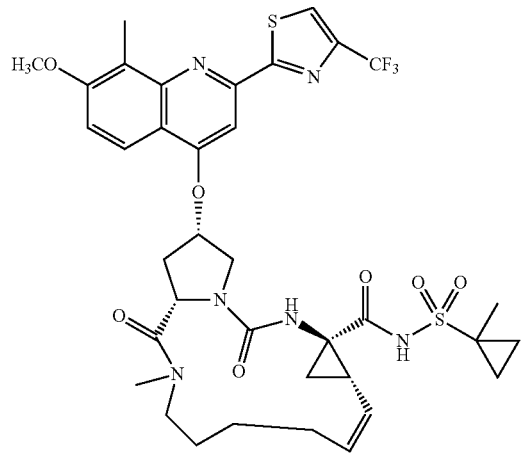
or
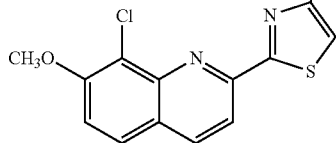
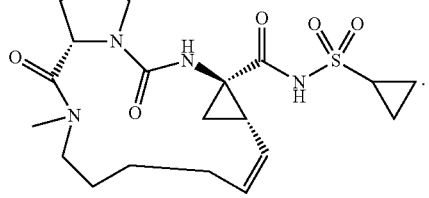
* * * * *